(12) United States Patent
Choi et al.

(10) Patent No.: US 9,163,259 B2
(45) Date of Patent: Oct. 20, 2015

(54) VIRAL VECTORS FOR THE TREATMENT OF RETINAL DYSTROPHY

(71) Applicants: Vivian Choi, Waltham, MA (US); Chad Eric Bigelow, Somerville, MA (US); Thaddeus Peter Dryja, Milton, MA (US); Seshidhar Reddy Police, Burlington, MA (US)

(72) Inventors: Vivian Choi, Waltham, MA (US); Chad Eric Bigelow, Somerville, MA (US); Thaddeus Peter Dryja, Milton, MA (US); Seshidhar Reddy Police, Burlington, MA (US)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 13/873,558

(22) Filed: Apr. 30, 2013

(65) Prior Publication Data

US 2014/0017201 A1    Jan. 16, 2014

Related U.S. Application Data

(60) Provisional application No. 61/776,167, filed on Mar. 11, 2013, provisional application No. 61/642,630, filed on May 4, 2012.

(51) Int. Cl.

| | |
|---|---|
| *C12N 15/00* | (2006.01) |
| *C12N 15/86* | (2006.01) |
| *C07H 21/04* | (2006.01) |
| *A61K 48/00* | (2006.01) |
| *A61K 38/17* | (2006.01) |
| *C07K 14/47* | (2006.01) |
| *C12N 15/79* | (2006.01) |

(52) U.S. Cl.
CPC ............ *C12N 15/86* (2013.01); *A61K 38/1709* (2013.01); *A61K 48/005* (2013.01); *A61K 48/0058* (2013.01); *C07K 14/47* (2013.01); *C07H 21/04* (2013.01); *C12N 15/79* (2013.01); *C12N 2750/14343* (2013.01); *C12N 2750/14345* (2013.01); *C12N 2750/14371* (2013.01); *C12N 2810/6027* (2013.01)

(58) Field of Classification Search
CPC ......... C12N 15/79; C12N 15/86; C07H 21/04
USPC ...................... 435/320.1, 456; 536/23.5, 24.1
See application file for complete search history.

(56) References Cited

U.S. PATENT DOCUMENTS

| | | |
|---|---|---|
| 2007/0258950 A1 | 11/2007 | Auricchio et al. |
| 2010/0297084 A1 | 11/2010 | Bennett et al. |
| 2012/0141422 A1 | 6/2012 | Barkats |

FOREIGN PATENT DOCUMENTS

| | | |
|---|---|---|
| EP | 2287323 A1 | 2/2011 |
| WO | 00/15822 A2 | 3/2000 |
| WO | 2004/084951 A2 | 3/2004 |
| WO | 2011/034947 A2 | 3/2011 |

OTHER PUBLICATIONS

Rolling et al., 2004, US 20040208847 A1.*
Sullivan, Sean M., 2005, US 20050090646 A1.*
Trinklein et al., 2009, GenEmbl Accession No. JB105613, computer printout pp. 8-9.*
Hollander et al., Journal of Clinical Investigation; vol. 120; No. 9: 3042-3053 (Sep. 2010).
Yokoi et al.; "Ocular Gene Transfer with Self-Complementary AAV Vectors" IOVS, vol. 48, No. 7: 3324-3328 (Jul. 2007).
Humbert et al. "Homozygous Deletion Related to Alu Repeats in RLBP1 Causes Retinitis Punctata Albescens" IOVS, vol. 47, No. 11: 4719-4724 (Nov. 2006).
Yin et al.; "Intraviteral Injection of AAV2 Transduces Macaque Inner Retina" IOVS, vol. 52, No. 5: 2775-2783 (Apr. 2011).
Aartsen et al.; "GFAP-Driven GFP Expression in Activated Mouse Muller Glial Cells Aligning Retinal Blood Vessels Following Intravitreal Injection of AAV2/6 Vectors" PLoS ONE, vol. 5, Issue 8, e12387: 1-12 (Aug. 2010).
Giove et al., "Transduction of the inner mouse retina using AAVrh8 and AAVrh10 via intravitreal injection" Experimental Eye Research 91: 652-659 (2010).
Klimczak et al.; "A Novel Adeno-Associated Viral Variant for Efficient and Selective Intravitreal Transduction of Rat Muller Cells" PLoS ONE, vol. 4, Issue 10, e7467: 1-10 (Oct. 2009).
Vazquez-Chona et al.; "Rlbp1 Promoter Drives Robust Muller Glial GFP Expression in Transgenic Mice" IOVS, vol. 50, No. 8: 3996-4003 (Aug. 2009).
McCarty, "Self-complementary AAV Vectors; Advances and Applications" www.moleculartherapy.org, vol. 16, No. 10: 1648-1656 (Oct. 2008).
Geller et al., "In vitro analysis of promoter activity in Muller cells" Molecular Vision 2008, 14: 691-705.
Burstedt, et al., Ocular phenotype of bothnia dystrophy, an autosomal recessive retinitis pigmentosa associated with an R234W mutation in the RLBP1 gene. Arch Ophthalmol. Feb. 2001;119(2):260-7.
Burstedt et al., Self-reported quality of life in patients with retinitis pigmentosa and maculopathy of Bothnia type. Clin Ophthalmol. Mar. 24, 2010;4:147-54.
Choi et al., Production of recombinant adeno-associated viral vectors for in vitro and in vivo use. Curr Protoc Mol Biol. Apr. 2007;Chapter 16:Unit 16.25, Supplement 78.
Choi et al., AAV hybrid serotypes: improved vectors for gene delivery. Curr Gene Ther. Jun. 2005;5(3):299-310.
Demirci et al., A novel compound heterozygous mutation in the cellular retinaldehyde-binding protein gene (RLBP1) in a patient with retinitis punctata albescens. Am J Ophthalmol. Jul. 2004;138(1):171-3.
Eichers et al., Newfoundland rod-cone dystrophy, an early-onset retinal dystrophy, is caused by splice-junction mutations in RLBP1. Am J Hum Genet. Apr. 2002;70(4):955-64.
Ferrari et al., New developments in the generation of Ad-free, high-titer rAAV gene therapy vectors. Nat Med. Nov. 1997;3(11):1295-7.
Fishman et al., Novel mutations in the cellular retinaldehyde-binding protein gene (RLBP1) associated with retinitis punctata albescens: evidence of interfamilial genetic heterogeneity and fundus changes in heterozygotes. Arch Ophthalmol. Jan. 2004;122(1):70-5.

(Continued)

*Primary Examiner* — Shin Lin Chen
(74) *Attorney, Agent, or Firm* — Forrester J. Liddle

(57) ABSTRACT

The present invention relates to viral vectors that are capable of delivering a heterologous gene to the retina and in particular delivering RLBP1 to RPE and Müller cells of the retina. The invention also relates nucleic acids useful for producing viral vectors, compositions comprising the viral vectors and uses of the compositions and viral vectors. The invention also relates to methods of delivering and/or expressing a heterologous gene to the retina, improving the rate of dark adaption in a subject and treating RLBP1-associated retinal dystrophy.

9 Claims, 7 Drawing Sheets

(56) References Cited

OTHER PUBLICATIONS

Golovleva et al., Retinitis Pigmentosa in Northern Sweden—From Gene to Treatment. Advances in Ophthalmology. Mar. 2012;25:451-72.

Golovleva et al., Mutation spectra in autosomal dominant and recessive retinitis pigmentosa in northern Sweden. Adv Exp Med Biol. 2010;664:255-62.

Grieger et al., Production and characterization of adeno-associated viral vectors. Nat Protoc. 2006;1(3):1412-28.

He et al., Bothnia dystrophy is caused by domino-like rearrangements in cellular retinaldehyde-binding protein mutant R234W. Proc Natl Acad Sci U S A. Nov. 3, 2009;106(44):18545-50.

Jacobson et al., Safety of recombinant adeno-associated virus type 2-RPE65 vector delivered by ocular subretinal injection. Mol Ther. Jun. 2006;13(6):1074-84.

Katsanis et al., Fundus albipunctatus and retinitis punctata albescens in a pedigree with an R150Q mutation in RLBP1. Clin Genet. Jun. 2001;59(6):424-9.

Köhn et al., Carrier of R14W in carbonic anhydrase IV presents Bothnia dystrophy phenotype caused by two allelic mutations in RLBP1. Invest Ophthalmol Vis Sci. Jul. 2008;49(7):3172-7.

Lock et al., Rapid, simple, and versatile manufacturing of recombinant adeno-associated viral vectors at scale. Hum Gene Ther. Oct. 2010;21(10):1259-71.

Maw et al., Mutation of the gene encoding cellular retinaldehyde-binding protein in autosomal recessive retinitis pigmentosa. Nat Genet. Oct. 1997;17(2):198-200.

McCarty et al., Adeno-associated virus terminal repeat (TR) mutant generates self-complementary vectors to overcome the rate-limiting step to transduction in vivo. Gene Ther. Dec. 2003;10(26):2112-8.

Morimura et al., Recessive mutations in the RLBP1 gene encoding cellular retinaldehyde-binding protein in a form of retinitis punctate albescens. Invest Ophthalmol Vis Sci. Apr. 1999;40(5):1000-4.

Muzyczka et al., Chapter 69: Parvoviridae: The viruses and their replication. Fields Virology. Aug. 2001, 4$^{th}$ Edition. Lippincott Williams & Wilkins. 27 pages.

Naz et al., Mutations in RLBP1 associated with fundus albipunctatus in consanguineous Pakistani families. Br J Ophthalmol. Jul. 2011;95(7):1019-24.

Nojima et al., Clinical features of a Japanese case with Bothnia dystrophy. Ophthalmic Genet. Jun. 2012;33(2):83-8.

Phelan et al., A brief review of retinitis pigmentosa and the identified retinitis pigmentosa genes. Mol Vis. Jul. 8, 2000;6:116-24.

Roman et al., Electroretinographic analyses of Rpe65-mutant rd12 mice: developing an in vivo bioassay for human gene therapy trials of Leber congenital amaurosis. Mol Vis. Sep. 18, 2007;13:1701-10.

Saari et al., Cellular retinaldehyde-binding protein is expressed by oligodendrocytes in optic nerve and brain. Glia. Nov. 1997;21(3):259-68.

Saari et al., Visual cycle impairment in cellular retinaldehyde binding protein (CRALBP) knockout mice results in delayed dark adaptation. Neuron. Mar. 2001;29(3):739-48.

Samulski et al., Rescue of adeno-associated virus from recombinant plasmids: gene correction within the terminal repeats of AAV. Cell. May 1983;33(1):135-43.

Schmidt et al., Adeno-associated virus type 12 (AAV12): a novel AAV serotype with sialic acid-and heparan sulfate proteoglycan-independent transduction activity. J Virol. Feb. 2008;82(3):1399-406.

Smith et al., A simplified baculovirus-AAV expression vector system coupled with one-step affinity purification yields high-titer rAAV stocks from insect cells. Mol Ther. Nov. 2009;17(11):1888-96.

Travis et al., Diseases caused by defects in the visual cycle: retinoids as potential therapeutic agents. Annu Rev Pharmacol Toxicol. 2007;47:469-512.

Vandenberghe et al., Efficient serotype-dependent release of functional vector into the culture medium during adeno-associated virus manufacturing. Hum Gene Ther. Oct. 2010;21(10):1251-7.

Wang et al., The cone-specific visual cycle. Prog Retin Eye Res. Mar. 2011;30(2):115-28.

\* cited by examiner

1A

1B

Dark adaptation in RLBP1 -/- and +/+ mice.

3A

3B

3C

3D

4A

4B

5A

5B

SEQUENCE LISTING

```
<160> NUMBER OF SEQ ID NOS: 71

<210> SEQ ID NO 1
<211> LENGTH: 103
<212> TYPE: DNA
<213> ORGANISM: Artificial Sequence
<220> FEATURE:
<223> OTHER INFORMATION: Description of Artificial Sequence: Synthetic
``` polynucleotide

<400> SEQUENCE: 1
cgcgctcgct cgctcactga ggccgcccgg gcaaagcccg ggcgtcgggc gacctttggt    60
cgcccggcct cagtgagcga gcgagcgcgc agagagggag tgg    103

<210> SEQ ID NO 2
<211> LENGTH: 119
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
ctgcgcgctc gctcgctcac tgaggccgcc cgggcgtcgg gcgacctttg gtcgcccggc    60
ctcagtgagc gagcgagcgc gcagagaggg agtggccaac tccatcacta ggggttcct    119

<210> SEQ ID NO 3
<211> LENGTH: 590
<212> TYPE: DNA
<213> ORGANISM: Homo sapiens

<400> SEQUENCE: 3
ttgtcctctc cctgcttggc cttaaccagc cacatttctc aactgacccc actcactgca    60
gaggtgaaaa ctaccatgcc aggtcctgct ggctggggga ggggtgggca ataggcctgg    120
atttgccaga gctgccactg tagatgtagt catatttacg atttccttc acctcttatt    180 accctggtgg tggtggtggg ggggggggg tgctctctca gcaacccac cccgggatct    240 tgaggagaaa gagggcagag aaaagaggga atgggactgg cccagatccc agccccacag    300
ccgggcttcc acatggccga gcaggaactc cagagcagga gcacacaaag gagggctttg    360
atgcgcctcc agccaggccc aggcctctcc cctctcccct ttctctctgg gtcttccttt    420
gccccactga gggcctcctg tgagcccgat ttaacgaaa ctgtgggcgg tgagaagttc    480
cttatgacac actaatccca acctgctgac cggaccacgc ctccagcgga gggaaccctct    540 agagctccag gacattcagg taccaggtag ccccaaggag gagctgccga    590

<210> SEQ ID NO 4
<211> LENGTH: 183
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
aactgaaaaa ccagaaagtt aactggtaag tttagtcttt ttgtctttta tttcaggtcc    60
cggatccggt ggtggtgcaa atcaaagaac tgctcctcag tggatgttgc ctttacttct    120
aggcctgtac ggaagtgtta cttctgctct aaaagctgcg gaattgtacc cgccccggga    180
tcc    183

<210> SEQ ID NO 5
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

```
gccacc                                                                       6
```

<210> SEQ ID NO 6
<211> LENGTH: 954
<212> TYPE: DNA
<213> ORGANISM: Homo sapiens

<400> SEQUENCE: 6

```
atgtcagaag gggtgggcac gttccgcatg gtacctgaag aggaacagga gctccgtgcc          60
caactggagc agctcacaac caaggaccat ggacctgtct ttggcccgtg cagccagctg         120
ccccgccaca ccttgcagaa ggccaaggat gagctgaacg agagagagga gacccgggag         180
gaggcagtgc gagagctgca ggagatggtg caggcgcagg cggcctcggg ggaggagctg         240
gcggtggccg tggcggagag ggtgcaagag aaggacagcg gcttcttcct gcgcttcatc         300
cgcgcacgga agttcaacgt gggccgtgcc tatgagctgc tcagaggcta tgtgaatttc         360
cggctgcagt accctgagct cttgtgacagc ctgtccccag aggctgtccg ctgcaccatt         420
gaagctggct accctggtgt cctctctagt cgggacaagt atggccgagt ggtcatgctc         480
ttcaacattg agaactggca aagtcaagaa atcacctttg atgagatctt gcaggcatat         540
tgcttcatcc tggagaagct gctggagaat gaggaaactc aaatcaatgg cttctgcatc         600
attgagaact tcaagggctt taccatgcag caggctgcta gtctccggac ttcagatctc         660
aggaagatgg tggacatgct ccaggattcc ttcccagccc ggttcaaagc catccacttc         720
atccaccagc catggtactt caccacgacc tacaatgtgg tcaagccctt cttgaagagc         780
aagctgcttg agagggtctt tgtccacggg gatgacctt tctggtttcta ccaggagatc         840
gatgagaaca tcctgccctc tgacttcggg ggcacgctgc ccaagtatga tgccaaggcc         900
gttgctgagc agctctttgg cccccaggcc caagctgaga cacagccctt ctga              954
```

<210> SEQ ID NO 7
<211> LENGTH: 317
<212> TYPE: PRT
<213> ORGANISM: Homo sapiens

<400> SEQUENCE: 7

```
Met Ser Glu Gly Val Gly Thr Phe Arg Met Val Pro Glu Glu Gln
1               5                   10                  15

Glu Leu Arg Ala Gln Leu Glu Gln Leu Thr Thr Lys Asp His Gly Pro
            20                  25                  30

Val Phe Gly Pro Cys Ser Gln Leu Pro Arg His Thr Leu Gln Lys Ala
        35                  40                  45

Lys Asp Glu Leu Asn Glu Arg Glu Glu Thr Arg Glu Glu Ala Val Arg
    50                  55                  60

Glu Leu Gln Glu Met Val Gln Ala Gln Ala Ala Ser Gly Glu Glu Leu
65                  70                  75                  80

Ala Val Ala Val Ala Glu Arg Val Gln Glu Lys Asp Ser Gly Phe Phe
                85                  90                  95

Leu Arg Phe Ile Arg Ala Arg Lys Phe Asn Val Gly Arg Ala Tyr Glu
            100                 105                 110

Leu Leu Arg Gly Tyr Val Asn Phe Arg Leu Gln Tyr Pro Glu Leu Phe
        115                 120                 125

Asp Ser Leu Ser Pro Glu Ala Val Arg Cys Thr Ile Glu Ala Gly Tyr
    130                 135                 140
```

```
Pro Gly Val Leu Ser Ser Arg Asp Lys Tyr Gly Arg Val Val Met Leu
145                 150                 155                 160

Phe Asn Ile Glu Asn Trp Gln Ser Gln Glu Ile Thr Phe Asp Glu Ile
                165                 170                 175

Leu Gln Ala Tyr Cys Phe Ile Leu Glu Lys Leu Leu Glu Asn Glu Glu
            180                 185                 190

Thr Gln Ile Asn Gly Phe Cys Ile Ile Glu Asn Phe Lys Gly Phe Thr
        195                 200                 205

Met Gln Gln Ala Ala Ser Leu Arg Thr Ser Asp Leu Arg Lys Met Val
    210                 215                 220

Asp Met Leu Gln Asp Ser Phe Pro Ala Arg Phe Lys Ala Ile His Phe
225                 230                 235                 240

Ile His Gln Pro Trp Tyr Phe Thr Thr Thr Tyr Asn Val Val Lys Pro
                245                 250                 255

Phe Leu Lys Ser Lys Leu Leu Glu Arg Val Phe Val His Gly Asp Asp
            260                 265                 270

Leu Ser Gly Phe Tyr Gln Glu Ile Asp Glu Asn Ile Leu Pro Ser Asp
        275                 280                 285

Phe Gly Gly Thr Leu Pro Lys Tyr Asp Gly Lys Ala Val Ala Glu Gln
    290                 295                 300

Leu Phe Gly Pro Gln Ala Gln Ala Glu Asn Thr Ala Phe
305                 310                 315

<210> SEQ ID NO 8
<211> LENGTH: 236
<212> TYPE: DNA
<213> ORGANISM: Simian virus 40

<400> SEQUENCE: 8
gatcataatc agccatacca catttgtaga ggttttactt gctttaaaaa acctcccaca    60 cctcccctg aacctgaaac ataaaatgaa tgcaattgtt gttgttaact tgtttattgc    120
agcttataat ggttacaaat aaagcaatag catcacaaat ttcacaaata agcattttt    180 ttcactgcat tctagttgtg gtttgtccaa actcatcaat gtatcttatc atgtct       236

<210> SEQ ID NO 9
<211> LENGTH: 130
<212> TYPE: DNA
<213> ORGANISM: Adeno-associated virus

<400> SEQUENCE: 9
aggaacccct agtgatggag ttggccactc cctctctgcg cgctcgctcg ctcactgagg    60
ccgggcgacc aaaggtcgcc cgacgcccgg gctttgcccg gcggcctca gtgagcgagc    120 gagcgcgcag                                                          130

<210> SEQ ID NO 10
<211> LENGTH: 3157
<212> TYPE: DNA
<213> ORGANISM: Homo sapiens

<400> SEQUENCE: 10
ttgtcctctc cctgcttggc cttaaccagc cacatttctc aactgacccc actcactgca    60
gaggtgaaaa ctaccatgcc aggtcctgct ggctggggga ggggtgggca ataggcctgg    120
atttgccaga gctgccactg tagatgtagt catatttacg atttcccttc acctcttatt    180
accctggtgg tggtggtggg ggggggggg tgctctctca gcaaccccac cccgggatct    240
```

-continued

```
tgaggagaaa gagggcagag aaaagaggga atgggactgg cccagatccc agccccacag    300
ccgggcttcc acatggccga gcaggaactc cagagcagga gcacacaaag gagggctttg    360
atgcgcctcc agccaggccc aggcctctcc cctctcccct ttctctctgg gtcttccttt    420
gccccactga gggcctcctg tgagcccgat ttaacggaaa ctgtgggcgg tgagaagttc    480
cttatgacac actaatccca acctgctgac cggaccacgc ctccagcgga gggaacctct    540
agagctccag gacattcagg taccaggtag ccccaaggag gagctgccga cctggcaggt    600
aagtcaatac ctggggcttg cctgggccag ggagcccagg actggggtga ggactcaggg    660
gagcagggag accacgtccc aagatgcctg taaaactgaa accacctggc cattctccag    720
gttgagccag accaatttga tggcagattt agcaaataaa aatacaggac acccagttaa    780
atgtgaattt cagatgaaca gcaaatactt ttttagtatt aaaaaagttc acatttaggc    840
tcacgcctgt aatcccagca ctttgggagg ccgaggcagg cagatcacct gaggtcagga    900
gttcgagacc agcctggcca acatggtgaa accccatctc cactaaaaat accaaaaatt    960
agccaggcgt gctggtgggc acctgtagtt ccagctactc aggaggctaa ggcaggagaa   1020
ttgcttgaac ctggggaggca gaggttgcag tgagctgaga tcgcaccatt gcactctagc   1080
ctgggcgaca agaacaaaac tccatctcaa aaaaaaaaaa aaaaaaaaag ttcacattta   1140
actgggcatt ctgtatttaa ttggtaatct gagatggcag ggaacagcat cagcatggtg   1200
tgagggatag gcatttttttc attgtgtaca gcttgtaaat cagtattttt aaaactcaaa   1260
gttaatggct tgggcatatt tagaaaagag ttgccgcacg gacttgaacc ctgtattcct   1320
aaaatctagg atcttgttct gatggtctgc acaactggct gggggtgtcc agccactgtc   1380
cctcttgcct gggctcccca gggcagttct gtcagcctct ccatttccat tcctgttcca   1440
gcaaaaccca actgatagca cagcagcatt tcagcctgtc tacctctgtg cccacatacc   1500
tggatgtcta ccagccagaa aggtggctta gatttggttc ctgtgggtgg attatggccc   1560
ccagaacttc cctgtgcttg ctgggggtgt ggagtggaaa gagcaggaaa tgggggaccc   1620
tccgatactc tatgggggtc ctccaagtct cttttgtgcaa gttagggtaa taatcaatat   1680
ggagctaaga aagagaaggg gaactatgct ttagaacagg acactgtgcc aggagcattg   1740
cagaaattat atggttttca cgacagttct tttttggtagg tactgttatt atcctcagtt   1800
tgcagatgag gaaactgaga cccagaaagg ttaaataact tgctagggtc acacaagtca   1860
taactgacaa agcctgattc aaacccaggt ctccctaacc tttaaggttt ctatgacgcc   1920
agctctccta gggagtttgt cttcagatgt cttggctcta ggtgtcaaaa aaagacttgg   1980
tgtcaggcag gcataggttc aagtcccaac tctgtcactt accaactgtg actaggtgat   2040
tgaactgacc atggaacctg gtcacatgca ggagcaggat ggtgaagggt tcttgaaggc   2100
acttaggcag gacatttagg caggagagaa aacctggaaa cagaagagct gtctccaaaa   2160
atacccactg gggaagcagg ttgtcatgtg ggccatgaat gggacctgtt ctggtaacca   2220
agcattgctt atgtgtccat tacatttcat aacacttcca tcctacttta cagggaacaa   2280
ccaagactgg ggttaaatct cacagcctgc aagtggaaga gaagaacttg aacccaggtc   2340
caacttttgc gccacagcag gctgcctctt ggtcctgaca ggaagtcaca acttgggtct   2400
gagtactgat ccctggctat ttttttggctg tgttaccttg gacaagtcac ttattcctcc   2460
tcccgtttcc tcctatgtaa aatggaaata ataatgttga ccctgggtct gagagagtgg   2520
atttgaaagt acttagtgca tcacaaagca cagaacacac ttccagtctc gtgattatgt   2580
acttatgtaa ctggtcatca cccatcttga gaatgaatgc attggggaaa gggccatcca   2640
```

```
ctaggctgcg aagtttctga gggactcctt cgggctggag aaggatggcc acaggaggga    2700
ggagagattg ccttatcctg cagtgatcat gtcattgaga acagagccag attcttttt    2760 tcctggcagg gccaacttgt tttaacatct aaggactgag ctatttgtgt ctgtgccctt    2820
tgtccaagca gtgtttccca aagtgtagcc caagaaccat ctccctcaga gccaccagga    2880
agtgctttaa attgcaggtt cctaggccac agcctgcacc tgcagagtca gaatcatgga    2940
ggttgggacc caggcacctg cgtttctaac aaatgcctcg ggtgattctg atgcaattga    3000
aagtttgaga tccacagttc tgagacaata acagaatggt ttttctaacc cctgcagccc    3060
tgacttccta tcctagggaa ggggccggct ggagaggcca ggacagagaa agcagatccc    3120 ttcttttttcc aaggactctg tgtcttccat aggcaac                           3157

<210> SEQ ID NO 11
<211> LENGTH: 1585
<212> TYPE: DNA
<213> ORGANISM: Homo sapiens

<400> SEQUENCE: 11
tacgtaatat ttattgaagt ttaatattgt gtttgtgata cagaagtatt tgctttaatt      60
ctaaataaaa attttatgct tttattgctg gtttaagaag atttggatta tccttgtact     120
ttgaggagaa gttcttatt tgaaatattt tggaaacagg tcttttaatg tggaaagata     180
gatattaatc tcctcttcta ttactctcca agatccaaca aaagtgatta taccccccaa     240
aatatgatgg tagtatctta tactaccatc atttttatagg catgggctc ttagctgcaa     300 ataatggaac taactctaat aaagcagaac gcaaatattg taaatattag agagctaaca     360
atctctggga tggctaaagg atggagcttg gaggctaccc agccagtaac aatattccgg     420
gctccactgt tgaatggaga cactacaact gccttggatg ggcagagata ttatggatgc     480
taagccccag gtgctaccat taggacttct accactgtcc ctaacgggtg agcccatca     540 catgcctatg ccctcactgt aaggaaatga agctactgtt gtatatcttg ggaagcactt     600
ggattaattg ttatacagtt tgttgaaga agaccccctag ggtaagtagc cataactgca     660
cactaaattt aaaattgtta atgagtttct caaaaaaaat gttaaggttg ttagctggta     720
tagtatatat cttgcctgtt ttccaaggac ttctttgggc agtaccttgt ctgtgctggc     780
aagcaactga gacttaatga aagagtattg gagatatgaa tgaattgatg ctgtatactc     840
tcagagtgcc aaacatatac caatggacaa gaaggtgagg cagagagcag acaggcatta     900
gtgacaagca aagatatgca gaatttcatt ctcagcaaat caaagtcct caacctggtt     960 ggaagaatat tggcactgaa tggtatcaat aaggttgcta gagagggtta gaggtgcaca    1020
atgtgcttcc ataacatttt atacttctcc aatcttagca ctaatcaaac atggttgaat    1080
actttgttta ctataactct tacagagtta agatctgt gaagacaggg acagggacaa    1140
tacccatctc tgtctggttc ataggtggta tgtaatagat atttttaaaa ataagtgagt    1200
taatgaatga gggtgagaat gaaggcacag aggtattagg gggaggtggg cccagagaa    1260 tggtgccaag gtccagtggg gtgactggga tcagctcagg cctgacgctg gccactccca    1320
cctagctcct ttcttctaa tctgttctca ttctccttgg gaaggattga ggtctctgga    1380
aaacagccaa acaactgtta tgggaacagc aagcccaaat aaagccaagc atcaggggga    1440
tctgagagct gaaagcaact tctgttcccc ctccctcagc tgaaggggtg gggaagggct    1500
cccaaagcca taactccttt taagggattt agaaggcata aaaaggcccc tggctgagaa    1560
```

```
cttccttctt cattctgcag ttggt                                      1585
```

<210> SEQ ID NO 12
<211> LENGTH: 628
<212> TYPE: DNA
<213> ORGANISM: Homo sapiens

<400> SEQUENCE: 12

```
tacgtaattc tgtcatttta ctagggtgat gaaattccca agcaacacca tccttttcag   60
ataagggcac tgaggctgag agaggagctg aaacctaccc ggcgtcacca cacacaggtg  120
gcaaggctgg gaccagaaac caggactgtt gactgcagcc cggtattcat tctttccata  180
gcccacaggg ctgtcaaaga ccccagggcc tagtcagagg ctcctccttc ctggagagtt  240
cctggcacag aagttgaagc tcagcacagc ccctaaccc ccaactctct ctgcaaggcc   300
tcaggggtca gaacactggt ggagcagatc ctttagcctc tggattttag ggccatggta  360
gaggggggtgt tgccctaaat tccagccctg gtctcagccc aacaccctcc aagaagaaat  420
tagagggcc atgccaggc tgtgctagcc gttgcttctg agcagattac aagaagggac    480
taagacaagg actcctttgt ggaggtcctg gcttagggag tcaagtgacg gcggctcagc  540
actcacgtgg gcagtgccag cctctaagag tgggcagggg cactggccac agagtcccag  600
ggagtcccac cagcctagtc gccagacc                                    628
```

<210> SEQ ID NO 13
<211> LENGTH: 2454
<212> TYPE: DNA
<213> ORGANISM: Homo sapiens

<400> SEQUENCE: 13

```
gggccccggt gttatctcat tctttttcct cctctgtaag ttgacatgtg atgtgggaac   60
aaaggggata aagtcattat tttgtgctaa aatcgtaatt ggagaggacc tcctgttagc  120
tgggctttct tctatttatt gtggtggtta ctggagttcc ttcttctagt tttaggatat  180
atatatatat ttttttttttt tctttccctg aagatataat aatatatata cttctgaaga  240
ttgagatttt taaattagtt gtattgaaaa ctagctaatc agcaatttaa ggctagcttg  300
agacttatgt cttgaatttg ttttttgtagg ctccaaaacc aaggagggag tggtgcatgg  360
tgtggcaaca ggtaagctcc attgtgctta tatccaaaga tgatatttaa agtatctagt  420
gattagtgtg gcccagtatt caagattcct atgaaattgt aaaacaatca ctgagcattc  480
taagaacata tcagtcttat tgaaactgaa ttctttataa agtattttta aaaaggtaaa  540
tattgattat aaataaaaaa tatacttgcc aagaataatg agggctttga attgataagc  600
tatgtttaat ttatagtaag tgggcattta aatattctga ccaaaaatgt attgacaaac  660
tgctgacaaa ataaaaatgt gaatattgcc ataattttaa aaaagagta  aaatttctgt   720
tgattacagt aaaatatttt gaccttaaat tatgttgatt acaatattcc tttgataatt  780
cagagtgcat ttcaggaaac acccttggac agtcagtaaa ttgtttattg tatttatctt  840
tgtattgtta tggtatagct atttgtacaa atattattgt gcaattatta catttctgat  900
tatattattc atttggccta aatttaccaa gaatttgaac aagtcaatta ggtttacaat  960
caagaaatat caaaaatgat gaaaaggatg ataatcatca tcagatgttg aggaagatga 1020
cgatgagagt gccagaaata gagaaatcaa aggagaacca aaatttaaca aattaaaagc 1080
ccacagactt gctgtaatta agttttctgt tgtaagtact ccacgtttcc tggcagatgt 1140
ggtgaagcaa aagatataat cagaaatata atttatatga tcggaaagca ttaaacacaa 1200
```

```
tagtgcctat acaaataaaa tgttcctatc actgacttct aaaatggaaa tgaggacaat    1260
gatatgggaa tcttaataca gtgttgtgga taggactaaa acacaggag tcagatcttc     1320 ttggttcaac ttcctgctta ctccttacca gctgtgtgtt ttttgcaagg ttcttcacct    1380
ctatgtgatt tagcttcctc atctataaaa taattcagtg aattaatgta cacaaaacat    1440
ctggaaaaca aaagcaaaca atatgtattt tataagtgtt acttatagtt ttatagtgaa    1500
ctttcttgtg caacattttt acaactagtg gagaaaaata tttctttaaa tgaatacttt    1560
tgatttaaaa atcagagtgt aaaaataaaa cagactcctt tgaaactagt tctgttagaa    1620
gttaattgtg cacctttaat gggctctgtt gcaatccaac agagaagtag ttaagtaagt    1680
ggactatgat ggcttctagg gacctcctat aaatatgata ttgtgaagca tgattataat    1740
aagaactaga taacagacag gtggagactc cactatctga agagggtcaa cctagatgaa    1800
tggtgttcca tttagtagtt gaggaagaac ccatgaggtt tagaaagcag acaagcatgt    1860
ggcaagttct ggagtcagtg gtaaaaatta aagaacccaa ctattactgt cacctaatga    1920
tctaatggag actgtggaga tgggctgcat ttttttaatc ttctccagaa tgccaaaatg    1980
taaacacata tctgtgtgtg tgtgtgtgtg tgtgtgtgtg tgtgagagag agagagagag    2040
agagagagac tgaagtttgt acaattagac attttataaa atgttttctg aaggacagtg    2100
gctcacaatc ttaagtttct aacattgtac aatgttggga gactttgtat actttatttt    2160
ctctttagca tattaaggaa tctgagatgt cctacagtaa agaaatttgc attacatagt    2220
taaaatcagg gttattcaaa ctttttgatt attgaaacct ttcttcatta gttactaggg    2280
ttgaatgaaa ctagtgttcc acagaaaact atgggaaatg ttgctaggca gtaaggacat    2340
ggtgatttca gcatgtgcaa tatttacagc gattgcaccc atggaccacc ctggcagtag    2400
tgaaataacc aaaaatgctg tcataactag tatggctatg agaaacacat tggg           2454

<210> SEQ ID NO 14
<211> LENGTH: 1503
<212> TYPE: DNA
<213> ORGANISM: Homo sapiens

<400> SEQUENCE: 14
attctccagg ttgagccaga ccaatttgat ggtagattta gcaaataaaa atacaggaca     60
cccagttaaa tgtgaatttc cgatgaacag caaatacttt tttagtatta aaaagttca     120 catttaggct cacgcctgta atcccagcac tttgggaggc cgaggcaggc agatcacctg    180
aggtcaggag ttcgagacca gcctggccaa catggtgaaa ccccatctcc actaaaaata    240
ccaaaaatta gccaggcgtg ctggtgggca cctgtagttc cagctactca ggaggctaag    300
gcaggagaat tgcttgaacc tgggaggcag aggttgcagt gagctgagat cgcaccattg    360
cactctagcc tgggcgacaa gaacaaaact ccatctcaaa aaaaaaaaaa aaaaaaagt    420 tcacattta ctgggcattc tgtatttaat tggtaatctg agatggcagg gaacagcatc     480
agcatggtgt gagggatagg catttttttca ttgtgtacag cttgtaaatc agtattttta    540
aaactcaaag ttaatggctt gggcatattt agaaaagagt tgccgcacgg acttgaaccc    600
tgtattccta aaatctagga tcttgttctg atggtctgca caactggctg ggggtgtcca    660
gccactgtcc ctcttgcctg ggctccccag ggcagttctg tcagcctctc catttccatt    720
cctgttccag caaaacccaa ctgatagcac agcagcattt cagcctgtct acctctgtgc    780
ccacatacct ggatgtctac cagccagaaa ggtggcttag atttggttcc tgtgggtgga    840
```

```
ttatggcccc cagaacttcc ctgtgcttgc tgggggtgtg gagtggaaag agcaggaaat      900
ggggacccct ccgatactct atggggtcc tccaagtctc tttgtgcaag ttagggtaat       960
aatcaatatg gagctaagaa agagaagggg aactatgctt tagaacagga cactgtgcca     1020
ggagcattgc agaaattata tggttttcac gacagttctt tttggtaggt actgttatta    1080
tcctcagttt gcagatgagg aaactgagac ccagaaaggt taaataactt gctagggtca    1140
cacaagtcat aactgacaaa gcctgattca aacccaggtc tccctaacct ttaaggtttc    1200
tatgacgcca gctctcctag ggagtttgtc ttcagatgtc ttggctctag gtgtcaaaaa    1260
aagacttggt gtcaggcagg cataggttca agtcccaact ctgtcactta ccaactgtga    1320
ctaggtgatt gaactgacca tggaacctgg tcacatgcag gagcaggatg gtgaagggtt    1380
cttgaaggca cttaggcagg acatttaggc aggagagaaa acctggaaac agaagagctg    1440
tctccaaaaa tacccactgg ggaagcaggt tgtcatgtgg gccatgaatg ggacctgttc    1500
tgg                                                                    1503
```

<210> SEQ ID NO 15
<211> LENGTH: 2619
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 15

```
ctgcctgcag gggcgcctga tgcggtattt tctccttacg catctgtgcg gtatttcaca      60
ccgcatacgt caaagcaacc atagtacgcg ccctgtagcg gcgcattaag cgcggcgggt     120
gtggtggtta cgcgcagcgt gaccgctaca cttgccagcg ccttagcgcc cgctcctttc     180
gctttcttcc cttcctttct cgccacgttc gccggctttc cccgtcaagc tctaaatcgg    240
gggctccctt tagggttccg atttagtgct ttacggcacc tcgaccccaa aaaacttgat    300
ttgggtgatg gttcacgtag tgggccatcg ccctgataga cggttttttcg ccctttgacg    360
ttggagtcca cgttctttaa tagtggactc ttgttccaaa ctggaacaac actcaactct    420
atctcgggct attcttttga tttataaggg attttgccga tttcggtcta ttggttaaaa    480
aatgagctga tttaacaaaa atttaacgcg aattttaaca aaatattaac gtttacaatt    540
ttatggtgca ctctcagtac aatctgctct gatgccgcat agttaagcca gccccgacac    600
ccgccaacac ccgctgacgc gccctgacgg gcttgtctgc tcccggcatc cgcttacaga    660
caagctgtga ccgtctccgg gagctgcatg tgtcagaggt tttcaccgtc atcaccgaaa    720
cgcgcgagac gaaagggcct cgtgatacgc ctatttttat aggttaatgt catgataata    780
atggtttctt agacgtcagg tggcactttt cggggaaatg tgcgcggaac ccctatttgt    840
ttatttttct aaatacattc aaatatgtat ccgctcatga caataaacc ctgataaatg     900
cttcaataat attgaaaaag gaagagtatg agtattcaac atttccgtgt cgcccttatt     960
cccttttttg cggcattttg ccttcctgtt tttgctcacc cagaaacgct ggtgaaagta    1020
aaagatgctg aagatcagtt gggtgcacga gtgggttaca tcgaactgga tctcaacagc    1080
ggtaagatcc ttgagagttt tcgccccgaa gaacgttttc caatgatgag cacttttaaa    1140
gttctgctat gtggcgcggt attatcccgt attgacgccg ggcaagagca actcggtcgc    1200
cgcatacact attctcagaa tgacttggtt gagtactcac cagtcacaga aaagcatctt    1260
acggatggca tgacagtaag agaattatgc agtgctgcca taaccatgag tgataacact    1320
```

```
gcggccaact tacttctgac aacgatcgga ggaccgaagg agctaaccgc ttttttgcac    1380
aacatggggg atcatgtaac tcgccttgat cgttgggaac cggagctgaa tgaagccata    1440
ccaaacgacg agcgtgacac cacgatgcct gtagcaatgg caacaacgtt gcgcaaacta    1500
ttaactggcg aactacttac tctagcttcc cggcaacaat taatagactg gatggaggcg    1560
gataaagttg caggaccact ctgcgctcg gcccttccgg ctggctggtt tattgctgat    1620
aaatctggag ccggtgagcg tgggtctcgc ggtatcattg cagcactggg gccagatggt    1680
aagccctccc gtatcgtagt tatctacacg acggggagtc aggcaactat ggatgaacga    1740
aatagacaga tcgctgagat aggtgcctca ctgattaagc attggtaact gtcagaccaa    1800
gtttactcat atatacttta gattgattta aaacttcatt tttaatttaa aaggatctag    1860
gtgaagatcc tttttgataa tctcatgacc aaaatccctt aacgtgagtt ttcgttccac    1920
tgagcgtcag accccgtaga aaagatcaaa ggatcttctt gaaatccttt ttttctgcgc    1980
gtaatctgct gcttgcaaac aaaaaaacca ccgctaccag cggtggtttg tttgccggat    2040
caagagctac caactctttt tccgaaggta actggcttca gcagagcgca gataccaaat    2100
actgttcttc tagtgtagcc gtagttaggc caccacttca agaactctgt agcaccgcct    2160
acatacctcg ctctgctaat cctgttacca gtggctgctg ccagtggcga taagtcgtgt    2220
cttaccgggt tggactcaag acgatagtta ccggataagg cgcagcggtc gggctgaacg    2280
gggggttcgt gcacacagcc cagcttggag cgaacgacct acaccgaact gagatacccta   2340 cagcgtgagc tatgagaaag cgccacgctt cccgaaggga gaaaggcgga caggtatccg    2400
gtaagcggca gggtcggaac aggagagcgc acgagggagc ttccaggggg aaacgcctgg    2460
tatctttata gtcctgtcgg gtttcgccac ctctgacttg agcgtcgatt tttgtgatgc    2520
tcgtcagggg gcggagcct atggaaaaac gccagcaacg cggccttttt acggttcctg     2580
gccttttgct ggccttttgc tcacatgtcc tgcaggcag                           2619
```

<210> SEQ ID NO 16
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16

```
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact    120 agggggttcct                                                           130
```

<210> SEQ ID NO 17
<211> LENGTH: 145
<212> TYPE: DNA
<213> ORGANISM: Adeno-associated virus

<400> SEQUENCE: 17

```
ttggccactc cctctctgcg cgctcgctcg ctcactgagg ccgggcgacc aaaggtcgcc      60
cgacgcccgg gctttgcccg gcggcctca gtgagcgagc gagcgcgcag agagggagtg     120
gccaactcca tcactagggg ttcct                                           145
```

<210> SEQ ID NO 18
<211> LENGTH: 2208
<212> TYPE: DNA

<213> ORGANISM: Adeno-associated virus

<400> SEQUENCE: 18

| | | | | | |
|---|---|---|---|---|---|
| atggctgccg | atggttatct | tccagattgg | ctcgaggaca | ctctctctga | aggaataaga | 60 |
| cagtggtgga | agctcaaacc | tggcccacca | ccaccaaagc | ccgcagagcg | cataaggac | 120 |
| gacagcaggg | gtcttgtgct | tcctgggtac | aagtaccctcg | gacccttcaa | cggactcgac | 180 |
| aagggagagc | cggtcaacga | ggcagacgcc | gcggccctcg | agcacgacaa | agcctacgac | 240 |
| cggcagctcg | acagcggaga | caacccgtac | ctcaagtaca | accacgccga | cgcggagttt | 300 |
| caggagcgcc | ttaaagaaga | tacgtctttt | gggggcaacc | tcggacgagc | agtcttccag | 360 |
| gcgaaaaaga | gggttcttga | acctctgggc | ctggttgagg | aacctgttaa | gacggctccg | 420 |
| ggaaaaaaga | ggccggtaga | gcactctcct | gtggagccag | actcctcctc | gggaaccgga | 480 |
| aaggcgggcc | agcagcctgc | aagaaaaaga | ttgaattttg | gtcagactgg | agacgcagac | 540 |
| tcagtacctg | accccagcc | tctcggacag | ccaccagcag | cccctctgg | tctgggaact | 600 |
| aatacgatgg | ctacaggcag | tggcgcacca | atggcagaca | ataacgaggg | cgccgacgga | 660 |
| gtgggtaatt | cctcgggaaa | ttggcattgc | gattccacat | ggatgggcga | cagagtcatc | 720 |
| accaccagca | cccgaacctg | ggcctgccc | acctacaaca | accacctcta | caaacaaatt | 780 |
| tccagccaat | caggagcctc | gaacgacaat | cactactttg | gctacagcac | cccttggggg | 840 |
| tattttgact | tcaacagatt | ccactgccac | ttttcaccac | gtgactggca | agactcatc | 900 |
| aacaacaact | ggggattccg | acccaagaga | ctcaacttca | agctctttaa | cattcaagtc | 960 |
| aaagaggtca | cgcagaatga | cggtacgacg | acgattgcca | ataaccttac | cagcacggtt | 1020 |
| caggtgttta | ctgactcgga | gtaccagctc | ccgtacgtcc | tcggctcggc | gcatcaagga | 1080 |
| tgcctcccgc | cgttcccagc | agacgtcttc | atggtgccac | agtatggata | cctcaccctg | 1140 |
| aacaacggga | gtcaggcagt | aggacgctct | tcattttact | gcctggagta | ctttccttct | 1200 |
| cagatgctgc | gtaccggaaa | caactttacc | ttcagctaca | cttttgagga | cgttcctttc | 1260 |
| cacagcagct | acgctcacag | ccagagtctg | gaccgtctca | tgaatcctct | catcgaccag | 1320 |
| tacctgtatt | acttgagcag | aacaaacact | ccaagtggaa | ccaccacgca | gtcaaggctt | 1380 |
| cagtttctc | aggccggagc | gagtgacatt | cgggaccagt | ctaggaactg | gcttcctgga | 1440 |
| ccctgttacc | gccagcagcg | agtatcaaag | acatctgcgg | ataacaacaa | cagtgaatac | 1500 |
| tcgtggactg | gagctaccaa | gtaccacctc | aatggcagag | actctctggt | gaatccgggc | 1560 |
| ccggccatgg | caagccacaa | ggacgatgaa | gaaaagtttt | tcctcagag | cggggttctc | 1620 |
| atctttggga | agcaaggctc | agagaaaaca | aatgtggaca | ttgaaaaggt | catgattaca | 1680 |
| gacgaagagg | aaatcaggac | aaccaatccc | gtggctacgg | agcagtatgg | ttctgtatct | 1740 |
| accaacctcc | agagaggcaa | cagacaagca | gctaccgcag | atgtcaacac | acaaggcgtt | 1800 |
| cttccaggca | tggtctggca | ggacagagat | gtgtaccttc | aggggcccat | ctgggcaaag | 1860 |
| attccacaca | cggacggaca | ttttcacccc | tctcccctca | tgggtggatt | cggacttaaa | 1920 |
| caccctcctc | acagattct | catcaagaac | accccggtac | ctgcgaatcc | ttcgaccacc | 1980 |
| ttcagtgcgg | caaagtttgc | ttccttcatc | acacagtact | ccacgggaca | ggtcagcgtg | 2040 |
| gagatcgagt | gggagctgca | gaaggaaaac | agcaaacgct | ggaatcccga | aattcagtac | 2100 |
| acttccaact | acaacaagtc | tgttaatgtg | gactttactg | tggacactaa | tggcgtgtat | 2160 |
| tcagagcctc | gccccattgg | caccagatac | ctgactcgta | atctgtaa | | 2208 |

-continued

```
<210> SEQ ID NO 19
<211> LENGTH: 735
<212> TYPE: PRT
<213> ORGANISM: Adeno-associated virus

<400> SEQUENCE: 19

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380
```

```
Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
            405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
            565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
    610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
            645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
    690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
            725                 730                 735

<210> SEQ ID NO 20
<211> LENGTH: 2217
<212> TYPE: DNA
<213> ORGANISM: Adeno-associated virus

<400> SEQUENCE: 20
atggctgccg atggttatct tccagattgg ctcgaggaca acctctctga gggcattcgc      60
gagtggtggg cgctgaaacc tggagccccg aagcccaaag ccaaccagca aaagcaggac     120
gacgccgggg gtctggtgct tcctggctac aagtacctcg gacccttcaa cggactcgac     180
```

```
aaggggggagc ccgtcaacgc ggcggacgca gcggccctcg agcacgacaa ggcctacgac      240
cagcagctgc aggcgggtga caatccgtac ctgcggtata accacgccga cgccgagttt      300
caggagcgtc tgcaagaaga tacgtctttt gggggcaacc tcgggcgagc agtcttccag      360
gccaagaagc gggttctcga acctctcggt ctggttgagg aaggcgctaa gacggctcct      420
ggaaagaaga gaccggtaga gccatcaccc cagcgttctc cagactcctc tacgggcatc      480
ggcaagaaag ccaacagcc cgccagaaaa agactcaatt ttggtcagac tggcgactca      540
gagtcagttc cagaccctca acctctcgga gaacctccag cagcgccctc tggtgtggga      600
cctaatacaa tggctgcagg cggtggcgca ccaatggcag acaataacga aggcgccgac      660
ggagtgggta gttcctcggg aaattggcat gcgattcca catggctggg cgacagagtc       720
atcaccacca gcacccgaac ctgggccctg cccacctaca caaccaccct ctacaagcaa      780
atctccaacg ggacatcggg aggagccacc aacgacaaca cctacttcgg ctacagcacc      840 cctgggggt attttgactt taacagattc cactgccact tttcaccacg tgactggcag      900
cgactcatca acaacaactg gggattccgg cccaagagac tcagcttcaa gctcttcaac      960
atccaggtca aggaggtcac gcagaatgaa ggcaccaaga ccatcgccaa taacctcacc     1020
agcaccatcc aggtgtttac ggactcggag taccagctgc cgtacgttct cggctctgcc     1080
caccagggct gctgcctcc gttcccggcg gacgtgttca tgattcccca gtacggctac     1140
ctaacactca acaacggtag tcaggccgtg gacgctcct ccttctactg cctggaatac     1200
tttccttcgc agatgctgag aaccggcaac aacttccagt ttacttacac cttcgaggac     1260
gtgcctttcc acagcagcta cgcccacagc cagagcttgg accggctgat gaatcctctg     1320
attgaccagt acctgtacta cttgtctcgg actcaaacaa caggaggcac ggcaaatacg     1380
cagactctgg gcttcagcca aggtgggcct aatacaatgg ccaatcaggc aaagaactgg     1440
ctgccaggac cctgttaccg ccaacaacgc gtctcaacga caaccgggca aaacaacaat     1500
agcaactttg cctggactgc tgggaccaaa taccatctga atggaagaaa ttcattggct     1560
aatcctggca tcgctatggc aacacacaaa gacgacgagg agcgtttttt tcccagtaac     1620
gggatcctga ttttttggcaa acaaaatgct gccagagaca atgcggatta cagcgatgtc     1680
atgctcacca gcgaggaaga aatcaaaaacc actaaccctg tggctacaga ggaatacggt     1740
atcgtggcag ataacttgca gcagcaaaac acggctcctc aaattggaac tgtcaacagc     1800
cagggggcct acccggtat ggtctggcag aaccgggacg tgtacctgca gggtcccatc     1860
tgggccaaga ttcctcacac ggacggcaac ttccaccccgt ctccgctgat gggcggcttt     1920
ggcctgaaac atcctccgcc tcagatcctg atcaagaaca cgcctgtacc tgcggatcct     1980
ccgaccacct tcaaccagtc aaagctgaac tctttcatca cgcaatacag caccggacag     2040
gtcagcgtgg aaattgaatg ggagctgcag aaggaaaaca gcaagcgctg gaaccccgag     2100
atccagtaca cctccaacta ctacaaatct acaagtgtgg actttgctgt taatacagaa     2160
ggcgtgtact ctgaaccccg ccccattggc acccgttacc tcacccgtaa tctgtaa       2217
```

<210> SEQ ID NO 21
<211> LENGTH: 738
<212> TYPE: PRT
<213> ORGANISM: Adeno-associated virus

<400> SEQUENCE: 21

```
Met Ala Ala Asp Gly Tyr Leu Pro Asp Trp Leu Glu Asp Asn Leu Ser
1               5                   10                  15
```

```
Glu Gly Ile Arg Glu Trp Trp Ala Leu Lys Pro Gly Ala Pro Lys Pro
             20                  25                  30

Lys Ala Asn Gln Gln Lys Gln Asp Asp Gly Arg Gly Leu Val Leu Pro
         35                  40                  45

Gly Tyr Lys Tyr Leu Gly Pro Phe Asn Gly Leu Asp Lys Gly Glu Pro
     50                  55                  60

Val Asn Ala Ala Asp Ala Ala Leu Glu His Asp Lys Ala Tyr Asp
 65                  70                  75                  80

Gln Gln Leu Gln Ala Gly Asp Asn Pro Tyr Leu Arg Tyr Asn His Ala
                 85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430
```

Leu Asp Arg Leu Met Asn Pro Leu Ile Asp Gln Tyr Leu Tyr Tyr Leu
            435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Arg Val Ser Thr Thr Thr Gly
                485                 490                 495

Gln Asn Asn Asn Ser Asn Phe Ala Trp Thr Ala Gly Thr Lys Tyr His
                500                 505                 510

Leu Asn Gly Arg Asn Ser Leu Ala Asn Pro Gly Ile Ala Met Ala Thr
            515                 520                 525

His Lys Asp Asp Glu Glu Arg Phe Phe Pro Ser Asn Gly Ile Leu Ile
        530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
            610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 22
<211> LENGTH: 1616
<212> TYPE: DNA
<213> ORGANISM: Unknown
<220> FEATURE:
<223> OTHER INFORMATION: Description of Unknown: CVM enhancer and CBA
      promoter polynucleotide

<400> SEQUENCE: 22
actagttatt aatagtaatc aattacgggg tcattagttc atagcccata tatggagttc    60
cgcgttacat aacttacggt aaatggcccg cctggctgac cgcccaacga ccccgccca    120 ttgacgtcaa taatgacgta tgttcccata gtaacgccaa tagggacttt ccattgacgt   180
caatgggtgg agtatttacg gtaaactgcc cacttggcag tacatcaagt gtatcatatg   240
ccaagtacgc ccctattga cgtcaatgac ggtaaatggc ccgcctggca ttatgcccag    300

```
tacatgacct tatgggactt cctacttgg cagtacatct acgtattagt catcgctatt      360
accatggtcg aggtgagccc cacgttctgc ttcactctcc ccatctcccc ccctccccca      420
cccccaattt tgtatttatt tatttttaa ttattttgtg cagcgatggg ggcgggggg       480 gggggggggc gcgcgccagg cggggcgggg cgggcgagg ggcggggcgg ggcgaggcgg      540
agaggtgcgg cggcagccaa tcagagcggc gcgctccgaa agtttccttt tatggcgagg      600
cggcggcggg ggcggcccta taaaaagcga agcgcgcggc gggcggggag tcgctgcgac      660
gctgccttcg ccccgtgccc cgctccgccg ccgcctcgcg ccgcccgccc cggctctgac      720
tgaccgcgtt actcccacag gtgagcgggc gggacggccc ttctcctccg ggctgtaatt      780
agcgcttggt ttaatgacgg cttgtttctt ttctgtggct gcgtgaaagc cttgaggggc      840
tccgggaggg cccttttgtgc ggggggagcg gctcggggg tgcgtgcgtg tgtgtgtgcg      900
tggggagcgc cgcgtgcggc tccgcgctgc ccggcggctg tgagcgctgc gggcgcggcg      960
cggggctttg tgcgctccgc agtgtgcgcg aggggagcgc ggccggggc ggtgccccgc     1020 ggtgcggggg gggctgcgag gggaacaaag gctgcgtgcg gggtgtgtgc gtgggggggt     1080
gagcaggggg tgtgggcgcg tcggtcgggc tgcaaccccc cctgcacccc cctccccgag     1140
ttgctgagca cggcccggct tcgggtgcgg ggctccgtac ggggcgtggc gcggggctcg     1200
ccgtgccggg cgggggtgg cggcaggtgg gggtgccggg cggggcgggg ccgcctcggg     1260
ccggggaggg ctcgggggag gggcgcggcg gcccccggag cgccggcggc tgtcgaggcg     1320
cggcgagccg cagccattgc cttttatggt aatcgtgcga gagggcgcag ggacttcctt     1380
tgtcccaaat ctgtgcggag ccgaaatctg ggaggcgccg ccgcaccccc tctagcgggc     1440
gcggggcgaa gcggtgcggc gccggcagga aggaaatggg cggggagggc cttcgtgcgt     1500
cgccgcgccg ccgtccccctt ctccctctcc agcctcgggg ctgtccgcgg ggggacggct     1560
gccttcgggg gggacggggc agggcggggt tcggcttctg gcgtgtgacc ggcggc        1616
```

<210> SEQ ID NO 23
<211> LENGTH: 1503
<212> TYPE: DNA
<213> ORGANISM: Homo sapiens

<400> SEQUENCE: 23

```
ccagaacagg tcccattcat ggcccacatg acaacctgct tccccagtgg gtattttgg        60 agacagctct tctgtttcca ggttttctct cctgcctaaa tgtcctgcct aagtgccttc      120 aagaacccctt caccatcctg ctcctgcatg tgaccaggtt ccatggtcag ttcaatcacc      180
tagtcacagt tggtaagtga cagagttggg acttgaacct atgcctgcct gacaccaagt      240 cttttttga cacctagagc caagacatct gaagacaaac tccctaggag agctggcgtc      300
atagaaacct taaaggttag ggagacctgg gtttgaatca ggctttgtca gttatgactt      360
gtgtgaccct agcaagttat ttaacctttc tgggtctcag tttcctcatc tgcaaactga      420
ggataataac agtacctacc aaaaagaact gtcgtgaaaa ccatataatt tctgcaatgc      480
tcctggcaca gtgtcctgtt ctaaagcata gttccccttc tctttcttag ctccatattg      540
attattaccc taacttgcac aaagagactt ggaggacccc catagagtat cggagggtcc      600
cccatttcct gctctttcca ctccacaccc ccagcaagca cagggaagtt ctggggggcca      660 taatccaccc acaggaacca aatctaagcc acctttctgg ctggtagaca tccaggtatg      720
tgggcacaga ggtagacagg ctgaaatgct gctgtgctat cagttgggtt ttgctggaac      780
```

| | |
|---|---|
| aggaatggaa atggagaggc tgacagaact gccctgggga gcccaggcaa gagggacagt | 840 |
| ggctggacac ccccagccag ttgtgcagac catcagaaca agatcctaga ttttaggaat | 900 |
| acagggttca gtccgtgcg gcaactcttt tctaaatatg cccaagccat taactttgag | 960 |
| ttttaaaaat actgatttac aagctgtaca caatgaaaaa atgcctatcc ctcacaccat | 1020 |
| gctgatgctg ttccctgcca tctcagatta ccaattaaat acagaatgcc cagttaaatg | 1080 |
| tgaactttt ttttttttt tttttgaga tggagttttg ttcttgtcgc ccaggctaga | 1140 |
| gtgcaatggt gcgatctcag ctcactgcaa cctctgcctc ccaggttcaa gcaattctcc | 1200 |
| tgccttagcc tcctgagtag ctggaactac aggtgcccac cagcacgcct ggctaatttt | 1260 |
| tggtattttt agtggagatg gggtttcacc atgttggcca ggctggtctc gaactcctga | 1320 |
| cctcaggtga tctgcctgcc tcggcctccc aaagtgctgg gattacaggc gtgagcctaa | 1380 |
| atgtgaactt ttttaatact aaaaaagtat ttgctgttca tcggaaattc acatttaact | 1440 |
| gggtgtcctg tattttatt tgctaaatct accatcaaat tggtctggct caacctggag | 1500 |
| aat | 1503 |

<210> SEQ ID NO 24
<211> LENGTH: 720
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 24

| | |
|---|---|
| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca cccctgaccta cggcgtgcag tgcttcagcc gctacccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagca cccagtccgc cctgagcaaa gaccccaacg agaagcgcga tcacatggtc | 660 |
| ctgctggagt tcgtgaccgc cgccgggatc actctcggca tggacgagct gtacaagtaa | 720 |

<210> SEQ ID NO 25
<211> LENGTH: 239
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile

```
                35                  40                  45
Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
        130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235

<210> SEQ ID NO 26
<211> LENGTH: 4949
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
ctgcgcgctc gctcgctcac tgaggccgcc cgggcaaagc ccgggcgtcg ggcgaccttt      60
ggtcgcccgg cctcagtgag cgagcgagcg cgcagagagg gagtgggggta ccacgcgttt    120 gtcctctccc tgcttggcct taaccagcca catttctcaa ctgaccccac tcactgcaga    180
ggtgaaaact accatgccag gtcctgctgg ctggggagg ggtgggcaat aggcctggat     240
ttgccagagc tgccactgta gatgtagtca tatttacgat ttcccttcac ctcttattac    300
cctggtggtg gtggtggggg ggggggggtg ctctctcagc aaccccaccc cgggatcttg    360
aggagaaaga gggcagagaa aagagggaat gggactggcc cagatcccag ccccacagcc    420
gggcttccac atggccgagc aggaactcca gagcaggagc acacaaagga gggctttgat    480
gcgcctccag ccaggcccag gcctctcccc tctcccctttt ctctctgggt cttcctttgc   540
cccactgagg gcctcctgtg agcccgattt aacggaaact gtgggcggtg agaagttcct    600
tatgacacac taatcccaac ctgctgaccg gaccacgcct ccagcggagg gaacctctag    660
agctccagga cattcaggta ccaggtagcc ccaaggagga gctgccgaat cgatggatcg    720
ggaactgaaa aaccagaaag ttaactggta agtttagtct ttttgtcttt tatttcaggt    780
cccggatccg gtggtggtgc aaatcaaaga actgctcctc agtggatgtt gcctttactt    840
ctaggcctgt acggaagtgt tacttctgct ctaaaagctg cggaattgta cccgccccgg    900
```

```
gatccatcga ttgaattcgc caccatgtca aaggggtgg gcacgttccg catggtacct   960
gaagaggaac aggagctccg tgcccaactg gagcagctca caaccaagga ccatggacct  1020
gtctttggcc cgtgcagcca gctgccccgc acaccttgc agaaggccaa ggatgagctg   1080
aacgagagag aggagacccg ggaggaggca gtgcgagagc tgcaggagat ggtgcaggcg  1140
caggcggcct cggggagga gctggcggtg ccgtggcgg agagggtgca agagaaggac    1200
agcggcttct tcctgcgctt catccgcgca cggaagttca acgtgggccg tgcctatgag  1260
ctgctcagag gctatgtgaa tttccggctg cagtaccctg agctctttga cagcctgtcc  1320
ccagaggctg tccgctgcac cattgaagct ggctaccctg gtgtcctctc tagtcgggac  1380
aagtatggcc gagtggtcat gctcttcaac attgagaact ggcaaagtca agaaatcacc  1440
tttgatgaga tcttgcaggc atattgcttc atcctggaga gctgctgga gaatgaggaa   1500
actcaaatca atggcttctg catcattgag aacttcaagg gctttaccat gcagcaggct  1560
gctagtctcc ggacttcaga tctcaggaag atggtggaca tgctccagga ttccttccca  1620
gcccggttca aagccatcca cttcatccac cagccatggt acttcaccac gacctacaat  1680
gtggtcaagc ccttcttgaa gagcaagctg cttgagaggg tctttgtcca cggggatgac  1740
cttctctggtt tctaccagga gatcgatgag aacatcctgc cctctgactt cggggcacg   1800
ctgcccaagt atgatggcaa ggccgttgct gagcagctct ttggccccca ggcccaagct  1860
gagaacacag ccttctgagg atcgtaccgg tcgacctgca gaagcttgcc tcgagcagcg  1920
ctgctcgaga gatctggatc ataatcagcc ataccacatt tgtagaggtt ttacttgctt  1980
taaaaacct cccacacctc cccctgaacc tgaaacataa aatgaatgca attgttgttg   2040
ttaacttgtt tattgcagct tataatggtt acaataaag caatagcatc acaaatttca    2100
caaataaagc attttttca ctgcattcta gttgtggttt gtccaaactc atcaatgtat    2160
cttatcatgt ctggtaacca cgtgcggacc gagcggccgc aggaacccct agtgatggag   2220
ttggccactc cctctctgcg cgctcgctcg ctcactgagg ccgggcgacc aaaggtcgcc   2280
cgacgcccgg gctttgcccg gcggcctca gtgagcgagc gagcgcgcag ctgcctgcag    2340
gggcgcctga tgcggtattt tctccttacg catctgtgcg gtatttcaca ccgcatacgt   2400
caaagcaacc atagtacgcg ccctgtagcg gcgcattaag cgcggcgggt gtggtggtta   2460
cgcgcagcgt gaccgctaca cttgccagcg ccttagcgcc cgctcctttc gctttcttcc   2520
cttcctttct cgccacgttc gccggctttc cccgtcaagc tctaaatcgg ggctcccctt   2580
tagggttccg atttagtgct ttacggcacc tcgaccccaa aaaacttgat tgggtgatg    2640
gttcacgtag tgggccatcg ccctgataga cggtttttcg ccctttgacg ttggagtcca   2700
cgttctttaa tagtggactc ttgttccaaa ctggaacaac actcaactct atctcgggct   2760
attcttttga tttataaggg attttgccga tttcggtcta ttggttaaaa aatgagctga   2820
tttaacaaaa attttaacg aattttaaca aatattaac gtttacaatt ttatggtgca    2880
ctctcagtac aatctgctct gatgccgcat agttaagcca gccccgacac ccgccaacac   2940
ccgctgacgc gccctgacgg gcttgtctgc tcccggcatc cgcttacaga caagctgtga   3000
ccgtctccgg gagctgcatg tgtcagaggt tttcaccgtc atcaccgaaa cgcgcgagac   3060
gaaagggcct cgtgatacgc ctatttttat aggttaatgt catgataata atggtttctt   3120
agacgtcagg tggcactttt cggggaaatg tgcgcggaac ccctatttgt ttatttttct   3180
aaatacattc aaatatgtat ccgctcatga gacaataacc ctgataaatg cttcaataat   3240
attgaaaaag gaagagtatg agtattcaac atttccgtgt cgcccttatt cccttttttg   3300
```

-continued

```
cggcattttg ccttcctgtt tttgctcacc cagaaacgct ggtgaaagta aaagatgctg      3360
aagatcagtt gggtgcacga gtgggttaca tcgaactgga tctcaacagc ggtaagatcc      3420
ttgagagttt tcgccccgaa gaacgttttc caatgatgag cacttttaaa gttctgctat      3480
gtggcgcggt attatcccgt attgacgccg ggcaagagca actcggtcgc cgcatacact      3540
attctcagaa tgacttggtt gagtactcac cagtcacaga aaagcatctt acggatggca      3600
tgacagtaag agaattatgc agtgctgcca taaccatgag tgataacact gcggccaact      3660
tacttctgac aacgatcgga ggaccgaagg agctaaccgc ttttttgcac aacatggggg      3720
atcatgtaac tcgccttgat cgttgggaac cggagctgaa tgaagccata ccaaacgacg      3780
agcgtgacac cacgatgcct gtagcaatgg caacaacgtt gcgcaaacta ttaactggcg      3840
aactacttac tctagcttcc cggcaacaat taatagactg gatggaggcg gataaagttg      3900
caggaccact tctgcgctcg gcccttccgg ctggctggtt tattgctgat aaatctggag      3960
ccggtgagcg tgggtctcgc ggtatcattg cagcactggg gccagatggt aagccctccc      4020
gtatcgtagt tatctacacg acggggagtc aggcaactat ggatgaacga aatagacaga      4080
tcgctgagat aggtgcctca ctgattaagc attggtaact gtcagaccaa gtttactcat      4140
atatacttta gattgattta aaacttcatt tttaatttaa aaggatctag gtgaagatcc      4200
tttttgataa tctcatgacc aaaatccctt aacgtgagtt ttcgttccac tgagcgtcag      4260
accccgtaga aaagatcaaa ggatcttctt gaaatccttt ttttctgcgc gtaatctgct      4320
gcttgcaaac aaaaaaacca ccgctaccag cggtggtttg tttgccggat caagagctac      4380
caactctttt tccgaaggta actggcttca gcagagcgca gataccaaat actgttcttc      4440
tagtgtagcc gtagttaggc caccacttca agaactctgt agcaccgcct acatacctcg      4500
ctctgctaat cctgttacca gtggctgctg ccagtggcga taagtcgtgt cttaccgggt      4560
tggactcaag acgatagtta ccggataagg cgcagcggtc gggctgaacg gggggttcgt      4620
gcacacagcc cagcttggag cgaacgacct acaccgaact gagataccta cagcgtgagc      4680
tatgagaaag cgccacgctt cccgaaggga gaaaggcgga caggtatccg gtaagcggca      4740
gggtcggaac aggagagcgc acgagggagc ttccaggggg aaacgcctgg tatctttata      4800
gtcctgtcgg gtttcgccac ctctgacttg agcgtcgatt tttgtgatgc tcgtcagggg      4860
ggcggagcct atgaaaaac gccagcaacg cggccttttt acggttcctg gccttttgct      4920
ggccttttgc tcacatgtcc tgcaggcag                                       4949
```

<210> SEQ ID NO 27
<211> LENGTH: 7330
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 27

```
ctgcgcgctc gctcgctcac tgaggccgcc cgggcgtcgg gcgacctttg gtcgcccggc        60
ctcagtgagc gagcgagcgc gcagagaggg agtggccaac tccatcacta ggggttcctg       120
cggccgcacg cagcttttgt cctctccctg cttggcctta accagccaca tttctcaact       180
gaccccactc actgcagagg tgaaaactac catgccaggt cctgctggct gggggagggg       240
tgggcaatag gctggatttt gccagagctg ccactgtaga tgtagtcata tttacgattt       300
cccttcacct cttattaccc tggtggtggt ggtggggggg gggggtgct ctctcagcaa       360
```

```
ccccaccccg ggatcttgag gagaaagagg gcagagaaaa gagggaatgg gactggccca     420
gatcccagcc ccacagccgg gcttccacat ggccgagcag gaactccaga gcaggagcac     480
acaaaggagg gctttgatgc gcctccagcc aggcccaggc ctctcccctc tccccttttct    540 ctctgggtct tcctttgccc cactgagggc ctcctgtgag cccgatttaa cggaaactgt     600
gggcggtgag aagttcctta tgacacacta atcccaacct gctgaccgga ccacgcctcc     660
agcggaggga acctctagag ctccaggaca ttcaggtacc aggtagcccc aaggaggagc     720
tgccgacctg gcaggtaagt caatacctgg ggcttgcctg gccagggag cccaggactg      780 gggtgaggac tcaggggagc agggagacca cgtcccaaga tgcctgtaaa actgaaacca    840
cctggccatt ctccaggttg agccagacca atttgatggc agatttagca aataaaaata    900
caggacaccc agtaaatgt gaatttcaga tgaacagcaa atactttttt agtattaaaa      960
aagttcacat ttaggctcac gcctgtaatc ccagcacttt gggaggccga ggcaggcaga    1020
tcacctgagg tcaggagttc gagaccagcc tggccaacat ggtgaaaccc catctccact    1080
aaaaatacca aaaattagcc aggcgtgctg gtgggcacct gtagttccag ctactcagga    1140
ggctaaggca ggagaattgc ttgaacctgg gaggcagagg ttgcagtgag ctgagatcgc    1200
accattgcac tctagcctgg gcgacaagaa caaaactcca tctcaaaaaa aaaaaaaaaa    1260
aaaaagttca catttaactg ggcattctgt atttaattgg taatctgaga tggcagggaa    1320
cagcatcagc atggtgtgag ggataggcat tttttcattg tgtacagctt gtaaatcagt    1380 attttttaaaa ctcaaagtta atggcttggg catatttaga aaagagttgc cgcacggact    1440
tgaaccctgt attcctaaaa tctaggatct tgttctgatg gtctgcacaa ctggctgggg    1500
gtgtccagcc actgtccctc ttgcctgggc tccccagggc agttctgtca gcctctccat    1560
ttccattcct gttccagcaa aacccaactg atagcacagc agcatttcag cctgtctacc    1620
tctgtgccca catacctgga tgtctaccag ccagaaaggt ggcttagatt tggttcctgt    1680
gggtggatta tggcccccag aacttccctg tgcttgctgg gggtgtggag tggaaagagc    1740
aggaaatggg ggaccctccg atactctatg ggggtcctcc aagtctcttt gtgcaagtta    1800
gggtaataat caatatggag ctaagaaaga gaagggaaac tatgctttag aacaggacac    1860
tgtgccagga gcattgcaga aattatatgg ttttcacgac agttcttttt ggtaggtact    1920
gttattatcc tcagttttgca gatgaggaaa ctgagaccca gaaaggttaa ataacttgct    1980
agggtcacac aagtcataac tgacaaagcc tgattcaaac ccaggtctcc ctaacccttta   2040 aggtttctat gacgccagct ctcctaggga gtttgtcttc agatgtcttg gctctaggtg    2100
tcaaaaaaag acttggtgtc aggcaggcat aggttcaagt cccaactctg tcacttacca    2160
actgtgacta ggtgattgaa ctgaccatgg aacctggtca catgcaggag caggatggtg    2220
aagggttctt gaaggcactt aggcaggaca tttaggcagg agagaaaacc tggaaacaga    2280
agagctgtct ccaaaaatac ccactgggga agcaggttgt catgtgggcc atgaatggga    2340
cctgttctgg taaccaagca ttgcttatgt gtccattaca tttcataaca cttccatcct    2400
actttacagg gaacaaccaa gactgggggtt aaatctcaca gcctgcaagt ggaagagaag   2460
aacttgaacc caggtccaac ttttgcgcca cagcaggctg cctcttggtc ctgacaggaa    2520
gtcacaactt gggtctgagt actgatccct ggctattttt tggctgtgtt accttggaca    2580
agtcacttat tcctcctccc gtttcctcct atgtaaaatg gaataataa tgttgaccct     2640 gggtctgaga gagtggattt gaaagtactt agtgcatcac aaagcacaga acacacttcc    2700
```

```
agtctcgtga ttatgtactt atgtaactgg tcatcaccca tcttgagaat gaatgcattg   2760
gggaaagggc catccactag gctgcgaagt ttctgaggga ctccttcggg ctggagaagg   2820
atggccacag gagggaggag agattgcctt atcctgcagt gatcatgtca ttgagaacag   2880
agccagattc ttttttttcct ggcagggcca acttgtttta acatctaagg actgagctat   2940
ttgtgtctgt gcccttttgtc caagcagtgt ttcccaaagt gtagcccaag aaccatctcc   3000
ctcagagcca ccaggaagtg ctttaaattg caggttccta ggccacagcc tgcacctgca   3060
gagtcagaat catggaggtt gggacccagg cacctgcgtt tctaacaaat gcctcgggtg   3120
attctgatgc aattgaaagt ttgagatcca cagttctgag acaataacag aatggttttt   3180 ctaaccctg cagccctgac ttcctatcct agggaagggg ccggctggag aggccaggac   3240
agagaaagca gatcccttct ttttccaagg actctgtgtc ttccataggc aacgaattcg   3300
ccaccatgtc agaaggggtg ggcacgttcc gcatggtacc tgaagaggaa caggagctcc   3360
gtgcccaact ggagcagctc acaaccaagg accatggacc tgtctttggc ccgtgcagcc   3420
agctgccccg ccacaccttg cagaaggcca aggatgagct gaacgagaga gaggagaccc   3480
gggaggaggc agtgcgagag ctgcaggaga tggtgcaggc gcaggcggcc tcggggagg   3540 agctggcggt ggccgtggcg gagagggtgc aagagaagga cagcggcttc ttcctgcgct   3600
tcatccgcgc acggaagttc aacgtgggcc gtgcctatga gctgctcaga ggctatgtga   3660
atttccggct gcagtaccct gagctctttg acagcctgtc cccagaggct gtccgctgca   3720
ccattgaagc tggctaccct ggtgtcctct ctagtcggga caagtatggc cgagtggtca   3780
tgctcttcaa cattgagaac tggcaaagtc aagaaatcac ctttgatgag atcttgcagg   3840
catattgctt catcctggag aagctgctgg agaatgagga aactcaaatc aatggcttct   3900
gcatcattga gaacttcaag ggcttttacca tgcagcaggc tgctagtctc cggacttcag   3960
atctcaggaa gatggtggac atgctccagg attccttccc agcccggttc aaagccatcc   4020
acttcatcca ccagccatgg tacttcacca cgacctacaa tgtggtcaag cccttcttga   4080
agagcaagct gcttgagagg gtctttgtcc acggggatga cctttctggt ttctaccagg   4140
agatcgatga gaacatcctg ccctctgact tcggggcac gctgcccaag tatgatggca   4200
aggccgttgc tgagcagctc tttggccccc aggcccaagc tgagaacaca gccttctgag   4260
gatcgtaccg gtcgacctgc agaagcttgc ctcgagcagc gctgctcgag agatctggat   4320
cataatcagc cataccacat ttgtagaggt tttacttgct ttaaaaaacc tcccacacct   4380
ccccctgaac ctgaaacata aaatgaatgc aattgttgtt gttaacttgt ttattgcagc   4440
ttataatggt tacaaataaa gcaatagcat cacaaatttc acaaataaag cattttttc   4500 actgcattct agttgtggtt tgtccaaact catcaatgta tcttatcatg tctggtaacc   4560
acgtgcggac cgagcggccg caggaacccc tagtgatgga gttggccact ccctctctgc   4620
gcgctcgctc gctcactgag gccgggcgac caaaggtcgc ccgacgcccg gctttgccc   4680 gggcggcctc agtgagcgag cgagcgcgca gctgcctgca ggggcgcctg atgcggtatt   4740
ttctccttac gcatctgtgc ggtatttcac accgcatacg tcaaagcaac catagtacgc   4800
gccctgtagc ggcgcattaa gcgcggcggg tgtggtggtt acgcgcagcg tgaccgctac   4860
acttgccagc gccttagcgc ccgctccttt cgctttcttc ccttcctttc tcgccacgtt   4920
cgccggcttt ccccgtcaag ctctaaatcg ggggctccct ttagggttcc gatttagtgc   4980
tttacggcac ctcgacccca aaaaacttga tttgggtgat ggttcacgta gtgggccatc   5040
gccctgatag acggtttttc gccctttgac gttggagtcc acgttcttta atagtggact   5100
```

```
cttgttccaa actggaacaa cactcaactc tatctcgggc tattcttttg atttataagg    5160
gattttgccg atttcggtct attggttaaa aaatgagctg atttaacaaa aatttaacgc    5220
gaattttaac aaaatattaa cgtttacaat tttatggtgc actctcagta caatctgctc    5280
tgatgccgca tagttaagcc agccccgaca cccgccaaca cccgctgacg cgccctgacg    5340
ggcttgtctg ctcccggcat ccgcttacag acaagctgtg accgtctccg ggagctgcat    5400
gtgtcagagg ttttcaccgt catcaccgaa acgcgcgaga cgaaagggcc tcgtgatacg    5460 cctatttta taggttaatg tcatgataat aatggtttct tagacgtcag gtggcacttt    5520
tcggggaaat gtgcgcggaa cccctatttg tttatttttc taaatacatt caaatatgta    5580
tccgctcatg agacaataac cctgataaat gcttcaataa tattgaaaaa ggaagagtat    5640
gagtattcaa catttccgtg tcgcccttat tcccttttt gcggcatttt gccttcctgt    5700
ttttgctcac ccagaaacgc tggtgaaagt aaaagatgct gaagatcagt tgggtgcacg    5760
agtgggttac atcgaactgg atctcaacag cggtaagatc cttgagagtt tcgccccga    5820 agaacgtttt ccaatgatga gcacttttaa agttctgcta tgtggcgcgg tattatcccg    5880
tattgacgcc gggcaagagc aactcggtcg ccgcatacac tattctcaga atgacttggt    5940
tgagtactca ccagtcacag aaaagcatct tacggatggc atgacagtaa gagaattatg    6000
cagtgctgcc ataaccatga gtgataacac tgcggccaac ttacttctga caacgatcgg    6060
aggaccgaag gagctaaccg cttttttgca caacatgggg gatcatgtaa ctcgccttga    6120
tcgttgggaa ccggagctga atgaagccat accaaacgac gagcgtgaca ccacgatgcc    6180
tgtagcaatg gcaacaacgt tgcgcaaact attaactggc gaactactta ctctagcttc    6240
ccggcaacaa ttaatagact ggatggaggc ggataaagtt gcaggaccac ttctgcgctc    6300
ggcccttccg gctggctggt ttattgctga taaatctgga gccggtgagc gtgggtctcg    6360
cggtatcatt gcagcactgg ggccagatgg taagccctcc cgtatcgtag ttatctacac    6420
gacggggagt caggcaacta tggatgaacg aaatagacag atcgctgaga taggtgcctc    6480
actgattaag cattggtaac tgtcagacca agtttactca tatatacttt agattgattt    6540
aaaacttcat ttttaattta aaaggatcta ggtgaagatc ctttttgata atctcatgac    6600
caaaatccct taacgtgagt tttcgttcca ctgagcgtca gaccccgtag aaaagatcaa    6660
aggatcttct tgaaatcctt ttttctgcg cgtaatctgc tgcttgcaaa caaaaaaacc    6720
accgctacca gcggtggttt gtttgccgga tcaagagcta ccaactcttt ttccgaaggt    6780
aactggcttc agcagagcgc agataccaaa tactgttctt ctagtgtagc cgtagttagg    6840
ccaccacttc aagaactctg tagcaccgcc tacatacctc gctctgctaa tcctgttacc    6900
agtggctgct gccagtggcg ataagtcgtg tcttaccggg ttggactcaa gacgatagtt    6960
accggataag gcgcagcggt cgggctgaac ggggggttcg tgcacacagc ccagcttgga    7020
gcgaacgacc tacaccgaac tgagatacct acagcgtgag ctatgagaaa gcgccacgct    7080
tcccgaaggg agaaaggcgg acaggtatcc ggtaagcggc agggtcggaa caggagagcg    7140
cacgagggag cttccagggg gaaacgcctg gtatctttat agtcctgtcg ggtttcgcca    7200
cctctgactt gagcgtcgat ttttgtgatg ctcgtcaggg gggcggagcc tatgaaaaa    7260 cgccagcaac gcggcctttt tacggttcct ggccttttgc tggccttttg ctcacatgtc    7320
ctgcaggcag                                                            7330
```

<210> SEQ ID NO 28

<211> LENGTH: 7264
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28

```
ctgcgcgctc gctcgctcac tgaggccgcc cgggcgtcgg gcgacctttg gtcgcccggc     60
ctcagtgagc gagcgagcgc gcagagaggg agtggccaac tccatcacta ggggttcctg    120
cggccgcacg cgttacgtaa tatttattga agtttaatat tgtgtttgtg atacagaagt    180
atttgcttta attctaaata aaaattttat gcttttattg ctggtttaag aagatttgga    240
ttatccttgt actttgagga gaagtttctt atttgaaata ttttggaaac aggtctttta    300
atgtggaaag atagatatta atctcctctt ctattactct ccaagatcca acaaaagtga    360
ttataccccc caaaatatga tggtagtatc ttatactacc atcatttatt aggcataggg    420
ctcttagctg caaataatgg aactaactct aataaagcag aacgcaaata ttgtaaatat    480
tagagagcta acaatctctg ggatggctaa aggatggagc ttggaggcta cccagccagt    540
aacaatattc cggggctccac tgttgaatgg agacactaca actgccttgg atgggcagag    600
atattatgga tgctaagccc caggtgctac cattaggact tctaccactg tccctaacgg    660
gtggagccca tcacatgcct atgccctcac tgtaaggaaa tgaagctact gttgtatatc    720
ttgggaagca cttggattaa ttgttataca gttttgttga agaagacccc tagggtaagt    780
agccataact gcacactaaa tttaaaattg ttaatgagtt tctcaaaaaa aatgttaagg    840
ttgttagctg gtatagtata tatcttgcct gttttccaag gacttctttg ggcagtacct    900
tgtctgtgct ggcaagcaac tgagacttaa tgaaagagta ttggagatat gaatgaattg    960
atgctgtata ctctcagagt gccaaacata taccaatgga caagaaggtg aggcagagag   1020
cagacaggca ttagtgacaa gcaaagatat gcagaatttc attctcagca aatcaaaagt   1080
cctcaacctg gttggaagaa tattggcact gaatggtatc aataaggttg ctagagaggg   1140
ttagaggtgc acaatgtgct tccataacat tttatacttc tccaatctta gcactaatca   1200
aacatggttg aatactttgt ttactataac tcttacagag ttataagatc tgtgaagaca   1260
gggacaggga caatacccat ctctgtctgg ttcataggtg gtatgtaata gatatttta    1320
aaaataagtg agttaatgaa tgaggtgag aatgaaggca cagaggtatt aggggaggt    1380
gggccccaga gaatggtgcc aaggtccagt ggggtgactg ggatcagctc aggcctgacg   1440
ctggccactc ccacctagct cctttctttc taatctgttc tcattctcct tgggaaggat   1500
tgaggtctct ggaaaacagc caaacaactg ttatgggaac agcaagccca aataaagcca   1560
agcatcaggg ggatctgaga gctgaaagca acttctgttc cccctccctc agctgaaggg   1620
gtggggaagg gctcccaaag ccataactcc tttaaggga tttagaaggc ataaaaaggc    1680
ccctggctga gaacttccctt cttcattctg cagttggtga attcgccacc atgtcagaag   1740
gggtgggcac gttccgcatg gtacctgaag aggaacagga gctccgtgcc caactggagc   1800
agctcacaac caaggaccat ggacctgtct ttggcccgtg cagccagctg cccgccaca    1860
ccttgcagaa ggccaaggat gagctgaacg agagagagga gacccgggag gaggcagtgc   1920
gagagctgca ggagatggtg caggcgcagg cggcctcggg ggaggagctg gcggtggccg   1980
tggcggagag ggtgcaagag aaggacacg gcttcttcct gcgcttcatc cgcgcacgga   2040
agttcaacgt gggccgtgcc tatgagctgc tcagaggcta tgtgaatttc cggctgcagt   2100
```

```
accctgagct ctttgacagc ctgtccccag aggctgtccg ctgcaccatt gaagctggct    2160
accctggtgt cctctctagt cgggacaagt atggccgagt ggtcatgctc ttcaacattg    2220
agaactggca aagtcaagaa atcacctttg atgagatctt gcaggcatat tgcttcatcc    2280
tggagaagct gctggagaat gaggaaactc aaatcaatgg cttctgcatc attgagaact    2340
tcaagggctt taccatgcag caggctgcta gtctccggac ttcagatctc aggaagatgg    2400
tggacatgct ccaggattcc ttcccagccc ggttcaaagc catccacttc atccaccagc    2460
catggtactt caccacgacc tacaatgtgg tcaagccctt cttgaagagc aagctgcttg    2520
agagggtctt tgtccacggg gatgaccttt ctggtttcta ccaggagatc gatgagaaca    2580
tcctgccctc tgacttcggg ggcacgctgc ccaagtatga tggcaaggcc gttgctgagc    2640
agctctttgg ccccaggcc caagctgaga cacagccctt gaggatct accggtcgac    2700 ctgcagaagc ttgcctcgag cagcgctgct cgagagatct ggatcataat cagccatacc    2760
acatttgtag aggttttact tgctttaaaa aacctcccac acctcccct gaacctgaaa    2820 cataaaatga atgcaattgt tgttgttaac ttgtttattg cagcttataa tggttacaaa    2880
taaagcaata gcatcacaaa tttcacaaat aaagcatttt tttcactgca ttctagttgt    2940
ggtttgtcca aactcatcaa tgtatcttat catgtctggt aaccattctc caggttgagc    3000
cagaccaatt tgatggtaga tttagcaaat aaaaatacag gacacccagt taaatgtgaa    3060
tttccgatga acagcaaata cttttttagt attaaaaaag ttcacattta ggctcacgcc    3120
tgtaatccca gcactttggg aggccgaggc aggcagatca cctgaggtca ggagttcgag    3180
accagcctgg ccaacatggt gaaacccat ctccactaaa ataccaaaa attagccagg    3240 cgtgctggtg ggcacctgta gttccagcta ctcaggaggc taaggcagga gaattgcttg    3300
aacctgggag gcagaggttg cagtgagctg agatcgcacc attgcactct agcctgggcg    3360
acaagaacaa aactccatct caaaaaaaaa aaaaaaaaa aagttcacat ttaactgggc    3420
attctgtatt taattggtaa tctgagatgg caggaacag catcagcatg gtgtgaggga    3480
taggcatttt ttcattgtgt acagcttgta aatcagtatt tttaaaactc aaagttaatg    3540
gcttgggcat atttagaaaa gagttgccgc acggacttga accctgtatt cctaaaatct    3600
aggatcttgt tctgatggtc tgcacaactg gctgggggtg tccagccact gtccctcttg    3660
cctgggctcc ccagggcagt tctgtcagcc tctccatttc cattcctgtt ccagcaaaac    3720
ccaactgata gcacagcagc atttcagcct gtctacctct gtgcccacat acctggatgt    3780
ctaccagcca gaaaggtggc ttagatttgg ttcctgtggg tggattatgg ccccagaac    3840 ttccctgtgc ttgctggggg tgtggagtgg aaagagcagg aaatggggga ccctccgata    3900
ctctatgggg gtcctccaag tctctttgtg caagttaggg taataatcaa tatggagcta    3960
agaaagagaa ggggaactat gctttagaac aggacactgt gccaggagca ttgcagaaat    4020
tatatggttt tcacgacagt tctttttggt aggtactgtt attatcctca gtttgcagat    4080
gaggaaactg agacccagaa aggttaaata acttgctagg tcacacaag tcataactga    4140 caaagcctga ttcaaaccca ggtctcccta acctttaagg tttctatgac gccagctctc    4200
ctagggagtt tgtcttcaga tgtcttggct ctaggtgtca aaaaagact tggtgtcagg    4260 caggcatagg ttcaagtccc aactctgtca cttaccaact gtgactaggt gattgaactg    4320
accatggaac ctggtcacat gcaggagcag gatggtgaag ggttcttgaa ggcacttagg    4380
caggacattt aggcaggaga gaaaacctgg aaacagaaga gctgtctcca aaaataccca    4440
ctggggaagc aggttgtcat gtgggccatg aatgggacct gttctggggt aaccacgtgc    4500
```

```
ggaccgagcg gccgcaggaa cccctagtga tggagttggc cactccctct ctgcgcgctc    4560
gctcgctcac tgaggccggg cgaccaaagg tcgcccgacg cccgggcttt gcccgggcgg    4620
cctcagtgag cgagcgagcg cgcagctgcc tgcaggggcg cctgatgcgg tattttctcc    4680
ttacgcatct gtgcggtatt tcacaccgca tacgtcaaag caaccatagt acgcgccctg    4740
tagcggcgca ttaagcgcgg cgggtgtggt ggttacgcgc agcgtgaccg ctacacttgc    4800
cagcgcctta gcgcccgctc ctttcgcttt cttcccttcc tttctcgcca cgttcgccgg    4860
ctttccccgt caagctctaa atcgggggct ccctttaggg ttccgattta gtgctttacg    4920
gcacctcgac cccaaaaaac ttgatttggg tgatggttca cgtagtgggc catcgccctg    4980
atagacggtt tttcgccctt gacgttgga gtccacgttc tttaatagtg gactcttgtt    5040
ccaaactgga caacactca actctatctc gggctattct tttgatttat aagggatttt    5100
gccgatttcg gtctattggt taaaaaatga gctgatttaa caaaaattta cgcgaatt    5160
taacaaaata ttaacgttta caattttatg gtgcactctc agtacaatct gctctgatgc    5220
cgcatagtta agccagcccc gacacccgcc aacacccgct gacgcgccct gacgggcttg    5280
tctgctcccg gcatccgctt acagacaagc tgtgaccgtc tccggagct gcatgtgtca    5340
gaggttttca ccgtcatcac cgaaacgcgc gagacgaaag gcctcgtga tacgcctatt    5400
tttataggtt aatgtcatga taataatggt ttcttagacg tcaggtggca cttttcgggg    5460
aaatgtgcgc ggaaccccta tttgtttatt tttctaaata cattcaaata tgtatccgct    5520
catgagacaa taaccctgat aaatgcttca ataatattga aaaggaaga gtatgagtat    5580
tcaacatttc cgtgtcgccc ttattccctt ttttgcggca ttttgccttc ctgttttttgc    5640
tcacccagaa acgctggtga agtaaaaga tgctgaagat cagttgggtg cacgagtggg    5700
ttacatcgaa ctggatctca acagcggtaa gatccttgag agttttcgcc ccgaagaacg    5760
ttttccaatg atgagcactt ttaaagttct gctatgtggc gcggtattat cccgtattga    5820
cgccgggcaa gagcaactcg gtcgccgcat acactattct cagaatgact tggttgagta    5880
ctcaccagtc acagaaaagc atcttacgga tggcatgaca gtaagagaat tatgcagtgc    5940
tgccataacc atgagtgata acactgcggc caacttactt ctgacaacga tcggaggacc    6000
gaaggagcta accgcttttt tgcacaacat gggggatcat gtaactcgcc ttgatcgttg    6060
ggaaccggag ctgaatgaag ccataccaaa cgacgagcgt gacaccacga tgcctgtagc    6120
aatggcaaca acgttgcgca aactattaac tggcgaacta cttactctag cttcccggca    6180
acaattaata gactggatgg aggcggataa agttgcagga ccacttctgc gctcggccct    6240
tccggctggc tggtttattg ctgataaatc tggagccggt gagcgtgggt ctcgcggtat    6300
cattgcagca ctggggccag atggtaagcc ctcccgtatc gtagttatct acacgacggg    6360
gagtcaggca actatggatg aacgaaatag acagatcgct gagataggtg cctcactgat    6420
taagcattgg taactgtcag accaagttta ctcatatata ctttagattg atttaaaact    6480
tcatttttaa tttaaaagga tctaggtgaa gatccttttt gataatctca tgaccaaaat    6540
cccttaacgt gagttttcgt tccactgagc gtcagacccc gtagaaaaga tcaaaggatc    6600
ttcttgaaat cctttttttc tgcgcgtaat ctgctgcttg caaacaaaaa aaccaccgct    6660
accagcggtg gtttgtttgc cggatcaaga gctaccaact cttttttccga aggtaactgg    6720
cttcagcaga gcgcagatac caaatactgt tcttctagtg tagccgtagt taggccacca    6780
cttcaagaac tctgtagcac cgcctacata cctcgctctg ctaatcctgt taccagtggc    6840
```

```
tgctgccagt ggcgataagt cgtgtcttac cgggttggac tcaagacgat agttaccgga   6900
taaggcgcag cggtcgggct gaacgggggg ttcgtgcaca cagcccagct tggagcgaac   6960
gacctacacc gaactgagat acctacagcg tgagctatga gaaagcgcca cgcttcccga   7020
agggagaaag gcggacaggt atccggtaag cggcagggtc ggaacaggag agcgcacgag   7080
ggagcttcca gggggaaacg cctggtatct ttatagtcct gtcgggtttc gccacctctg   7140
acttgagcgt cgatttttgt gatgctcgtc aggggggcgg agcctatgga aaaacgccag   7200
caacgcggcc ttttacggt tcctggcctt ttgctggcct tttgctcaca tgtcctgcag   7260
gcag                                                                 7264

<210> SEQ ID NO 29
<211> LENGTH: 7321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
ctgcgcgctc gctcgctcac tgaggccgcc cgggcgtcgg gcgacctttg gtcgcccggc     60
ctcagtgagc gagcgagcgc gcagagaggg agtggccaac tccatcacta ggggttcctg    120
cggccgcacg cgtactagtt attaatagta atcaattacg gggtcattag ttcatagccc    180
atatatggag ttccgcgtta cataacttac ggtaaatggc ccgcctggct gaccgcccaa    240
cgacccccgc ccattgacgt caataatgac gtatgttccc atagtaacgc caatagggac    300
tttccattga cgtcaatggg tggagtattt acggtaaact gcccacttgg cagtacatca    360
agtgtatcat atgccaagta cgccccctat tgacgtcaat gacggtaaat ggcccgcctg    420
gcattatgcc cagtacatga ccttatggga ctttcctact tggcagtaca tctacgtatt    480
agtcatcgct attaccatgg tcgaggtgag ccccacgttc tgcttcactc tccccatctc    540
ccccccctcc ccaccccaa ttttgtattt atttattttt taattatttt gtgcagcgat    600 ggggcggg ggggggggg ggcgcgcgcc aggcggggcg gggcggggcg agggcgggg    660 cggggcgagg cggagaggtg cggcggcagc caatcagagc ggcgcgctcc gaaagtttcc    720
ttttatggcg aggcggcggc ggcggcggcc ctataaaaag cgaagcgcgc ggcgggcggg    780
gagtcgctgc gacgctgcct tcgccccgtg ccccgctccg ccgccgcctc gcgccgcccg    840
ccccggctct gactgaccgc gttactccca caggtgagcg ggcgggacgg cccttctcct    900
ccgggctgta attagcgctt ggtttaatga cggcttgttt cttttctgtg gctgcgtgaa    960
agccttgagg ggctccggga gggccctttg tgcgggggga gcggctcggg gggtgcgtgc   1020
gtgtgtgtgt gcgtggggag cgccgcgtgc ggctccgcgc tgcccggcgg ctgtgagcgc   1080
tgcgggcgcg gcgcggggct ttgtgcgctc cgcagtgtgc gcgaggggag cgcggccggg   1140
ggcggtgccc cgcggtgcgg ggggggctgc gaggggaaca aaggctgcgt gcggggtgtg   1200
tgcgtggggg ggtgagcagg gggtgtgggc gcgtcggtcg ggctgcaacc cccctgcac   1260 ccccctcccc gagttgctga gcacggcccg gcttcgggtg cggggctccg tacggggcgt   1320
ggcgcggggc tcgccgtgcc gggcgggggg tggcggcagg tgggggtgcc gggcggggcg   1380
gggccgcctc gggccgggga gggctcgggg gaggggcgcg gcggccccg gagcgccggc   1440 ggctgtcgag gcgcggcgag ccgcagccat tgccttttat ggtaatcgtg cgagagggcg   1500
cagggacttc ctttgtccca aatctgtgcg gagccgaaat ctgggaggcg ccgccgcacc   1560
```

```
ccctctagcg ggcgcggggc gaagcggtgc ggcgccggca ggaaggaaat gggcggggag    1620
ggccttcgtg cgtcgccgcg ccgccgtccc cttctccctc tccagcctcg gggctgtccg    1680
cgggggacg gctgccttcg gggggacgg ggcagggcgg ggttcggctt ctggcgtgtg      1740
accggcggca tcgattgaat tcgccaccat gtcagaaggg gtgggcacgt tccgcatggt    1800
acctgaagag gaacaggagc tccgtgccca actggagcag ctcacaacca aggaccatgg    1860
acctgtcttt ggcccgtgca gccagctgcc ccgccacacc ttgcagaagg ccaaggatga    1920
gctgaacgag agagaggaga cccgggagga ggcagtgcga gagctgcagg agatggtgca    1980
ggcgcaggcg gcctcggggg aggagctggc ggtggccgtg gcggagaggg tgcaagagaa    2040
ggacagcggc ttcttcctgc gcttcatccg cgcacggaag ttcaacgtgg gccgtgccta    2100
tgagctgctc agaggctatg tgaatttccg gctgcagtac cctgagctct ttgacagcct    2160
gtccccagag gctgtccgct gcaccattga agctggctac cctggtgtcc tctctagtcg    2220
ggacaagtat ggccgagtgg tcatgctctt caacattgag aactggcaaa gtcaagaaat    2280
cacctttgat gagatcttgc aggcatattg cttcatcctg gagaagctgc tggagaatga    2340
ggaaactcaa atcaatggct tctgcatcat tgagaacttc aagggcttta ccatgcagca    2400
ggctgctagt ctccggactt cagatctcag gaagatggtg gacatgctcc aggattcctt    2460
cccagcccgg ttcaaagcca tccacttcat ccaccagcca tggtacttca ccacgaccta    2520
caatgtggtc aagcccttct tgaagagcaa gctgcttgag agggtctttg tccacgggga    2580
tgaccttttct ggtttctacc aggagatcga tgagaacatc ctgccctctg acttcggggg    2640
cacgctgccc aagtatgatg gcaaggccgt tgctgagcag ctctttggcc cccaggccca    2700
agctgagaac acagccttct gaggatcgta ccggtcgacc tgcagaagct tgcctcgagc    2760
agcgctgctc gagagatctg gatcataatc agccatacca catttgtaga ggttttactt    2820
gctttaaaaa acctcccaca cctcccctg aacctgaaac ataaaatgaa tgcaattgtt    2880
gttgttaact tgtttattgc agcttataat ggttacaaat aaagcaatag catcacaaat    2940
ttcacaaata aagcattttt ttcactgcat tctagttgtg gtttgtccaa actcatcaat    3000
gtatcttatc atgtctggta ctagggttac cccagaacag gtcccattca tggcccacat    3060
gacaacctgc ttccccagtg ggtatttttg gagacagctc ttctgtttcc aggttttctc    3120
tcctgcctaa atgtcctgcc taagtgcctt caagaaccct tcaccatcct gctcctgcat    3180
gtgaccaggt tccatggtca gttcaatcac ctagtcacag ttggtaagtg acagagttgg    3240
gacttgaacc tatgcctgcc tgacaccaag tcttttttg acaccttagag ccaagacatc    3300
tgaagacaaa ctccctagga gagctggcgt catagaaacc ttaaaggtta gggagacctg    3360
ggtttgaatc aggctttgtc agttatgact tgtgtgaccc tagcaagtta tttaaccttt    3420
ctgggtctca gtttcctcat ctgcaaactg aggataataa cagtacctac caaaaagaac    3480
tgtcgtgaaa accatataat ttctgcaatg ctcctggcac agtgtcctgt tctaaagcat    3540
agttcccctt ctctttctta gctccatatt gattattacc ctaacttgca caaagagact    3600
tggaggaccc ccatagagta tcggagggtc ccccatttcc tgctctttcc actccacacc    3660
cccagcaagc acaggaagt tctgggggcc ataatccacc cacaggaacc aaatctaagc    3720
cacctttctg gctggtagac atccaggtat gtgggcacag aggtagacag gctgaaatgc    3780
tgctgtgcta tcagttgggt tttgctggaa caggaatgga aatggagagg ctgacagaac    3840
tgccctgggg agcccaggca agagggacag tggctggaca ccccccagcca gttgtgcaga    3900
ccatcagaac aagatcctag atttttaggaa tacagggttc aagtccgtgc ggcaactctt    3960
```

```
ttctaaatat gcccaagcca ttaactttga gttttaaaaa tactgattta caagctgtac    4020
acaatgaaaa aatgcctatc cctcacacca tgctgatgct gttccctgcc atctcagatt    4080
accaattaaa tacagaatgc ccagttaaat gtgaactttt tttttttttt ttttttgag    4140 atggagtttt gttcttgtcg cccaggctag agtgcaatgg tgcgatctca gctcactgca    4200
acctctgcct cccaggttca agcaattctc ctgccttagc ctcctgagta gctggaacta    4260
caggtgccca ccagcacgcc tggctaattt ttggtatttt tagtggagat ggggtttcac    4320
catgttggcc aggctggtct cgaactcctg acctcaggtg atctgcctgc ctcggcctcc    4380
caaagtgctg ggattacagg cgtgagccta aatgtgaact tttttaatac taaaaaagta    4440
tttgctgttc atcggaaatt cacatttaac tgggtgtcct gtatttttat ttgctaaatc    4500
taccatcaaa ttggtctggc tcaacctgga gaatggttac cctaggtaac cacgtgcgga    4560
ccgagcggcc gcaggaaccc ctagtgatgg agttggccac tccctctctg cgcgctcgct    4620
cgctcactga ggccgggcga ccaaaggtcg cccgacgccc gggctttgcc cgggcggcct    4680
cagtgagcga gcgagcgcgc agctgcctgc agggcgcct gatgcggtat tttctcctta    4740
cgcatctgtg cggtatttca caccgcatac gtcaaagcaa ccatagtacg cgccctgtag    4800
cggcgcatta agcgcggcgg gtgtggtggt tacgcgcagc gtgaccgcta cacttgccag    4860
cgccttagcg cccgctcctt tcgctttctt cccttccttt ctcgccacgt tcgccggctt    4920
tccccgtcaa gctctaaatc gggggctccc tttagggttc cgatttagtg ctttacggca    4980
cctcgacccc aaaaaacttg atttgggtga tggttcacgt agtgggccat cgccctgata    5040
gacggttttt cgccctttga cgttggagtc cacgttcttt aatagtggac tcttgttcca    5100
aactggaaca acactcaact ctatctcggg ctattctttt gatttataag gattttgcc    5160 gatttcggtc tattggttaa aaaatgagct gatttaacaa aaatttaacg cgaattttaa    5220
caaaatatta acgtttacaa ttttatggtg cactctcagt acaatctgct ctgatgccgc    5280
atagttaagc cagccccgac acccgccaac acccgctgac gcgccctgac gggcttgtct    5340
gctcccggca tccgcttaca gacaagctgt gaccgtctcc gggagctgca tgtgtcagag    5400
gttttcaccg tcatcaccga aacgcgcgag acgaaagggc ctcgtgatac gcctattttt    5460
ataggttaat gtcatgataa taatggtttc ttagacgtca ggtggcactt ttcggggaaa    5520
tgtgcgcgga accctatt gtttatttt ctaaatacat tcaaatatgt atccgctcat    5580
gagacaataa ccctgataaa tgcttcaata atattgaaaa aggaagagta tgagtattca    5640
acatttccgt gtcgcccta ttccctttt tgcggcattt tgccttcctg tttttgctca    5700
cccagaaacg ctggtgaaag taaaagatgc tgaagatcag ttgggtgcac gagtgggtta    5760
catcgaactg gatctcaaca gcggtaagat ccttgagagt tttcgccccg aagaacgttt    5820
tccaatgatg agcactttta aagttctgct atgtggcgcg gtattatccc gtattgacgc    5880
cgggcaagag caactcggtc gccgcataca ctattctcag aatgacttgg ttgagtactc    5940
accagtcaca gaaaagcatc ttacggatgg catgacagta agagaattat gcagtgctgc    6000
cataaccatg agtgataaca ctgcggccaa cttacttctg acaacgatcg gaggaccgaa    6060
ggagctaacc gcttttttgc acaacatggg ggatcatgta actcgccttg atcgttggga    6120
accggagctg aatgaagcca taccaaacga cgagcgtgac accacgatgc ctgtagcaat    6180
ggcaacaacg ttgcgcaaac tattaactgg cgaactactt actctagctt cccggcaaca    6240
attaatagac tggatggagg cggataaagt tgcaggacca cttctgcgct cggcccttcc    6300
```

-continued

```
ggctggctgg tttattgctg ataaatctgg agccggtgag cgtgggtctc gcggtatcat    6360
tgcagcactg gggccagatg gtaagccctc ccgtatcgta gttatctaca cgacggggag    6420
tcaggcaact atggatgaac gaaatagaca gatcgctgag ataggtgcct cactgattaa    6480
gcattggtaa ctgtcagacc aagtttactc atatatactt tagattgatt taaaacttca    6540
ttttaatttt aaaaggatct aggtgaagat cctttttgat aatctcatga ccaaaatccc    6600
ttaacgtgag ttttcgttcc actgagcgtc agaccccgta gaaaagatca aaggatcttc    6660
ttgaaatcct ttttttctgc gcgtaatctg ctgcttgcaa acaaaaaaac caccgctacc    6720
agcggtggtt tgtttgccgg atcaagagct accaactctt tttccgaagg taactggctt    6780
cagcagagcg cagataccaa atactgttct tctagtgtag ccgtagttag gccaccactt    6840
caagaactct gtagcaccgc ctacatacct cgctctgcta atcctgttac cagtggctgc    6900
tgccagtggc gataagtcgt gtcttaccgg gttggactca agacgatagt taccggataa    6960
ggcgcagcgg tcgggctgaa cggggggttc gtgcacacag cccagcttgg agcgaacgac    7020
ctacaccgaa ctgagatacc tacagcgtga gctatgagaa agcgccacgc ttcccgaagg    7080
gagaaaggcg gacaggtatc cggtaagcgg cagggtcgga acaggagagc gcacgaggga    7140
gcttccaggg ggaaacgcct ggtatcttta tagtcctgtc gggtttcgcc acctctgact    7200
tgagcgtcga ttttgtgat gctcgtcagg ggggcggagc ctatggaaaa acgccagcaa    7260
cgcggccttt ttacggttcc tggccttttg ctggcctttt gctcacatgt cctgcaggca    7320
g                                                                     7321
```

<210> SEQ ID NO 30
<211> LENGTH: 6492
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 30

```
ctgcgcgctc gctcgctcac tgaggccgcc cgggcgtcgg gcgacctttg gtcgcccggc      60
ctcagtgagc gagcgagcgc gcagagaggg agtggccaac tccatcacta ggggttcctg     120
cggccgcacg cgtttgtcct ctccctgctt ggccttaacc agccacattt ctcaactgac     180
cccactcact gcagaggtga aaactaccat gccaggtcct gctggctggg ggaggggtgg     240
gcaataggcc tggatttgcc agagctgcca ctgtagatgt agtcatattt acgatttccc     300
ttcacctctt attaccctgg tggtggtggt gggggggggg gggtgctctc tcagcaaccc     360
caccccggga tcttgaggag aaagagggca gagaaaagag ggaatgggac tggcccagat     420
cccagcccca cagccgggct tccacatggc cgagcaggaa ctccagagca ggagcacaca     480
aaggagggct ttgatgcgcc tccagccagg cccaggcctc tccctctcc ctttctctc      540 tgggtcttcc tttgccccac tgagggcctc ctgtgagccc gatttaacgg aaactgtggg     600
cggtgagaag ttccttatga cacactaatc ccaacctgct gaccggacca cgcctccagc     660
ggagggaacc tctagagctc caggacattc aggtaccagg tagccccaag gaggagctgc     720
cgaatcgatg gatcgggaac tgaaaaacca gaaagttaac tggtaagttt agtctttttg     780
tcttttattt caggtcccgg atccggtggt ggtgcaaatc aaagaactgc tcctcagtgg     840
atgttgcctt tacttctagg cctgtacgga agtgttactt ctgctctaaa agctgcggaa     900
ttgtacccgc cccgggatcc atcgattgaa ttcgccacca tgtcagaagg ggtgggcacg     960
```

```
ttccgcatgg tacctgaaga ggaacaggag ctccgtgccc aactggagca gctcacaacc    1020
aaggaccatg gacctgtctt tggcccgtgc agccagctgc cccgccacac cttgcagaag    1080
gccaaggatg agctgaacga gagagaggag acccgggagg aggcagtgcg agagctgcag    1140
gagatggtgc aggcgcaggc ggcctcgggg gaggagctgg cggtgccgt ggcggagagg     1200 gtgcaagaga aggacagcgg cttcttcctg cgcttcatcc gcgcacggaa gttcaacgtg    1260
ggccgtgcct atgagctgct cagaggctat gtgaatttcc ggctgcagta ccctgagctc    1320
tttgacagcc tgtccccaga ggctgtccgc tgcaccattg aagctggcta ccctggtgtc    1380
ctctctagtc gggacaagta tggccgagtg gtcatgctct tcaacattga gaactggcaa    1440
agtcaagaaa tcacctttga tgagatcttg caggcatatt gcttcatcct ggagaagctg    1500
ctggagaatg aggaaactca aatcaatggc ttctgcatca ttgagaactt caagggcttt    1560
accatgcagc aggctgctag tctccggact tcagatctca ggaagatggt ggacatgctc    1620
caggattcct tcccagcccg gttcaaagcc atccacttca tccaccagcc atggtacttc    1680
accacgacct acaatgtggt caagcccttc ttgaagagca gctgcttga gagggtcttt      1740 gtccacgggg atgacctttc tggtttctac caggagatcg atgagaacat cctgccctct    1800
gacttcgggg gcacgctgcc caagtatgat ggcaaggccg ttgctgagca gctctttggc    1860
ccccaggccc aagctgagaa cacagccttc tgaggatcgt accggtcgac ctgcagaagc    1920
ttgcctcgag cagcgctgct cgagagatct ggatcataat cagccatacc acatttgtag    1980
aggttttact tgctttaaaa aacctcccac acctcccct gaacctgaaa cataaaatga     2040
atgcaattgt tgttgttaac ttgtttattg cagcttataa tggttacaaa taaagcaata    2100
gcatcacaaa tttcacaaat aaagcatttt tttcactgca ttctagttgt ggtttgtcca    2160
aactcatcaa tgtatcttat catgtctggt actagggtta ccccagaaca ggtcccattc    2220
atggcccaca tgacaacctg cttccccagt gggtattttt ggagacagct cttctgtttc    2280
caggttttct ctcctgccta aatgtcctgc ctaagtgcct tcaagaaccc ttcaccatcc    2340
tgctcctgca tgtgaccagg ttccatggtc agttcaatca cctagtcaca gttggtaagt    2400
gacagagttg ggacttgaac ctatgcctgc ctgacaccaa gtcttttttt gacacctaga    2460
gccaagacat ctgaagacaa actccctagg agagctggcg tcatagaaac cttaaaggtt    2520
agggagacct gggtttgaat caggcttgt cagttatgac ttgtgtgacc ctagcaagtt     2580
atttaacctt tctgggtctc agtttcctca tctgcaaact gaggataata acagtaccta    2640
ccaaaaagaa ctgtcgtgaa aaccatataa tttctgcaat gctcctggca cagtgtcctg    2700
ttctaaagca tagttccccct tctctttctt agctccatat tgattattac cctaacttgc    2760
acaaagagac ttggaggacc cccatagagt atcggagggt cccccatttc ctgctctttc    2820
cactccacac ccccagcaag cacagggaag ttctgggggc cataatccac ccacaggaac    2880
caaatctaag ccacctttct ggctggtaga catccaggta tgtgggcaca gaggtagaca    2940
ggctgaaatg ctgctgtgct atcagttggg ttttgctgga acaggaatgg aaatggagag    3000
gctgacagaa ctgccctggg gagcccaggc aagagggaca gtggctggac accccagcc    3060 agttgtgcag accatcagaa caagatccta gattttagga atacagggtt caagtccgtg    3120
cggcaactct tttctaaata tgcccaagcc attaactttg agttttaaaa atactgattt    3180
acaagctgta cacaatgaaa aaatgcctat ccctcacacc atgctgatgc tgttccctgc    3240
catctcagat taccaattaa atacagaatg cccagttaaa tgtgaacttt tttttttttt    3300
ttttttttga gatggagttt tgttcttgtc gcccaggcta gagtgcaatg gtgcgatctc    3360
```

```
agctcactgc aacctctgcc tcccaggttc aagcaattct cctgccttag cctcctgagt   3420
agctggaact acaggtgccc accagcacgc ctggctaatt tttggtattt ttagtggaga   3480
tggggtttca ccatgttggc caggctggtc tcgaactcct gacctcaggt gatctgcctg   3540
cctcggcctc ccaaagtgct gggattacag gcgtgagcct aaatgtgaac tttttaata   3600
ctaaaaagt atttgctgtt catcggaaat tcacatttaa ctgggtgtcc tgtattttta   3660
tttgctaaat ctaccatcaa attggtctgg ctcaacctgg agaatggtta ccctaggtaa   3720
ccacgtgcgg accgagcggc cgcaggaacc cctagtgatg gagttggcca ctccctctct   3780
gcgcgctcgc tcgctcactg aggccgggcg accaaaggtc gcccgacgcc cgggctttgc   3840
ccgggcggcc tcagtgagcg agcgagcgcg cagctgcctg caggggcgcc tgatgcggta   3900
ttttctcctt acgcatctgt gcggtatttc acaccgcata cgtcaaagca accatagtac   3960
gcgccctgta gcggcgcatt aagcgcggcg ggtgtggtgg ttacgcgcag cgtgaccgct   4020
acacttgcca gcgccttagc gcccgctcct ttcgctttct tcccttcctt tctcgccacg   4080
ttcgccggct ttccccgtca gctctaaat cgggggctcc ctttagggtt ccgatttagt    4140
gctttacggc acctcgaccc caaaaaactt gatttgggtg atggttcacg tagtgggcca   4200
tcgccctgat agacggtttt tcgccctttg acgttggagt ccacgttctt aatagtgga   4260
ctcttgttcc aaactggaac aacactcaac tctatctcgg ctattctttt gatttataa    4320
gggattttgc cgatttcggt ctattggtta aaaatgagc tgatttaaca aaaatttaac    4380
gcgaattta acaaaatatt aacgtttaca attttatggt gcactctcag tacaatctgc    4440
tctgatgccg catagttaag ccagccccga cacccgccaa cacccgctga cgcgccctga   4500
cgggcttgtc tgctcccggc atccgcttac agacaagctg tgaccgtctc cgggagctgc   4560
atgtgtcaga ggttttcacc gtcatcaccg aaacgcgcga cgaaaggg cctcgtgata    4620
cgcctatttt tataggttaa tgtcatgata ataatggttt cttagacgtc aggtggcact   4680
tttcggggaa atgtgcgcgg aaccctatt tgtttatttt tctaaataca ttcaaatatg   4740
tatccgctca tgagacaata accctgataa atgcttcaat aatattgaaa aggaagagt    4800
atgagtattc aacatttccg tgtcgccctt attcccttttt ttgcggcatt ttgccttcct   4860
gttttgctc acccagaaac gctggtgaaa gtaaaagatg ctgaagatca gttgggtgca   4920
cgagtgggtt acatcgaact ggatctcaac agcggtaaga tccttgagag ttttcgcccc   4980
gaagaacgtt ttccaatgat gagcactttt aaagttctgc tatgtggcgc ggtattatcc   5040
cgtattgacg ccgggcaaga gcaactcggt cgccgcatac actattctca gaatgacttg   5100
gttgagtact caccagtcac agaaaagcat cttacggatg gcatgacagt aagagaatta   5160
tgcagtgctg ccataaccat gagtgataac actgcggcca acttacttct gacaacgatc   5220
ggaggaccga aggagctaac cgcttttttg cacaacatgg gggatcatgt aactcgcctt   5280
gatcgttggg aaccggagct gaatgaagcc ataccaaacg acgagcgtga ccaccacgat   5340
cctgtagcaa tggcaacaac gttgcgcaaa ctattaactg gcgaactact tactctagct   5400
tcccggcaac aattaataga ctggatggag gcggataaag ttgcaggacc acttctgcgc   5460
tcggcccttc cggctggctg gtttattgct gataaatctg gagccggtga gcgtgggtct   5520
cgcggtatca ttgcagcact ggggccagat ggtaagccct cccgtatcgt agttatctac   5580
acgacgggga gtcaggcaac tatggatgaa cgaaatagac agatcgctga gataggtgcc   5640
tcactgatta agcattggta actgtcagac caagtttact catatatact ttagattgat   5700
```

```
ttaaaacttc attttaatt taaaaggatc taggtgaaga tccttttga taatctcatg    5760 accaaaatcc cttaacgtga gttttcgttc cactgagcgt cagacccgt agaaaagatc    5820 aaaggatctt cttgaaatcc tttttttctg cgcgtaatct gctgcttgca acaaaaaaa    5880 ccaccgctac cagcggtggt ttgtttgccg gatcaagagc taccaactct ttttccgaag    5940
gtaactggct tcagcagagc gcagatacca aatactgttc ttctagtgta gccgtagtta    6000
ggccaccact tcaagaactc tgtagcaccg cctacatacc tcgctctgct aatcctgtta    6060
ccagtggctg ctgccagtgg cgataagtcg tgtcttaccg ggttggactc aagacgatag    6120
ttaccggata aggcgcagcg gtcgggctga acggggggtt cgtgcacaca gcccagcttg    6180
gagcgaacga cctacaccga actgagatac ctacagcgtg agctatgaga aagcgccacg    6240
cttcccgaag ggagaaaggc ggacaggtat ccggtaagcg gcagggtcgg aacaggagag    6300
cgcacgaggg agcttccagg gggaaacgcc tggtatcttt atagtcctgt cgggtttcgc    6360
cacctctgac ttgagcgtcg attttgtga tgctcgtcag ggggcggag cctatggaaa    6420 aacgccagca acgcggcctt tttacggttc ctggccttt gctggccttt tgctcacatg    6480
tcctgcaggc ag                                                       6492

<210> SEQ ID NO 31
<211> LENGTH: 4741
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
cgcgctcgct cgctcactga ggccgcccgg gcaaagcccg ggcgtcgggc gacctttggt      60
cgcccggcct cagtgagcga gcgagcgcgc agagaggag tggggtacca cgcgtttgtc     120
ctctccctgc ttggccttaa ccagccacat ttctcaactg accccactca ctgcagaggt     180
gaaaactacc atgccaggtc ctgctggctg ggggaggggt gggcaatagg cctggatttg     240
ccagagctgc cactgtagat gtagtcatat ttacgatttc ccttcacctc ttattaccct     300
ggtggtggtg gtgggggggg ggggtgctc tctcagcaac cccaccccgg gatcttgagg     360
agaaagaggg cagagaaaag agggaatggg actggcccag atcccagccc cacagccggg     420
cttccacatg gccgagcagg aactccagag caggagcaca caaggagggg ctttgatgcg     480
cctccagcca ggcccaggcc tctcccctct cccctttctc tctgggtctt cctttgcccc     540
actgagggcc tcctgtgagc ccgatttaac ggaaactgtg ggcggtgaga agttccttat     600
gacacactaa tcccaacctg ctgaccggac cacgcctcca gcggagggaa cctctagagc     660
tccaggacat tcaggtacca ggtagccca aggaggagct gccgaatcga tggatcggga     720
actgaaaaac cagaaagtta actggtaagt ttagtctttt tgtctttat ttcaggtccc     780 ggatccggtg gtggtgcaaa tcaaagaact gctcctcagt ggatgttgcc tttacttcta     840
ggcctgtacg gaagtgttac ttctgctcta aaagctgcgg aattgtaccc gccccgggat     900
ccatcgattt aattccccgg ggatcctcta gagtcgaaat tcgccaccat ggtgagcaag     960
ggcgaggagc tgttcaccgg ggtggtgccc atcctggtcg agctggacgg cgacgtaaac    1020
ggccacaagt tcagcgtgtc cggcgagggc gagggcgatg ccacctacgg caagctgacc    1080
ctgaagttca tctgcaccac cggcaagctg cccgtgccct ggcccaccct cgtgaccacc    1140
ctgacctacg gcgtgcagtg cttcagccgc taccccgacc acatgaagca gcacgacttc    1200
```

```
ttcaagtccg ccatgcccga aggctacgtc caggagcgca ccatcttctt caaggacgac    1260
ggcaactaca agacccgcgc cgaggtgaag ttcgagggcg acaccctggt gaaccgcatc    1320
gagctgaagg gcatcgactt caaggaggac ggcaacatcc tggggcacaa gctggagtac    1380
aactacaaca gccacaacgt ctatatcatg gccgacaagc agaagaacgg catcaaggtg    1440
aacttcaaga tccgccacaa catcgaggac ggcagcgtgc agctcgccga ccactaccag    1500
cagaacaccc ccatcggcga cggccccgtg ctgctgcccg acaaccacta cctgagcacc    1560
cagtccgccc tgagcaaaga ccccaacgag aagcgcgatc acatggtcct gctggagttc    1620
gtgaccgccg ccgggatcac tctcggcatg gacgagctgt acaagtaata gggtaccggt    1680
cgacctgcag aagcttgcct cgagcagcgc tgctcgagag atctggatca taatcagcca    1740
taccacattt gtagaggttt tacttgcttt aaaaaacctc ccacacctcc ccctgaacct    1800
gaaacataaa atgaatgcaa ttgttgttgt taacttgttt attgcagctt ataatggtta    1860
caaataaagc aatagcatca caaatttcac aaataaagca tttttttcac tgcattctag    1920
ttgtggtttg tccaaactca tcaatgtatc ttatcatgtc tggtaaccac gtgcggaccg    1980
agcggccgca ggaaccccta gtgatggagt tggccactcc ctctctgcgc gctcgctcgc    2040
tcactgaggc cgggcgacca aggtcgcccg acgcccggg ctttgccgg gcggcctcag     2100
tgagcgagcg agcgcgcagc tgcctgcagg ggcgcctgat gcggtatttt ctccttacgc    2160
atctgtgcgg tatttcacac cgcatacgtc aaagcaacca tagtacgcgc cctgtagcgg    2220
cgcattaagc gcggcgggtg tggtggttac gcgcagcgtg accgctacac ttgccagcgc    2280
cttagcgccc gctcctttcg ctttcttccc ttcctttctc gccacgttcg ccggcttttcc   2340
ccgtcaagct ctaaatcggg ggctcccttt agggttccga tttagtgctt tacggcacct    2400
cgaccccaaa aaacttgatt tgggtgatgg ttcacgtagt gggccatcgc cctgatagac    2460
ggttttcgc cctttgacgt tggagtccac gttctttaat agtggactct tgttccaaac     2520
tggaacaaca ctcaactcta tctcgggcta ttcttttgat ttataaggga ttttgccgat    2580
ttcggtctat tggttaaaaa atgagctgat ttaacaaaaa tttaacgcga attttaacaa    2640
aatattaacg tttacaattt tatggtgcac tctcagtaca atctgctctg atgccgcata    2700
gttaagccag ccccgacacc cgccaacacc cgctgacgcg ccctgacggg cttgtctgct    2760
cccggcatcc gcttacagac aagctgtgac cgtctccggg agctgcatgt gtcagaggtt    2820
ttcaccgtca tcaccgaaac gcgcgagacg aaagggcctc gtgatacgcc tatttttata    2880
ggttaatgtc atgataataa tggtttctta gacgtcaggt ggcactttc ggggaaatgt     2940
gcgcggaacc cctatttgtt tatttttcta aatacattca aatatgtatc cgctcatgag    3000
acaataaccc tgataaatgc ttcaataata ttgaaaaagg aagagtatga gtattcaaca    3060
tttccgtgtc gcccttattc ccttttttgc ggcattttgc cttcctgttt ttgctcaccc    3120
agaaacgctg gtgaaagtaa aagatgctga agatcagttg ggtgcacgag tgggttacat    3180
cgaactggat ctcaacagcg gtaagatcct tgagagtttt cgccccgaag aacgttttcc    3240
aatgatgagc acttttaaag ttctgctatg tggcgcggta ttatcccgta ttgacgccgg    3300
gcaagagcaa ctcggtcgcc gcatacacta ttctcagaat gacttggttg agtactcacc    3360
agtcacagaa aagcatctta cggatggcat gacagtaaga gaattatgca gtgctgccat    3420
aaccatgagt gataacactg cggccaactt acttctgaca acgatcggag gaccgaagga    3480
gctaaccgct tttttgcaca acatggggga tcatgtaact cgccttgatc gttgggaacc    3540
ggagctgaat gaagccatac caaacgacga gcgtgacacc acgatgcctg tagcaatggc    3600
```

```
aacaacgttg cgcaaactat taactggcga actacttact ctagcttccc ggcaacaatt    3660
aatagactgg atggaggcgg ataaagttgc aggaccactt ctgcgctcgg cccttccggc    3720
tggctggttt attgctgata aatctggagc cggtgagcgt gggtctcgcg gtatcattgc    3780
agcactgggg ccagatggta agccctcccg tatcgtagtt atctacacga cggggagtca    3840
ggcaactatg gatgaacgaa atagacagat cgctgagata ggtgcctcac tgattaagca    3900
ttggtaactg tcagaccaag tttactcata tatactttag attgatttaa aacttcattt    3960
ttaatttaaa aggatctagg tgaagatcct tttttgataat ctcatgacca aaatccctta    4020
acgtgagttt tcgttccact gagcgtcaga ccccgtagaa aagatcaaag gatcttcttg    4080
aaatcctttt tttctgcgcg taatctgctg cttgcaaaca aaaaaaccac cgctaccagc    4140
ggtggtttgt ttgccggatc aagagctacc aactctttttt ccgaaggtaa ctggcttcag    4200
cagagcgcag ataccaaata ctgttcttct agtgtagccg tagttaggcc accacttcaa    4260
gaactctgta gcaccgccta catacctcgc tctgctaatc ctgttaccag tggctgctgc    4320
cagtggcgat aagtcgtgtc ttaccgggtt ggactcaaga cgatagttac cggataaggc    4380
gcagcggtcg ggctgaacgg ggggttcgtg cacacagccc agcttggagc gaacgaccta    4440
caccgaactg agatacctac agcgtgagct atgagaaagc gccacgcttc ccgaagggag    4500
aaaggcggac aggtatccgg taagcggcag ggtcggaaca ggagagcgca cgagggagct    4560
tccaggggga aacgcctggt atctttatag tcctgtcggg tttcgccacc tctgacttga    4620
gcgtcgattt ttgtgatgct cgtcaggggg gcggagccta tggaaaaacg ccagcaacgc    4680 ggcctttttta cggttcctgg ccttttgctg gccttttgct cacatgtcct gcaggcagct    4740
g                                                                   4741
```

<210> SEQ ID NO 32
<211> LENGTH: 7122
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 32

```
ctgcgcgctc gctcgctcac tgaggccgcc cgggcgtcgg gcgacctttg gtcgcccggc     60
ctcagtgagc gagcgagcgc gcagagaggg agtggccaac tccatcacta ggggttcctg    120
cggccgcacg cagcttttgt cctctcccctg cttggcctta accagccaca tttctcaact    180
gaccccactc actgcagagg tgaaaactac catgccaggt cctgctggct gggggagggg    240
tgggcaatag gcctggattt gccagagctg ccactgtaga tgtagtcata tttacgattt    300
cccttcacct cttattaccc tggtggtggt ggtggggggg gggggtgct ctctcagcaa     360 ccccacccccg ggatcttgag gagaaagagg gcagagaaaa gagggaatgg gactggccca    420
gatcccagcc ccacagccgg gcttccacat ggccgagcag gaactccaga gcaggagcac    480
acaaaggagg gctttgatgc gcctccagcc aggcccaggc ctctcccctc tccccttttct    540 ctctgggtct tcctttgccc cactgagggc ctcctgtgag cccgatttaa cggaaactgt    600
gggcggtgag aagttcctta tgacacacta atcccaacct gctgaccgga ccacgcctcc    660
agcggaggga acctctagag ctccaggaca ttcaggtacc aggtagcccc aaggaggagc    720
tgccgacctg gcaggtaagt caatacctgg ggcttgcctg ggccagggag cccaggactg    780
gggtgaggac tcaggggagc agggagacca cgtcccaaga tgcctgtaaa actgaaacca    840
```

```
cctggccatt ctccaggttg agccagacca atttgatggc agatttagca aataaaaata    900
caggacaccc agttaaatgt gaatttcaga tgaacagcaa atacttttt agtattaaaa    960
aagttcacat ttaggctcac gcctgtaatc ccagcacttt gggaggccga ggcaggcaga   1020
tcacctgagg tcaggagttc gagaccagcc tggccaacat ggtgaaaccc catctccact   1080
aaaaatacca aaaattagcc aggcgtgctg gtgggcacct gtagttccag ctactcagga   1140
ggctaaggca ggagaattgc ttgaacctgg gaggcagagg ttgcagtgag ctgagatcgc   1200
accattgcac tctagcctgg gcgacaagaa caaaactcca tctcaaaaaa aaaaaaaaa    1260
aaaaagttca catttaactg ggcattctgt atttaattgg taatctgaga tggcagggaa   1320
cagcatcagc atggtgtgag ggataggcat ttttcattg tgtacagctt gtaaatcagt   1380
attttaaaa ctcaaagtta atggcttggg catatttaga aaagagttgc cgcacggact   1440
tgaaccctgt attcctaaaa tctaggatct tgttctgatg gtctgcacaa ctggctgggg   1500
gtgtccagcc actgtccctc ttgcctgggc tccccagggc agttctgtca gcctctccat   1560
ttccattcct gttccagcaa acccaactg atagcacagc agcatttcag cctgtctacc   1620
tctgtgccca catacctgga tgtctaccag ccagaaaggt ggcttagatt tggttcctgt   1680
gggtggatta tggcccccag aacttccctg tgcttgctgg gggtgtggag tggaaagagc   1740
aggaaatggg ggaccctccg atactctatg ggggtcctcc aagtctcttt gtgcaagtta   1800
gggtaataat caatatggag ctaagaaaga aaggggaac tatgctttag aacaggacac    1860
tgtgccagga gcattgcaga aattatatgg ttttcacgac agttctttt ggtaggtact    1920
gttattatcc tcagtttgca gatgaggaaa ctgagaccca gaaaggttaa ataacttgct   1980
agggtcacac aagtcataac tgacaaagcc tgattcaaac ccaggtctcc ctaacctta    2040
aggtttctat gacgccagct ctcctaggga gtttgtcttc agatgtcttg gctctaggtg   2100
tcaaaaaaag acttggtgtc aggcaggcat aggttcaagt cccaactctg tcacttacca   2160
actgtgacta ggtgattgaa ctgaccatgg aacctggtca catgcaggag caggatggtg   2220
aagggttctt gaaggcactt aggcaggaca tttaggcagg agagaaaacc tggaaacaga   2280
agagctgtct ccaaaaatac ccactgggga agcaggttgt catgtgggcc atgaatggga   2340
cctgttctgg taaccaagca ttgcttatgt gtccattaca tttcataaca cttccatcct   2400
actttacagg gaacaaccaa gactgggggtt aaatctcaca gcctgcaagt ggaagagaag   2460
aacttgaacc caggtccaac ttttgcgcca cagcaggctg cctcttggtc ctgacaggaa   2520
gtcacaactt gggtctgagt actgatccct ggctattttt tggctgtgtt accttggaca   2580
agtcacttat tcctcctccc gtttcctcct atgtaaaatg gaaataataa tgttgaccct   2640
gggtctgaga gagtggattt gaaagtactt agtgcatcac aaagcacaga acacacttcc   2700
agtctcgtga ttatgtactt atgtaactgg tcatcaccca tcttgagaat gaatgcattg   2760
gggaagggc catccactag gctgcgaagt ttctgaggga ctccttcggg ctggagaagg    2820
atggccacag gagggaggag agattgcctt atcctgcagt gatcatgtca ttgagaacag   2880
agccagattc tttttttcct ggcagggcca acttgtttta acatctaagg actgagctat   2940
ttgtgtctgt gccctttgtc caagcagtgt ttcccaaagt gtagcccaag aaccatctcc   3000
ctcagagcca ccaggaagtg ctttaaattg caggttccta ggccacagcc tgcacctgca   3060
gagtcagaat catggaggtt gggacccagg cacctgcgtt tctaacaaat gcctcgggtg   3120
attctgatgc aattgaaagt ttgagatcca cagttctgag acaataacag aatggttttt   3180
```

```
ctaacccctg cagccctgac ttcctatcct agggaagggg ccggctggag aggccaggac    3240
agagaaagca gatcccttct ttttccaagg actctgtgtc ttccataggc aacgaattcc    3300
ccggggatcc tctagagtcg aaattcgcca ccatggtgag caagggcgag gagctgttca    3360
ccggggtggt gcccatcctg gtcgagctgg acggcgacgt aaacggccac aagttcagcg    3420
tgtccggcga gggcgagggc gatgccacct acggcaagct gaccctgaag ttcatctgca    3480
ccaccggcaa gctgcccgtg ccctggccca cccttgtgac cacactgacc tacggcgtgc    3540
agtgcttcag ccgctacccc gaccacatga agcagcacga cttcttcaag tccgccatgc    3600
ccgaaggcta cgtccaggag cgcaccatct tcttcaagga cgacggcaac tacaagaccc    3660
gcgccgaggt gaagttcgag ggcgacaccc tggtgaaccg catcgagctg aagggcatcg    3720
acttcaagga ggacggcaac atcctggggc acaagctgga gtacaactac aacagccaca    3780
acgtctatat catggccgac aagcagaaga acggcatcaa ggtgaacttc aagatccgcc    3840
acaacatcga ggacggcagc gtgcagctcg ccgaccacta ccagcagaac acccccatcg    3900
gcgacggccc cgtgctgctg cccgacaacc actacctgag cacccagtcc gccctgagca    3960
aagaccccaa cgagaagcgc gatcacatgg tcctgctgga gttcgtgacc gccgccggga    4020
tcactctcgg catggacgag ctgtacaagt aatagggtac cggtcgacct gcagaagctt    4080
gcctcgagca gcgctgctcg agagatctgg atcataatca gccataccac atttgtagag    4140
gttttacttg ctttaaaaaa cctcccacac ctccccctga acctgaaaca taaaatgaat    4200
gcaattgttg ttgttaactt gtttattgca gcttataatg gttacaaata agcaatagc    4260 atcacaaatt tcacaaataa agcatttttt tcactgcatt ctagttgtgg tttgtccaaa    4320
ctcatcaatg tatcttatca tgtctggtaa ccacgtgcgg accgagcggc cgcaggaacc    4380
cctagtgatg gagttggcca ctccctctct gcgcgctcgc tcgctcactg aggccgggcg    4440
accaaaggtc gcccgacgcc cgggctttgc ccgggcggcc tcagtgagcg agcgagcgcg    4500
cagctgcctg caggggcgcc tgatgcggta ttttctcctt acgcatctgt gcggtatttc    4560
acaccgcata cgtcaaagca accatagtac gcgccctgta gcggcgcatt aagcgcggcg    4620
ggtgtggtgg ttacgcgcag cgtgaccgct acacttgcca gcgccttagc gcccgctcct    4680
ttcgctttct tcccttcctt tctcgccacg ttcgccggct ttccccgtca gctctaaat    4740 cgggggctcc ctttagggtt ccgatttagt gctttacggc acctcgaccc caaaaaactt    4800
gatttgggtg atggttcacg tagtgggcca tcgccctgat agacggtttt tcgccctttg    4860
acgttggagt ccacgttctt taatagtgga ctcttgttcc aaactggaac aacactcaac    4920
tctatctcgg gctattcttt tgatttataa gggattttgc cgatttcggt ctattggtta    4980
aaaaatgagc tgatttaaca aaaatttaac gcgaatttta caaaatatt aacgtttaca    5040 attttatggt gcactctcag tacaatctgc tctgatgccg catagttaag ccagccccga    5100
cacccgccaa cacccgctga cgcgccctga cgggcttgtc tgctcccggc atccgcttac    5160
agacaagctg tgaccgtctc cgggagctgc atgtgtcaga ggttttcacc gtcatcaccg    5220
aaacgcgcga gacgaaaggg cctcgtgata cgcctatttt tataggttaa tgtcatgata    5280
ataatggttt cttagacgtc aggtggcact ttcggggaaa tgtgcgcgg aacccctatt    5340 tgtttatttt tctaaataca ttcaaatatg tatccgctca tgagacaata accctgataa    5400
atgcttcaat aatattgaaa aaggaagagt atgagtattc aacatttccg tgtcgccctt    5460 attcccttttt ttgcggcatt ttgccttcct gttttgctc acccagaaac gctggtgaaa    5520
gtaaaagatg ctgaagatca gttgggtgca cgagtgggtt acatcgaact ggatctcaac    5580
```

| | |
|---|---|
| agcggtaaga tccttgagag ttttcgcccc gaagaacgtt ttccaatgat gagcacttt | 5640 |
| aaagttctgc tatgtggcgc ggtattatcc cgtattgacg ccgggcaaga gcaactcggt | 5700 |
| cgccgcatac actattctca gaatgacttg gttgagtact caccagtcac agaaaagcat | 5760 |
| cttacggatg gcatgacagt aagagaatta tgcagtgctg ccataaccat gagtgataac | 5820 |
| actgcggcca acttacttct gacaacgatc ggaggaccga aggagctaac cgcttttttg | 5880 |
| cacaacatgg gggatcatgt aactcgcctt gatcgttggg aaccggagct gaatgaagcc | 5940 |
| ataccaaacg acgagcgtga caccacgatg cctgtagcaa tggcaacaac gttgcgcaaa | 6000 |
| ctattaactg gcgaactact tactctagct tcccggcaac aattaataga ctggatggag | 6060 |
| gcggataaag ttgcaggacc acttctgcgc tcggcccttc cggctggctg gtttattgct | 6120 |
| gataaatctg gagccggtga gcgtgggtct cgcggtatca ttgcagcact ggggccagat | 6180 |
| ggtaagccct cccgtatcgt agttatctac acgacgggga gtcaggcaac tatggatgaa | 6240 |
| cgaaatagac agatcgctga gataggtgcc tcactgatta gcattggtaa actgtcagac | 6300 |
| caagtttact catatatact ttagattgat ttaaaacttc attttaatt taaaaggatc | 6360 |
| taggtgaaga tcctttttga taatctcatg accaaaatcc cttaacgtga gttttcgttc | 6420 |
| cactgagcgt cagaccccgt agaaaagatc aaaggatctt cttgaaatcc ttttttctg | 6480 |
| cgcgtaatct gctgcttgca acaaaaaaa ccaccgctac cagcggtggt ttgtttgccg | 6540 |
| gatcaagagc taccaactct ttttccgaag gtaactggct tcagcagagc gcagatacca | 6600 |
| aatactgttc ttctagtgta gccgtagtta ggccaccact tcaagaactc tgtagcaccg | 6660 |
| cctacatacc tcgctctgct aatcctgtta ccagtggctg ctgccagtgg cgataagtcg | 6720 |
| tgtcttaccg ggttggactc aagacgatag ttaccggata aggcgcagcg gtcgggctga | 6780 |
| acgggggtt cgtgcacaca gcccagcttg gagcgaacga cctacaccga actgagatac | 6840 |
| ctacagcgtg agctatgaga aagcgccacg cttcccgaag ggagaaaggc ggacaggtat | 6900 |
| ccggtaagcg gcagggtcgg aacaggagag cgcacgaggg agcttccagg gggaaacgcc | 6960 |
| tggtatcttt atagtcctgt cgggtttcgc cacctctgac ttgagcgtcg attttgtga | 7020 |
| tgctcgtcag gggggcggag cctatggaaa aacgccagca acgcggcctt tttacggttc | 7080 |
| ctggcctttt gctggccttt tgctcacatg tcctgcaggc ag | 7122 |

<210> SEQ ID NO 33
<211> LENGTH: 7162
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 33

| | |
|---|---|
| ctgcgcgctc gctcgctcac tgaggccgcc cgggcgtcgg gcgacctttg gtcgcccggc | 60 |
| ctcagtgagc gagcgagcgc gcagagaggg agtggccaac tccatcacta ggggttcctg | 120 |
| cggccgcacg cgtgacgtcg tttaaacggg ccccggtgtt atctcattct ttttctcct | 180 |
| ctgtaagttg acatgtgatg tgggaacaaa ggggataaag tcattatttt gtgctaaaat | 240 |
| cgtaattgga gaggacctcc tgttagctgg gctttcttct atttattgtg gtggttactg | 300 |
| gagttccttc ttctagtttt aggatatata tatattttt ttttttttct ttccctgaag | 360 |
| atataataat atatatactt ctgaagattg agatttttaa attagttgta ttgaaaacta | 420 |
| gctaatcagc aatttaaggc tagcttgaga cttatgtctt gaatttgttt ttgtaggctc | 480 |

```
caaaaccaag gagggagtgg tgcatggtgt ggcaacaggt aagctccatt gtgcttatat      540
ccaaagatga tatttaaagt atctagtgat tagtgtggcc cagtattcaa gattcctatg      600
aaattgtaaa acaatcactg agcattctaa gaacatatca gtcttattga aactgaattc      660
tttataaagt atttttaaaa aggtaaatat tgattataaa taaaaatat acttgccaag       720 aataatgagg gctttgaatt gataagctat gtttaattta tagtaagtgg gcatttaaat      780
attctgacca aaaatgtatt gacaaactgc tgacaaaaat aaaatgtgaa tattgccata     840
attttaaaaa aagagtaaaa tttctgttga ttacagtaaa atattttgac cttaaattat     900
gttgattaca atattccttt gataattcag agtgcatttc aggaaacacc cttggacagt     960
cagtaaattg tttattgtat ttatctttgt attgttatgg tatagctatt tgtacaaata    1020
ttattgtgca attattacat ttctgattat attattcatt tggcctaaat ttaccaagaa    1080
tttgaacaag tcaattaggt ttacaatcaa gaaatatcaa aaatgatgaa aaggatgata    1140
atcatcatca gatgttgagg aagatgacga tgagagtgcc agaaatagag aaatcaaagg    1200
agaaccaaaa tttaacaaat taaaagccca cagacttgct gtaattaagt tttctgttgt    1260
aagtactcca cgtttcctgg cagatgtggt gaagcaaaag atataatcag aaatataatt    1320
tatatgatcg gaaagcatta aacacaatag tgcctataca aataaaatgt tcctatcact    1380
gacttctaaa atggaaatga ggacaatgat atgggaatct taatacagtg ttgtggatag    1440
gactaaaaac acaggagtca gatcttcttg gttcaacttc ctgcttactc cttaccagct    1500
gtgtgttttt tgcaaggttc ttcacctcta tgtgatttag cttcctcatc tataaaataa    1560
ttcagtgaat taatgtacac aaaacatctg gaaaacaaaa gcaaacaata tgtattttat    1620
aagtgttact tatagttta tagtgaactt tcttgtgcaa cattttaca actagtggag       1680 aaaaatattt ctttaaatga atactttga tttaaaaatc agagtgtaaa aataaaacag      1740
actcctttga aactagttct gttagaagtt aattgtgcac ctttaatggg ctctgttgca    1800
atccaacaga gaagtagtta agtaagtgga ctatgatggc ttctagggac ctcctataaa    1860
tatgatattg tgaagcatga ttataataag aactagataa cagacaggtg gagactccac    1920
tatctgaaga gggtcaacct agatgaatgg tgttccattt agtagttgag gaagaaccca    1980
tgaggtttag aaagcagaca agcatgtggc aagttctgga gtcagtggta aaaattaaag    2040
aacccaacta ttactgtcac ctaatgatct aatggagact gtggagatgg gctgcatttt    2100
tttaatcttc tccagaatgc caaaatgtaa acacatatct gtgtgtgtgt gtgtgtgtgt    2160
gtgtgtgtgt gagagagaga gagagagaga gagagactga agtttgtaca attagacatt    2220
ttataaaatg ttttctgaag gacagtggct cacaatctta agtttctaac attgtacaat    2280
gttgggagac tttgtatact ttattttctc tttagcatat taaggaatct gagatgtcct    2340
acagtaaaga aatttgcatt acatagttaa aatcagggtt attcaaactt tttgattatt    2400
gaaacctttc ttcattagtt actagggttg aatgaaacta gtgttccaca gaaaactatg    2460
ggaaatgttg ctaggcagta aggacatggt gatttcagca tgtgcaatat ttacagcgat    2520
tgcacccatg gaccaccctg gcagtagtga aataaccaaa aatgctgtca taactagtat    2580
ggctatgaga aacacattgg gcagaagctt gcctcgagca gcgctgctcg agagatctgg    2640
atcataatca gccataccac atttgtagag gttttacttg ctttaaaaaa cctcccacac    2700 ctcccctga acctgaaaca taaaatgaat gcaattgttg ttgttaactt gtttattgca    2760
gcttataatg gttacaaata aagcaatagc atcacaaatt tcacaaataa agcattttt    2820
```

```
tcactgcatt ctagttgtgg tttgtccaaa ctcatcaatg tatcttatca tgtctggtaa    2880
ccattctcca ggttgagcca gaccaatttg atggtagatt tagcaaataa aaatacagga    2940
cacccagtta aatgtgaatt tccgatgaac agcaaatact ttttagtat taaaaaagtt    3000
cacatttagg ctcacgcctg taatcccagc actttgggag gccgaggcag gcagatcacc    3060
tgaggtcagg agttcgagac cagcctggcc aacatggtga accccatct ccactaaaaa    3120
taccaaaaat tagccaggcg tgctggtggg cacctgtagt tccagctact caggaggcta    3180
aggcaggaga attgcttgaa cctgggaggc agaggttgca gtgagctgag atcgcaccat    3240
tgcactctag cctgggcgac aagaacaaaa ctccatctca aaaaaaaaa aaaaaaaaa    3300
gttcacattt aactgggcat tctgtattta attggtaatc tgagatggca gggaacagca    3360
tcagcatggt gtgagggata ggcattttt cattgtgtac agcttgtaaa tcagtatttt    3420
taaaactcaa agttaatggc ttgggcatat ttagaaaaga gttgccgcac ggacttgaac    3480
cctgtattcc taaaatctag gatcttgttc tgatggtctg cacaactggc tgggggtgtc    3540
cagccactgt ccctcttgcc tgggctcccc agggcagttc tgtcagcctc tccatttcca    3600
ttcctgttcc agcaaaaccc aactgatagc acagcagcat ttcagcctgt ctacctctgt    3660
gcccacatac ctggatgtct accagccaga aaggtggctt agatttggtt cctgtgggtg    3720
gattatggcc cccagaactt ccctgtgctt gctggggtg tggagtggaa agagcaggaa    3780
atgggggacc ctccgatact ctatgggggt cctccaagtc tctttgtgca gttaggta    3840
ataatcaata tggagctaag aaagagaagg ggaactatgc tttagaacag gacactgtgc    3900
caggagcatt gcagaaatta tatggttttc acgacagttc ttttggtag gtactgttat    3960
tatcctcagt ttgcagatga ggaaactgag acccagaaag gttaaataac ttgctagggt    4020
cacacaagtc ataactgaca aagcctgatt caaacccagg tctccctaac ctttaaggtt    4080
tctatgacgc cagctctcct agggagtttg tcttcagatg tcttggctct aggtgtcaaa    4140
aaaagacttg gtgtcaggca ggcataggtt caagtcccaa ctctgtcact taccaactgt    4200
gactaggtga ttgaactgac catggaacct ggtcacatgc aggagcagga tggtgaaggg    4260
ttcttgaagg cacttaggca ggacatttag gcaggagaga aaacctggaa acagaagagc    4320
tgtctccaaa aatacccact ggggaagcag gttgtcatgt gggccatgaa tgggacctgt    4380
tctgggtaa ccacgtgcgg accgagcggc cgcaggaacc cctagtgatg gagttggcca    4440
ctccctctct gcgcgctcgc tcgctcactg aggccgggcg accaaaggtc gcccgacgcc    4500
cgggctttgc ccgggcggcc tcagtgagcg agcgagcgcg cagctgcctg caggggcgcc    4560
tgatgcggta ttttctcctt acgcatctgt gcggtatttc acaccgcata cgtcaaagca    4620
accatagtac gcgccctgta gcggcgcatt aagcgcggcg ggtgtggtgg ttacgcgcag    4680
cgtgaccgct acacttgcca gcgccttagc gcccgctcct ttcgctttct tcccttcctt    4740
tctcgccacg ttcgccggct ttccccgtca gctctaaat cggggctcc ctttagggtt    4800
ccgatttagt gctttacggc acctcgaccc caaaaaactt gatttgggtg atggttcacg    4860
tagtgggcca tcgccctgat agacggtttt tcgccctttg acgttggagt ccacgttctt    4920
taatagtgga ctcttgttcc aaactggaac aacactcaac tctatctcgg gctattcttt    4980
tgatttataa gggattttgc cgatttcggt ctattggtta aaaatgagc tgatttaaca    5040
aaaatttaac gcgaatttta acaaaatatt aacgtttaca attttatggt gcactctcag    5100
tacaatctgc tctgatgccg catagttaag ccagccccga cacccgccaa cacccgctga    5160
cgcgccctga cgggcttgtc tgctcccggc atccgcttac agacaagctg tgaccgtctc    5220
```

```
cgggagctgc atgtgtcaga ggttttcacc gtcatcaccg aaacgcgcga gacgaaaggg     5280
cctcgtgata cgcctatttt tataggttaa tgtcatgata ataatggttt cttagacgtc     5340
aggtggcact tttcggggaa atgtgcgcgg aaccoctatt tgtttatttt tctaaataca     5400
ttcaaatatg tatccgctca tgagacaata accctgataa atgcttcaat aatattgaaa     5460
aaggaagagt atgagtattc aacatttccg tgtcgccctt attcccttt ttgcggcatt      5520 ttgccttcct gttttgctc acccagaaac gctggtgaaa gtaaaagatg ctgaagatca      5580
gttgggtgca cgagtgggtt acatcgaact ggatctcaac agcggtaaga tccttgagag     5640
ttttcgcccc gaagaacgtt ttccaatgat gagcactttt aaagttctgc tatgtggcgc     5700
ggtattatcc cgtattgacg ccgggcaaga gcaactcggt cgccgcatac actattctca     5760
gaatgacttg gttgagtact caccagtcac agaaaagcat cttacggatg gcatgacagt     5820
aagagaatta tgcagtgctg ccataaccat gagtgataac actgcggcca acttacttct     5880
gacaacgatc ggaggaccga aggagctaac cgcttttttg cacaacatgg ggatcatgt      5940 aactcgcctt gatcgttggg aaccggagct gaatgaagcc ataccaaacg acgagcgtga     6000
caccacgatg cctgtagcaa tggcaacaac gttgcgcaaa ctattaactg gcgaactact     6060
tactctagct tcccggcaac aattaataga ctggatggag gcggataaag ttgcaggacc     6120
acttctgcgc tcggcccttc cggctggctg gtttattgct gataaatctg gagccggtga     6180
gcgtgggtct cgcggtatca ttgcagcact ggggccagat ggtaagccct cccgtatcgt     6240
agttatctac acgacgggga gtcaggcaac tatggatgaa cgaaatagac agatcgctga     6300
gataggtgcc tcactgatta agcattggta actgtcagac caagtttact catatatact     6360
ttagattgat ttaaaacttc atttttaatt taaaaggatc taggtgaaga tcctttttga     6420
taatctcatg accaaaatcc cttaacgtga gttttcgttc cactgagcgt cagaccccgt     6480
agaaaagatc aaaggatctt cttgaaatcc ttttttctg cgcgtaatct gctgcttgca      6540
aacaaaaaaa ccaccgctac cagcggtggt ttgtttgccg gatcaagagc taccaactct     6600
ttttccgaag gtaactggct tcagcagagc gcagatacca atactgttc ttctagtgta      6660 gccgtagtta ggccaccact tcaagaactc tgtagcaccg cctacatacc tcgctctgct     6720
aatcctgtta ccagtggctg ctgccagtgg cgataagtcg tgtcttaccg ggttggactc     6780
aagacgatag ttaccggata aggcgcagcg gtcgggctga acggggggtt cgtgcacaca     6840
gcccagcttg gagcgaacga cctacaccga actgagatac ctacagcgtg agctatgaga     6900
aagcgccacg cttcccgaag ggagaaaggc ggacaggtat ccggtaagcg cagggtcgg     6960 aacaggagag cgcacgaggg agcttccagg gggaaacgcc tggtatcttt atagtcctgt     7020
cgggtttcgc cacctctgac ttgagcgtcg attttgtga tgctcgtcag ggggcggag      7080 cctatggaaa aacgccagca acgcggcctt tttacggttc ctggcctttt gctggccttt     7140
tgctcacatg tcctgcaggc ag                                              7162
```

<210> SEQ ID NO 34
<211> LENGTH: 7057
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

```
ctgcgcgctc gctcgctcac tgaggccgcc cgggcgtcgg gcgacctttg gtcgcccggc       60
```

```
ctcagtgagc gagcgagcgc gcagagaggg agtggccaac tccatcacta ggggttcctg    120
cggccgcacg cgttacgtaa tatttattga agtttaatat tgtgtttgtg atacagaagt    180
atttgcttta attctaaata aaaattttat gcttttattg ctggtttaag aagatttgga    240
ttatccttgt actttgagga aagtttctt atttgaaata ttttggaaac aggtctttta     300
atgtggaaag atagatatta atctcctctt ctattactct ccaagatcca acaaaagtga    360
ttataccccc caaaatatga tggtagtatc ttatactacc atcattttat aggcataggg    420
ctcttagctg caaataatgg aactaactct aataaagcag aacgcaaata ttgtaaatat    480
tagagagcta acaatctctg ggatggctaa aggatggagc ttggaggcta cccagccagt    540
aacaatattc cgggctccac tgttgaatgg agacactaca actgccttgg atgggcagag    600
atattatgga tgctaagccc caggtgctac cattaggact tctaccactg tccctaacgg    660
gtggagccca tcacatgcct atgccctcac tgtaaggaaa tgaagctact gttgtatatc    720
ttgggaagca cttggattaa ttgttataca gttttgttga agaaccccc tagggtaagt    780 agccataact gcacactaaa tttaaaattg ttaatgagtt tctcaaaaaa aatgttaagg    840
ttgttagctg gtatagtata tatcttgcct gttttccaag gacttctttg ggcagtacct    900
tgtctgtgct ggcaagcaac tgagacttaa tgaaagagta ttggagatat gaatgaattg    960
atgctgtata ctctcagagt gccaaacata taccaatgga caagaaggtg aggcagagag   1020
cagacaggca ttagtgacaa gcaaagatat gcagaatttc attctcagca aatcaaaagt   1080
cctcaacctg gttggaagaa tattggcact gaatggtatc aataaggttg ctagagaggg   1140
ttagaggtgc acaatgtgct tccataacat tttatacttc tccaatctta gcactaatca   1200
aacatggttg aatactttgt ttactataac tcttacagag ttataagatc tgtgaagaca   1260
gggacaggga caatacccat ctctgtctgg ttcataggtg gtatgtaata gatattttta   1320
aaaataagtg agttaatgaa tgagggtgag aatgaaggca cagaggtatt aggggggaggt   1380 gggccccaga gaatggtgcc aaggtccagt ggggtgactg ggatcagctc aggcctgacg   1440
ctggccactc ccacctagct cctttctttc taatctgttc tcattctcct tgggaaggat   1500
tgaggtctct ggaaaacagc caaacaactg ttatgggaac agcaagccca aataaagcca   1560
agcatcaggg ggatctgaga gctgaaagca acttctgttc cccctccctc agctgaaggg   1620
gtggggaagg gctcccaaag ccataactcc tttttaaggga tttagaaggc ataaaaaggc   1680
ccctggctga gaacttcctt cttcattctg cagttggtga attccccggg gatcctctag   1740
agtcgaaatt cgccaccatg gtgagcaagg gcgaggagct gttcaccggg gtggtgccca   1800
tcctggtcga gctggacggc gacgtaaacg gccacaagtt cagcgtgtcc ggcgagggcg   1860
agggcgatgc cacctacggc aagctgaccc tgaagttcat ctgcaccacc ggcaagctgc   1920
ccgtgccctg gcccaccctc gtgaccaccc tgacctacgg cgtgcagtgc ttcagccgct   1980
accccgacca catgaagcag cacgacttct tcaagtccgc catgcccgaa ggctacgtcc   2040
aggagcgcac catcttcttc aaggacgacg gcaactacaa gacccgcgcc gaggtgaagt   2100
tcgagggcga cacactggtg aaccgcatcg agctgaaggg catcgacttc aaggaggacg   2160
gcaacatcct ggggcacaag ctggagtaca actacaacag ccacaacgtc tatatcatgg   2220
ccgacaagca gaagaacggc atcaaggtga acttcaagat ccgccacaac atcgaggacg   2280
gcagcgtgca gctcgccgac cactaccagc agaacacccc catcggcgac ggccccgtgc   2340
tgctgcccga caaccactac ctgagcaccc agtccgccct gagcaaagac cccaacgaga   2400
```

```
agcgcgatca catggtcctg ctggagttcg tgaccgccgc cgggatcact ctcggcatgg    2460
acgagctgta caagtaatag ggtaccggtc gacctgcaga agcttgcctc gagcagcgct    2520
gctcgagaga tctggatcat aatcagccat accacatttg tagaggtttt acttgcttta    2580
aaaaacctcc cacacctccc cctgaacctg aaacataaaa tgaatgcaat tgttgttgtt    2640
aacttgttta ttgcagctta taatggttac aaataaagca atagcatcac aaatttcaca    2700
aataaagcat ttttttcact gcattctagt tgtggtttgt ccaaactcat caatgtatct    2760
tatcatgtct ggtaaccatt ctccaggttg agccagacca atttgatggt agatttagca    2820
aataaaaata caggacaccc agttaaatgt gaatttccga tgaacagcaa atactttttt    2880
agtattaaaa aagttcacat ttaggctcac gcctgtaatc ccagcacttt gggaggccga    2940
ggcaggcaga tcacctgagg tcaggagttc gagaccagcc tggccaacat ggtgaaaccc    3000
catctccact aaaaatacca aaattagcc aggcgtgctg gtgggcacct gtagttccag    3060
ctactcagga ggctaaggca ggagaattgc ttgaacctgg gaggcagagg ttgcagtgag    3120
ctgagatcgc accattgcac tctagcctgg gcgacaagag caaaactcca tctcaaaaaa    3180
aaaaaaaaaa aaaagttca catttaactg gcattctgt atttaattgg taatctgaga    3240
tggcagggaa cagcatcagc atggtgtgag ggataggcat tttttcattg tgtacagctt    3300
gtaaatcagt attttaaaa ctcaaagtta atggcttggg catatttaga aaagagttgc    3360
cgcacggact tgaaccctgt attcctaaaa tctaggatct tgttctgatg gtctgcacaa    3420
ctggctgggg gtgtccagcc actgtccctc ttgcctgggc tccccagggc agttctgtca    3480
gcctctccat ttccattcct gttccagcaa aacccaactg atagcacagc agcatttcag    3540
cctgtctacc tctgtgccca catacctgga tgtctaccag ccagaaaggt ggcttagatt    3600
tggttcctgt gggtggatta tggccccag aacttccctg tgcttgctgg gggtgtggag    3660
tggaaagagc aggaaatggg ggaccctccg atactctatg ggggtcctcc aagtctcttt    3720
gtgcaagtta gggtaataat caatatggag ctaagaaaga gaaggggaac tatgctttag    3780
aacaggacac tgtgccagga gcattgcaga aattatatgg ttttcacgac agttcttttt    3840
ggtaggtact gttattatcc tcagtttgca gatgaggaaa ctgagaccca gaaaggttaa    3900
ataacttgct agggtcacac aagtcataac tgacaaagcc tgattcaaac ccaggtctcc    3960 ctaacctta aggtttctat gacgccagct ctcctaggga gtttgtcttc agatgtcttg    4020
gctctaggtg tcaaaaaag acttggtgtc aggcaggcat aggttcaagt cccaactctg    4080
tcacttacca actgtgacta ggtgattgaa ctgaccatgg aacctggtca catgcaggag    4140
caggatggtg aagggttctt gaaggcactt aggcaggaca tttaggcagg agagaaaacc    4200
tggaaacaga gagctgtct ccaaaaatac ccactgggga gcaggttgt catgtgggcc    4260 atgaatggga cctgttctgg ggtaaccacg tgcggaccga gcggccgcag gaacccctag    4320
tgatggagtt ggccactccc tctctgcgcg ctcgctcgct cactgaggcc gggcgaccaa    4380
aggtcgcccg acgccgggc tttgcccggg cggcctcagt gagcgagcga gcgcgcagct    4440
gcctgcaggg gcgcctgatg cggtattttc tccttacgca tctgtgcggt atttcacacc    4500
gcatacgtca aagcaaccat agtacgcgcc ctgtagcggc gcattaagcg cggcgggtgt    4560
ggtggttacg cgcagcgtga ccgctacact tgccagcgcc ttagcgcccg ctcctttcgc    4620
tttcttccct tcctttctcg ccacgttcgc cggctttccc cgtcaagctc taaatcgggg    4680
gctcccttta gggttccgat ttagtgcttt acggcacctc gaccccaaaa aacttgattt    4740
gggtgatggt tcacgtagtg ggccatcgcc ctgatagacg gtttttcgcc ctttgacgtt    4800
```

```
ggagtccacg ttctttaata gtggactctt gttccaaact ggaacaacac tcaactctat    4860
ctcgggctat tcttttgatt tataagggat tttgccgatt tcggtctatt ggttaaaaaa    4920
tgagctgatt taacaaaaat ttaacgcgaa ttttaacaaa atattaacgt ttacaatttt    4980
atggtgcact ctcagtacaa tctgctctga tgccgcatag ttaagccagc ccgacaccc     5040 gccaacaccc gctgacgcgc cctgacgggc ttgtctgctc ccggcatccg cttacagaca    5100
agctgtgacc gtctccggga gctgcatgtg tcagaggttt tcaccgtcat caccgaaacg    5160
cgcgagacga aagggcctcg tgatacgcct atttttatag gttaatgtca tgataataat    5220
ggtttcttag acgtcaggtg gcacttttcg gggaaatgtg cgcggaaccc ctatttgttt    5280
atttttctaa atacattcaa atatgtatcc gctcatgaga cataaccct gataaatgct     5340 tcaataatat tgaaaaagga gagtatgag tattcaacat ttccgtgtcg ccttattcc      5400 cttttttgcg cattttgcc ttcctgtttt tgctcaccca gaaacgctgg tgaaagtaaa     5460
agatgctgaa gatcagttgg gtgcacgagt gggttacatc gaactggatc tcaacagcgg    5520
taagatcctt gagagtttc gccccgaaga acgttttcca atgatgagca cttttaaagt     5580
tctgctatgt ggcgcggtat tatcccgtat tgacgccggg caagagcaac tcggtcgccg    5640
catacactat tctcagaatg acttggttga gtactcacca gtcacagaaa agcatcttac    5700
ggatggcatg acagtaagag aattatgcag tgctgccata accatgagtg ataacactgc    5760
ggccaactta cttctgacaa cgatcggagg accgaaggag ctaaccgctt ttttgcacaa    5820
catgggggat catgtaactc gccttgatcg ttgggaaccg gagctgaatg aagccatacc    5880
aaacgacgag cgtgacacca cgatgcctgt agcaatggca acaacgttgc gcaaactatt    5940
aactggcgaa ctacttactc tagcttcccg gcaacaatta atagactgga tggaggcgga    6000
taaagttgca ggaccacttc tgcgctcggc ccttccggct ggctggttta ttgctgataa    6060
atctggagcc ggtgagcgtg ggtctcgcgg tatcattgca gcactgggc cagatggtaa     6120 gccctcccgt atcgtagtta tctacacgac ggggagtcag gcaactatgg atgaacgaaa    6180
tagacagatc gctgagatag gtgcctcact gattaagcat tggtaactgt cagaccaagt    6240
ttactcatat atactttaga ttgatttaaa acttcatttt taatttaaaa ggatctaggt    6300
gaagatcctt tttgataatc tcatgaccaa aatcccttaa cgtgagtttt cgttccactg    6360
agcgtcagac cccgtagaaa agatcaaagg atcttcttga atcctttttt ttctgcgcgt    6420
aatctgctgc ttgcaaacaa aaaaaccacc gctaccagcg gtggtttgtt tgccggatca    6480
agagctacca actctttttc cgaaggtaac tggcttcagc agagcgcaga taccaaatac    6540
tgttcttcta gtgtagccgt agttaggcca ccacttcaag aactctgtag caccgcctac    6600
atacctcgct ctgctaatcc tgttaccagt ggctgctgcc agtggcgata agtcgtgtct    6660
taccgggttg gactcaagac gatagttacc ggataaggcg cagcggtcgg gctgaacggg    6720
gggttcgtgc acacagccca gcttggagcg aacgacctac accgaactga gatacctaca    6780
gcgtgagcta tgagaaagcg ccacgcttcc cgaagggaga aaggcggaca ggtatccggt    6840
aagcggcagg gtcggaacag gagagcgcac gagggagctt ccagggggaa acgcctggta    6900
tctttatagt cctgtcgggt ttcgccacct ctgacttgag cgtcgatttt tgtgatgctc    6960 gtcaggggg cggagcctat ggaaaaacgc cagcaacgcg gcctttttac ggttcctggc     7020
cttttgctgg ccttttgctc acatgtcctg caggcag                             7057
```

<210> SEQ ID NO 35

<211> LENGTH: 6100
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 35

| | | | | | |
|---|---|---|---|---|---|
| ctgcgcgctc | gctcgctcac | tgaggccgcc | cgggcgtcgg | gcgacctttg | gtcgcccggc | 60 |
| ctcagtgagc | gagcgagcgc | gcagagaggg | agtggccaac | tccatcacta | ggggttcctg | 120 |
| cggccgcacg | cgttacgtaa | ttctgtcatt | ttactagggt | gatgaaattc | ccaagcaaca | 180 |
| ccatcctttt | cagataaggg | cactgaggct | gagagaggg | ctgaaaccta | cccggcgtca | 240 |
| ccacacacag | gtggcaaggc | tgggaccaga | aaccaggact | gttgactgca | gcccggtatt | 300 |
| cattctttcc | atagcccaca | gggctgtcaa | agacccagg | gcctagtcag | aggctcctcc | 360 |
| ttcctggaga | gttcctggca | cagaagttga | agctcagcac | agcccccctaa | ccccaactc | 420 |
| tctctgcaag | gcctcagggg | tcagaacact | ggtggagcag | atcctttagc | ctctggattt | 480 |
| tagggccatg | gtagaggggg | tgttgcccta | aattccagcc | ctggtctcag | cccaacaccc | 540 |
| tccaagaaga | aattagaggg | gccatggcca | ggctgtgcta | gccgttgctt | ctgagcagat | 600 |
| tacaagaagg | gactaagaca | aggactcctt | tgtggaggtc | ctggcttagg | gagtcaagtg | 660 |
| acggcggctc | agcactcacg | tgggcagtgc | cagcctctaa | gagtgggcag | ggcactggc | 720 |
| cacagagtcc | cagggagtcc | caccagccta | gtcgccagac | cgaattcccc | ggggatcctc | 780 |
| tagagtcgaa | attcgccacc | atggtgagca | agggcgagga | gctgttcacc | ggggtggtgc | 840 |
| ccatcctggt | cgagctggac | ggcgacgtaa | acggccacaa | gttcagcgtg | tccggcgagg | 900 |
| gcgagggcga | tgccacctac | ggcaagctga | ccctgaagtt | catctgcacc | accggcaagc | 960 |
| tgcccgtgcc | ctggcccacc | ctcgtgacca | ccctgaccta | cggcgtgcag | tgcttcagcc | 1020 |
| gctaccccga | ccacatgaag | cagcacgact | tcttcaagtc | cgccatgccc | gaaggctacg | 1080 |
| tccaggagcg | caccatcttc | ttcaaggacg | acggcaacta | caagacccgc | gccgaggtga | 1140 |
| agttcgaggg | cgacaccctg | gtgaaccgca | tcgagctgaa | gggcatcgac | ttcaaggagg | 1200 |
| acggcaacat | cctggggcac | aagctggagt | acaactacaa | cagccacaac | gtctatatca | 1260 |
| tggccgacaa | gcagaagaac | ggcatcaagg | tgaacttcaa | gatccgccac | aacatcgagg | 1320 |
| acggcagcgt | gcagctcgcc | gaccactacc | agcagaacac | cccatcggc | gacggccccg | 1380 |
| tgctgctgcc | cgacaaccac | tacctgagca | cccagtccgc | cctgagcaaa | gaccccaacg | 1440 |
| agaagcgcga | tcacatggtc | ctgctggagt | tcgtgaccgc | cgccgggatc | actctcggca | 1500 |
| tggacgagct | gtacaagtaa | tagggtaccg | gtcgacctgc | agaagcttgc | ctcgagcagc | 1560 |
| gctgctcgag | agatctggat | cataatcagc | cataccacat | tgtagaggt | tttacttgct | 1620 |
| ttaaaaaacc | tcccacacct | cccctgaac | ctgaaacata | aaatgaatgc | aattgttgtt | 1680 |
| gttaacttgt | ttattgcagc | ttataatggt | tacaaataaa | gcaatagcat | cacaaatttc | 1740 |
| acaaataaag | catttttttc | actgcattct | agttgtggtt | tgtccaaact | catcaatgta | 1800 |
| tcttatcatg | tctggtaacc | attctccagg | ttgagccaga | ccaatttgat | ggtagattta | 1860 |
| gcaaataaaa | atacaggaca | cccagttaaa | tgtgaatttc | cgatgaacag | caaatacttt | 1920 |
| tttagtatta | aaaaagttca | catttaggct | cacgcctgta | atcccagcac | tttgggaggc | 1980 |
| cgaggcaggc | agatcacctg | aggtcaggag | ttcgagacca | gcctggccaa | catggtgaaa | 2040 |
| ccccatctcc | actaaaaata | caaaaaatta | gccaggcgtg | ctggtgggca | cctgtagttc | 2100 |

```
cagctactca ggaggctaag gcaggagaat tgcttgaacc tgggaggcag aggttgcagt   2160
gagctgagat cgcaccattg cactctagcc tgggcgacaa gaacaaaact ccatctcaaa   2220
aaaaaaaaaa aaaaaaaagt tcacatttaa ctgggcattc tgtatttaat tggtaatctg   2280
agatggcagg gaacagcatc agcatggtgt gagggatagg cattttttca ttgtgtacag   2340
cttgtaaatc agtattttta aaactcaaag ttaatggctt gggcatattt agaaagagt    2400
tgccgcacgg acttgaaccc tgtattccta aaatctagga tcttgttctg atggtctgca   2460
caactggctg ggggtgtcca gccactgtcc ctcttgcctg ggctcccag ggcagttctg    2520
tcagcctctc catttccatt cctgttccag caaaacccaa ctgatagcac agcagcattt   2580
cagcctgtct acctctgtgc ccacatacct ggatgtctac cagccagaaa ggtggcttag   2640
atttggttcc tgtgggtgga ttatggcccc cagaacttcc ctgtgcttgc tggggtgtg    2700
gagtggaaag agcaggaaat gggggaccct ccgatactct atgggggtcc tccaagtctc   2760
tttgtgcaag ttagggtaat aatcaatatg gagctaagaa agagaagggg aactatgctt   2820
tagaacagga cactgtgcca ggagcattgc agaaattata tggttttcac gacagttctt   2880
tttggtaggt actgttatta tcctcagttt gcagatgagg aaactgagac ccagaaaggt   2940
taaataactt gctagggtca cacaagtcat aactgacaaa gcctgattca aacccaggtc   3000
tccctaacct ttaaggtttc tatgacgcca gctctcctag ggagtttgtc ttcagatgtc   3060
ttggctctag gtgtcaaaaa aagacttggt gtcaggcagg catagqttca agtcccaact   3120
ctgtcactta ccaactgtga ctaggtgatt gaactgacca tggaacctgg tcacatgcag   3180
gagcaggatg gtgaagggtt cttgaaggca cttaggcagg acatttaggc aggagagaaa   3240
acctggaaac agaagagctg tctccaaaaa tacccactgg ggaagcaggt tgtcatgtgg   3300
gccatgaatg ggacctgttc tggggtaacc acgtgcggac cgagcggccg caggaacccc   3360
tagtgatgga gttggccact ccctctctgc gcgctcgctc gctcactgag gccgggcgac   3420
caaaggtcgc ccgacgcccg ggcttttgccc gggcggcctc agtgagcgag cgagcgcgca   3480
gctgcctgca ggggcgcctg atgcggtatt ttctccttac gcatctgtgc ggtatttcac   3540
accgcatacg tcaaagcaac catagtacgc gccctgtagc ggcgcattaa gcgcggcggg   3600
tgtggtggtt acgcgcagcg tgaccgctac acttgccagc gccttagcgc ccgctccttt   3660
cgctttcttc ccttcctttc tcgccacgtt cgccggcttt ccccgtcaag ctctaaatcg   3720
ggggctccct ttagggttcc gatttagtgc tttacggcac ctcgacccca aaaaacttga   3780
tttgggtgat ggttcacgta gtgggccatc gccctgatag acggttttc gccctttgac   3840
gttggagtcc acgttcttta atagtggact cttgttccaa actggaacaa cactcaactc   3900
tatctcgggc tattcttttg atttataagg gattttgccg atttcggtct attggttaaa   3960
aaatgagctg atttaacaaa aatttaacgc gaattttaac aaaatattaa cgtttacaat   4020
tttatggtgc actctcagta caatctgctc tgatgccgca tagttaagcc agccccgaca   4080
cccgccaaca cccgctgacg cgccctgacg ggcttgtctg ctcccggcat ccgcttacag   4140
acaagctgtg accgtctccg ggagctgcat gtgtcagagg ttttcaccgt catcaccgaa   4200
acgcgcgaga cgaaagggcc tcgtgatacg cctatttta taggttaatg tcatgataat   4260
aatggtttct tagacgtcag gtggcacttt tcggggaaat gtgcgcggaa cccctatttg   4320
tttatttttc taaatacatt caaatatgta tccgctcatg agacaataac cctgataaat   4380
gcttcaataa tattgaaaaa ggaagagtat gagtattcaa catttccgtg tcgcccttat   4440
tccctttttt gcggcatttt gccttcctgt ttttgctcac ccagaaacgc tggtgaaagt   4500
```

| | | | | |
|---|---|---|---|---|
| aaaagatgct | gaagatcagt | tgggtgcacg | agtgggttac | atcgaactgg | atctcaacag | 4560 |
| cggtaagatc | cttgagagtt | ttcgccccga | agaacgtttt | ccaatgatga | gcacttttaa | 4620 |
| agttctgcta | tgtggcgcgg | tattatcccg | tattgacgcc | gggcaagagc | aactcggtcg | 4680 |
| ccgcatacac | tattctcaga | atgacttggt | tgagtactca | ccagtcacag | aaaagcatct | 4740 |
| tacggatggc | atgacagtaa | gagaattatg | cagtgctgcc | ataaccatga | gtgataacac | 4800 |
| tgcggccaac | ttacttctga | caacgatcgg | aggaccgaag | gagctaaccg | cttttttgca | 4860 |
| caacatgggg | gatcatgtaa | ctcgccttga | tcgttgggaa | ccggagctga | atgaagccat | 4920 |
| accaaacgac | gagcgtgaca | ccacgatgcc | tgtagcaatg | gcaacaacgt | tgcgcaaact | 4980 |
| attaactggc | gaactactta | ctctagcttc | ccggcaacaa | ttaatagact | ggatggaggc | 5040 |
| ggataaagtt | gcaggaccac | ttctgcgctc | ggcccttccg | gctggctggt | ttattgctga | 5100 |
| taaatctgga | gccggtgagc | gtgggtctcg | cggtatcatt | gcagcactgg | ggccagatgg | 5160 |
| taagccctcc | cgtatcgtag | ttatctacac | gacggggagt | caggcaacta | tggatgaacg | 5220 |
| aaatagacag | atcgctgaga | taggtgcctc | actgattaag | cattggtaac | tgtcagacca | 5280 |
| agtttactca | tatatacttt | agattgattt | aaaacttcat | ttttaattta | aaaggatcta | 5340 |
| ggtgaagatc | ctttttgata | atctcatgac | caaaatccct | taacgtgagt | tttcgttcca | 5400 |
| ctgagcgtca | gacccgtag | aaaagatcaa | aggatcttct | tgaaatcctt | ttttctgcg | 5460 |
| cgtaatctgc | tgcttgcaaa | caaaaaaacc | accgctacca | gcggtggttt | gtttgccgga | 5520 |
| tcaagagcta | ccaactcttt | ttccgaaggt | aactggcttc | agcagagcgc | agataccaaa | 5580 |
| tactgttctt | ctagtgtagc | cgtagttagg | ccaccacttc | aagaactctg | tagcaccgcc | 5640 |
| tacatacctc | gctctgctaa | tcctgttacc | agtggctgct | gccagtggcg | ataagtcgtg | 5700 |
| tcttaccggg | ttggactcaa | gacgatagtt | accggataag | gcgcagcggt | cgggctgaac | 5760 |
| ggggggttcg | tgcacacagc | ccagcttgga | gcgaacgacc | tacaccgaac | tgagatacct | 5820 |
| acagcgtgag | ctatgagaaa | gcgccacgct | tcccgaaggg | agaaaggcgg | acaggtatcc | 5880 |
| ggtaagcggc | agggtcggaa | caggagagcg | cacgagggag | cttccagggg | gaaacgcctg | 5940 |
| gtatctttat | agtcctgtcg | ggtttcgcca | cctctgactt | gagcgtcgat | ttttgtgatg | 6000 |
| ctcgtcaggg | gggcggagcc | tatggaaaaa | cgccagcaac | gcggcctttt | tacggttcct | 6060 |
| ggccttttgc | tggccttttg | ctcacatgtc | ctgcaggcag | | | 6100 |

```
<210> SEQ ID NO 36
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
```

| | | | | |
|---|---|---|---|---|
| ctgcgcgctc | gctcgctcac | tgaggccgcc | cgggcaaagc | ccgggcgtcg | ggcgaccttt | 60 |
| ggtcgcccgg | cctcagtgag | cgagcgagcg | cgcagagagg | gagtggccaa | ctccatcact | 120 |
| aggggttcct | | | | | 130 |

```
<210> SEQ ID NO 37
<211> LENGTH: 954
<212> TYPE: DNA
<213> ORGANISM: Macaca mulatta

<400> SEQUENCE: 37
```

-continued

```
atgtcagaag gggtgggcac gttccgcatg gtacctgaag aggaacagga gctccgtgcc      60
caactggagc agctcacaac caaggaccat ggacctgtct ttggcccgtg cagccagctg     120
ccccgccaca ccttgcagaa ggccaaagat gagctgaatg agagagagga gacccgggag     180
gaggcagtgc gagagctgca ggagatggtg caggcgcagg cggcctcggg ggaggagctg     240
gccgtggccg tggcggagag ggtgcaagag aaggacagcg gcttcttcct gcgcttcatc     300
cgcgcgcgaa agttcaacgt gggccgtgcc tatgagctgc tcagaggcta tgtgaatttc     360
cggctgcagt accctgagct ctttgacagc ctgtccccag aggctgtccg ctgtaccatt     420
gaagctggct accctggtgt cctctctagt cgggacaagt atggccgagt ggtcatgctc     480
ttcaacattg agaactggca aagtcaagaa atcaccttcg atgagatctt gcaggcatat     540
tgcttcatcc tggagaagct gctggagaat gaggaaactc aaattaatgg attctgcatc     600
attgagaact tcaagggctt taccatgcag caggctgcta gtctccgcac ttcagatctc     660
aggaagatgg tggacatgct ccaggattcc ttcccagccc ggttcaaagc catccacttc     720
atccaccagc catggtactt caccacgacc tacaatgtgg tcaagccctt cttgaagagc     780
aagctgcttg agagggtctt tgtccacggg gaggacctct ctggtttcta ccaggagatt     840
gatgagaaca tcctgccctc tgactttggg ggcacgctgc ccaagtatga tggcaaagct     900
gttgctgagc agctctttgg cccccgggcc caagctgaga cacagccctt ctga           954
```

<210> SEQ ID NO 38
<211> LENGTH: 317
<212> TYPE: PRT
<213> ORGANISM: Macaca mulatta

<400> SEQUENCE: 38

```
Met Ser Glu Gly Val Gly Thr Phe Arg Met Val Pro Glu Glu Gln
1               5                   10                  15

Glu Leu Arg Ala Gln Leu Glu Gln Leu Thr Thr Lys Asp His Gly Pro
            20                  25                  30

Val Phe Gly Pro Cys Ser Gln Leu Pro Arg His Thr Leu Gln Lys Ala
        35                  40                  45

Lys Asp Glu Leu Asn Glu Arg Glu Glu Thr Arg Glu Glu Ala Val Arg
    50                  55                  60

Glu Leu Gln Glu Met Val Gln Ala Gln Ala Ala Ser Gly Glu Glu Leu
65                  70                  75                  80

Ala Val Ala Val Ala Glu Arg Val Gln Glu Lys Asp Ser Gly Phe Phe
                85                  90                  95

Leu Arg Phe Ile Arg Ala Arg Lys Phe Asn Val Gly Arg Ala Tyr Glu
            100                 105                 110

Leu Leu Arg Gly Tyr Val Asn Phe Arg Leu Gln Tyr Pro Glu Leu Phe
        115                 120                 125

Asp Ser Leu Ser Pro Glu Ala Val Arg Cys Thr Ile Glu Ala Gly Tyr
    130                 135                 140

Pro Gly Val Leu Ser Ser Arg Asp Lys Tyr Gly Arg Val Val Met Leu
145                 150                 155                 160

Phe Asn Ile Glu Asn Trp Gln Ser Gln Glu Ile Thr Phe Asp Glu Ile
                165                 170                 175

Leu Gln Ala Tyr Cys Phe Ile Leu Glu Lys Leu Leu Glu Asn Glu Glu
            180                 185                 190

Thr Gln Ile Asn Gly Phe Cys Ile Ile Glu Asn Phe Lys Gly Phe Thr
        195                 200                 205
```

```
Met Gln Gln Ala Ala Ser Leu Arg Thr Ser Asp Leu Arg Lys Met Val
    210                 215                 220

Asp Met Leu Gln Asp Ser Phe Pro Ala Arg Phe Lys Ala Ile His Phe
225                 230                 235                 240

Ile His Gln Pro Trp Tyr Phe Thr Thr Thr Tyr Asn Val Val Lys Pro
                245                 250                 255

Phe Leu Lys Ser Lys Leu Leu Glu Arg Val Phe Val His Gly Glu Asp
            260                 265                 270

Leu Ser Gly Phe Tyr Gln Glu Ile Asp Glu Asn Ile Leu Pro Ser Asp
        275                 280                 285

Phe Gly Gly Thr Leu Pro Lys Tyr Asp Gly Lys Ala Val Ala Glu Gln
    290                 295                 300

Leu Phe Gly Pro Arg Ala Gln Ala Glu Asn Thr Ala Phe
305                 310                 315

<210> SEQ ID NO 39
<211> LENGTH: 954
<212> TYPE: DNA
<213> ORGANISM: Bos taurus

<400> SEQUENCE: 39
atgtcagagg gggcgggcac gttccgcatg gtccctgaag aggaacagga gctccgtgcc      60
caactggaga ggcttacgac caaagaccat ggacctgtct ttggcccgtg cagccagctg     120
ccccgccaca ccttgcagaa ggccaaggac gagctgaatg aaaaggaaga gacccgggaa     180
gaggcagtgc gggagctaca ggagctggtg caggcggagg ccgcctcggg gcaggagctg     240
gccgtggccg tggcggagag ggtgcaggga aaagacagtg ccttcttcct gcgcttcatc     300
cgcgcgcgca agttccacgt ggggcgcgcc tacgagctgc tcagaggcta cgtgaacttc     360
cggctgcagt acccagagct cttcgacagc ctgtccccag aggctgtccg ctgcaccgtt     420
gaggctggct accctggtgt cctctccacg cgggacaagt atggccgagt ggtcatgctc     480
ttcaatattg agaactggga ctctgaagaa atcacctttg atgagatctt gcaggcatac     540
tgcgtcatcc tggagaagct actggagaat gaggagactc aaattaatgg ctttttgcatc     600 attgagaact caagggcttc accatgcag caggctgccg acttcggcc ttccgatctc     660 agaaagatgg tggacatgct ccaggattcc ttcccagctc ggttcaaagc catccacttc     720
atctaccagc cctggtactt caccaccacc tacaacgtgg tcaagccctt cttgaagagc     780
aaattgctcc agagggtatt tgtccatgga agacctct ccagcttcta ccaggagttt     840
gacgaggaca tcctgccctc cgactttggg ggtacactgc caagtatga tggcaaggcc     900 gttgctgagc agctctttgg tcctcgggac caaactgaga acacagcctt ctga     954

<210> SEQ ID NO 40
<211> LENGTH: 317
<212> TYPE: PRT
<213> ORGANISM: Bos taurus

<400> SEQUENCE: 40

Met Ser Glu Gly Ala Gly Thr Phe Arg Met Val Pro Glu Glu Glu Gln
1               5                   10                  15

Glu Leu Arg Ala Gln Leu Glu Arg Leu Thr Thr Lys Asp His Gly Pro
            20                  25                  30

Val Phe Gly Pro Cys Ser Gln Leu Pro Arg His Thr Leu Gln Lys Ala
        35                  40                  45
```

```
Lys Asp Glu Leu Asn Glu Lys Glu Glu Thr Arg Glu Ala Val Arg
     50                  55                  60
Glu Leu Gln Glu Leu Val Gln Ala Glu Ala Ser Gly Gln Glu Leu
 65                  70                  75                  80
Ala Val Ala Val Ala Glu Arg Val Gln Gly Lys Asp Ser Ala Phe Phe
                 85                  90                  95
Leu Arg Phe Ile Arg Ala Arg Lys Phe His Val Gly Arg Ala Tyr Glu
                100                 105                 110
Leu Leu Arg Gly Tyr Val Asn Phe Arg Leu Gln Tyr Pro Glu Leu Phe
                115                 120                 125
Asp Ser Leu Ser Pro Glu Ala Val Arg Cys Thr Val Glu Ala Gly Tyr
    130                 135                 140
Pro Gly Val Leu Ser Thr Arg Asp Lys Tyr Gly Arg Val Val Met Leu
145                 150                 155                 160
Phe Asn Ile Glu Asn Trp Asp Ser Glu Glu Ile Thr Phe Asp Glu Ile
                165                 170                 175
Leu Gln Ala Tyr Cys Val Ile Leu Glu Lys Leu Leu Glu Asn Glu Glu
                180                 185                 190
Thr Gln Ile Asn Gly Phe Cys Ile Ile Glu Asn Phe Lys Gly Phe Thr
                195                 200                 205
Met Gln Gln Ala Ala Gly Leu Arg Pro Ser Asp Leu Arg Lys Met Val
    210                 215                 220
Asp Met Leu Gln Asp Ser Phe Pro Ala Arg Phe Lys Ala Ile His Phe
225                 230                 235                 240
Ile Tyr Gln Pro Trp Tyr Phe Thr Thr Thr Tyr Asn Val Val Lys Pro
                245                 250                 255
Phe Leu Lys Ser Lys Leu Leu Gln Arg Val Phe Val His Gly Glu Asp
                260                 265                 270
Leu Ser Ser Phe Tyr Gln Glu Phe Asp Glu Asp Ile Leu Pro Ser Asp
                275                 280                 285
Phe Gly Gly Thr Leu Pro Lys Tyr Asp Gly Lys Ala Val Ala Glu Gln
    290                 295                 300
Leu Phe Gly Pro Arg Asp Gln Thr Glu Asn Thr Ala Phe
305                 310                 315
```

<210> SEQ ID NO 41
<211> LENGTH: 954
<212> TYPE: DNA
<213> ORGANISM: Canis lupus

<400> SEQUENCE: 41

```
atgtcagaag gcgtgggcac attccgtgtg gtccctgaag aggaacagga gctccgtgcc      60
cagctggagc ggcttacaac caaggaccat gggcctgtct ttggcccttg cagccagctc     120
cctcgtcata ccttacagaa ggccaaggac gagctgaacg agagggagga gacccgggag     180
gaggtggtgc agagctgca ggagctggtg caggcacagg ctgccaccgg gcaggagctg     240
gccagggcgg tggctgagag ggtgcaggga agggacagtg ccttcttcct gcgcttcatc     300
cgcgcgcgga gttccatgt ggggcgtgcc tacgagctgc ttcgaggcta cgtgaacttc     360
cggctgcagt acccagagct cttcgacagc ctgtccctgg aggctgtccg ttgcaccgtc     420
gaggccggct atcctggggt cctccccagt cgggacaagt atggccgagt ggtcatgctc     480
ttcaacatcg agaactggga ctccgaagaa atcaccttcg atgagatctt gcaggcatat     540
tgtttcatcc tggagaagct actagagaat gaggaaactc aaattaatgg cttctgcatt     600
```

```
attgagaact ttaagggctt taccatgcag caggctgctg gacttcgggc ttccgatctc    660
aggaagatgg tggacatgct ccaggattcc ttcccagcgc ggttcaaagc catccacttc    720
attcaccaac catggtactt caccaccacc tacaacatgg tcaagcccct cctgaagaac    780
aagctgctcc aaagagtctt tgtccatgga gatgacctct ctggcttctt ccaggagatt    840
gatgaagaca tactgcccgc tgactttggg ggcacactgc ccaagtatga tggcaaggtg    900
gttgctgagc agctctttgg cccccgggcc caagctgaga cacagccttc tga           954
```

```
<210> SEQ ID NO 42
<211> LENGTH: 317
<212> TYPE: PRT
<213> ORGANISM: Canis lupus

<400> SEQUENCE: 42
```

```
Met Ser Glu Gly Val Gly Thr Phe Arg Val Pro Glu Glu Glu Gln
1               5                   10                  15

Glu Leu Arg Ala Gln Leu Glu Arg Leu Thr Thr Lys Asp His Gly Pro
            20                  25                  30

Val Phe Gly Pro Cys Ser Gln Leu Pro Arg His Thr Leu Gln Lys Ala
        35                  40                  45

Lys Asp Glu Leu Asn Glu Arg Glu Thr Arg Glu Glu Val Val Arg
50                  55                  60

Glu Leu Gln Glu Leu Val Gln Ala Gln Ala Thr Gly Gln Glu Leu
65                  70                  75                  80

Ala Arg Ala Val Ala Glu Arg Val Gln Gly Arg Asp Ser Ala Phe Phe
                85                  90                  95

Leu Arg Phe Ile Arg Ala Arg Lys Phe His Val Gly Arg Ala Tyr Glu
            100                 105                 110

Leu Leu Arg Gly Tyr Val Asn Phe Arg Leu Gln Tyr Pro Glu Leu Phe
        115                 120                 125

Asp Ser Leu Ser Leu Glu Ala Val Arg Cys Thr Val Glu Ala Gly Tyr
130                 135                 140

Pro Gly Val Leu Pro Ser Arg Asp Lys Tyr Gly Arg Val Val Met Leu
145                 150                 155                 160

Phe Asn Ile Glu Asn Trp Asp Ser Glu Glu Ile Thr Phe Asp Glu Ile
                165                 170                 175

Leu Gln Ala Tyr Cys Phe Ile Leu Glu Lys Leu Leu Glu Asn Glu Glu
            180                 185                 190

Thr Gln Ile Asn Gly Phe Cys Ile Ile Glu Asn Phe Lys Gly Phe Thr
        195                 200                 205

Met Gln Gln Ala Ala Gly Leu Arg Ala Ser Asp Leu Arg Lys Met Val
210                 215                 220

Asp Met Leu Gln Asp Ser Phe Pro Ala Arg Phe Lys Ala Ile His Phe
225                 230                 235                 240

Ile His Gln Pro Trp Tyr Phe Thr Thr Thr Tyr Asn Met Val Lys Pro
                245                 250                 255

Leu Leu Lys Asn Lys Leu Leu Gln Arg Val Phe Val His Gly Asp Asp
            260                 265                 270

Leu Ser Gly Phe Phe Gln Glu Ile Asp Glu Asp Ile Leu Pro Ala Asp
        275                 280                 285

Phe Gly Gly Thr Leu Pro Lys Tyr Asp Gly Lys Val Val Ala Glu Gln
    290                 295                 300

Leu Phe Gly Pro Arg Ala Gln Ala Glu Asn Thr Ala Phe
305                 310                 315
```

<210> SEQ ID NO 43
<211> LENGTH: 954
<212> TYPE: DNA
<213> ORGANISM: Rattus norvegicus

<400> SEQUENCE: 43

```
atgtcagagg gggtgggcac attccgaatg gtccctgaag aggagcagga gctccgggca      60
cagctagaac agctcacaac caaggatcat ggtcctgtct ttggcccatg cagccagctg     120
ccccgccaca ctttgcagaa ggctaaggat gagctgaatg aaagggagga aacccgggat     180
gaggcggtga gggagctaca ggagctggtc caggcacagg cagcttctgg ggaagagttg     240
gccgtggcag tggctgagag ggtgcaggca agagacagcg ccttcctcct gcgcttcatc     300
cgtgcccgaa agtttgatgt gggccgggct tatgagctgc tcaaaggcta tgtgaacttc     360
cggctccagt accctgaact cttcgatagc ctatctatgg aggctctccg ctgcactatc     420
gaggccggtt accctggtgt cctttccagt cgggacaagt atggtcgagt ggttatgctc     480
ttcaacattg aaaactggca ctgtgaagaa gtcacctttg atgagatctt acaggcatat     540
tgtttcattc tggagaaact gctggagaac gaggaaaccc aaatcaacgg cttctgtatt     600
gtggagaact tcaagggctt caccatgcag caggccgcgg gactccgccc ctccgatctc     660
aagaagatgg tggacatgct ccaggattca ttcccagcca ggttcaaagc tatccacttc     720
atccaccaac catggtactt caccaccact acaatgtgg tcaagcccct cttgaagaac      780
aagttgctac agagggtctt cgttcatgga gatgacctgg acggcttctt ccaggagatt     840
gatgagaata tcttgcctgc tgactttggg ggtacactgc ccaagtatga cggcaaagtt     900
gtcgctgagc agctcttcgg tccccggggtt gaggttgaga cacagccttt gtga            954
```

<210> SEQ ID NO 44
<211> LENGTH: 317
<212> TYPE: PRT
<213> ORGANISM: Rattus norvegicus

<400> SEQUENCE: 44

Met Ser Glu Gly Val Gly Thr Phe Arg Met Val Pro Glu Glu Gln
1               5                   10                  15

Glu Leu Arg Ala Gln Leu Glu Gln Leu Thr Thr Lys Asp His Gly Pro
            20                  25                  30

Val Phe Gly Pro Cys Ser Gln Leu Pro Arg His Thr Leu Gln Lys Ala
        35                  40                  45

Lys Asp Glu Leu Asn Glu Arg Glu Glu Thr Arg Asp Glu Ala Val Arg
    50                  55                  60

Glu Leu Gln Glu Leu Val Gln Ala Gln Ala Ala Ser Gly Glu Glu Leu
65                  70                  75                  80

Ala Val Ala Val Ala Glu Arg Val Gln Ala Arg Asp Ser Ala Phe Leu
                85                  90                  95

Leu Arg Phe Ile Arg Ala Arg Lys Phe Asp Val Gly Arg Ala Tyr Glu
            100                 105                 110

Leu Leu Lys Gly Tyr Val Asn Phe Arg Leu Gln Tyr Pro Glu Leu Phe
        115                 120                 125

Asp Ser Leu Ser Met Glu Ala Leu Arg Cys Thr Ile Glu Ala Gly Tyr
    130                 135                 140

Pro Gly Val Leu Ser Ser Arg Asp Lys Tyr Gly Arg Val Val Met Leu
145                 150                 155                 160

```
Phe Asn Ile Glu Asn Trp His Cys Glu Glu Val Thr Phe Asp Glu Ile
                165                 170                 175
Leu Gln Ala Tyr Cys Phe Ile Leu Glu Lys Leu Leu Glu Asn Glu Glu
            180                 185                 190
Thr Gln Ile Asn Gly Phe Cys Ile Val Glu Asn Phe Lys Gly Phe Thr
        195                 200                 205
Met Gln Gln Ala Ala Gly Leu Arg Pro Ser Asp Leu Lys Lys Met Val
    210                 215                 220
Asp Met Leu Gln Asp Ser Phe Pro Ala Arg Phe Lys Ala Ile His Phe
225                 230                 235                 240
Ile His Gln Pro Trp Tyr Phe Thr Thr Thr Tyr Asn Val Val Lys Pro
                245                 250                 255
Phe Leu Lys Asn Lys Leu Leu Gln Arg Val Phe Val His Gly Asp Asp
            260                 265                 270
Leu Asp Gly Phe Phe Gln Glu Ile Asp Glu Asn Ile Leu Pro Ala Asp
        275                 280                 285
Phe Gly Gly Thr Leu Pro Lys Tyr Asp Gly Lys Val Val Ala Glu Gln
    290                 295                 300
Leu Phe Gly Pro Arg Val Glu Val Glu Asn Thr Ala Leu
305                 310                 315

<210> SEQ ID NO 45
<211> LENGTH: 954
<212> TYPE: DNA
<213> ORGANISM: Mus musculus

<400> SEQUENCE: 45
atgtcagacg gggtgggcac tttccgcatg gttcctgaag aggagcagga gctccgagca      60
caactggagc agctcacaac caaggatcat ggtcctgtct ttggcccatg cagccagctg     120
ccccgccaca ctttgcagaa ggccaaggat gagctgaatg aaaaggagga gacccgggag     180
gaagcggtga gggagctaca ggagctggta caggcacagg cagcttctgg cgaggaattg     240
gccctggcag tggctgagag ggtgcaggca agagacagcg ccttcctcct gcgcttcatc     300
cgtgcccgca gttcgatgt gggtcgtgct tatgagctgc tcaaaggcta tgtgaacttc     360
cgcctccagt accctgaact cttcgatagt ctctccatgg aggctctccg ctgcactatc     420
gaggccggat accctggtgt cctttccagt cgggacaagt atggtcgagt ggttatgctc     480
ttcaacatcg aaaactggca ctgtgaagaa gtgacctttg atgagatctt acaggcatat     540
tgtttcattt tggagaaact gctggaaaat gaggaaaccc aaatcaacgg cttctgtatt     600
gttgagaact tcaagggctt caccatgcag caggcagcag ggctccgccc ctcggatctc     660
aagaagatgg tggacatgct ccaggattca ttcccagcca ggttcaaagc tatccacttc     720
atccaccagc catggtactt caccaccacc tataatgtgg tcaagccctt cttgaagaac     780
aagctgctac agagggtctt tgttcacgga gatgacctgg atggcttctt ccaggagatt     840
gatgagaaca tcctgcctgc tgactttggg ggtacactgc ccaagtacga cggcaaagtt     900
gttgctgagc agctctttgg tccccgggct gaagttgaga cacagcctt atga           954

<210> SEQ ID NO 46
<211> LENGTH: 317
<212> TYPE: PRT
<213> ORGANISM: Mus musculus

<400> SEQUENCE: 46

Met Ser Asp Gly Val Gly Thr Phe Arg Met Val Pro Glu Glu Glu Gln
```

```
  1               5                  10                 15
Glu Leu Arg Ala Gln Leu Glu Gln Leu Thr Thr Lys Asp His Gly Pro
                 20                 25                 30

Val Phe Gly Pro Cys Ser Gln Leu Pro Arg His Thr Leu Gln Lys Ala
                 35                 40                 45

Lys Asp Glu Leu Asn Glu Lys Glu Glu Thr Arg Glu Glu Ala Val Arg
 50                 55                 60

Glu Leu Gln Glu Leu Val Gln Ala Gln Ala Ser Gly Glu Glu Leu
 65                 70                 75                 80

Ala Leu Ala Val Ala Glu Arg Val Gln Ala Arg Asp Ser Ala Phe Leu
                 85                 90                 95

Leu Arg Phe Ile Arg Ala Arg Lys Phe Asp Val Gly Arg Ala Tyr Glu
                100                105                110

Leu Leu Lys Gly Tyr Val Asn Phe Arg Leu Gln Tyr Pro Glu Leu Phe
                115                120                125

Asp Ser Leu Ser Met Glu Ala Leu Arg Cys Thr Ile Glu Ala Gly Tyr
                130                135                140

Pro Gly Val Leu Ser Ser Arg Asp Lys Tyr Gly Arg Val Val Met Leu
145                 150                155                160

Phe Asn Ile Glu Asn Trp His Cys Glu Glu Val Thr Phe Asp Glu Ile
                165                170                175

Leu Gln Ala Tyr Cys Phe Ile Leu Glu Lys Leu Leu Glu Asn Glu Glu
                180                185                190

Thr Gln Ile Asn Gly Phe Cys Ile Val Glu Asn Phe Lys Gly Phe Thr
                195                200                205

Met Gln Gln Ala Ala Gly Leu Arg Pro Ser Asp Leu Lys Lys Met Val
                210                215                220

Asp Met Leu Gln Asp Ser Phe Pro Ala Arg Phe Lys Ala Ile His Phe
225                 230                235                240

Ile His Gln Pro Trp Tyr Phe Thr Thr Thr Tyr Asn Val Val Lys Pro
                245                250                255

Phe Leu Lys Asn Lys Leu Leu Gln Arg Val Phe Val His Gly Asp Asp
                260                265                270

Leu Asp Gly Phe Phe Gln Glu Ile Asp Glu Asn Ile Leu Pro Ala Asp
                275                280                285

Phe Gly Gly Thr Leu Pro Lys Tyr Asp Gly Lys Val Val Ala Glu Gln
                290                295                300

Leu Phe Gly Pro Arg Ala Glu Val Glu Asn Thr Ala Leu
305                 310                315

<210> SEQ ID NO 47
<211> LENGTH: 951
<212> TYPE: DNA
<213> ORGANISM: Gallus gallus

<400> SEQUENCE: 47
atgtctgctg ttacgggcac cttccgcatt gtctcggaag aggagcaggc gctgcgcacc      60
aaactggagc gcctcaccac caaggaccac ggccctgttt ttgggaggtg ccagcagatc     120 cccccctcaca ccctgcagaa ggcaaaagat gagctgaatg agacggagga gcagagggag     180
gcagcggtca aagcgctgcg ggagctggtg caggagcggg ccggcagcga ggatgtctgc     240
aaggcagtgg cagagaagat gcaggggaag gacgattcct tcttcctccg cttcatccgt     300 gccccgcaagt tgacgtgca cagggcctac gacctgctga aaggctatgt gaactttcgc     360
```

-continued

```
cagcaatacc ctgaactctt tgacaacctg accccgagg ccgtgcgcag caccatcgag    420
gcgggctacc ccggcatcct ggccagcagg gacaaatacg gcgggtagt gatgctcttc     480
aacatcgaga actgggacta cgaggagatc acctttgatg agatccttcg tgcctactgc   540
gttatcttgg agaagctgct ggaaaacgaa gagacccaga tcaatgggtt ctgcatcatt   600
gagaacttca agggcttcac catgcagcag gcatcaggga tcaaaccctc cgagctcaag   660
aagatggtgg acatgctaca ggactccttc ccagcgcggt tcaaagctgt ccacttcatc   720
caccagcect ggtacttcac cactacctac aacgtggtca aaccgttcct gaagagcaag   780
ctgctggaga gggtgtttgt gcacggcgag gagctgagt ccttctacca ggagatcgat    840
gctgacatac tgccagcaga cttcggtggc aacctgccca agtacgacgg caaagcaact   900
gcagagcagc tctttgggcc ccgcattgag gctgaagaca cggcacttta a            951
```

<210> SEQ ID NO 48
<211> LENGTH: 316
<212> TYPE: PRT
<213> ORGANISM: Gallus gallus

<400> SEQUENCE: 48

```
Met Ser Ala Val Thr Gly Thr Phe Arg Ile Val Ser Glu Glu Glu Gln
1               5                   10                  15

Ala Leu Arg Thr Lys Leu Glu Arg Leu Thr Thr Lys Asp His Gly Pro
            20                  25                  30

Val Phe Gly Arg Cys Gln Gln Ile Pro Pro His Thr Leu Gln Lys Ala
        35                  40                  45

Lys Asp Glu Leu Asn Glu Thr Glu Glu Gln Arg Glu Ala Ala Val Lys
    50                  55                  60

Ala Leu Arg Glu Leu Val Gln Glu Arg Ala Gly Ser Glu Asp Val Cys
65                  70                  75                  80

Lys Ala Val Ala Glu Lys Met Gln Gly Lys Asp Asp Ser Phe Phe Leu
                85                  90                  95

Arg Phe Ile Arg Ala Arg Lys Phe Asp Val His Arg Ala Tyr Asp Leu
            100                 105                 110

Leu Lys Gly Tyr Val Asn Phe Arg Gln Gln Tyr Pro Glu Leu Phe Asp
        115                 120                 125

Asn Leu Thr Pro Glu Ala Val Arg Ser Thr Ile Glu Ala Gly Tyr Pro
    130                 135                 140

Gly Ile Leu Ala Ser Arg Asp Lys Tyr Gly Arg Val Val Met Leu Phe
145                 150                 155                 160

Asn Ile Glu Asn Trp Asp Tyr Glu Glu Ile Thr Phe Asp Glu Ile Leu
                165                 170                 175

Arg Ala Tyr Cys Val Ile Leu Glu Lys Leu Leu Glu Asn Glu Glu Thr
            180                 185                 190

Gln Ile Asn Gly Phe Cys Ile Ile Glu Asn Phe Lys Gly Phe Thr Met
        195                 200                 205

Gln Gln Ala Ser Gly Ile Lys Pro Ser Glu Leu Lys Lys Met Val Asp
    210                 215                 220

Met Leu Gln Asp Ser Phe Pro Ala Arg Phe Lys Ala Val His Phe Ile
225                 230                 235                 240

His Gln Pro Trp Tyr Phe Thr Thr Thr Tyr Asn Val Val Lys Pro Phe
                245                 250                 255

Leu Lys Ser Lys Leu Leu Glu Arg Val Phe Val His Gly Glu Glu Leu
            260                 265                 270
```

```
Glu Ser Phe Tyr Gln Glu Ile Asp Ala Asp Ile Leu Pro Ala Asp Phe
            275                 280                 285

Gly Gly Asn Leu Pro Lys Tyr Asp Gly Lys Ala Thr Ala Glu Gln Leu
        290                 295                 300

Phe Gly Pro Arg Ile Glu Ala Glu Asp Thr Ala Leu
305                 310                 315

<210> SEQ ID NO 49
<211> LENGTH: 2659
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
```

| | | | | | |
|---|---|---|---|---|---|
| ctgcctgcag | ggttccatcc | caatggcgcg | tcaattcact | ggccgtcgtt | ttacaacgtc | 60 |
| gtgactggga | aaaccctggc | gttacccaac | ttaatcgcct | tgcagcacat | ccccctttcg | 120 |
| ccagctggcg | taatagcgaa | gaggcccgca | ccgatcgccc | ttcccaacag | ttgcgcagcc | 180 |
| tgaatggcga | atggcgcctg | atgcggtatt | ttctccttac | gcatctgtgc | ggtatttcac | 240 |
| accgcatatg | gtgcactctc | agtacaatct | gctctgatgc | cgcatagtta | agccagcccc | 300 |
| gacacccgcc | aacacccgct | gacgcgccct | gacgggcttg | tctgctcccg | gcatccgctt | 360 |
| acagacaagc | tgtgaccgtc | tccgggagct | gcatgtgtca | gaggttttca | ccgtcatcac | 420 |
| cgaaacgcgc | gagacgaaag | ggcctcgtga | tacgcctatt | tttataggtt | aatgtcatga | 480 |
| taataatggt | ttcttagacg | tcaggtggca | cttttcgggg | aaatgtgcgc | ggaacccta | 540 |
| tttgtttatt | tttctaaata | cattcaaata | tgtatccgct | catgagacaa | taaccctgat | 600 |
| aaatgcttca | ataatattga | aaaggaaga | gtatgagcca | tattcaacgg | gaaacgtctt | 660 |
| gctctaggcc | gcgattaaat | tccaacatgg | atgctgattt | atatgggtat | aaatgggctc | 720 |
| gcgataatgt | cgggcaatca | ggtgcgacaa | tctatcgatt | gtatgggaag | cccgatgcgc | 780 |
| cagagttgtt | tctgaaacat | ggcaaaggta | gcgttgccaa | tgatgttaca | gatgagatgg | 840 |
| tcagactaaa | ctggctgacg | gaatttatgc | ctcttccgac | catcaagcat | ttatccgta | 900 |
| ctcctgatga | tgcatggtta | ctcaccactg | cgatcctgg | aaaacagca | ttccaggtat | 960 |
| tagaagaata | tcctgattca | ggtgaaaata | ttgttgatgc | gctggcagtg | ttcctgcgcc | 1020 |
| ggttgcattc | gattcctgtt | tgtaattgtc | cttttaacag | cgatcgcgta | tttcgtctcg | 1080 |
| ctcaggcgca | atcacgaatg | aataacggtt | tggttgatgc | gagtgatttt | gatgacgagc | 1140 |
| gtaatggctg | gcctgttgaa | caagtctgga | aagaaatgca | taaacttttg | ccattctcac | 1200 |
| cggattcagt | cgtcactcat | ggtgatttct | cacttgataa | ccttattttt | gacgagggga | 1260 |
| aattaatagg | ttgtattgat | gttggacgag | tcggaatcgc | agaccgatac | caggatcttg | 1320 |
| ccatcctatg | gaactgcctc | ggtgagtttt | ctccttcatt | acagaaacgg | ctttttcaaa | 1380 |
| aatatggtat | tgataatcct | gatatgaata | aattgcagtt | tcatttgatg | ctcgatgagt | 1440 |
| ttttctaact | gtcagaccaa | gtttactcat | atatacttta | gattgattta | aaacttcatt | 1500 |
| tttaatttaa | aaggatctag | gtgaagatcc | ttttttgataa | tctcatgacc | aaaatccctt | 1560 |
| aacgtgagtt | ttcgttccac | tgagcgtcag | accccgtaga | aaagatcaaa | ggatcttctt | 1620 |
| gagatccttt | ttttctgcgc | gtaatctgct | gcttgcaaac | aaaaaaacca | ccgctaccag | 1680 |
| cggtggtttg | tttgccggat | caagagctac | caactctttt | tccgaaggta | actggcttca | 1740 |
| gcagagcgca | gataccaaat | actgttcttc | tagtgtagcc | gtagttaggc | caccacttca | 1800 |

```
agaactctgt agcaccgcct acatacctcg ctctgctaat cctgttacca gtggctgctg    1860
ccagtggcga taagtcgtgt cttaccgggt tggactcaag acgatagtta ccggataagg    1920
cgcagcggtc gggctgaacg gggggttcgt gcacacagcc cagcttggag cgaacgacct    1980
acaccgaact gagataccta cagcgtgagc tatgagaaag cgccacgctt cccgaaggga    2040
gaaaggcgga caggtatccg gtaagcggca gggtcggaac aggagagcgc acgagggagc    2100
ttccaggggg aaacgcctgg tatctttata gtcctgtcgg gtttcgccac ctctgacttg    2160
agcgtcgatt tttgtgatgc tcgtcagggg ggcggagcct atggaaaaac gccagcaacg    2220
cggccttttt acggttcctg gccttttgct ggccttttgc tcacatgttc tttcctgcgt    2280
tatcccctga ttctgtggat aaccgtatta ccgcctttga gtgagctgat accgctcgcc    2340
gcagccgaac gaccgagcgc agcgagtcag tgagcgagga gcggaagag cgcccaatac    2400 gcaaaccgcc tctccccgcg cgttggccga ttcattaatg cagctggcac gacaggtttc    2460
ccgactggaa agcgggcagt gagcgcaacg caattaatgt gagttagctc actcattagg    2520
caccccaggc tttacacttt atgcttccgg ctcgtatgtt gtgtggaatt gtgagcggat    2580
aacaatttca cacaggaaac agctatgacc atgattacgc caagctcggc gcgccattgg    2640
gatggaaccc tgcaggcag                                                2659
```

<210> SEQ ID NO 50
<211> LENGTH: 4989
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggggta ccacgcgttt    120
gtcctctccc tgcttggcct taaccagcca catttctcaa ctgaccccac tcactgcaga    180
ggtgaaaact accatgccag gtcctgctgg ctgggggagg ggtgggcaat aggcctggat    240
ttgccagagc tgccactgta gatgtagtca tatttacgat ttcccttcac ctcttattac    300
cctggtggtg gtggtggggg ggggggggtg ctctctcagc aacccacccc gggatcttg    360 aggagaaaga gggcagagaa aagagggaat gggactggcc cagatcccag ccccacagcc    420
gggcttccac atggccgagc aggaactcca gagcaggagc acacaaagga gggctttgat    480
gcgcctccag ccaggcccag gcctctcccc tctccccttt ctctctgggt cttcctttgc    540
cccactgagg gcctcctgtg agcccgattt aacggaaact gtgggcggtg agaagttcct    600
tatgacacac taatcccaac ctgctgaccg gaccacgcct ccagcggagg gaacctctag    660
agctccagga cattcaggta ccaggtagcc ccaaggagga gctgccgaat cgatggatcg    720
ggaactgaaa aaccagaaag ttaactggta agtttagtct ttttgtcttt tatttcaggt    780
cccggatccg gtggtggtgc aaatcaaaga actgctcctc agtggatgtt gcctttactt    840
ctaggcctgt acggaagtgt tacttctgct ctaaaagctg cggaattgta cccgccccgg    900
gatccatcga ttgaattcgc caccatgtca gaagggggtgg gcacgttccg catggtacct    960
gaagaggaac aggagctccg tgcccaactg gagcagctca caaccaagga ccatggacct   1020
gtctttggcc cgtgcagcca gctgccccgc cacaccttgc agaaggccaa ggatgagctg   1080
aacgagagag aggagaccccg ggaggaggca gtgcgagagc tgcaggagat ggtgcaggcg   1140
```

```
caggcggcct cggggagga gctggcggtg gccgtggcgg agagggtgca agagaaggac    1200
agcggcttct tcctgcgctt catccgcgca cggaagttca acgtgggccg tgcctatgag    1260
ctgctcagag gctatgtgaa tttccggctg cagtaccctg agctctttga cagcctgtcc    1320
ccagaggctg tccgctgcac cattgaagct ggctaccctg tgtcctctc tagtcggac     1380 aagtatggcc gagtggtcat gctcttcaac attgagaact ggcaaagtca agaaatcacc    1440
tttgatgaga tcttgcaggc atattgcttc atcctggaga gctgctgga gaatgaggaa     1500 actcaaatca atggcttctg catcattgag aacttcaagg ctttaccat gcagcaggct     1560 gctagtctcc ggacttcaga tctcaggaag atggtggaca tgctccagga ttccttccca    1620
gcccggttca aagccatcca cttcatccac cagccatggt acttcaccac gacctacaat    1680
gtggtcaagc ccttcttgaa gagcaagctg cttgagaggg tctttgtcca cggggatgac    1740 cttttctggtt tctaccagga gatcgatgag aacatcctgc cctctgactt cggggggcacg   1800 ctgcccaagt atgatggcaa ggccgttgct gagcagctct ttggcccccca ggcccaagct    1860 gagaacacag ccttctgagg atcgtaccgg tcgacctgca gaagcttgcc tcgagcagcg    1920
ctgctcgaga gatctggatc ataatcagcc ataccacatt tgtagaggtt ttacttgctt    1980
taaaaaacct cccacacctc cccctgaacc tgaaacataa aatgaatgca attgttgttg    2040
ttaacttgtt tattgcagct tataatggtt acaaataaag caatagcatc acaaatttca    2100
caaataaagc attttttttca ctgcattcta gttgtggttt gtccaaactc atcaatgtat    2160
cttatcatgt ctggtaacca cgtgcggacc gagcggccgc aggaacccct agtgatggag    2220
ttggccactc cctctctgcg cgctcgctcg ctcactgagg ccgggcgacc aaaggtcgcc    2280
cgacgcccgg gctttgcccg gcggcctca gtgagcgagc gagcgcgcag ctgcctgcag    2340
ggttccatcc caatggcgcg tcaattcact ggccgtcgtt ttacaacgtc gtgactggga    2400
aaaccctggc gttacccaac ttaatcgcct tgcagcacat ccccctttcg ccagctggcg    2460
taatagcgaa gaggcccgca ccgatcgccc ttcccaacag ttgcgcagcc tgaatggcga    2520
atggcgcctg atgcggtatt ttctccttac gcatctgtgc ggtatttcac accgcatatg    2580
gtgcactctc agtacaatct gctctgatgc cgcatagtta agccagcccc gacacccgcc    2640
aacacccgct gacgcgccct gacgggcttg tctgctcccg gcatccgctt acagacaagc    2700
tgtgaccgtc tccgggagct gcatgtgtca gaggttttca ccgtcatcac cgaaacgcgc    2760
gagacgaaag gcctcgtga tacgcctatt tttataggtt aatgtcatga taataatggt    2820
ttcttagacg tcaggtggca cttttcgggg aaatgtgcgc ggaacccccta tttgtttatt    2880 tttctaaata cattcaaata tgtatccgct catgagacaa taaccctgat aaatgcttca    2940
ataatattga aaaggaaga gtatgagcca tattcaacgg gaaacgtctt gctctaggcc    3000
gcgattaaat ccaacatgg atgctgattt atatgggtat aaatgggctc gcgataatgt    3060
cgggcaatca ggtgcgacaa tctatcgatt gtatgggaag cccgatgcgc cagagttgtt    3120
tctgaaacat ggcaaaggta gcgttgccaa tgatgttaca gatgagatgg tcagactaaa    3180
ctggctgacg gaatttatgc ctcttccgac catcaagcat tttatccgta ctcctgatga    3240
tgcatggtta ctcaccactg cgatcccctgg gaaaacagca ttccaggtat tagaagaata    3300
tcctgattca ggtgaaaata ttgttgatgc gctggcagtg ttcctgcgcc ggttgcattc    3360
gattcctgtt tgtaattgtc cttttaacag cgatcgcgta tttcgtctcg ctcaggcgca    3420
atcacgaatg aataacggtt tggttgatgc gagtgatttt gatgacgagc gtaatggctg    3480
```

-continued

| | |
|---|---|
| gcctgttgaa caagtctgga agaaatgca taaacttttg ccattctcac cggattcagt | 3540 |
| cgtcactcat ggtgatttct cacttgataa ccttattttt gacgagggga aattaatagg | 3600 |
| ttgtattgat gttggacgag tcggaatcgc agaccgatac caggatcttg ccatcctatg | 3660 |
| gaactgcctc ggtgagtttt ctccttcatt acagaaacgg cttttcaaa aatatggtat | 3720 |
| tgataatcct gatatgaata aattgcagtt tcatttgatg ctcgatgagt ttttctaact | 3780 |
| gtcagaccaa gtttactcat atactttta gattgattta aaacttcatt tttaatttaa | 3840 |
| aaggatctag gtgaagatcc ttttttgataa tctcatgacc aaaatccctt aacgtgagtt | 3900 |
| ttcgttccac tgagcgtcag accccgtaga aagatcaaa ggatcttctt gagatccttt | 3960 |
| ttttctgcgc gtaatctgct gcttgcaaac aaaaaaacca ccgctaccag cggtggtttg | 4020 |
| tttgccggat caagagctac caactctttt tccgaaggta actggcttca gcagagcgca | 4080 |
| gataccaaat actgttcttc tagtgtagcc gtagttaggc caccacttca agaactctgt | 4140 |
| agcaccgcct acatacctcg ctctgctaat cctgttacca gtggctgctg ccagtggcga | 4200 |
| taagtcgtgt cttaccgggt tggactcaag acgatagtta ccggataagg cgcagcggtc | 4260 |
| gggctgaacg gggggttcgt gcacacagcc cagcttggag cgaacgacct acaccgaact | 4320 |
| gagataccta cagcgtgagc tatgagaaag cgccacgctt cccgaaggga aaaggcgga | 4380 |
| caggtatccg gtaagcggca gggtcggaac aggagagcgc acgagggagc ttccaggggg | 4440 |
| aaacgcctgg tatctttata gtcctgtcgg gtttcgccac ctctgacttg agcgtcgatt | 4500 |
| tttgtgatgc tcgtcagggg ggcggagcct atggaaaaac gccagcaacg cggccttttt | 4560 |
| acggttcctg gccttttgct ggccttttgc tcacatgttc tttcctgcgt tatcccctga | 4620 |
| ttctgtggat aaccgtatta ccgcctttga gtgagctgat accgctcgcc gcagccgaac | 4680 |
| gaccgagcgc agcgagtcag tgagcgagga agcggaagag cgcccaatac gcaaaccgcc | 4740 |
| tctccccgcg cgttggccga ttcattaatg cagctggcac gacaggtttc ccgactggaa | 4800 |
| agcgggcagt gagcgcaacg caattaatgt gagttagctc actcattagg caccccaggc | 4860 |
| tttacacttt atgcttccgg ctcgtatgtt gtgtggaatt gtgagcggat aacaatttca | 4920 |
| cacaggaaac agctatgacc atgattacgc caagctcggc gcgccattgg gatggaaccc | 4980 |
| tgcaggcag | 4989 |

<210> SEQ ID NO 51
<211> LENGTH: 2327
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 51

| | |
|---|---|
| cgcgctcgct cgctcactga ggccgcccgg gcaaagcccg ggcgtcgggc gacctttggt | 60 |
| cgcccggcct cagtgagcga gcgagcgcgc agagagggag tggggtacca cgcgtttgtc | 120 |
| ctctcccctgc ttggccttaa ccagccacat ttctcaactg accccactca ctgcagaggt | 180 |
| gaaaactacc atgccaggtc ctgctggctg ggggaggggt gggcaatagg cctggatttg | 240 |
| ccagagctgc cactgtagat gtagtcatat ttacgatttc ccttcacctc ttattaccct | 300 |
| ggtggtggtg gtggggggg ggggtgctc tctcagcaac cccaccccgg gatcttgagg | 360 |
| agaaagaggg cagagaaaag agggaatggg actggcccag atcccagccc cacagccggg | 420 |
| cttccacatg gccgagcagg aactccagag caggagcaca caaggagggg ctttgatgcg | 480 |

```
cctccagcca ggcccaggcc tctcccctct ccccttctc tctgggtctt cctttgcccc      540
actgagggcc tcctgtgagc ccgatttaac ggaaactgtg ggcggtgaga agttccttat      600
gacacactaa tcccaacctg ctgaccggac cacgcctcca gcggagggaa cctctagagc      660
tccaggacat tcaggtacca ggtagcccca aggaggagct gccgaatcga tggatcggga      720
actgaaaaac cagaaagtta actggtaagt ttagtctttt tgtcttttat ttcaggtccc      780
ggatccggtg gtggtgcaaa tcaaagaact gctcctcagt ggatgttgcc tttacttcta      840
ggcctgtacg gaagtgttac ttctgctcta aaagctgcgg aattgtaccc gccccgggat      900
ccatcgattg aattcgccac catgtcagaa ggggtgggca cgttccgcat ggtacctgaa      960
gaggaacagg agctccgtgc ccaactggag cagctcacaa ccaaggacca tggacctgtc     1020
tttggcccgt gcagccagct gccccgccac accttgcaga aggccaagga tgagctgaac     1080
gagagagagg agacccggga ggaggcagtg cgagagctgc aggagatggt gcaggcgcag     1140
gcggcctcgg gggaggagct ggcggtggcc gtggcggaga gggtgcaaga aaggacagc      1200 ggcttcttcc tgcgcttcat ccgcgcacgg aagttcaacg tgggccgtgc ctatgagctg     1260
ctcagaggct atgtgaattt ccggctgcag taccctgagc tctttgacag cctgtcccca     1320
gaggctgtcc gctgcaccat tgaagctggc taccctggtg tcctctctag tcgggacaag     1380
tatggccgag tggtcatgct cttcaacatt gagaactggc aaagtcaaga aatcacctt      1440 gatgagatct tgcaggcata ttgcttcatc ctggagaagc tgctggagaa tgaggaaact     1500
caaatcaatg gcttctgcat cattgagaac ttcaagggct ttaccatgca gcaggctgct     1560
agtctccgga cttcagatct caggaagatg gtggacatgc tccaggattc cttcccagcc     1620
cggttcaaag ccatccactt catccaccag ccatggtact tcaccacgac ctacaatgtg     1680
gtcaagccct tcttgaagag caagctgctt gagagggtct ttgtccacgg ggatgacctt     1740
tctggtttct accaggagat cgatgagaac atcctgccct ctgacttcgg gggcacgctg     1800
cccaagtatg atggcaaggc cgttgctgag cagctctttg ccccaggc ccaagctgag       1860 aacacagcct tctgaggatc gtaccggtcg acctgcagaa gcttgcctcg agcagcgctg     1920
ctcgagagat ctggatcata atcagccata ccacatttgt agaggtttta cttgctttaa     1980
aaaacctccc acacctcccc ctgaacctga acataaaat gaatgcaatt gttgttgtta     2040
acttgtttat tgcagcttat aatggttaca aataaagcaa tagcatcaca aatttcacaa     2100
ataaagcatt ttttcactg cattctagtt gtggtttgtc caaactcatc aatgtatctt    2160
atcatgtctg gtaaccacgt gcggaccgag cggccgcagg aaccctagt gatggagttg     2220 gccactccct ctctgcgcgc tcgctcgctc actgaggccg ggcgaccaaa ggtcgcccga     2280
cgcccgggct tgcccgggc ggcctcagtg agcgagcgag cgcgcag                   2327
```

<210> SEQ ID NO 52
<211> LENGTH: 4711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

```
ctgcgcgctc gctcgctcac tgaggccgcc gggcgtcgg gcgacctttg gtcgcccggc       60
ctcagtgagc gagcgagcgc gcagagaggg agtggccaac tccatcacta ggggttcctg     120
cggccgcacg cagcttttgt cctctcccctg cttggcctta accagccaca tttctcaact    180
```

```
gaccccactc actgcagagg tgaaaactac catgccaggt cctgctggct gggggagggg    240
tgggcaatag gcctggattt gccagagctg ccactgtaga tgtagtcata tttacgattt    300
cccttcacct cttattaccc tggtggtggt ggtgggggggg gggggtgct ctctcagcaa    360 ccccaccccg ggatcttgag gagaaagagg gcagagaaaa gagggaatgg gactggccca    420
gatcccagcc ccacagccgg gcttccacat ggccgagcag gaactccaga gcaggagcac    480
acaaaggagg gctttgatgc gcctccagcc aggcccaggc ctctcccctc tccccttct    540 ctctgggtct tccttttgccc cactgagggc ctcctgtgag cccgatttaa cggaaactgt    600
gggcggtgag aagttcctta tgacacacta atcccaacct gctgaccgga ccacgcctcc    660
agcggaggga acctctagag ctccaggaca ttcaggtacc aggtagcccc aaggaggagc    720
tgccgacctg gcaggtaagt caatacctgg ggcttgcctg gccagggag cccaggactg    780 gggtgaggac tcagggagc agggagacca cgtcccaaga tgcctgtaaa actgaaacca    840
cctggccatt ctccaggttg agccagacca atttgatggc agatttagca aataaaaata    900
caggacaccc agttaaatgt gaatttcaga tgaacagcaa atacttttttt agtattaaaa    960 aagttcacat ttaggctcac gcctgtaatc ccagcacttt gggaggccga ggcaggcaga   1020
tcacctgagg tcaggagttc gagaccagcc tggccaacat ggtgaaaccc catctccact   1080
aaaaatacca aaaattagcc aggcgtgctg gtgggcacct gtagttccag ctactcagga   1140
ggctaaggca ggagaattgc ttgaacctgg gaggcagagg ttgcagtgag ctgagatcgc   1200
accattgcac tctagcctgg gcgacaagaa caaaactcca tctcaaaaaa aaaaaaaaaa   1260
aaaaagttca catttaactg ggcattctgt atttaattgg taatctgaga tggcagggaa   1320
cagcatcagc atggtgtgag ggataggcat ttttcattg tgtacagctt gtaaatcagt   1380 attttttaaaa ctcaaagtta atggcttggg catatttaga aaagagttgc cgcacggact   1440
tgaaccctgt attcctaaaa tctaggatct tgttctgatg gtctgcacaa ctggctgggg   1500
gtgtccagcc actgtccctc ttgcctgggc tccccagggc agttctgtca gcctctccat   1560
ttccattcct gttccagcaa aacccaactg atagcacagc agcatttcag cctgtctacc   1620
tctgtgccca catacctgga tgtctaccag ccagaaaggt ggcttagatt tggttcctgt   1680
gggtggatta tggcccccag aacttccctg tgcttgctgg gggtgtggag tggaaagagc   1740
aggaaatggg ggaccctccg atactctatg ggggtcctcc aagtctcttt gtgcaagtta   1800
gggtaataat caatatggag ctaagaaaga gaaggggaac tatgctttag aacaggacac   1860
tgtgccagga gcattgcaga aattatatgg ttttcacgac agttcttttt ggtaggtact   1920
gttattatcc tcagtttgca gatgaggaaa ctgagaccca gaaaggttaa ataacttgct   1980
agggtcacac aagtcataac tgacaaagcc tgattcaaac ccaggtctcc ctaaccttta   2040
aggtttctat gacgccagct ctcctaggga gtttgtcttc agatgtcttg gctctaggtg   2100
tcaaaaaaag acttggtgtc aggcaggcat aggttcaagt cccaactctg tcacttacca   2160
actgtgacta ggtgattgaa ctgaccatgg aacctggtca catgcaggag caggatggtg   2220
aagggttctt gaaggcactt aggcaggaca tttaggcagg agagaaaacc tggaaacaga   2280
agagctgtct ccaaaaatac ccactgggga agcaggttgt catgtgggcc atgaatggga   2340
cctgttctgg taaccaagca ttgcttatgt gtccattaca tttcataaca cttccatcct   2400
actttacagg gaacaaccaa gactggggtt aaatctcaca gcctgcaagt ggaagagaag   2460
aacttgaacc caggtccaac ttttgcgcca cagcaggctg cctcttggtc ctgacaggaa   2520
gtcacaactt gggtctgagt actgatccct ggctattttt tggctgtgtt accttggaca   2580
```

```
agtcacttat tcctcctccc gtttcctcct atgtaaaatg gaaataataa tgttgaccct    2640
gggtctgaga gagtggattt gaaagtactt agtgcatcac aaagcacaga acacacttcc    2700
agtctcgtga ttatgtactt atgtaactgg tcatcaccca tcttgagaat gaatgcattg    2760
gggaaagggc catccactag gctgcgaagt ttctgaggga ctccttcggg ctggagaagg    2820
atggccacag gagggaggag agattgcctt atcctgcagt gatcatgtca ttgagaacag    2880
agccagattc ttttttcct ggcagggcca acttgtttta acatctaagg actgagctat    2940
ttgtgtctgt gcccttttgtc caagcagtgt ttcccaaagt gtagcccaag aaccatctcc    3000
ctcagagcca ccaggaagtg ctttaaattg caggttccta ggccacagcc tgcacctgca    3060
gagtcagaat catggaggtt gggacccagg cacctgcgtt tctaacaaat gcctcgggtg    3120
attctgatgc aattgaaagt ttgagatcca cagttctgag acaataacag aatggttttt    3180
ctaacccctg cagccctgac ttcctatcct agggaagggg ccggctggag aggccaggac    3240
agagaaagca gatcccttct ttttccaagg actctgtgtc ttccataggc aacgaattcg    3300
ccaccatgtc agaaggggtg ggcacgttcc gcatggtacc tgaagaggaa caggagctcc    3360
gtgcccaact ggagcagctc acaaccaagg accatggacc tgtctttggc ccgtgcagcc    3420
agctgccccg ccacaccttg cagaaggcca aggatgagct gaacgagaga gaggagaccc    3480
gggaggaggc agtgcgagag ctgcaggaga tggtgcaggc gcaggcggcc tcggggggagg    3540 agctggcggt ggccgtggcg gagagggtgc aagagaagga cagcggcttc ttcctgcgct    3600
tcatccgcgc acggaagttc aacgtgggcc gtgcctatga gctgtcaga ggctatgtga    3660 atttccggct gcagtaccct gagctctttg acagcctgtc cccagaggct gtccgctgca    3720
ccattgaagc tggctaccct ggtgtcctct ctagtcggga caagtatggc cgagtggtca    3780
tgctcttcaa cattgagaac tggcaaagtc aagaaatcac ctttgatgag atcttgcagg    3840
catattgctt catcctggag aagctgctgg agaatgagga aactcaaatc aatggcttct    3900
gcatcattga aacttcaag ggcttttacca tgcagcaggc tgctagtctc cggacttcag    3960
atctcaggaa gatggtggac atgctccagg attccttccc agcccggttc aaagccatcc    4020
acttcatcca ccagccatgg tacttcacca cgacctacaa tgtggtcaag cccttcttga    4080
agagcaagct gcttgagagg gtctttgtcc acgggatga cctttctggt ttctaccagg    4140
agatcgatga gaacatcctg ccctctgact tcggggcac gctgcccaag tatgatggca    4200
aggccgttgc tgagcagctc tttggccccc aggcccaagc tgagaacaca gccttctgag    4260
gatcgtaccg gtcgacctgc agaagcttgc ctcgagcagc gctgctcgag agatctggat    4320
cataatcagc cataccacat ttgtagaggt tttacttgct ttaaaaaacc tcccacacct    4380
ccccctgaac ctgaaacata aaatgaatgc aattgttgtt gttaacttgt ttattgcagc    4440
ttataatggt tacaaataaa gcaatagcat cacaaatttc acaaataaag cattttttttc    4500 actgcattct agttgtggtt tgtccaaact catcaatgta tcttatcatg tctggtaacc    4560
acgtgcggac cgagcggccg caggaacccc tagtgatgga gttggccact ccctctctgc    4620
gcgctcgctc gctcactgag gccgggcgac caaaggtcgc ccgacgcccg ggctttgccc    4680
gggcggcctc agtgagcgag cgagcgcgca g                                    4711
```

<210> SEQ ID NO 53
<211> LENGTH: 4645
<212> TYPE: DNA
<213> ORGANISM: Artificial Sequence
<220> FEATURE:

<223> OTHER INFORMATION: Description of Artificial Sequence: Synthetic
polynucleotide

<400> SEQUENCE: 53

```
ctgcgcgctc gctcgctcac tgaggccgcc cgggcgtcgg gcgacctttg gtcgcccggc        60
ctcagtgagc gagcgagcgc gcagagaggg agtggccaac tccatcacta ggggttcctg       120
cggccgcacg cgttacgtaa tatttattga agtttaatat tgtgtttgtg atacagaagt       180
atttgcttta attctaaata aaatttttat gcttttattg ctggtttaag aagatttgga       240
ttatccttgt actttgagga gaagtttctt atttgaaata ttttggaaac aggtcttttA       300
atgtggaaag atagatatta atctcctctt ctattactct ccaagatcca acaaaagtga       360
ttataccccc caaaatatga tggtagtatc ttatactacc atcattttat aggcataggg       420
ctcttagctg caaataatgg aactaactct aataaagcag aacgcaaata ttgtaaatat       480
tagagagcta acaatctctg ggatggctaa aggatggagc ttggaggcta cccagccagt       540
aacaatattc cgggctccac tgttgaatgg agacactaca actgccttgg atgggcagag       600
atattatgga tgctaagccc caggtgctac cattaggact tctaccactg tccctaacgg       660
gtggagccca tcacatgcct atgccctcac tgtaaggaaa tgaagctact gttgtatatc       720
ttgggaagca cttggattaa ttgttataca gttttgttga agaagacccc tagggtaagt       780
agccataact gcacactaaa tttaaaattg ttaatgagtt tctcaaaaaa atgttaagg       840
ttgttagctg gtatagtata tatcttgcct gttttccaag gacttctttg ggcagtacct       900
tgtctgtgct ggcaagcaac tgagacttaa tgaaagagta ttggagatat gaatgaattg       960
atgctgtata ctctcagagt gccaaacata taccaatgga caagaaggtg aggcagagag      1020
cagacaggca ttagtgacaa gcaaagatat gcagaatttc attctcagca aatcaaaagt      1080
cctcaacctg gttggaagaa tattggcact gaatggtatc aataaggttg ctagagaggg      1140
ttagaggtgc acaatgtgct tccataacat tttatacttc tccaatctta gcactaatca      1200
aacatggttg aatactttgt ttactataac tcttacagag ttataagatc tgtgaagaca      1260
gggacaggga caatacccat ctctgtctgg ttcataggtg gtatgtaata gatattttta      1320
aaaataagtg agttaatgaa tgagggtgag aatgaaggca cagaggtatt agggggaggt      1380
gggccccaga gaatggtgcc aaggtccagt gggtgactg ggatcagctc aggcctgacg      1440
ctggccactc ccacctagct cctttctttc taatctgttc tcattctcct tgggaaggat      1500
tgaggtctct ggaaaacagc caaacaactg ttatgggaac agcaagccca aataaagcca      1560
agcatcaggg ggatctgaga gctgaaagca acttctgttc cccctccctc agctgaaggg      1620
gtggggaagg gctcccaaag ccataactcc ttttaaggga tttagaaggc ataaaaaggc      1680
ccctggctga gaacttcctt cttcattctg cagttggtga attcgccacc atgtcagaag      1740
gggtgggcac gttccgcatg gtacctgaag aggaacagga gctccgtgcc caactggagc      1800
agctcacaac caaggaccat ggacctgtct ttggcccgtg cagccagctg ccccgccaca      1860
ccttgcagaa ggccaaggat gagctgaacg agagagagga gacccgggag gaggcagtgc      1920
gagagctgca ggagatggtg caggcgcagg cggcctcggg ggaggagctg gcggtggccg      1980
tggcggagag ggtgcaagag aaggacacg gcttcttcct gcgcttcatc cgcgcacgga      2040
agttcaacgt gggccgtgcc tatgagctgc tcagaggcta tgtgaatttc ggctgcagt      2100
accctgagct ctttgacagc ctgtcccag aggctgtccg ctgcaccatt gaagctggct      2160
accctggtgt cctctctagt cgggacaagt atggccgagt ggtcatgctc ttcaacattg      2220
```

```
agaactggca aagtcaagaa atcacctttg atgagatctt gcaggcatat tgcttcatcc    2280
tggagaagct gctggagaat gaggaaactc aaatcaatgg cttctgcatc attgagaact    2340
tcaagggctt taccatgcag caggctgcta gtctccggac ttcagatctc aggaagatgg    2400
tggacatgct ccaggattcc ttcccagccc ggttcaaagc catccacttc atccaccagc    2460
catggtactt caccacgacc tacaatgtgg tcaagccctt cttgaagagc aagctgcttg    2520
agagggtctt tgtccacggg gatgaccttt ctggtttcta ccaggagatc gatgagaaca    2580
tcctgccctc tgacttcggg ggcacgctgc ccaagtatga tggcaaggcc gttgctgagc    2640
agctctttgg ccccaggcc caagctgaga cacagcctt ctgaggatct accggtcgac    2700
ctgcagaagc ttgcctcgag cagcgctgct cgagagatct ggatcataat cagccatacc    2760
acatttgtag aggttttact tgctttaaaa aacctcccac acctcccct gaacctgaaa    2820 cataaaatga atgcaattgt tgttgttaac ttgtttattg cagcttataa tggttacaaa    2880
taaagcaata gcatcacaaa tttcacaaat aaagcatttt tttcactgca ttctagttgt    2940
ggtttgtcca aactcatcaa tgtatcttat catgtctggt aaccattctc caggttgagc    3000
cagaccaatt tgatggtaga tttagcaaat aaaaatacag gacacccagt taaatgtgaa    3060
tttccgatga acagcaaata ctttttagt attaaaaaag ttcacattta ggctcacgcc    3120
tgtaatccca gcactttggg aggccgaggc aggcagatca cctgaggtca ggagttcgag    3180
accagcctgg ccaacatggt gaaacccat ctccactaaa ataccaaaa attagccagg    3240 cgtgctggtg ggcacctgta gttccagcta ctcaggaggc taaggcagga gaattgcttg    3300
aacctgggag gcagaggttg cagtgagctg agatcgcacc attgcactct agcctgggcg    3360
acaagaacaa aactccatct caaaaaaaaa aaaaaaaaa aagttcacat ttaactgggc    3420
attctgtatt taattggtaa tctgagatgg cagggaacag catcagcatg gtgtgaggga    3480
taggcatttt ttcattgtgt acagcttgta aatcagtatt tttaaaactc aaagttaatg    3540
gcttgggcat atttagaaaa gagttgccgc acggacttga accctgtatt cctaaaatct    3600
aggatcttgt tctgatggtc tgcacaactg gctgggggtg tccagccact gtccctcttg    3660
cctgggctcc ccagggcagt tctgtcagcc tctccatttc cattcctgtt ccagcaaaac    3720
ccaactgata gcacagcagc atttcagcct gtctacctct gtgcccacat acctggatgt    3780
ctaccagcca gaaaggtggc ttagatttgg ttcctgtggg tggattatgg cccccagaac    3840
ttccctgtgc ttgctggggg tgtggagtgg aaagagcagg aaatggggga ccctccgata    3900
ctctatgggg gtcctccaag tctctttgtg caagttaggg taataatcaa tatgagcta    3960 agaaagagaa ggggaactat gctttagaac aggacactgt gccaggagca ttgcagaaat    4020
tatatggttt tcacgacagt tctttttggt aggtactgtt attatcctca gtttgcagat    4080
gaggaaactg agacccagaa aggttaaata acttgctagg gtcacacaag tcataactga    4140
caaagcctga ttcaaaccca ggtctcccta acctttaagg tttctatgac gccagctctc    4200
ctagggagtt tgtcttcaga tgtcttggct ctaggtgtca aaaaaagact tggtgtcagg    4260
caggcatagg ttcaagtccc aactctgtca cttaccaact gtgactaggt gattgaactg    4320
accatggaac ctggtcacat gcaggagcag gatggtgaag ggttcttgaa ggcacttagg    4380
caggacattt aggcaggaga gaaaacctgg aaacagaaga gctgtctcca aaaatacccca    4440 ctggggaagc aggttgtcat gtgggccatg aatgggacct gttctggggt aaccacgtgc    4500
ggaccgagcg gccgcaggaa cccctagtga tggagttggc cactccctct ctgcgcgctc    4560
gctcgctcac tgaggccggg cgaccaaagg tcgcccgacg cccgggcttt gcccgggcgg    4620
```
cctcagtgag cgagcgagcg cgcag                                          4645

<210> SEQ ID NO 54
<211> LENGTH: 4702
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54

| | | | | | |
|---|---|---|---|---|---|
| ctgcgcgctc | gctcgctcac | tgaggccgcc | cgggcgtcgg | gcgacctttg | gtcgcccggc | 60 |
| ctcagtgagc | gagcgagcgc | gcagagaggg | agtggccaac | tccatcacta | ggggttcctg | 120 |
| cggccgcacg | cgtactagtt | attaatagta | atcaattacg | gggtcattag | ttcatagccc | 180 |
| atatatggag | ttccgcgtta | cataacttac | ggtaaatggc | ccgcctggct | gaccgcccaa | 240 |
| cgacccccgc | ccattgacgt | caataatgac | gtatgttccc | atagtaacgc | caatagggac | 300 |
| tttccattga | cgtcaatggg | tggagtattt | acggtaaact | gcccacttgg | cagtacatca | 360 |
| agtgtatcat | atgccaagta | cgccccctat | tgacgtcaat | gacggtaaat | ggcccgcctg | 420 |
| gcattatgcc | cagtacatga | ccttatggga | ctttcctact | tggcagtaca | tctacgtatt | 480 |
| agtcatcgct | attaccatgg | tcgaggtgag | ccccacgttc | tgcttcactc | tccccatctc | 540 |
| ccccccctcc | ccacccccaa | ttttgtattt | atttattttt | taattatttt | gtgcagcgat | 600 |
| ggggggcgggg | ggggggggggg | ggcgcgcgcc | aggcggggcg | gggcggggcg | aggggcgggg | 660 |
| cggggcgagg | cggagaggtg | cggcggcagc | caatcagagc | ggcgcgctcc | gaaagtttcc | 720 |
| ttttatggcg | aggcggcggc | ggcggcggcc | ctataaaaag | cgaagcgcgc | ggcgggcggg | 780 |
| gagtcgctgc | gacgctgcct | tcgccccgtg | ccccgctccg | ccgccgcctc | gcgccgcccg | 840 |
| ccccggctct | gactgaccgc | gttactccca | caggtgagcg | ggcgggacgg | cccttctcct | 900 |
| ccgggctgta | attagcgctt | ggtttaatga | cggcttgttt | cttttctgtg | gctgcgtgaa | 960 |
| agccttgagg | ggctccggga | gggccctttg | tgcgggggga | gcggctcggg | gggtgcgtgc | 1020 |
| gtgtgtgtgt | gcgtggggag | cgccgcgtgc | ggctccgcgc | tgcccggcgg | ctgtgagcgc | 1080 |
| tgcgggcgcg | gcgcggggct | tgtgcgctc | cgcagtgtgc | gcgaggggag | cgcggccggg | 1140 |
| ggcggtgccc | cgcggtgcgg | gggggctgc | gaggggaaca | aaggctgcgt | gcggggtgtg | 1200 |
| tgcgtggggg | ggtgagcagg | gggtgtgggc | gcgtcggtcg | ggctgcaacc | ccccctgcac | 1260 |
| ccccctcccc | gagttgctga | gcacggcccg | gcttcgggtg | cggggctccg | tacgggcgt | 1320 |
| ggcgcgggc | tcgccgtgcc | gggcgggggg | tggcggcagg | tgggggtgcc | gggcggggcg | 1380 |
| gggccgcctc | gggccgggga | gggctcgggg | gagggggcgcg | gcggcccccg | gagcgccggc | 1440 |
| ggctgtcgag | gcgcggcgag | ccgcagccat | tgccttttat | ggtaatcgtg | cgagagggcg | 1500 |
| cagggacttc | ctttgtccca | aatctgtgcg | gagccgaaat | ctgggaggcg | ccgccgcacc | 1560 |
| ccctctagcg | ggcgcgggc | gaagcggtgc | ggcgccggca | ggaaggaaat | gggcggggag | 1620 |
| ggccttcgtg | cgtcgccgcg | ccgccgtccc | cttctccctc | tccagcctcg | gggctgtccg | 1680 |
| cggggggacg | gctgccttcg | gggggacgg | ggcagggcgg | ggttcggctt | ctggcgtgtg | 1740 |
| accggcggca | tcgattgaat | tcgccaccat | gtcagaaggg | gtgggcacgt | tccgcatggt | 1800 |
| acctgaagag | gaacaggagc | tccgtgccca | actggagcag | ctcacaacca | aggaccatgg | 1860 |
| acctgtcttt | ggcccgtgca | gccagctgcc | ccgccacacc | ttgcagaagg | ccaaggatga | 1920 |
| gctgaacgag | agagaggaga | cccgggagga | ggcagtgcga | gagctgcagg | agatggtgca | 1980 |

-continued

```
ggcgcaggcg gcctcggggg aggagctggc ggtggccgtg gcggagaggg tgcaagagaa    2040
ggacagcggc ttcttcctgc gcttcatccg cgcacggaag ttcaacgtgg gccgtgccta    2100
tgagctgctc agaggctatg tgaatttccg gctgcagtac cctgagctct ttgacagcct    2160
gtccccagag gctgtccgct gcaccattga agctggctac cctggtgtcc tctctagtcg    2220
ggacaagtat ggccgagtgg tcatgctctt caacattgag aactggcaaa gtcaagaaat    2280
cacctttgat gagatcttgc aggcatattg cttcatcctg gagaagctgc tggagaatga    2340
ggaaactcaa atcaatggct ctgcatcat tgagaacttc aagggcttta ccatgcagca    2400
ggctgctagt ctccggactt cagatctcag gaagatggtg gacatgctcc aggattcctt    2460
cccagcccgg ttcaaagcca tccacttcat ccaccagcca tggtacttca ccacgaccta    2520
caatgtggtc aagcccttct gaagagcaa gctgcttgag agggtctttg tccacgggga    2580
tgacctttct ggtttctacc aggagatcga tgagaacatc ctgccctctg acttcggggg    2640
cacgctgccc aagtatgatg gcaaggccgt tgctgagcag ctctttggcc cccaggccca    2700
agctgagaac acagccttct gaggatcgta ccggtcgacc tgcagaagct tgcctcgagc    2760
agcgctgctc gagagatctg gatcataatc agccatacca catttgtaga ggttttactt    2820
gctttaaaaa acctcccaca cctcccctg aacctgaaac ataaaatgaa tgcaattgtt    2880
gttgttaact tgtttattgc agcttataat ggttacaaat aaagcaatag catcacaaat    2940
ttcacaaata aagcattttt ttcactgcat tctagttgtg gtttgtccaa actcatcaat    3000
gtatcttatc atgtctggta ctagggttac cccagaacag gtcccattca tggcccacat    3060
gacaacctgc ttccccagtg ggtattttg gagacagctc ttctgtttcc aggttttctc    3120
tcctgcctaa atgtcctgcc taagtgcctt caagaaccct tcaccatcct gctcctgcat    3180
gtgaccaggt tccatggtca gttcaatcac ctagtcacag ttggtaagtg acagagttgg    3240
gacttgaacc tatgcctgcc tgacaccaag tcttttttttg acaccagag ccaagacatc    3300 tgaagacaaa ctccctagga gagctggcgt catagaaacc ttaaaggtta gggagacctg    3360
ggtttgaatc aggctttgtc agttatgact tgtgtgaccc tagcaagtta tttaacctttt    3420 ctgggtctca gtttcctcat ctgcaaactg aggataataa cagtacctac caaaaagaac    3480
tgtcgtgaaa accatataat ttctgcaatg ctccctggcac agtgtcctgt tctaaagcat    3540
agttcccctt ctctttctta gctccatatt gattattacc ctaacttgca caagagact    3600 tggaggaccc ccatagagta tcggagggtc cccatttcc tgctctttcc actccacacc    3660
cccagcaagc acagggaagt tctggggcc ataatccacc cacaggaacc aaatctaagc    3720
cacctttctg gctggtagac atccaggtat gtgggcacag aggtagacag gctgaaatgc    3780
tgctgtgcta tcagttgggt tttgctggaa caggaatgga aatggagagg ctgacagaac    3840
tgccctgggg agcccaggca agagggacag tggctggaca ccccccagcca gttgtgcaga    3900 ccatcagaac aagatcctag atttttaggaa tacagggttc aagtccgtgc ggcaactctt    3960
ttctaaatat gcccaagcca ttaactttga gttttaaaaa tactgattta caagctgtac    4020
acaatgaaaa aatgcctatc cctcacacca tgctgatgct gttccctgcc atctcagatt    4080
accaattaaa tacagaatgc ccagttaaat gtgaactttt tttttttttt tttttttgag    4140
atggagtttt gttcttgtcg cccaggctag agtgcaatgg tgcgatctca gctcactgca    4200
acctctgcct cccaggttca agcaattctc ctgccttagc ctcctgagta gctgaaacta    4260
caggtgccca ccagcacgcc tggctaattt ttggtatttt tagtggagat ggggtttcac    4320
```

| | |
|---|---|
| catgttggcc aggctggtct cgaactcctg acctcaggtg atctgcctgc ctcggcctcc | 4380 |
| caaagtgctg ggattacagg cgtgagccta aatgtgaact tttttaatac taaaaaagta | 4440 |
| tttgctgttc atcggaaatt cacatttaac tgggtgtcct gtattttttat ttgctaaatc | 4500 |
| taccatcaaa ttggtctggc tcaacctgga gaatggttac cctaggtaac cacgtgcgga | 4560 |
| ccgagcggcc gcaggaaccc ctagtgatgg agttggccac tccctctctg cgcgctcgct | 4620 |
| cgctcactga ggccgggcga ccaaaggtcg cccgacgccc gggctttgcc cgggcggcct | 4680 |
| cagtgagcga gcgagcgcgc ag | 4702 |

<210> SEQ ID NO 55
<211> LENGTH: 3873
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 55

| | |
|---|---|
| ctgcgcgctc gctcgctcac tgaggccgcc cgggcgtcgg gcgacctttg gtcgcccggc | 60 |
| ctcagtgagc gagcgagcgc gcagagaggg agtggccaac tccatcacta ggggttcctg | 120 |
| cggccgcacg cgtttgtcct ctccctgctt ggccttaacc agccacattt ctcaactgac | 180 |
| cccactcact gcagaggtga aaactaccat gccaggtcct gctggctggg ggaggggtgg | 240 |
| gcaataggcc tggatttgcc agagctgcca ctgtagatgt agtcatattt acgatttccc | 300 |
| ttcacctctt attaccctgg tggtggtggt gggggggggg gggtgctctc tcagcaaccc | 360 |
| caccccggga tcttgaggag aaagagggca gagaaaagag ggaatgggac tggcccagat | 420 |
| cccagcccca cagccgggct tccacatggc cgagcaggaa ctccagagca ggagcacaca | 480 |
| aaggagggct ttgatgcgcc tccagccagg cccaggcctc tccctctcc cctttctctc | 540 |
| tgggtcttcc tttgccccac tgagggcctc ctgtgagccc gatttaacgg aaactgtggg | 600 |
| cggtgagaag ttccttatga cacactaatc ccaacctgct gaccggacca cgcctccagc | 660 |
| ggagggaacc tctagagctc caggacattc aggtaccagg tagccccaag gaggagctgc | 720 |
| cgaatcgatg gatcgggaac tgaaaaacca gaaagttaac tggtaagttt agtcttttttg | 780 |
| tcttttattt caggtcccgg atccggtggt ggtgcaaatc aaagaactgc tcctcagtgg | 840 |
| atgttgcctt tacttctagg cctgtacgga agtgttactt ctgctctaaa agctgcggaa | 900 |
| ttgtacccgc cccgggatcc atcgattgaa ttcgccacca tgtcagaagg ggtgggcacg | 960 |
| ttccgcatgg tacctgaaga ggaacaggag ctccgtgccc aactgagcag gctcacaacc | 1020 |
| aaggaccatg gacctgtctt tggcccgtgc agccagctgc ccgccacac cttgcagaag | 1080 |
| gccaaggatg agctgaacga gagagaggag acccggagg aggcagtgcg agagctgcag | 1140 |
| gagatggtgc aggcgcaggc ggcctcgggg gaggagctgg cggtggccgt ggcggagagg | 1200 |
| gtgcaagaga aggacagcgg cttcttcctg cgcttcatcc gcgcacggaa gttcaacgtg | 1260 |
| ggccgtgcct atgagctgct cagaggctat gtgaatttcc ggctgcagta ccctgagctc | 1320 |
| tttgacagcc tgtccccaga ggctgtccgc tgcaccattg aagctggcta ccctggtgtc | 1380 |
| ctctctagtc gggacaagta tggccgagtg gtcatgctct tcaacattga gaactggcaa | 1440 |
| agtcaagaaa tcacctttga tgagatcttg caggcatatt gcttcatcct ggagaagctg | 1500 |
| ctggagaatg aggaaactca aatcaatggc ttctgcatca ttgagaactt caagggcttt | 1560 |
| accatgcagc aggctgctag tctccggact tcagatctca ggaagatggt ggacatgctc | 1620 |

```
caggattcct tcccagcccg gttcaaagcc atccacttca tccaccagcc atggtacttc    1680
accacgacct acaatgtggt caagcccttc ttgaagagca agctgcttga gagggtcttt    1740
gtccacgggg atgacctttc tggtttctac caggagatcg atgagaacat cctgccctct    1800
gacttcgggg gcacgctgcc caagtatgat ggcaaggccg ttgctgagca gctcttggc    1860 ccccaggccc aagctgagaa cacagccttc tgaggatcgt accggtcgac ctgcagaagc    1920
ttgcctcgag cagcgctgct cgagagatct ggatcataat cagccatacc acatttgtag    1980
aggttttact tgctttaaaa aacctcccac acctccccct gaacctgaaa cataaaatga    2040
atgcaattgt tgttgttaac ttgtttattg cagcttataa tggttacaaa taaagcaata    2100
gcatcacaaa tttcacaaat aaagcatttt tttcactgca ttctagttgt ggtttgtcca    2160
aactcatcaa tgtatcttat catgtctggt actagggtta ccccagaaca ggtcccattc    2220
atggcccaca tgacaacctg cttccccagt gggtattttt ggagacagct cttctgtttc    2280
caggttttct ctcctgccta aatgtcctgc ctaagtgcct tcaagaaccc ttcaccatcc    2340
tgctcctgca tgtgaccagg ttccatggtc agttcaatca cctagtcaca gttggtaagt    2400
gacagagttg ggacttgaac ctatgcctgc ctgacaccaa gtctttttttt gacacctaga    2460 gccaagacat ctgaagacaa actccctagg agagctggcg tcatagaaac cttaaaggtt    2520
agggagacct gggtttgaat caggctttgt cagttatgac ttgtgtgacc ctagcaagtt    2580
atttaacctt tctgggtctc agtttcctca tctgcaaact gaggataata acagtaccta    2640
ccaaaaagaa ctgtcgtgaa aaccatataa tttctgcaat gctcctggca cagtgtcctg    2700
ttctaaagca tagttcccct tctctttctt agctccatat tgattattac cctaacttgc    2760
acaaagagac ttggaggacc cccatagagt atcggagggt cccccatttc ctgctctttc    2820
cactccacac ccccagcaag cacagggaag ttctgggggc cataatccac ccacaggaac    2880
caaatctaag ccacctttct ggctggtaga catccaggta tgtgggcaca gaggtagaca    2940
ggctgaaatg ctgctgtgct atcagttggg ttttgctgga acaggaatgg aaatggagag    3000
gctgacagaa ctgccctggg gagcccaggc aagagggaca gtggctggac ccccagcc    3060 agttgtgcag accatcagaa caagatccta gattttagga atacagggtt caagtccgtg    3120
cggcaactct tttctaaata tgcccaagcc attaactttg agttttaaaa atactgattt    3180
acaagctgta cacaatgaaa aaatgcctat ccctcacacc atgctgatgc tgttccctgc    3240
catctcagat taccaattaa atacagaatg cccagttaaa tgtgaacttt ttttttttt    3300 tttttttga gatggagttt tgttcttgtc gcccaggcta gagtgcaatg gtgcgatctc    3360
agctcactgc aacctctgcc tcccaggttc aagcaattct cctgccttag cctcctgagt    3420
agctggaact acaggtgccc accagcacgc ctggctaatt tttggtattt ttagtggaga    3480
tggggtttca ccatgttggc caggctggtc tcgaactcct gacctcaggt gatctgcctg    3540
cctcggcctc ccaaagtgct gggattacag gcgtgagcct aaatgtgaac ttttttaata    3600 ctaaaaagt atttgctgtt catcggaaat tcacatttaa ctgggtgtcc tgtattttta    3660
tttgctaaat ctaccatcaa attggtctgg ctcaacctgg agaatggtta ccctaggtaa    3720
ccacgtgcgg accgagcggc cgcaggaacc cctagtgatg gagttggcca ctccctctct    3780
gcgcgctcgc tcgctcactg aggccgggcg accaaggtc gcccgacgcc cgggctttgc    3840
ccgggcggcc tcagtgagcg agcgagcgcg cag                                 3873

<210> SEQ ID NO 56
<211> LENGTH: 2119
```

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

| | |
|---|---:|
| cgcgctcgct cgctcactga ggccgcccgg gcaaagcccg ggcgtcgggc gacctttggt | 60 |
| cgcccggcct cagtgagcga gcgagcgcgc agagagggag tggggtacca cgcgtttgtc | 120 |
| ctctccctgc ttggccttaa ccagccacat ttctcaactg accccactca ctgcagaggt | 180 |
| gaaaactacc atgccaggtc ctgctggctg ggggaggggt gggcaatagg cctggatttg | 240 |
| ccagagctgc cactgtagat gtagtcatat ttacgatttc ccttcacctc ttattaccct | 300 |
| ggtggtggtg gtggggggggg ggggtgctc tctcagcaac cccacccgg gatcttgagg | 360 |
| agaaagaggg cagagaaaag agggaatggg actggcccag atcccagccc acagccggg | 420 |
| cttccacatg gccgagcagg aactccagag caggagcaca caaggagggg ctttgatgcg | 480 |
| cctccagcca ggcccaggcc tctccctct ccctttctc tctgggtctt cctttgcccc | 540 |
| actgagggcc tcctgtgagc ccgatttaac ggaaactgtg ggcggtgaga agttccttat | 600 |
| gacacactaa tcccaacctg ctgaccggac cacgcctcca gcggagggaa cctctagagc | 660 |
| tccaggacat tcaggtacca ggtagcccca aggaggagct gccgaatcga tggatcggga | 720 |
| actgaaaaac cagaaagtta actggtaagt ttagtctttt tgtctttat ttcaggtccc | 780 |
| ggatccggtg gtggtgcaaa tcaaagaact gctcctcagt ggatgttgcc tttacttcta | 840 |
| ggcctgtacg gaagtgttac ttctgctcta aaagctgcgg aattgtaccc gccccgggat | 900 |
| ccatcgattg aattccccgg ggatcctcta gagtcgaaat tcgccaccat ggtgagcaag | 960 |
| ggcgaggagc tgttcaccgg ggtggtgccc atcctggtcg agctggacgg cgacgtaaac | 1020 |
| ggccacaagt tcagcgtgtc cggcgagggc gagggcgatg ccacctacgg caagctgacc | 1080 |
| ctgaagttca tctgcaccac cggcaagctg cccgtgccct ggcccaccct cgtgaccacc | 1140 |
| ctgacctacg gcgtgcagtg cttcagccgc taccccgacc acatgaagca gcacgacttc | 1200 |
| ttcaagtccg ccatgcccga aggctacgtc caggagcgca ccatcttctt caaggacgac | 1260 |
| ggcaactaca agacccgcgc cgaggtgaag ttcgagggcg acaccctggt gaaccgcatc | 1320 |
| gagctgaagg gcatcgactt caaggaggac ggcaacatcc tggggcacaa gctggagtac | 1380 |
| aactacaaca gccacaacgt ctatatcatg gccgacaagc agaagaacgg catcaaggtg | 1440 |
| aacttcaaga tccgccacaa catcgaggac ggcagcgtgc agctcgccga ccactaccag | 1500 |
| cagaacaccc ccatcggcga cggccccgtg ctgctgcccg acaaccacta cctgagcacc | 1560 |
| cagtccgccc tgagcaaaga ccccaacgag aagcgcgatc acatggtcct gctggagttc | 1620 |
| gtgaccgccg ccgggatcac tctcggcatg gacgagctgt acaagtaata gggtaccggt | 1680 |
| cgacctgcag aagcttgcct cgagcagcgc tgctcgagag atctggatca taatcagcca | 1740 |
| taccacattt gtagaggttt tacttgcttt aaaaaacctc ccacacctcc ccctgaacct | 1800 |
| gaaacataaa atgaatgcaa ttgttgttgt taacttgttt attgcagctt ataatggtta | 1860 |
| caaataaagc aatagcatca caaatttcac aaataaagca ttttttttcac tgcattctag | 1920 |
| ttgtggtttg tccaaactca tcaatgtatc ttatcatgtc tggtaaccac gtgcggaccg | 1980 |
| agcggccgca ggaaccccta gtgatggagt tggccactcc ctctctgcgc gctcgctcgc | 2040 |
| tcactgaggc cgggcgacca aaggtcgccc gacgcccggg ctttgcccgg gcggcctcag | 2100 |
| tgagcgagcg agcgcgcag | 2119 |

<210> SEQ ID NO 57
<211> LENGTH: 4503
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 57

```
ctgcgcgctc gctcgctcac tgaggccgcc cgggcgtcgg gcgacctttg gtcgcccggc      60
ctcagtgagc gagcgagcgc gcagagaggg agtggccaac tccatcacta ggggttcctg     120
cggccgcacg cagcttttgt cctctccctg cttggcctta accagccaca tttctcaact     180
gaccccactc actgcagagg tgaaaactac catgccaggt cctgctggct ggggagggg      240
tgggcaatag gcctggattt gccagagctg ccactgtaga tgtagtcata tttacgattt     300
cccttcacct cttattaccc tgtggtggt ggtgggggg ggggggtgct ctctcagcaa       360
ccccaccccg ggatcttgag gagaaagagg gcagagaaaa gagggaatgg gactggccca     420
gatcccagcc ccacagccgg gcttccacat ggccgagcag gaactccaga gcaggagcac     480
acaaggagg gctttgatgc gcctccagcc aggcccaggc ctctcccctc tccctttct       540
ctctgggtct tcctttgccc cactgagggc ctcctgtgag cccgatttaa cggaaactgt     600
gggcggtgag aagttcctta tgacacacta atcccaacct gctgaccgga ccacgcctcc     660
agcggaggga acctctagag ctccaggaca ttcaggtacc aggtagcccc aaggaggagc     720
tgccgacctg gcaggtaagt caatacctgg ggcttgcctg gccagggag cccaggactg      780
gggtgaggac tcaggggagc agggagacca cgtcccaaga tgcctgtaaa actgaaacca     840
cctggccatt ctccaggttg agccagacca atttgatggc agatttagca aataaaaata     900
caggacaccc agttaaatgt gaatttcaga tgaacagcaa atactttttt agtattaaaa     960
aagttcacat ttaggctcac gcctgtaatc ccagcacttt gggaggccga ggcaggcaga    1020
tcacctgagg tcaggagttc gagaccagcc tggccaacat ggtgaaaccc catctccact    1080
aaaaatacca aaaattagcc aggcgtgctg gtgggcacct gtagttccag ctactcagga    1140
ggctaaggca ggagaattgc ttgaacctgg gaggcagagg ttgcagtgag ctgagatcgc    1200
accattgcac tctagcctgg gcgacaagaa caaaactcca tctcaaaaaa aaaaaaaaa     1260
aaaaagttca catttaactg ggcattctgt atttaattgg taatctgaga tggcagggaa    1320
cagcatcagc atggtgtgag ggataggcat ttttttcattg tgtacagctt gtaaatcagt    1380
attttttaaaa ctcaaagtta atggcttggg catatttaga aaagagttgc cgcacggact    1440
tgaaccctgt attcctaaaa tctaggatct tgttctgatg gtctgcacaa ctggctgggg    1500
gtgtccagcc actgtccctc ttgcctgggc tcccagggc agttctgtca gcctctccat    1560
ttccattcct gttccagcaa aacccaactg atagcacagc agcatttcag cctgtctacc    1620
tctgtgccca catacctgga tgtctaccag ccagaaaggt ggcttagatt tggttcctgt    1680
gggtggatta tggcccccag aacttccctg tgcttgctgg gggtgtggag tggaaagagc    1740
aggaaatggg ggaccctccg atactctatg ggggtcctcc aagtctcttt gtgcaagtta    1800
gggtaataat caatatggag ctaagaaaga gaaggggaac tatgctttag aacaggacac    1860
tgtgccagga gcattgcaga aattatatgg ttttcacgac agttcttttt ggtaggtact    1920
gttattatcc tcagtttgca gatgaggaaa ctgagaccca gaaaggttaa ataacttgct    1980
agggtcacac aagtcataac tgacaaagcc tgattcaaac ccaggtctcc ctaaccttta    2040
```

```
aggtttctat gacgccagct ctcctaggga gtttgtcttc agatgtcttg gctctaggtg    2100
tcaaaaaaag acttggtgtc aggcaggcat aggttcaagt cccaactctg tcacttacca    2160
actgtgacta ggtgattgaa ctgaccatgg aacctggtca catgcaggag caggatggtg    2220
aagggttctt gaaggcactt aggcaggaca tttaggcagg agagaaaacc tggaaacaga    2280
agagctgtct ccaaaaatac ccactgggga agcaggttgt catgtgggcc atgaatggga    2340
cctgttctgg taaccaagca ttgcttatgt gtccattaca tttcataaca cttccatcct    2400
actttacagg gaacaaccaa gactggggtt aaatctcaca gcctgcaagt ggaagagaag    2460
aacttgaacc caggtccaac ttttgcgcca cagcaggctg cctcttggtc ctgacaggaa    2520
gtcacaactt gggtctgagt actgatccct ggctattttt tggctgtgtt accttggaca    2580
agtcacttat tcctcctccc gtttcctcct atgtaaaatg gaataataaa tgttgaccct    2640
gggtctgaga gagtggattt gaaagtactt agtgcatcac aaagcacaga acacacttcc    2700
agtctcgtga ttatgtactt atgtaactgg tcatcaccca tcttgagaat gaatgcattg    2760
gggaaagggc catccactag gctgcgaagt ttctgaggga ctccttcggg ctggagaagg    2820
atggccacag gagggaggag agattgcctt atcctgcagt gatcatgtca ttgagaacag    2880
agccagattc ttttttttcct ggcagggcca acttgtttta acatctaagg actgagctat    2940
ttgtgtctgt gcccttttgtc caagcagtgt ttcccaaagt gtagcccaag aaccatctcc    3000
ctcagagcca ccaggaagtg ctttaaattg caggttccta ggccacagcc tgcacctgca    3060
gagtcagaat catggaggtt gggacccagg cacctgcgtt tctaacaaat gcctcgggtg    3120
attctgatgc aattgaaagt ttgagatcca cagttctgag acaataacag aatggttttt    3180
ctaacccctg cagccctgac ttcctatcct agggaagggg ccggctggag aggccaggac    3240
agagaaagca gatcccttct tttccaagg actctgtgtc ttccataggc aacgaattcc    3300
ccggggatcc tctagagtcg aaattcgcca ccatggtgag caaggcgag gagctgttca    3360
ccggggtggt gcccatcctg gtcgagctgg acggcgacgt aaacggccac aagttcagcg    3420
tgtccggcga gggcgagggc gatgccacct acggcaagct gaccctgaag ttcatctgca    3480
ccaccggcaa gctgcccgtg ccctggccca ccctcgtgac caccctgacc tacggcgtgc    3540
agtgcttcag ccgctacccc gaccacatga gcagcacga cttcttcaag tccgccatgc    3600
ccgaaggcta cgtccaggag cgcaccatct tcttcaagga cgacggcaac tacaagaccc    3660
gcgccgaggt gaagttcgag ggcgacaccc tggtgaaccg catcgagctg aagggcatcg    3720
acttcaagga ggacggcaac atcctggggc acaagctgga gtacaactac aacagccaca    3780
acgtctatat catggccgac aagcagaaga acggcatcaa ggtgaacttc aagatccgcc    3840
acaacatcga ggacggcagc gtgcagctcg ccgaccacta ccagcagaac ccccatcg    3900
gcgacggccc cgtgctgctg cccgacaacc actacctgag cacccagtcc gccctgagca    3960
aagaccccaa cgagaagcgc gatcacatgg tcctgctgga gttcgtgacc gccgccggga    4020
tcactctcgg catggacgag ctgtacaagt aatagggtac cggtcgacct gcagaagctt    4080
gcctcgagca gcgctgctcg agagatctgg atcataatca gccataccac atttgtagag    4140
gttttacttg ctttaaaaaa cctcccacac ctccccctga acctgaaaca taaaatgaat    4200
gcaattgttg ttgttaactt gtttattgca gcttataatg gttacaaata aagcaatagc    4260
atcacaaatt tcacaaataa agcatttttt tcactgcatt ctagttgtgg tttgtccaaa    4320
ctcatcaatg tatcttatca tgtctggtaa ccacgtgcgg accgagcggc cgcaggaacc    4380
```

```
cctagtgatg gagttggcca ctccctctct gcgcgctcgc tcgctcactg aggccgggcg    4440
accaaaggtc gcccgacgcc cgggctttgc ccgggcggcc tcagtgagcg agcgagcgcg    4500
cag                                                                  4503

<210> SEQ ID NO 58
<211> LENGTH: 4543
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58
ctgcgcgctc gctcgctcac tgaggccgcc cgggcgtcgg gcgacctttg gtcgcccggc      60
ctcagtgagc gagcgagcgc gcagagaggg agtggccaac tccatcacta ggggttcctg     120
cggccgcacg cgtgacgtcg tttaaacggg ccccggtgtt atctcattct ttttctcct      180 ctgtaagttg acatgtgatg tgggaacaaa ggggataaag tcattatttt gtgctaaaat     240
cgtaattgga gaggacctcc tgttagctgg gctttcttct atttattgtg gtggttactg     300
gagttccttc ttctagtttt aggatatata tatatatttt ttttttttct ttccctgaag     360 ataataat atatatactt ctgaagattg agattttaa attagttgta ttgaaaacta       420
gctaatcagc aatttaaggc tagcttgaga cttatgtctt gaatttgttt ttgtaggctc     480
caaaaccaag gagggagtgg tgcatggtgt ggcaacaggt aagctccatt gtgcttatat     540
ccaaagatga tatttaaagt atctagtgat tagtgtggcc cagtattcaa gattcctatg     600
aaattgtaaa acaatcactg agcattctaa gaacatatca gtcttattga aactgaattc     660
tttataaagt attttttaaaa aggtaaatat tgattataaa taaaaaatat acttgccaag    720
aataatgagg gctttgaatt gataagctat gtttaattta tagtaagtgg gcatttaaat    780
attctgacca aaaatgtatt gacaaactgc tgacaaaaat aaaatgtgaa tattgccata    840
attttaaaaa aagagtaaaa tttctgttga ttacagtaaa atattttgac cttaaattat    900
gttgattaca atattccttt gataattcag agtgcatttc aggaaacacc cttggacagt    960
cagtaaattg tttattgtat ttatctttgt attgttatgg tatagctatt tgtacaaata    1020
ttattgtgca attattacat ttctgattat attattcatt tggcctaaat ttaccaagaa    1080
tttgaacaag tcaattaggt ttacaatcaa gaaatatcaa aaatgatgaa aaggatgata    1140
atcatcatca gatgttgagg aagatgacga tgagagtgcc agaaatagag aaatcaaagg    1200
agaaccaaaa tttaacaaat taaaagccca cagacttgct gtaattaagt tttctgttgt    1260
aagtactcca cgtttcctgg cagatgtggt gaagcaaaag atataatcag aaatataatt    1320
tatatgatcg gaaagcatta aacacaatag tgcctataca aataaaatgt tcctatcact    1380
gacttctaaa atggaaatga ggacaatgat atgggaatct taatacagtg ttgtggatag    1440
gactaaaaac acaggagtca gatcttcttg gttcaacttc ctgcttactc cttaccagct    1500
gtgtgttttt tgcaaggttc ttcacctcta tgtgatttag cttcctcatc tataaaataa    1560
ttcagtgaat taatgtacac aaaacatctg gaaaacaaaa gcaaacaata tgtattttat    1620
aagtgttact tatagttta tagtgaactt tcttgtgcaa cattttttaca actagtggag    1680 aaaaatattt ctttaaatga atactttga tttaaaaatc agagtgtaaa aataaaacag    1740
actcctttga aactagttct gttagaagtt aattgtgcac ctttaatggg ctctgttgca    1800
atccaacaga gaagtagtta agtaagtgga ctatgatggc ttctagggac ctcctataaa    1860
```

```
tatgatattg tgaagcatga ttataataag aactagataa cagacaggtg gagactccac     1920
tatctgaaga gggtcaacct agatgaatgg tgttccattt agtagttgag gaagaaccca     1980
tgaggtttag aaagcagaca agcatgtggc aagttctgga gtcagtggta aaaattaaag     2040
aacccaacta ttactgtcac ctaatgatct aatggagact gtggagatgg gctgcatttt     2100
tttaatcttc tccagaatgc caaaatgtaa acacatatct gtgtgtgtgt gtgtgtgtgt     2160
gtgtgtgtgt gagagagaga gagagagaga gagagactga agtttgtaca attagacatt     2220
ttataaaatg ttttctgaag gacagtggct cacaatctta agtttctaac attgtacaat     2280
gttgggagac tttgtatact ttattttctc tttagcatat taaggaatct gagatgtcct     2340
acagtaaaga aatttgcatt acatagttaa aatcagggtt attcaaactt tttgattatt     2400
gaaacctttc ttcattagtt actagggttg aatgaaacta gtgttccaca gaaaactatg     2460
ggaaatgttg ctaggcagta aggacatggt gatttcagca tgtgcaatat ttacagcgat     2520
tgcacccatg gaccaccctg gcagtagtga ataaccaaa aatgctgtca taactagtat      2580
ggctatgaga aacacattgg gcagaagctt gcctcgagcc gcgctgctcg agagatctgg     2640
atcataatca gccataccac atttgtagag gttttacttg ctttaaaaaa cctcccacac     2700
ctccccctga acctgaaaca taaatgaat gcaattgttg ttgttaactt gtttattgca      2760
gcttataatg gttacaaata aagcaatagc atcacaaatt tcacaaataa agcatttttt     2820
tcactgcatt ctagttgtgg tttgtccaaa ctcatcaatg tatcttatca tgtctggtaa     2880
ccattctcca ggttgagcca gaccaatttg atggtagatt tagcaaataa aaatacagga     2940
cacccagtta aatgtgaatt tccgatgaac agcaaatact tttttagtat taaaaaagtt     3000
cacatttagg ctcacgcctg taatcccagc actttgggag gccgaggcag gcagatcacc     3060
tgaggtcagg agttcgagac cagcctggcc aacatggtga aaccccatct ccactaaaaa     3120
taccaaaaat tagccaggcg tgctggtggg cacctgtagt tccagctact caggaggcta     3180
aggcaggaga attgcttgaa cctgggaggc agaggttgca gtgagctgag atcgcaccat     3240
tgcactctag cctgggcgac aagaacaaaa ctccatctca aaaaaaaaa aaaaaaaaaa      3300
gttcacattt aactgggcat tctgtattta attggtaatc tgagatggca gggaacagca     3360
tcagcatggt gtgagggata ggcatttttt cattgtgtac agcttgtaaa tcagtatttt     3420
taaaactcaa agttaatggc ttgggcatat ttagaaaaga gttgccgcac ggacttgaac     3480
cctgtattcc taaaatctag gatcttgttc tgatggtctg cacaactggc tgggggtgtc     3540
cagccactgt ccctcttgcc tgggctcccc agggcagttc tgtcagcctc tccatttcca     3600
ttcctgttcc agcaaaaccc aactgatagc acagcagcat ttcagcctgt ctacctctgt     3660
gcccacatac ctggatgtct accagccaga aaggtggctt agatttggtt cctgtgggtg     3720
gattatggcc cccagaactt ccctgtgctt gctggggtg tggagtggaa agagcaggaa      3780
atggggacc ctccgatact ctatgggggt cctccaagtc tctttgtgca agttagggta      3840
ataatcaata tggagctaag aaagagaagg ggaactatgc tttagaacag gacactgtgc     3900
caggagcatt gcagaaatta tatggttttc acgacagttc ttttttggtag gtactgttat    3960
tatcctcagt ttgcagatga ggaaactgag acccagaaag gttaaataac ttgctagggt     4020
cacacaagtc ataactgaca aagcctgatt caaacccagg tctccctaac ctttaaggtt     4080
tctatgacgc cagctctcct agggagtttg tcttcagatg tcttggctct aggtgtcaaa     4140
aaaagacttg gtgtcaggca ggcataggtt caagtcccaa ctctgtcact taccaactgt     4200
gactaggtga ttgaactgac catggaacct ggtcacatgc aggagcagga tggtgaaggg     4260
```

```
ttcttgaagg cacttaggca ggacatttag gcaggagaga aaacctggaa acagaagagc    4320
tgtctccaaa atacccact ggggaagcag gttgtcatgt gggccatgaa tgggacctgt    4380
tctggggtaa ccacgtgcgg accgagcggc cgcaggaacc cctagtgatg gagttggcca    4440
ctccctctct gcgcgctcgc tcgctcactg aggccgggcg accaaaggtc gcccgacgcc    4500
cgggctttgc ccgggcggcc tcagtgagcg agcgagcgcg cag                     4543
```

<210> SEQ ID NO 59
<211> LENGTH: 4438
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 59

```
ctgcgcgctc gctcgctcac tgaggccgcc cgggcgtcgg gcgacctttg gtcgcccggc     60
ctcagtgagc gagcgagcgc gcagagaggg agtggccaac tccatcacta ggggttcctg    120
cggccgcacg cgttacgtaa tatttattga agtttaatat tgtgtttgtg atacagaagt    180
atttgcttta attctaaata aaaatttttat gcttttattg ctggtttaag aagatttgga    240
ttatccttgt actttgagga gaagtttctt atttgaaata ttttggaaac aggtctttta    300
atgtggaaag atagatatta atctcctctt ctattactct ccaagatcca acaaaagtga    360
ttataccccc caaaatatga tggtagtatc ttatactacc atcattttat aggcataggg    420
ctcttagctg caaataatgg aactaactct aataaagcag aacgcaaata ttgtaaatat    480
tagagagcta acaatctctg ggatggctaa aggatggagc ttggaggcta cccagccagt    540
aacaatattc cggctccac tgttgaatgg agacactaca actgccttgg atgggcagag    600
atattatgga tgctaagccc caggtgctac cattaggact tctaccactg tccctaacgg    660
gtggagccca tcacatgcct atgccctcac tgtaaggaaa tgaagctact gttgtatatc    720
ttgggaagca cttggattaa ttgttataca gttttgttga agaagacccc tagggtaagt    780
agccataact gcacactaaa tttaaaattg ttaatgagtt tctcaaaaaa atgttaagg    840 ttgttagctg gtatagtata tatcttgcct gtttttccaag gacttctttg ggcagtacct    900
tgtctgtgct ggcaagcaac tgagacttaa tgaaagagta ttggagatat gaatgaattg    960
atgctgtata ctctcagagt gccaaacata taccaatgga caagaaggtg aggcagagag   1020
cagacaggca ttagtgacaa gcaaagatat gcagaatttc attctcagca aatcaaaagt   1080
cctcaacctg gttggaagaa tattggcact gaatggtatc aataaggttg ctagagaggg   1140
ttagaggtgc acaatgtgct tccataacat tttatacttc tccaatctta gcactaatca   1200
aacatggttg aatactttgt ttactataac tcttacagag ttataagatc tgtgaagaca   1260
gggacaggga caatacccat ctctgtctgg ttcataggtg gtatgtaata gatattttta   1320
aaaataagtg agttaatgaa tgagggtgag aatgaaggca cagaggtatt aggggagggt   1380
gggccccaga gaatggtgcc aaggtccagt ggggtgactg ggatcagctc aggcctgacg   1440
ctggccactc ccacctagct cctttctttc taatctgttc tcattctcct tgggaaggat   1500
tgaggtctct ggaaaacagc caaacaactg ttatgggaac agcaagccca aataaagcca   1560
agcatcaggg ggatctgaga gctgaaagca acttctgttc ccctcccctc agctgaaggg   1620
gtggggaagg gctcccaaag ccataactcc ttttaaggga tttagaaggc ataaaaaggc   1680
ccctggctga gaacttcctt cttcattctg cagttggtga attccccggg gatcctctag   1740
```

```
agtcgaaatt cgccaccatg gtgagcaagg gcgaggagct gttcaccggg gtggtgccca   1800
tcctggtcga gctggacggc gacgtaaacg gccacaagtt cagcgtgtcc ggcgagggcg   1860
agggcgatgc cacctacggc aagctgaccc tgaagttcat ctgcaccacc ggcaagctgc   1920
ccgtgccctg gcccaccctc gtgaccaccc tgacctacgg cgtgcagtgc ttcagccgct   1980
accccgacca catgaagcag cacgacttct tcaagtccgc catgcccgaa ggctacgtcc   2040
aggagcgcac catcttcttc aaggacgacg gcaactacaa gacccgcgcc gaggtgaagt   2100
tcgagggcga caccctggtg aaccgcatcg agctgaaggg catcgacttc aaggaggacg   2160
gcaacatcct gggcacaag ctggagtaca actacaacag ccacaacgtc tatatcatgg   2220
ccgacaagca gaagaacggc atcaaggtga acttcaagat ccgccacaac atcgaggacg   2280
gcagcgtgca gctcgccgac cactaccagc agaacacccc catcggcgac ggccccgtgc   2340
tgctgcccga caaccactac ctgagcaccc agtccgccct gagcaaagac cccaacgaga   2400
agcgcgatca catggtcctg ctggagttcg tgaccgccgc cgggatcact ctcggcatgg   2460
acgagctgta caagtaatag ggtaccggtc gacctgcaga agcttgcctc gagcagcgct   2520
gctcgagaga tctggatcat aatcagccat accacatttg tagaggtttt acttgcttta   2580
aaaaacctcc cacacctccc cctgaacctg aaacataaaa tgaatgcaat tgttgttgtt   2640
aacttgttta ttgcagctta taatggttac aaataaagca atagcatcac aaatttcaca   2700
aataaagcat ttttttcact gcattctagt tgtggtttgt ccaaactcat caatgtatct   2760
tatcatgtct ggtaaccatt ctccaggttg agccagacca atttgatggt agatttagca   2820
aataaaaata caggacaccc agttaaatgt gaatttccga tgaacagcaa atacttttt   2880 agtattaaaa aagttcacat ttaggctcac gcctgtaatc ccagcacttt gggaggccga   2940
ggcaggcaga tcacctgagg tcaggagttc gagaccagcc tggccaacat ggtgaaaccc   3000
catctccact aaaaatacca aaaattagcc aggcgtgctg gtgggcacct gtagttccag   3060
ctactcagga ggctaaggca ggagaattgc ttgaacctgg gaggcagagg ttgcagtgag   3120
ctgagatcgc accattgcac tctagcctgg gcgacaagaa caaaactcca tctcaaaaaa   3180
aaaaaaaaaa aaaaagttca catttaactg ggcattctgt atttaattgg taatctgaga   3240
tggcagggaa cagcatcagc atggtgtgag ggataggcat ttttcattg tgtacagctt   3300 gtaaatcagt attttaaaa ctcaaagtta atggcttggg catatttaga aaagagttgc   3360
cgcacggact tgaaccctgt attcctaaaa tctaggatct tgttctgatg gtctgcacaa   3420
ctggctgggg gtgtccagcc actgtccctc ttgcctgggc tccccagggc agttctgtca   3480
gcctctccat ttccattcct gttccagcaa aacccaactg atagcacagc agcatttcag   3540
cctgtctacc tctgtgccca cataccggga tgtctaccag ccagaaaggt ggcttagatt   3600
tggttcctgt gggtggatta tggcccccag aacttccctg tgcttgctgg gggtgtggag   3660
tggaaagagc aggaaatggg ggaccctccg atactctatg ggggtcctcc aagtctcttt   3720
gtgcaagtta gggtaataat caatatggag ctaagaaaga gaaggggaac tatgctttag   3780
aacaggacac tgtgccagga gcattgcaga aattatatgg ttttcacgac agttcttttt   3840
ggtaggtact gttattatcc tcagtttgca gatgaggaaa ctgagaccca gaaaggttaa   3900
ataacttgct agggtcacac aagtcataac tgacaaagcc tgattcaaac ccaggtctcc   3960
ctaaccttta aggtttctat gacgccagct ctcctaggga gtttgtcttc agatgtcttg   4020
gctctaggtg tcaaaaaaag acttggtgtc aggcaggcat aggttcaagt cccaactctg   4080
```

-continued

| | |
|---|---|
| tcacttacca actgtgacta ggtgattgaa ctgaccatgg aacctggtca catgcaggag | 4140 |
| caggatggtg aagggttctt gaaggcactt aggcaggaca tttaggcagg agagaaaacc | 4200 |
| tggaaacaga agagctgtct ccaaaaatac ccactgggga agcaggttgt catgtgggcc | 4260 |
| atgaatggga cctgttctgg ggtaaccacg tgcggaccga gcggccgcag gaacccctag | 4320 |
| tgatggagtt ggccactccc tctctgcgcg ctcgctcgct cactgaggcc gggcgaccaa | 4380 |
| aggtcgcccg acgcccgggc tttgcccggg cggcctcagt gagcgagcga gcgcgcag | 4438 |

<210> SEQ ID NO 60
<211> LENGTH: 3481
<212> TYPE: DNA
<213> ORGANISM: Artificial Sequence
<220> FEATURE:
<223> OTHER INFORMATION: Description of Artificial Sequence: Synthetic
   polynucleotide

<400> SEQUENCE: 60

| | |
|---|---|
| ctgcgcgctc gctcgctcac tgaggccgcc cgggcgtcgg gcgacctttg gtcgcccggc | 60 |
| ctcagtgagc gagcgagcgc gcagagaggg agtggccaac tccatcacta ggggttcctg | 120 |
| cggccgcacg cgttacgtaa ttctgtcatt ttactagggt gatgaaattc ccaagcaaca | 180 |
| ccatcctttt cagataaggg cactgaggct gagagaggag ctgaaaccta cccggcgtca | 240 |
| ccacacacag gtggcaaggc tgggaccaga aaccaggact gttgactgca gcccggtatt | 300 |
| cattctttcc atagcccaca gggctgtcaa agaccccagg gcctagtcag aggctcctcc | 360 |
| ttcctggaga gttcctggca cagaagttga agctcagcac agcccctaa ccccaactc | 420 |
| tctctgcaag gcctcagggg tcagaacact ggtggagcag atcctttagc ctctggattt | 480 |
| tagggccatg gtagagggg tgttgcccta aattccagcc ctggtctcag cccaacaccc | 540 |
| tccaagaaga aattagaggg gccatggcca ggctgtgcta gccgttgctt ctgagcagat | 600 |
| tacaagaagg gactaagaca aggactcctt tgtggaggtc ctggcttagg gagtcaagtg | 660 |
| acggcggctc agcactcacg tgggcagtgc cagcctctaa gagtgggcag gggcactggc | 720 |
| cacagagtcc cagggagtcc caccagccta gtcgccagac cgaattcccc ggggatcctc | 780 |
| tagagtcgaa attcgccacc atggtgagca agggcgagga gctgttcacc ggggtggtgc | 840 |
| ccatcctggt cgagctggac ggcgacgtaa acggccacaa gttcagcgtg tccggcgagg | 900 |
| gcgagggcga tgccacctac ggcaagctga ccctgaagtt catctgcacc accggcaagc | 960 |
| tgcccgtgcc ctggcccacc ctcgtgacca ccctgaccta cggcgtgcag tgcttcagcc | 1020 |
| gctaccccga ccacatgaag cagcacgact tcttcaagtc cgccatgccc gaaggctacg | 1080 |
| tccaggagcg caccatcttc ttcaaggacg acggcaacta caagacccgc gccgaggtga | 1140 |
| agttcgaggg cgacaccctg gtgaaccgca tcgagctgaa gggcatcgac ttcaaggagg | 1200 |
| acggcaacat cctggggcac aagctggagt acaactacaa cagccacaac gtctatatca | 1260 |
| tggccgacaa gcagaagaac ggcatcaagg tgaacttcaa gatccgccac aacatcgagg | 1320 |
| acggcagcgt gcagctcgcc gaccactacc agcagaacac ccccatcggc gacggccccg | 1380 |
| tgctgctgcc cgacaaccac tacctgagca cccagtccgc cctgagcaaa gaccccaacg | 1440 |
| agaagcgcga tcacatggtc ctgctggagt tcgtgaccgc cgccgggatc actctcggca | 1500 |
| tggacgagct gtacaagtaa tagggtaccg gtcgacctgc agaagcttgc ctcgagcagc | 1560 |
| gctgctcgag agatctggat cataatcagc cataccacat ttgtagaggt tttacttgct | 1620 |
| ttaaaaaacc tcccacacct cccctgaac ctgaaacata aaatgaatgc aattgttgtt | 1680 |

```
gttaacttgt ttattgcagc ttataatggt tacaaataaa gcaatagcat cacaaatttc    1740
acaaataaag catttttttc actgcattct agttgtggtt tgtccaaact catcaatgta    1800
tcttatcatg tctggtaacc attctccagg ttgagccaga ccaatttgat ggtagattta    1860
gcaaataaaa atacaggaca cccagttaaa tgtgaatttc cgatgaacag caaatacttt    1920
tttagtatta aaaagttca catttaggct cacgcctgta atcccagcac tttgggaggc    1980
cgaggcaggc agatcacctg aggtcaggag ttcgagacca gcctggccaa catggtgaaa    2040
ccccatctcc actaaaaata ccaaaaatta gccaggcgtg ctggtgggca cctgtagttc    2100
cagctactca ggaggctaag gcaggagaat tgcttgaacc tgggaggcag aggttgcagt    2160
gagctgagat cgcaccattg cactctagcc tgggcgacaa gaacaaaact ccatctcaaa    2220
aaaaaaaaaa aaaaaaaagt tcacatttaa ctgggcattc tgtatttaat tggtaatctg    2280
agatggcagg aacagcatc agcatggtgt gagggatagg catttttttca ttgtgtacag    2340 cttgtaaatc agtattttta aaactcaaag ttaatggctt gggcatattt agaaaagagt    2400
tgccgcacgg acttgaaccc tgtattccta aaatctagga tcttgttctg atggtctgca    2460
caactggctg ggggtgtcca gccactgtcc ctcttgcctg gctccccag ggcagttctg    2520 tcagcctctc catttccatt cctgttccag caaaacccaa ctgatagcac agcagcattt    2580
cagcctgtct acctctgtgc ccacatacct ggatgtctac cagccagaaa ggtggcttag    2640
atttggttcc tgtgggtgga ttatggcccc cagaacttcc ctgtgcttgc tgggggtgtg    2700
gagtggaaag agcaggaaat gggggaccct ccgatactct atgggggtcc tccaagtctc    2760
tttgtgcaag ttagggtaat aatcaatatg gagctaagaa agagaagggg aactatgctt    2820
tagaacagga cactgtgcca ggagcattgc agaaattata tggttttcac gacagttctt    2880
tttggtaggt actgttatta tcctcagttt gcagatgagg aaactgagac ccagaaaggt    2940
taaataactt gctagggtca cacaagtcat aactgacaaa gcctgattca aacccaggtc    3000
tccctaacct ttaaggtttc tatgacgcca gctctcctag ggagtttgtc ttcagatgtc    3060
ttggctctag gtgtcaaaaa aagacttggt gtcaggcagg cataggttca agtcccaact    3120
ctgtcactta ccaactgtga ctaggtgatt gaactgacca tggaacctgg tcacatgcag    3180
gagcaggatg gtgaagggtt cttgaaggca cttaggcagg acatttaggc aggagagaaa    3240
acctggaaac agaagagctg tctccaaaaa tacccactgg ggaagcaggt tgtcatgtgg    3300
gccatgaatg ggacctgttc tggggtaacc acgtgcggac cgagcggccg caggaacccc    3360
tagtgatgga gttggccact ccctctctgc gcgctcgctc gctcactgag gccgggcgac    3420
caaaggtcgc ccgacgcccg ggctttgccc gggcggcctc agtgagcgag cgagcgcgca    3480
g                                                                    3481
```

<210> SEQ ID NO 61
<211> LENGTH: 2327
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 61

```
cgcgctcgct cgctcactga ggccgcccgg gcaaagcccg ggcgtcgggc gacctttggt      60 cgccggcct cagtgagcga gcgagcgcgc agagagggag tggggtacca cgcgtttgtc     120
ctctccctgc ttggccttaa ccagccacat ttctcaactg accccactca ctgcagaggt     180
```

```
gaaaactacc atgccaggtc ctgctggctg ggggaggggt gggcaatagg cctggatttg      240
ccagagctgc cactgtagat gtagtcatat ttacgatttc ccttcacctc ttattaccct      300
ggtggtggtg gtggggggg ggggtgctc tctcagcaac cccacccgg gatcttgagg         360
agaaagaggg cagagaaaag agggaatggg actggcccag atcccagccc cacagccggg      420
cttccacatg gccgagcagg aactccagag caggagcaca caaggagggg ctttgatgcg      480
cctccagcca ggcccaggcc tctccctct cccctttctc tctgggtctt cctttgcccc       540
actgagggcc tcctgtgagc ccgatttaac ggaaactgtg ggcggtgaga agttccttat      600
gacacactaa tcccaacctg ctgaccggac cacgcctcca gcggagggaa cctctagagc      660
tccaggacat tcaggtacca ggtagccccca aggaggagct gccgaatcga tggatcggga    720
actgaaaaac cagaaagtta actggtaagt ttagtctttt tgtctttat ttcaggtccc       780
ggatccggtg gtggtgcaaa tcaaagaact gctcctcagt ggatgttgcc tttacttcta     840
ggcctgtacg gaagtgttac ttctgctcta aaagctgcgg aattgtaccc gccccgggat     900
ccatcgattg aattcgccac catgtcagaa ggggtgggca cgttccgcat ggtacctgaa     960
gaggaacagg agctccgtgc ccaactggag cagctcacaa ccaaggacca tggacctgtc    1020
tttggcccgt gcagccagct gccccgccac accttgcaga aggccaagga tgagctgaac   1080
gagagagagg agacccggga ggaggcagtg cgagagctgc aggagatggt gcaggcgcag   1140
gcggcctcgg gggaggagct ggcggtgcc gtggcggaga gggtgcaaga aaggacagc      1200
ggcttcttcc tgcgcttcat ccgcgcacgg aagttcaacg tgggccgtgc ctatgagctg   1260
ctcagaggct atgtgaattt ccggctgcag taccctgagc tctttgacag cctgtcccca   1320
gaggctgtcc gctgcaccat tgaagctggc taccctggtg tcctctctag tcgggacaag   1380
tatgccgag tggtcatgct cttcaacatt gagaactggc aaagtcaaga aatcacctt    1440
gatgagatct tgcaggcata ttgcttcatc ctggagaagc tgctggagaa tgaggaaact   1500
caaatcaatg gcttctgcat cattgagaac ttcaagggct ttaccatgca gcaggctgct   1560
agtctccgga cttcagatct caggaagatg gtggacatgc tccaggattc cttcccagcc   1620
cggttcaaag ccatccactt catccaccag ccatggtact tcaccacgac ctacaatgtg   1680
gtcaagccct tcttgaagag caagctgctt gagagggtct ttgtccacgg ggatgacctt   1740
tctggttctc accaggagat cgatgagaac atcctgccct ctgacttcgg ggcacgctg    1800
cccaagtatg atggcaaggc cgttgctgag cagctctttg gccccaggc caagctgag    1860
aacacagcct tctgaggatc gtaccggtcg acctgcagaa gcttgcctcg agcagcgctg   1920
ctcgagagat ctggatcata atcagccata ccacatttgt agaggtttta cttgctttaa   1980
aaaacctccc acacctcccc ctgaacctga aacataaaat gaatgcaatt gttgttgtta   2040
acttgtttat tgcagcttat aatggttaca aataaagcaa tagcatcaca aatttcacaa   2100
ataaagcatt tttttcactg cattctagtt gtggtttgtc caaactcatc aatgtatctt   2160
atcatgtctg gtaaccacgt gcggaccgag cggccgcagg aaccccctagt gatggagttg   2220
gccactccct ctctgcgcgc tcgctcgctc actgaggccg ggcgaccaaa ggtcgcccga   2280
cgcccgggct tgcccgggc ggcctcagtg agcgagcgag cgcgcag                  2327
```

<210> SEQ ID NO 62
<211> LENGTH: 236
<212> TYPE: DNA
<213> ORGANISM: Simian virus 40

<400> SEQUENCE: 62

```
agacatgata agatacattg atgagtttgg acaaaccaca actagaatgc agtgaaaaaa    60
atgctttatt tgtgaaattt gtgatgctat tgctttattt gtaaccatta taagctgcaa   120
taaacaagtt aacaacaaca attgcattca ttttatgttt caggttcagg gggaggtgtg   180
ggaggttttt taaagcaagt aaaacctcta caaatgtggt atggctgatt atgatc       236
```

<210> SEQ ID NO 63
<211> LENGTH: 954
<212> TYPE: DNA
<213> ORGANISM: Homo sapiens

<400> SEQUENCE: 63

```
tcagaaggct gtgttctcag cttgggcctg ggggccaaag agctgctcag caacggcctt    60
gccatcatac ttgggcagcg tgcccccgaa gtcagagggc aggatgttct catcgatctc   120
ctggtagaaa ccagaaaggt catccccgtg acaaagacc ctctcaagca gcttgctctt   180
caagaagggc ttgaccacat tgtaggtcgt ggtgaagtac catggctggt ggatgaagtg   240
gatggctttg aaccgggctg ggaaggaatc ctggagcatg tccaccatct tcctgagatc   300
tgaagtccgg agactagcag cctgctgcat ggtaaagccc ttgaagttct caatgatgca   360
gaagccattg atttgagttt cctcattctc cagcagcttc tccaggatga agcaatatgc   420
ctgcaagatc tcatcaaagg tgatttcttg actttgccag ttctcaatgt tgaagagcat   480
gaccactcgg ccatacttgt cccgactaga gaggacacca gggtagccag cttcaatggt   540
gcagcggaca gcctctgggg acaggctgtc aaagagctca gggtactgca gccggaaatt   600
cacatagcct ctgagcagct cataggcacg gcccacgttg aacttccgtg cgcggatgaa   660
gcgcaggaag aagccgctgt ccttctcttg caccctctcc gccacggcca ccgccagctc   720
ctcccccgag gccgctgcg cctgcaccat ctcctgcagc tctcgcactg cctcctcccg   780
ggtctcctct ctctcgttca gctcatcctt ggccttctgc aaggtgtggc ggggcagctg   840
gctgcacggg ccaaagacag gtccatggtc cttggttgtg agctgctcca gttgggcacg   900
gagctcctgt tcctcttcag gtaccatgcg gaacgtgccc accccttctg acat          954
```

<210> SEQ ID NO 64
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64

```
ggtggc                                                                 6
```

<210> SEQ ID NO 65
<211> LENGTH: 183
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65

```
ggatcccggg gcgggtacaa ttccgcagct tttagagcag aagtaacact tccgtacagg    60
cctagaagta aaggcaacat ccactgagga gcagttcttt gatttgcacc accaccggat   120
ccgggacctg aaataaaaga caaaaagact aaacttacca gttaactttc tggtttttca   180
```

<210> SEQ ID NO 66
<211> LENGTH: 590
<212> TYPE: DNA
<213> ORGANISM: Homo sapiens

<400> SEQUENCE: 66

```
tcggcagctc ctccttgggg ctacctggta cctgaatgtc ctggagctct agaggttccc      60
tccgctggag gcgtggtccg gtcagcaggt tgggattagt gtgtcataag gaacttctca     120
ccgcccacag tttccgttaa atcgggctca caggaggccc tcagtggggc aaaggaagac     180
ccagagagaa aggggagagg ggagaggcct gggcctggct ggaggcgcat caaagccctc     240
ctttgtgtgc tcctgctctg gagttcctgc tcggccatgt ggaagcccgg ctgtggggct     300
gggatctggg ccagtcccat tccctctttt ctctgccctc tttctcctca agatcccggg     360
gtggggttgc tgagagagca ccccccccc cccaccacca ccaccagggt aataagaggt     420
gaagggaaat cgtaaatatg actacatcta cagtggcagc tctggcaaat ccaggcctat     480
tgcccacccc tccccagcc agcaggacct ggcatggtag ttttcacctc tgcagtgagt     540
ggggtcagtt gagaaatgtg gctggttaag gccaagcagg gagaggacaa                590
```

<210> SEQ ID NO 67
<211> LENGTH: 720
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 67

```
ttacttgtac agctcgtcca tgccgagagt gatcccggcg gcggtcacga actccagcag      60
gaccatgtga tcgcgcttct cgttggggtc tttgctcagg gcggactggg tgctcaggta     120
gtggttgtcg ggcagcagca cggggccgtc gccgatgggg tgttctgct ggtagtggtc     180
ggcgagctgc acgctgccgt cctcgatgtt gtggcggatc ttgaagttca ccttgatgcc     240
gttcttctgc ttgtcggcca tgatatagac gttgtggctg ttgtagttgt actccagctt     300
gtgccccagg atgttgccgt cctccttgaa gtcgatgccc ttcagctcga tgcggttcac     360
cagggtgtcg ccctcgaact tcacctcggc gcggtcttg tagttgccgt cgtccttgaa     420
gaagatggtg cgctcctgga cgtagccttc gggcatggcg gacttgaaga agtcgtgctg     480
cttcatgtgt tcggggtagc ggctgaagca ctgcacgccg taggtcaggg tggtcacgag     540
ggtgggccag ggcacgggca gcttgccggt ggtgcagatg aacttcaggg tcagcttgcc     600
gtaggtggca tcgccctcgc cctcgccgga cacgctgaac ttgtggccgt ttacgtcgcc     660
gtccagctcg accaggatgg gcaccacccc ggtgaacagc tcctcgccct tgctcaccat     720
```

<210> SEQ ID NO 68
<211> LENGTH: 598
<212> TYPE: PRT
<213> ORGANISM: Adeno-associated virus

<400> SEQUENCE: 68

Met Ala Pro Gly Lys Lys Arg Pro Val Glu His Ser Pro Val Glu Pro
1               5                   10                  15

Asp Ser Ser Gly Thr Gly Lys Ala Gly Gln Gln Pro Ala Arg Lys
            20                  25                  30

```
Arg Leu Asn Phe Gly Gln Thr Gly Asp Ala Asp Ser Val Pro Asp Pro
     35                  40                  45

Gln Pro Leu Gly Gln Pro Pro Ala Ala Pro Ser Gly Leu Gly Thr Asn
 50                  55                  60

Thr Met Ala Thr Gly Ser Gly Ala Pro Met Ala Asp Asn Asn Glu Gly
 65                  70                  75                  80

Ala Asp Gly Val Gly Asn Ser Ser Gly Asn Trp His Cys Asp Ser Thr
                 85                  90                  95

Trp Met Gly Asp Arg Val Ile Thr Thr Ser Thr Arg Thr Trp Ala Leu
                100                 105                 110

Pro Thr Tyr Asn Asn His Leu Tyr Lys Gln Ile Ser Ser Gln Ser Gly
             115                 120                 125

Ala Ser Asn Asp Asn His Tyr Phe Gly Tyr Ser Thr Pro Trp Gly Tyr
 130                 135                 140

Phe Asp Phe Asn Arg Phe His Cys His Phe Ser Pro Arg Asp Trp Gln
145                 150                 155                 160

Arg Leu Ile Asn Asn Asn Trp Gly Phe Arg Pro Lys Arg Leu Asn Phe
                165                 170                 175

Lys Leu Phe Asn Ile Gln Val Lys Glu Val Thr Gln Asn Asp Gly Thr
            180                 185                 190

Thr Thr Ile Ala Asn Asn Leu Thr Ser Thr Val Gln Val Phe Thr Asp
        195                 200                 205

Ser Glu Tyr Gln Leu Pro Tyr Val Leu Gly Ser Ala His Gln Gly Cys
    210                 215                 220

Leu Pro Pro Phe Pro Ala Asp Val Phe Met Val Pro Gln Tyr Gly Tyr
225                 230                 235                 240

Leu Thr Leu Asn Asn Gly Ser Gln Ala Val Gly Arg Ser Ser Phe Tyr
                245                 250                 255

Cys Leu Glu Tyr Phe Pro Ser Gln Met Leu Arg Thr Gly Asn Asn Phe
            260                 265                 270

Thr Phe Ser Tyr Thr Phe Glu Asp Val Pro Phe His Ser Ser Tyr Ala
        275                 280                 285

His Ser Gln Ser Leu Asp Arg Leu Met Asn Pro Leu Ile Asp Gln Tyr
    290                 295                 300

Leu Tyr Tyr Leu Ser Arg Thr Asn Thr Pro Ser Gly Thr Thr Thr Gln
305                 310                 315                 320

Ser Arg Leu Gln Phe Ser Gln Ala Gly Ala Ser Asp Ile Arg Asp Gln
                325                 330                 335

Ser Arg Asn Trp Leu Pro Gly Pro Cys Tyr Arg Gln Gln Arg Val Ser
            340                 345                 350

Lys Thr Ser Ala Asp Asn Asn Asn Ser Glu Tyr Ser Trp Thr Gly Ala
        355                 360                 365

Thr Lys Tyr His Leu Asn Gly Arg Asp Ser Leu Val Asn Pro Gly Pro
    370                 375                 380

Ala Met Ala Ser His Lys Asp Asp Glu Glu Lys Phe Phe Pro Gln Ser
385                 390                 395                 400

Gly Val Leu Ile Phe Gly Lys Gln Gly Ser Glu Lys Thr Asn Val Asp
                405                 410                 415

Ile Glu Lys Val Met Ile Thr Asp Glu Glu Ile Arg Thr Thr Asn
            420                 425                 430

Pro Val Ala Thr Glu Gln Tyr Gly Ser Val Ser Thr Asn Leu Gln Arg
        435                 440                 445

Gly Asn Arg Gln Ala Ala Thr Ala Asp Val Asn Thr Gln Gly Val Leu
```

```
            450                 455                 460
Pro Gly Met Val Trp Gln Asp Arg Asp Val Tyr Leu Gln Gly Pro Ile
465                 470                 475                 480

Trp Ala Lys Ile Pro His Thr Asp Gly His Phe His Pro Ser Pro Leu
                485                 490                 495

Met Gly Gly Phe Gly Leu Lys His Pro Pro Gln Ile Leu Ile Lys
                500                 505                 510

Asn Thr Pro Val Pro Ala Asn Pro Ser Thr Thr Phe Ser Ala Ala Lys
            515                 520                 525

Phe Ala Ser Phe Ile Thr Gln Tyr Ser Thr Gly Gln Val Ser Val Glu
        530                 535                 540

Ile Glu Trp Glu Leu Gln Lys Glu Asn Ser Lys Arg Trp Asn Pro Glu
545                 550                 555                 560

Ile Gln Tyr Thr Ser Asn Tyr Asn Lys Ser Val Asn Val Asp Phe Thr
                565                 570                 575

Val Asp Thr Asn Gly Val Tyr Ser Glu Pro Arg Pro Ile Gly Thr Arg
            580                 585                 590

Tyr Leu Thr Arg Asn Leu
        595

<210> SEQ ID NO 69
<211> LENGTH: 533
<212> TYPE: PRT
<213> ORGANISM: Adeno-associated virus

<400> SEQUENCE: 69

Met Ala Thr Gly Ser Gly Ala Pro Met Ala Asp Asn Asn Glu Gly Ala
1               5                   10                  15

Asp Gly Val Gly Asn Ser Ser Gly Asn Trp His Cys Asp Ser Thr Trp
            20                  25                  30

Met Gly Asp Arg Val Ile Thr Thr Ser Thr Arg Thr Trp Ala Leu Pro
        35                  40                  45

Thr Tyr Asn Asn His Leu Tyr Lys Gln Ile Ser Ser Gln Ser Gly Ala
    50                  55                  60

Ser Asn Asp Asn His Tyr Phe Gly Tyr Ser Thr Pro Trp Gly Tyr Phe
65                  70                  75                  80

Asp Phe Asn Arg Phe His Cys His Phe Ser Pro Arg Asp Trp Gln Arg
                85                  90                  95

Leu Ile Asn Asn Asn Trp Gly Phe Arg Pro Lys Arg Leu Asn Phe Lys
            100                 105                 110

Leu Phe Asn Ile Gln Val Lys Glu Val Thr Gln Asn Asp Gly Thr Thr
        115                 120                 125

Thr Ile Ala Asn Asn Leu Thr Ser Thr Val Gln Val Phe Thr Asp Ser
    130                 135                 140

Glu Tyr Gln Leu Pro Tyr Val Leu Gly Ser Ala His Gln Gly Cys Leu
145                 150                 155                 160

Pro Pro Phe Pro Ala Asp Val Phe Met Val Pro Gln Tyr Gly Tyr Leu
                165                 170                 175

Thr Leu Asn Asn Gly Ser Gln Ala Val Gly Arg Ser Ser Phe Tyr Cys
            180                 185                 190

Leu Glu Tyr Phe Pro Ser Gln Met Leu Arg Thr Gly Asn Asn Phe Thr
        195                 200                 205

Phe Ser Tyr Thr Phe Glu Asp Val Pro Phe His Ser Ser Tyr Ala His
    210                 215                 220
```

```
Ser Gln Ser Leu Asp Arg Leu Met Asn Pro Leu Ile Asp Gln Tyr Leu
225                 230                 235                 240

Tyr Tyr Leu Ser Arg Thr Asn Thr Pro Ser Gly Thr Thr Thr Gln Ser
            245                 250                 255

Arg Leu Gln Phe Ser Gln Ala Gly Ala Ser Asp Ile Arg Asp Gln Ser
        260                 265                 270

Arg Asn Trp Leu Pro Gly Pro Cys Tyr Arg Gln Gln Arg Val Ser Lys
    275                 280                 285

Thr Ser Ala Asp Asn Asn Ser Glu Tyr Ser Trp Thr Gly Ala Thr
290                 295                 300

Lys Tyr His Leu Asn Gly Arg Asp Ser Leu Val Asn Pro Gly Pro Ala
305                 310                 315                 320

Met Ala Ser His Lys Asp Asp Glu Glu Lys Phe Phe Pro Gln Ser Gly
                325                 330                 335

Val Leu Ile Phe Gly Lys Gln Gly Ser Glu Lys Thr Asn Val Asp Ile
            340                 345                 350

Glu Lys Val Met Ile Thr Asp Glu Glu Ile Arg Thr Thr Asn Pro
        355                 360                 365

Val Ala Thr Glu Gln Tyr Gly Ser Val Ser Thr Asn Leu Gln Arg Gly
370                 375                 380

Asn Arg Gln Ala Ala Thr Ala Asp Val Asn Thr Gln Gly Val Leu Pro
385                 390                 395                 400

Gly Met Val Trp Gln Asp Arg Asp Val Tyr Leu Gln Gly Pro Ile Trp
                405                 410                 415

Ala Lys Ile Pro His Thr Asp Gly His Phe His Pro Ser Pro Leu Met
            420                 425                 430

Gly Gly Phe Gly Leu Lys His Pro Pro Gln Ile Leu Ile Lys Asn
        435                 440                 445

Thr Pro Val Pro Ala Asn Pro Ser Thr Thr Phe Ser Ala Ala Lys Phe
450                 455                 460

Ala Ser Phe Ile Thr Gln Tyr Ser Thr Gly Gln Val Ser Val Glu Ile
465                 470                 475                 480

Glu Trp Glu Leu Gln Lys Glu Asn Ser Lys Arg Trp Asn Pro Glu Ile
                485                 490                 495

Gln Tyr Thr Ser Asn Tyr Asn Lys Ser Val Asn Val Asp Phe Thr Val
            500                 505                 510

Asp Thr Asn Gly Val Tyr Ser Glu Pro Arg Pro Ile Gly Thr Arg Tyr
        515                 520                 525

Leu Thr Arg Asn Leu
530

<210> SEQ ID NO 70
<211> LENGTH: 601
<212> TYPE: PRT
<213> ORGANISM: Adeno-associated virus

<400> SEQUENCE: 70

Met Ala Pro Gly Lys Lys Arg Pro Val Glu Pro Ser Pro Gln Arg Ser
1               5                   10                  15

Pro Asp Ser Ser Thr Gly Ile Gly Lys Lys Gly Gln Gln Pro Ala Arg
            20                  25                  30

Lys Arg Leu Asn Phe Gly Gln Thr Gly Asp Ser Glu Ser Val Pro Asp
        35                  40                  45

Pro Gln Pro Leu Gly Glu Pro Pro Ala Ala Pro Ser Gly Val Gly Pro
    50                  55                  60
```

```
Asn Thr Met Ala Ala Gly Gly Ala Pro Met Ala Asp Asn Asn Glu
 65                  70                  75                  80

Gly Ala Asp Gly Val Gly Ser Ser Ser Gly Asn Trp His Cys Asp Ser
             85                  90                  95

Thr Trp Leu Gly Asp Arg Val Ile Thr Thr Ser Thr Arg Thr Trp Ala
            100                 105                 110

Leu Pro Thr Tyr Asn Asn His Leu Tyr Lys Gln Ile Ser Asn Gly Thr
            115                 120                 125

Ser Gly Gly Ala Thr Asn Asp Asn Thr Tyr Phe Gly Tyr Ser Thr Pro
            130                 135                 140

Trp Gly Tyr Phe Asp Phe Asn Arg Phe His Cys His Phe Ser Pro Arg
145                 150                 155                 160

Asp Trp Gln Arg Leu Ile Asn Asn Asn Trp Gly Phe Arg Pro Lys Arg
                165                 170                 175

Leu Ser Phe Lys Leu Phe Asn Ile Gln Val Lys Glu Val Thr Gln Asn
                180                 185                 190

Glu Gly Thr Lys Thr Ile Ala Asn Asn Leu Thr Ser Thr Ile Gln Val
            195                 200                 205

Phe Thr Asp Ser Glu Tyr Gln Leu Pro Tyr Val Leu Gly Ser Ala His
210                 215                 220

Gln Gly Cys Leu Pro Pro Phe Pro Ala Asp Val Phe Met Ile Pro Gln
225                 230                 235                 240

Tyr Gly Tyr Leu Thr Leu Asn Asn Gly Ser Gln Ala Val Gly Arg Ser
                245                 250                 255

Ser Phe Tyr Cys Leu Glu Tyr Phe Pro Ser Gln Met Leu Arg Thr Gly
                260                 265                 270

Asn Asn Phe Gln Phe Thr Tyr Thr Phe Glu Asp Val Pro Phe His Ser
                275                 280                 285

Ser Tyr Ala His Ser Gln Ser Leu Asp Arg Leu Met Asn Pro Leu Ile
            290                 295                 300

Asp Gln Tyr Leu Tyr Tyr Leu Ser Arg Thr Gln Thr Thr Gly Gly Thr
305                 310                 315                 320

Ala Asn Thr Gln Thr Leu Gly Phe Ser Gln Gly Gly Pro Asn Thr Met
                325                 330                 335

Ala Asn Gln Ala Lys Asn Trp Leu Pro Gly Pro Cys Tyr Arg Gln Gln
            340                 345                 350

Arg Val Ser Thr Thr Thr Gly Gln Asn Asn Asn Ser Asn Phe Ala Trp
            355                 360                 365

Thr Ala Gly Thr Lys Tyr His Leu Asn Gly Arg Asn Ser Leu Ala Asn
            370                 375                 380

Pro Gly Ile Ala Met Ala Thr His Lys Asp Asp Glu Glu Arg Phe Phe
385                 390                 395                 400

Pro Ser Asn Gly Ile Leu Ile Phe Gly Lys Gln Asn Ala Ala Arg Asp
                405                 410                 415

Asn Ala Asp Tyr Ser Asp Val Met Leu Thr Ser Glu Glu Ile Lys
            420                 425                 430

Thr Thr Asn Pro Val Ala Thr Glu Glu Tyr Gly Ile Val Ala Asp Asn
            435                 440                 445

Leu Gln Gln Gln Asn Thr Ala Pro Gln Ile Gly Thr Val Asn Ser Gln
            450                 455                 460

Gly Ala Leu Pro Gly Met Val Trp Gln Asn Arg Asp Val Tyr Leu Gln
465                 470                 475                 480
```

```
Gly Pro Ile Trp Ala Lys Ile Pro His Thr Asp Gly Asn Phe His Pro
                485                 490                 495

Ser Pro Leu Met Gly Gly Phe Gly Leu Lys His Pro Pro Gln Ile
        500                 505                 510

Leu Ile Lys Asn Thr Pro Val Pro Ala Asp Pro Pro Thr Thr Phe Asn
            515                 520                 525

Gln Ser Lys Leu Asn Ser Phe Ile Thr Gln Tyr Ser Thr Gly Gln Val
        530                 535                 540

Ser Val Glu Ile Glu Trp Glu Leu Gln Lys Glu Asn Ser Lys Arg Trp
545                 550                 555                 560

Asn Pro Glu Ile Gln Tyr Thr Ser Asn Tyr Tyr Lys Ser Thr Ser Val
                565                 570                 575

Asp Phe Ala Val Asn Thr Glu Gly Val Tyr Ser Glu Pro Arg Pro Ile
            580                 585                 590

Gly Thr Arg Tyr Leu Thr Arg Asn Leu
        595                 600

<210> SEQ ID NO 71
<211> LENGTH: 535
<212> TYPE: PRT
<213> ORGANISM: Adeno-associated virus

<400> SEQUENCE: 71

Met Ala Ala Gly Gly Ala Pro Met Ala Asp Asn Asn Glu Gly Ala
1               5                   10                  15

Asp Gly Val Gly Ser Ser Ser Gly Asn Trp His Cys Asp Ser Thr Trp
            20                  25                  30

Leu Gly Asp Arg Val Ile Thr Thr Ser Thr Arg Thr Trp Ala Leu Pro
        35                  40                  45

Thr Tyr Asn Asn His Leu Tyr Lys Gln Ile Ser Asn Gly Thr Ser Gly
    50                  55                  60

Gly Ala Thr Asn Asp Asn Thr Tyr Phe Gly Tyr Ser Thr Pro Trp Gly
65                  70                  75                  80

Tyr Phe Asp Phe Asn Arg Phe His Cys His Phe Ser Pro Arg Asp Trp
                85                  90                  95

Gln Arg Leu Ile Asn Asn Asn Trp Gly Phe Arg Pro Lys Arg Leu Ser
            100                 105                 110

Phe Lys Leu Phe Asn Ile Gln Val Lys Glu Val Thr Gln Asn Glu Gly
        115                 120                 125

Thr Lys Thr Ile Ala Asn Asn Leu Thr Ser Thr Ile Gln Val Phe Thr
    130                 135                 140

Asp Ser Glu Tyr Gln Leu Pro Tyr Val Leu Gly Ser Ala His Gln Gly
145                 150                 155                 160

Cys Leu Pro Pro Phe Pro Ala Asp Val Phe Met Ile Pro Gln Tyr Gly
                165                 170                 175

Tyr Leu Thr Leu Asn Asn Gly Ser Gln Ala Val Gly Arg Ser Ser Phe
            180                 185                 190

Tyr Cys Leu Glu Tyr Phe Pro Ser Gln Met Leu Arg Thr Gly Asn Asn
        195                 200                 205

Phe Gln Phe Thr Tyr Thr Phe Glu Asp Val Pro Phe His Ser Ser Tyr
    210                 215                 220

Ala His Ser Gln Ser Leu Asp Arg Leu Met Asn Pro Leu Ile Asp Gln
225                 230                 235                 240

Tyr Leu Tyr Tyr Leu Ser Arg Thr Gln Thr Thr Gly Gly Thr Ala Asn
                245                 250                 255
```

```
Thr Gln Thr Leu Gly Phe Ser Gln Gly Gly Pro Asn Thr Met Ala Asn
            260             265             270
Gln Ala Lys Asn Trp Leu Pro Gly Pro Cys Tyr Arg Gln Gln Arg Val
        275             280             285
Ser Thr Thr Thr Gly Gln Asn Asn Asn Ser Asn Phe Ala Trp Thr Ala
    290             295             300
Gly Thr Lys Tyr His Leu Asn Gly Arg Asn Ser Leu Ala Asn Pro Gly
305             310             315             320
Ile Ala Met Ala Thr His Lys Asp Asp Glu Glu Arg Phe Phe Pro Ser
                325             330             335
Asn Gly Ile Leu Ile Phe Gly Lys Gln Asn Ala Ala Arg Asp Asn Ala
            340             345             350
Asp Tyr Ser Asp Val Met Leu Thr Ser Glu Glu Glu Ile Lys Thr Thr
            355             360             365
Asn Pro Val Ala Thr Glu Glu Tyr Gly Ile Val Ala Asp Asn Leu Gln
    370             375             380
Gln Gln Asn Thr Ala Pro Gln Ile Gly Thr Val Asn Ser Gln Gly Ala
385             390             395             400
Leu Pro Gly Met Val Trp Gln Asn Arg Asp Val Tyr Leu Gln Gly Pro
                405             410             415
Ile Trp Ala Lys Ile Pro His Thr Asp Gly Asn Phe His Pro Ser Pro
            420             425             430
Leu Met Gly Gly Phe Gly Leu Lys His Pro Pro Pro Gln Ile Leu Ile
            435             440             445
Lys Asn Thr Pro Val Pro Ala Asp Pro Pro Thr Thr Phe Asn Gln Ser
    450             455             460
Lys Leu Asn Ser Phe Ile Thr Gln Tyr Ser Thr Gly Gln Val Ser Val
465             470             475             480
Glu Ile Glu Trp Glu Leu Gln Lys Glu Asn Ser Lys Arg Trp Asn Pro
                485             490             495
Glu Ile Gln Tyr Thr Ser Asn Tyr Tyr Lys Ser Thr Ser Val Asp Phe
            500             505             510
Ala Val Asn Thr Glu Gly Val Tyr Ser Glu Pro Arg Pro Ile Gly Thr
        515             520             525
Arg Tyr Leu Thr Arg Asn Leu
530             535
```

VIRAL VECTORS FOR THE TREATMENT OF RETINAL DYSTROPHY

RELATED APPLICATIONS

This application claims priority to U.S. Provisional Application No. 61/642,630 filed May 4, 2012 and U.S. Provisional Application No. 61/776,167 filed Mar. 11, 2013, the contents of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Aug. 16, 2013 is named PAT055109-US-NP_SL.txt and is 253,289 bytes in size.

BACKGROUND OF THE INVENTION

Retinitis pigmentosa (RP) refers to a group of inherited degenerations of the photoreceptor cells (rods and cones) of the retina leading to visual loss and blindness. Mutations in any of a wide variety of genes can cause RP, including genes encoding proteins that are involved in phototransduction (the process by which the energy of a photon of light is converted in the photoreceptor cell outer segment into a neuronal signal), the visual cycle (production and recycling of vitamin A in the retina), photoreceptor structure, and transcription factors (Phelan and Bok, 2000).

RLBP1-associated retinal dystrophy is a rare form of RP caused by mutations in the retinaldehyde binding protein 1 (RLBP1) gene on chromosome 15. Mutations in this gene cause absence of or dysfunction of cellular retinaldehyde-binding protein (CRALBP), a protein that is important in the visual cycle (He et al 2009). CRALBP is expressed in retinal pigment epithelium (RPE) and Müller cells, ciliary epithelium, iris, cornea, pineal gland and a subset of oligodendrocytes of the optic nerve and brain (Saari et al 1997). CRALBP accepts 11-cis-retinol from the isomerase RPE65 and acts as a carrier of this substrate for 11-cis-retinol dehydrogenase (RDH5) to convert the substrate into 11-cis-retinal. The rate of chromophore regeneration is severely reduced in the absence of functional CRALBP (Travis et al 2007). The function of CRALBP outside the RPE is not well understood, but it has been suggested that CRALBP in the Müller cells supports a cone-specific visual pathway that permits cone cells to quickly adapt to a wide range of light intensities (Wang and Kefalov 2011).

RLBP1-associated retinal dystrophy is characterized by early severe night blindness and slow dark adaptation, followed by progressive loss of visual acuity, visual fields and color vision leading to legal blindness typically around middle adulthood. The fundus appearance is characterized by yellow or white spots in the retina. The reduction in visual acuity and visual field significantly impacts patients' quality of life (Burstedt and Mönestam, 2010).

The most common RLBP1 mutations leading to RLBP1-associated retinal dystrophy are recessive mutations, designated R234W and M226K (Golovleva I and Burstedt M 2012). RLBP1-associated retinal dystrophy caused by 1 or both of these recessive missense mutations is also known as Bothnia Dystrophy. Several other loss-of-function mutations in the RLBP1 gene have been reported to lead to RLBP1-associated retinal dystrophy. For example, splice-junction mutations in RLBP1 cause rod-cone dystrophy in Newfoundland. Currently there is no treatment available for RLBP1-associated retinal dystrophy (Eichers et al 2002).

The present invention is based in part on the discovery that expression of RLBP1 from recombinant adeno-associated viral vectors (rAAV) having a combination of selected promoter, AAV genome and capsid serotype provides a potent and efficacious treatment for RLBP1-associated retinal dystrophy.

SUMMARY OF THE INVENTION

The present invention relates generally to recombinant viral vectors and methods of using recombinant viral vectors to express proteins in the retina of subjects suffering from retinal diseases and blindness.

The present invention relates to viral vectors that are capable of delivering a heterologous gene to the retina. The present invention also relates to viral vectors that are capable of directing a heterologous gene to RPE and Müller cells of the retina. The present invention further relates to viral vectors that are recombinant adeno-associated viral vectors (rAAV). In certain embodiments the rAAV viral vector may be selected from among any AAV serotype known in the art, including, without limitation, AAV1-AAV12. In certain embodiments, the rAAV vector capsid is an AAV2 serotype. In certain other embodiments, the rAAV vector capsid is an AAV8 serotype.

The invention relates, in part, to viral vectors carrying a single stranded vector genome. In the single stranded viral vector, the vector genome can include a 5' ITR, a recombinant nucleotide sequence comprising an RLBP1 coding sequence, and a 3' ITR. The recombinant nucleic acid sequence of the vector genome can also include a promoter as described herein. In one aspect, the promoter is an RLBP1 (long) promoter (SEQ ID NO: 10), in another aspect the promoter is an RLBP1 (short) promoter (SEQ ID NO: 3). In certain specific aspects of the invention, the vector genome comprises, in the 5' to 3' direction, nucleic acid sequences selected from: a) SEQ ID NO: 2, 10, 5, 6, 8, and 9; b) SEQ ID NO: 2, 11, 5, 6, 8, 14, 9; c) SEQ ID NO: 2, 22, 5, 6, 8, 23, and 9; and d) SEQ ID NO: 2, 3, 4, 5, 6, 8, 23, and 9.

The invention also relates, in part, to viral vectors carrying a self-complementary genome. The self-complementary vector genome can include, from 5' to 3', a 5' ITR, a first recombinant nucleotide sequence, a non-resolvable ITR (e.g.: ΔITR), a second recombinant nucleotide sequence, and a 3' ITR, wherein the first and second recombinant nucleotide sequences are self-complementary. The second recombinant nucleotide sequence comprises in the 5' to 3' direction, a promoter, an RLBP1 coding sequence and an SV40 polyA sequence. The promoter can be an RLBP1 promoter and, further, can be the RLBP1 (short) promoter (SEQ ID NO: 3). In certain aspects of the invention, the second recombinant nucleotide sequence comprises nucleic acid sequences in the 5' to 3' direction of SEQ ID NO: 3, 4, 5, 6, and 8 and the first recombinant nucleotide sequence comprises sequences that are self-complementary to, or the reverse complement of, the second recombinant sequence, for example, SEQ ID NOs: 62, 63, 64, 65, and 66. The invention also relates to a viral vector comprising a self-complementary vector genome wherein the genome comprises, nucleic acid sequences in the 5' to 3' direction of: SEQ ID NOs: 36, 62, 63, 64, 65, 66, 1, 3, 4, 5, 6, 8, and 9. The self-complementary vector genome described above can be packaged in an AAV capsid that is selected from any AAV serotype known in the art, including but not limited to AAV1-12. In one aspect, the self-complementary genome is packaged in an AAV8 capsid. In another aspect, the self-complementary genome is packaged in an AAV2 capsid.

The present invention also relates to a viral vector capable of directing expression of a heterologous gene to RPE and Müller cells of the retina. It is contemplated that the viral vector capsid is an AAV2 or an AAV8 serotype capsid and that the viral vector comprises a vector genome, wherein the heterologous gene is operably linked to an RLBP1 promoter. It is further contemplated that the RLBP1 promoter is the RLBP1 (short) promoter (SEQ ID NO: 3) or the RLBP1 (long) promoter (SEQ ID NO: 10). In another aspect of the invention it is contemplated that the heterologous gene to be expressed in RPE and Müller cells is an RLBP1 coding sequence having for example, the sequence of SEQ ID NO: 6.

The present invention also relates to a viral vector capable of directing expression of a heterologous gene to RPE and Müller cells of the retina, wherein the viral vector capsid is an AAV8 serotype capsid and that the viral vector comprises a self-complementary vector genome wherein a heterologous gene is operably linked to an RLBP1 promoter. It is further contemplated that the RLBP1 promoter is the RLBP1 (short) promoter (SEQ ID NO: 3). In another aspect of the invention it is contemplated that the heterologous gene to be expressed in RPE and Müller cells is an RLBP1 coding sequence having for example, the sequence of SEQ ID NO: 6.

The invention also relates to a composition comprising a viral vector described herein, as well as viral vector compositions in combination with a pharmaceutically acceptable carrier. Specifically, the invention further relates to compositions comprising the viral vectors as described in Table 4. The invention still further relates to compositions comprising viral vectors that can be generated using the plasmids described in Table 2, in conjunction with rAAV production methods known in the art and described herein. The compositions described herein are useful for treating a subject having RLBP1 associated retinal dystrophy and/or improving the rate of dark adaption in a subject having RLBP1-associated retinal dystrophy.

The present invention also relates to nucleic acids that can be used, with the rAAV production methods known in the art and described herein, for the generation of the viral vectors described herein. The invention relates to nucleic acids comprising a gene cassette, wherein the gene cassette comprises, in the 5' to 3' direction: (i) a 5' ITR or a non-resolvable ITR, (ii) a recombinant nucleotide sequence comprising an RLBP1 coding sequence, and (iii) a 3' ITR. It is contemplated that the nucleic acid may comprise a gene cassette comprising a nucleic acid sequence selected from SEQ ID NOs: 51, 52, 53, 54, and 55. It is contemplated that the nucleic acids of the invention may be plasmids. It is further contemplated that the nucleic acid may be a plasmid comprising a nucleic acid sequence selected from SEQ ID NOs: 26, 27, 28, 29, 30 and 50.

In certain specific aspects of the invention, the nucleic acid can comprise a gene cassette comprising sequences in the 5' to 3' direction that are selected from: a) a) SEQ ID NO: 2, 10, 5, 6, 8, and 9, b) SEQ ID NO: 2, 11, 5, 6, 8, 14 and 9, c) SEQ ID NO: 2, 22, 5, 6, 8, 23 and 9, d) SEQ ID NO: 2, 3, 4, 5, 6, 8, 23 and 9, or e) SEQ ID NO: 1, 3, 4, 5, 6, 8, and 9.

The invention also relates to nucleic acids comprising a gene cassette, wherein the gene cassette comprises, in the 5' to 3' direction: (i) a 5' ITR, (ii) a recombinant nucleotide sequence comprising a promoter operably linked to reporter gene, and (iii) a 3' ITR. It is contemplated that the nucleic acid may comprise a gene cassette comprising a nucleic acid sequence selected from SEQ ID NOs: 56, 57, 59 and 60. It is further contemplated that nucleic acid may be a plasmid comprising a nucleic acid sequence selected from SEQ ID NOs: 31, 32, 34 and 35.

The invention also relates to methods of treating a subject having RLBP1-associated retinal dystrophy wherein the method comprises administering to a subject in need thereof, a composition comprising a viral vector as described herein.

The invention also relates to a method of improving the rate of dark adaption in a subject having RLBP1-associated retinal dystrophy, wherein the method comprises administering to a subject in need thereof, a composition comprising a viral vector as described herein.

The invention still further relates to a method of directing expression of an RLBP1 coding sequence in RPE and Müller cells in the retina of a subject having RLBP1-associated retinal dystrophy, wherein the method comprises the step of contacting the retina of the subject, with a viral vector comprising an AAV8 or AAV2 serotype capsid and a vector genome comprising an RLBP1 coding sequence operably linked to an RLBP1 promoter, such as, for example, the RLBP1(short) (SEQ ID NO: 3) or RLBP1(long) (SEQ ID NO: 10) promoters as described herein.

The invention still further relates to a method of delivering an RLBP1 coding sequence in RPE and Müller cells in the retina of a subject having RLBP1-associated retinal dystrophy, wherein the method comprises the step of contacting the retina of the subject, with a viral vector comprising an AAV8 or AAV2 serotype capsid and a vector genome comprising an RLBP1 coding sequence operably linked to an RLBP1 promoter, such as, for example, the RLBP1(short) (SEQ ID NO: 3) or RLBP1(long) (SEQ ID NO: 10) promoters as described herein.

The invention also includes a viral vector as described in Table 1, or 4, as well as a plasmid described in Table 2.

DEFINITIONS

Unless defined otherwise, all technical and scientific terms used herein have the same meaning as commonly understood by those of ordinary skill in the art to which this invention pertains.

The term "capsid" refers to the protein coat of the virus or viral vector. The term "AAV capsid" refers to the protein coat of the adeno-associated virus (AAV), which is composed of a total of 60 subunits; each subunit is an amino acid sequence, which can be viral protein 1(VP1), VP2 or VP3 (Muzyczka N and Berns K I 2001).

The term "gene cassette" refers to a manipulatable fragment of DNA carrying, and capable of expressing, one or more genes, or coding sequences, of interest between one or more sets of restriction sites. A gene cassette can be transferred from one DNA sequence (often in a plasmid vector) to another by 'cutting' the fragment out using restriction enzymes and ligating it back into a new context, for example into a new plasmid backbone.

The term "heterologous gene" or "heterologous nucleotide sequence" will typically refer to a gene or nucleotide sequence that is not naturally-occurring in the virus. Alternatively, a heterologous gene or nucleotide sequence may refer to a viral sequence that is placed into a non-naturally occurring environment (e.g.: by association with a promoter with which it is not naturally associated in the virus).

The terms "ITR" or "inverted terminal repeat" refer to the stretch of nucleic acid sequences that exist in Adeno-Associated Viruses (AAV) and/or recombinant Adeno-Associated Viral Vectors (rAAV) that can form a T-shaped palindromic structure, that is required for completing AAV lytic and latent life cycles (Muzyczka N and Berns K I 2001). The term "non-resolvable ITR" refers to a modified ITR such that the resolution by the Rep protein is reduced. A non-resolvable ITR can be an ITR sequence without the terminal resolution site (TRS) which leads to low or no resolution of the non-resolvable ITR and would yield 90-95% of self-complementary AAV vectors (McCarty et al 2003). A specific example of a non-resolvable ITR is "ΔITR", having a sequence of SEQ ID NO: 1.

The term "operably linked" refers to a functional relationship between two or more polynucleotide (e.g., DNA) segments. Typically, the term refers to the functional relationship of a transcriptional regulatory sequence to a sequence to be transcribed. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribable sequence are contiguous to the transcribable sequence, i.e., they are cis-acting. However, some transcriptional regulatory sequences, such as enhancers, need not be physically contiguous or located in close proximity to the coding sequences whose transcription they enhance.

The term "promoter" refers to a sequence that regulates transcription of an operably-linked gene, or nucleotide sequence encoding a protein, etc. Promoters provide the sequence sufficient to direct transcription, as well as, the recognition sites for RNA polymerase and other transcription factors required for efficient transcription and can direct cell specific expression. In addition to the sequence sufficient to direct transcription, a promoter sequence of the invention can also include sequences of other regulatory elements that are involved in modulating transcription (e.g.: enhancers, kozak sequences and introns). Examples of promoters known in the art and useful in the viral vectors described herein, include the CMV promoter, CBA promoter, smCBA promoter and those promoters derived from an immunoglobulin gene, SV40, or other tissue specific genes (e.g: RLBP1, RPE, VMD2). Specific promoters may also include those described in Table 1, for example, the "RLBP1 (short)" promoter (SEQ ID NO: 3), the "RLBP1 (long)" promoter (SEQ ID NO: 10), RPE65 promoter (SEQ ID NO: 11), VMD2 promoter (SEQ ID NO: 12), and the CMV enhancer+CBA promoter (SEQ ID NO: 22). In addition, standard techniques are known in the art for creating functional promoters by mixing and matching known regulatory elements. "Truncated promoters" may also be generated from promoter fragments or by mix and matching fragments of known regulatory elements; for example the smCBA promoter is a truncated form of the CBA promoter.

The term "RLBP1" refers to the "Retinaldehyde Binding Protein 1". The human RLBP1 gene is found on chromosome 15 and has the nucleic acid coding sequence as set out in Table 1: SEQ ID NO: 6. The "RLBP1 gene product" is also known as, "cellular retinaldehyde binding protein" or "CRALBP" and is the protein encoded by the RLBP1 gene. The human RLBP1 gene product (hCRALBP) has the amino acid sequence as set out in Table 1: SEQ ID NO: 7. Examples of RLBP1 coding sequences and RLBP1 gene products from other species can be found in Table 1 (e.g.: SEQ ID NOs: 37-48). The term "RLBP1 coding sequence" or "RLBP1 GENE CDS" or "RLBP1 CDS" refers to the nucleic acid sequence that encodes the RLBP1 gene product. One of skill in the art would understand that an RLBP1 coding sequence may include any nucleic acid sequence that encodes an RLBP1 gene product. The RLBP1 coding sequence may or may not include intervening regulatory elements (e.g.: introns, enhancers, or other non-coding sequences).

The term "subject" includes human and non-human animals. Non-human animals include all vertebrates (e.g.: mammals and non-mammals) such as, non-human primates (e.g.: cynomolgus monkey), mice, rats, sheep, dogs, cows, chickens, amphibians, and reptiles. Except when noted, the terms "patient" or "subject" are used herein interchangeably.

As used herein, the term "treating" or "treatment" of any disease or disorder (e.g., retinitis pigmentosa, RBLP1-associated retinal dystrophy) refers, to ameliorating the disease or disorder such as by slowing or arresting or reducing the development of the disease or at least one of the clinical symptoms thereof. "Treating" or "treatment" can also refer to alleviating or ameliorating at least one physical parameter including those which may not be discernible by the patient. "Treating" or "treatment" can also refer to modulating the disease or disorder, either physically, (e.g., stabilization of a discernible symptom), physiologically, (e.g., stabilization of a physical parameter), or both. More specifically, "treatment" of RLBP1-associated retinal dystrophy means any action that results in the improvement or preservation of visual function and/or regional anatomy in a subject having RLBP1-associated retinal dystrophy. "Preventing or "prevention" as used herein, refers to preventing or delaying the onset or development or progression of the disease or disorder. "Prevention" as it relates to RLBP1-associated retinal dystrophy means any action that prevents or slows a worsening in visual function, retinal anatomy, and/or an RLBP1-associated retinal dystrophy disease parameter, as described below, in a patient with RLBP1-associated retinal dystrophy and at risk for said worsening. Methods for assessing treatment and/or prevention of disease are known in the art and described herein below.

The term "virus vector" or "viral vector" is intended to refer to a non-wild-type recombinant viral particle (e.g.: a parvovirus, etc.) that functions as a gene delivery vehicle and which comprises a recombinant viral genome packaged within a viral (e.g.: AAV) capsid. A specific type of virus vector may be a "recombinant adeno-associated virus vector", or "rAAV vector". The recombinant viral genome packaged in the a viral vector is also referred to herein as the "vector genome".

DETAILED DESCRIPTION

Figure 1:
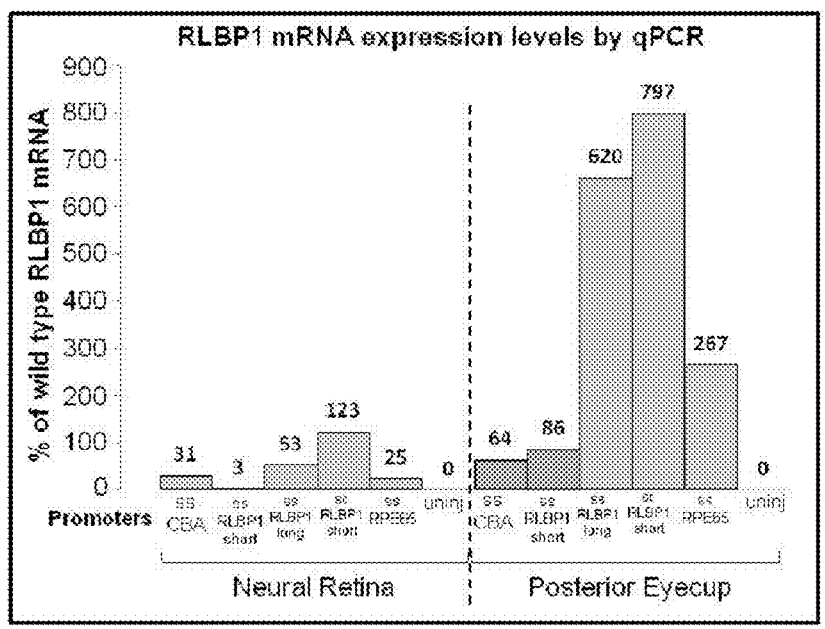
FIG. 1. Relative expression of vector-mediated human RLBP1 mRNA compared to endogenous mouse RLBP1 mRNA in eyes injected with various viral vectors at the dosage of $1 \times 10^9$ (1A) and $1 \times 10^8$ (1B) vector genome (vg) particles per eye.
Figure 1:
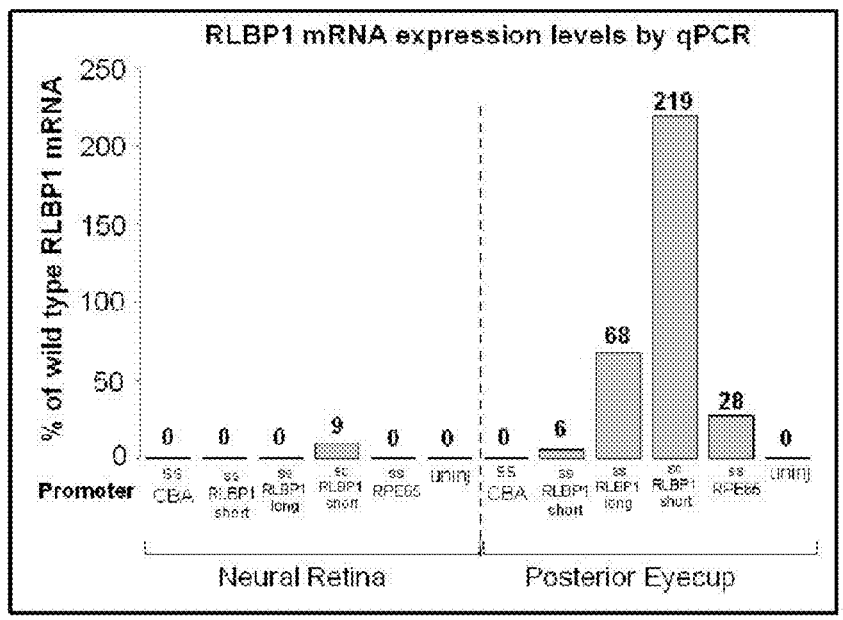

The present invention is based, in part, on the discovery of viral vectors that express a heterologous gene in RPE and Müller cells of the retina. The invention also relates both to single stranded and self-complementary viral vectors with a heterologous gene expressing the RLBP1 gene product (CRALBP).

Accordingly, the present invention provides recombinant viral vectors that direct expression of the RLBP1 coding sequence to the retina, viral vector compositions, plasmids useful for generating the viral vectors, methods of delivering an RLBP1 coding sequence to the retina, methods of expressing an RLBP1 coding sequence in RPE and Müller cells of the retina, and methods of use of such viral vectors.

Except as otherwise indicated, standard methods known to those skilled in the art may be used for the construction of recombinant parvovirus and rAAV vectors, using recombinant plasmids carrying a viral gene cassette, packaging plasmids expressing the parvovirus rep and/or cap sequences, as well as transiently and stably transfected packaging cells. Such techniques are known to those skilled in the art. (e.g.: SAMBROOK et al., MOLECULAR CLONING: A LABORATORY MANUAL 2nd Ed. (Cold Spring Harbor, N.Y., 1989); Choi V W et al. CURRENT PROTOCOLS IN MOLECULAR BIOLOGY (2007)).

1. Viral Vectors

The present invention is related to viral vectors that direct expression of a heterologous gene to the retina. In certain aspects of the invention, expression is directed to RPE and Müller cells of the retina. A variety of viral vectors known in the art may be adapted by one of skill in the art for use in the present invention, for example, recombinant adeno-associated viruses, recombinant adenoviruses, recombinant retroviruses, recombinant poxviruses, recombinant baculoviruses, etc.

In particular, it is contemplated that the viral vector of the invention may be a recombinant adeno-associated (rAAV) vector. AAVs are small, single-stranded DNA viruses which require helper virus to facilitate efficient replication (Muzyczka N and Berns K I 2001). The viral vector comprises a vector genome and a protein capsid. The viral vector capsid may be supplied from any of the AAV serotypes known in the art, including presently identified human and non-human AAV serotypes and AAV serotypes yet to be identified (See: Choi V W et al 2005, Schmidt et al 2008). Virus capsids may be mixed and matched with other vector components to form a hybrid viral vector, for example the ITRs and capsid of the viral vector may come from different AAV serotypes. In one aspect, the ITRs can be from an AAV2 serotype while the capsid is from, for example, an AAV2 or AAV8 serotype. In addition, one of skill in the art would recognize that the vector capsid may also be a mosaic capsid (e.g.: a capsid composed of a mixture of capsid proteins from different serotypes), or even a chimeric capsid (e.g.: a capsid protein containing a foreign or unrelated protein sequence for generating markers and/or altering tissue tropism). It is contemplated that the viral vector of the invention may comprise an AAV2 capsid. It is further contemplated that the invention may comprise an AAV8 capsid.

The invention relates, in part, to viral vectors wherein the vector genome is single stranded. In certain aspects, the invention is related to a single stranded vector genome comprising, in the 5' to 3' direction: (i) a 5' ITR, (ii) a recombinant nucleotide sequence comprising an RLBP1 coding sequence, and (iii) a 3' ITR. In certain aspects of the invention the recombinant nucleotide sequence comprises in the 5' to 3' direction: (i) a promoter, (ii) an RLBP1 coding sequence, and (iii) an SV40 polyA sequence. In certain aspects, the promoter may be an RLBP1 (short) promoter, an RLBP1 (long) promoter, or a truncated promoter of RLBP1. In particular, the invention relates to a single stranded vector genome comprising a recombinant nucleotide sequence comprising in the 5' to 3' direction: an RLBP1 (long) promoter (SEQ ID NO:10), an RLBP1 coding sequence, and an SV40 polyA sequence. In addition, the invention also relates to a single stranded vector genome comprising a recombinant nucleotide sequence comprising in the 5' to 3' direction: an RLBP1 (short) promoter (SEQ ID NO: 3), an RLBP1 coding sequence, and an SV40 polyA sequence. Certain aspects of the invention further relate to a single stranded vector genome comprising a recombinant nucleotide sequence packaged in an AAV2 or AAV8 capsid.

In certain aspects of the invention the viral vector comprises an AAV2 capsid (encoded by SEQ ID NO: 18) and a vector genome comprising in the 5' to 3 direction nucleotide sequences selected from the following: a) SEQ ID NO: 2, 10, 5, 6, 8, and 9; b) SEQ ID NO: 2, 11, 5, 6, 8, 14, 9; c) SEQ ID NO: 2, 22, 5, 6, 8, 23, and 9; and d) SEQ ID NO: 2, 3, 4, 5, 6, 8, 23, and 9. In certain aspects the AAV2 capsid comprises capsid proteins VP1, VP2 and VP3 having an amino acid sequence of SEQ ID NO: 19, 68, and 69, respectively. In certain other aspects the AAV2 capsid may comprise subcombinations of capsid proteins VP1, VP2 and/or VP3.

In certain aspects of the invention the viral vector comprises an AAV8 capsid (encoded by SEQ ID NO: 20) and a vector genome comprising in the 5' to 3' direction nucleotide sequences selected from the following: a) SEQ ID NO: 2, 10, 5, 6, 8, and 9; b) SEQ ID NO: 2, 11, 5, 6, 8, 14, 9; c) SEQ ID NO: 2, 22, 5, 6, 8, 23, and 9; and d) SEQ ID NO: 2, 3, 4, 5, 6, 8, 23, and 9. In certain aspects the AAV8 capsid comprises capsid proteins VP1, VP2 and VP3 having an amino acid sequence of SEQ ID NO: 21, 70, and 71. In certain other aspects the AAV8 capsid may comprise subcombinations of capsid proteins VP1, VP2 and/or VP3.

The viral vector can also be an AAV vector comprising a self-complementary genome. Self-complementary rAAV vectors have been previously described in the art (U.S. Pat. No. 7,465,583 and McCarty 2008) and may be adapted for use in the present invention. A self-complementary genome comprises a 5' ITR and a 3' ITR (i.e.: resolvable ITR or wild-type ITR) at either end of the genome and a non-resolvable ITR (e.g.: ΔITR, as described herein) interposed between the 5' and 3' ITRs. Each portion of the genome (i.e. between each resolvable ITR and non-resolvable ITR) comprises a recombinant nucleotide sequence, wherein each half (i.e.: the first recombinant nucleotide sequence and the second recombinant nucleotide sequence) is complementary to the other, or self-complementary. In other words, the self-complementary vector genome is essentially an inverted repeat with the two halves joined by the non-resolvable ITR. In certain aspects the invention is related to a self-complementary vector genome comprising, in the 5' to 3' direction, (i) a 5' ITR, (ii) a first recombinant nucleotide sequence, (iii) a non-resolvable ITR, (iv) a second recombinant nucleotide sequence, and (v) a 3' ITR. In a certain aspect of the invention the second recombinant nucleotide sequence of the vector genome comprises, an RLBP1 promoter, an RLBP1 coding sequence, and an SV40 polyA sequence and the first recombinant nucleotide sequence is self-complementary to the second nucleotide sequence. In certain specific aspects the RLBP1 promoter has the nucleotide sequence of SEQ ID NO: 3. In certain aspects of the invention, the second recombinant nucleotide sequence comprises nucleic acid sequences in the 5' to 3' direction of SEQ ID NO: 3, 4, 5, 6, and 8 and the first recombinant nucleotide sequence comprises sequences that are self-complementary to, or the reverse complement of, the second recombinant sequence, for example, SEQ ID NOs: 62, 63, 64, 65, and 66. It is also contemplated that the viral vector of the invention may comprise a self-complementary genome wherein the first recombinant nucleotide sequence of the vector genome comprises, an RLBP1 promoter, an RLBP1 coding sequence, and an SV40 polyA sequence and the second recombinant nucleotide sequence is self-complementary to the first recombinant nucleotide sequence.

In certain aspects of the invention the self-complementary viral vector comprises an AAV2 capsid (encoded by SEQ ID NO: 18) and a vector genome comprising a nucleotide sequence comprising sequences in the 5' to 3' direction SEQ ID NO: 36, SEQ ID NO: 62, SEQ ID NO: 63, SEQ ID NO: 64, SEQ ID NO: 65, SEQ ID NO: 66, SEQ ID NO: 1, SEQ ID NO: 3, SEQ ID NO: 4, SEQ ID NO: 5, SEQ ID NO: 6, SEQ ID NO: 8, and SEQ ID NO: 9. In certain aspects the AAV2 capsid comprises capsid proteins VP1, VP2 and VP3 having an amino acid sequence of SEQ ID NO: 19, 68, and 69, respectively. In certain other aspects the AAV2 capsid may comprise subcombinations of capsid proteins VP1, VP2 and/or VP3.

In certain aspects of the invention the self-complementary viral vector comprises an AAV8 capsid (encoded by SEQ ID NO: 20) and a vector genome comprising a nucleotide sequence comprising sequences in the 5' to 3' direction SEQ ID NO: 36, SEQ ID NO: 62, SEQ ID NO: 63, SEQ ID NO: 64, SEQ ID NO: 65, SEQ ID NO: 66, SEQ ID NO: 1, SEQ ID NO: 3, SEQ ID NO: 4, SEQ ID NO: 5, SEQ ID NO: 6, SEQ ID NO: 8, and SEQ ID NO: 9. In certain aspects the AAV8 capsid comprises capsid proteins VP1, VP2 and VP3 having an amino acid sequence of SEQ ID NO: 21, 70, and 71. In certain other aspects the AAV8 capsid may comprise subcombinations of capsid proteins VP1, VP2 and/or VP3.

Thus, the invention also relates to viral vectors as described herein, comprising a truncated promoter of RLBP1.

The invention further relates to a viral vector that directs expression of a heterologous gene to RPE and Müller cells of the retina, wherein the viral vector comprises an AAV8 capsid and a vector genome comprising an RLBP1 (short) promoter (SEQ ID NO:3) operably linked to a heterologous gene. In certain aspects of the invention, the vector genome is a self-complementary genome.

The invention also relates to methods of expressing RLBP1 in RPE cells and Müller cells of the retina. In certain aspects of the invention the method comprises contacting the retinal cells with a viral vector comprising an AAV capsid and a vector genome comprising an RLBP1 coding sequence operably linked to an RLBP1 promoter, which may be an RLBP1 (short) promoter (SEQ ID NO:3). In certain aspects of the invention the AAV capsid is AAV2. In certain other aspects, the AAV capsid is AAV8. In other aspects of the invention the method comprises contacting the retinal cells with a viral vector comprising an AAV capsid and a vector genome comprising an RLBP1 coding sequence operably linked to an RLBP1 promoter, which may be an RLBP1 (long) promoter (SEQ ID NO: 10). In certain aspects of the invention the AAV capsid is AAV2. In certain other aspects, the AAV capsid is AAV8.

Methods for generating viral vectors are well known in the art and would allow for the skilled artisan to generate the viral vectors of the invention (see, e.g., U.S. Pat. No. 7,465,583), including the viral vectors described in Table 4, using the plasmids described in Table 2 and the Examples.

In general, methods of producing rAAV vectors are applicable to producing the viral vectors of the invention; the primary difference between the methods is the structure of the genetic elements to be packaged. To produce a viral vector according to the present invention, sequences of the genetic elements and plasmids as described in table 2 can be used to produce the encapsidated viral genome.

The genetic elements as described in table 2 are in the context of a circular plasmid, but one of skill in the art will appreciated that a DNA substrate may be provided in any form known in the art, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like). Alternatively, the genetic elements in table 2 necessary to produce the viral vectors described herein may be stably incorporated into the genome of a packaging cell.

The viral vector particles according to the invention may be produced by any method known in the art, e.g., by introducing the sequences to be replicated and packaged into a permissive or packaging cell, as those terms are understood in the art (e.g., a "permissive" cell can be infected or transduced by the virus; a "packaging" cell is a stably transformed cell providing helper functions).

In one embodiment, a method is provided for producing an RLBP1 viral vector, wherein the method comprises providing to a cell permissive for parvovirus replication: (a) a nucleotide sequence containing the genetic elements for producing a vector genome of the invention (as described in detail below and in table 2); (b) nucleotide sequences sufficient for replication of the vector genome sequence in (a) to produce a vector genome; (c) nucleotide sequences sufficient to package the vector genome into a parvovirus capsid, under conditions sufficient for virus vectors comprising the vector genome encapsidated within the parvovirus capsid to be produced in the cell. Preferably, the parvovirus replication and/or capsid coding sequences are AAV sequences.

Any method of introducing the nucleotide sequence carrying the gene cassettes described below into a cellular host for replication and packaging may be employed, including but not limited to, electroporation, calcium phosphate precipitation, microinjection, cationic or anionic liposomes, and liposomes in combination with a nuclear localization signal.

Viral vectors described herein may be produced using methods known in the art, such as, for example, triple transfection or baculovirus mediated virus production. Any suitable permissive or packaging cell known in the art may be employed to produce the vectors. Mammalian cells are preferred. Also preferred are trans-complementing packaging cell lines that provide functions deleted from a replication-defective helper virus, e.g., 293 cells or other E1a trans-complementing cells. Also preferred are mammalian cells or cell lines that are defective for DNA repair as known in the art, as these cell lines will be impaired in their ability to correct the mutations introduced into the plasmids described herein.

The gene cassette may contain some or all of the parvovirus (e.g., AAV) cap and rep genes. Preferably, however, some or all of the cap and rep functions are provided in trans by introducing a packaging vector(s) encoding the capsid and/or Rep proteins into the cell. Most preferably, the gene cassette does not encode the capsid or Rep proteins. Alternatively, a packaging cell line is used that is stably transformed to express the cap and/or rep genes (see, e.g., Gao et al., (1998)

Human Gene Therapy 9:2353; Inoue et al., (1998) J. Virol. 72:7024; U.S. Pat. No. 5,837,484; WO 98/27207; U.S. Pat. No. 5,658,785; WO 96/17947).

In addition, helper virus functions are preferably provided for the virus vector to propagate new virus particles. Both adenovirus and herpes simplex virus may serve as helper viruses for AAV. See, e.g., BERNARD N. FIELDS et al., VIROLOGY, volume 2, chapter 69 (3d ed., Lippincott-Raven Publishers). Exemplary helper viruses include, but are not limited to, Herpes simplex (HSV) varicella zoster, cytomegalovirus, and Epstein-Barr virus. The multiplicity of infection (MOI) and the duration of the infection will depend on the type of virus used and the packaging cell line employed. Any suitable helper vector may be employed. Preferably, the helper vector is a plasmid, for example, as described by Xiao et al., (1998) J. Virology 72:2224. The vector can be introduced into the packaging cell by any suitable method known in the art, as described above.

Vector stocks free of contaminating helper virus may be obtained by any method known in the art. For example, recombinant single stranded or self complementary virus and helper virus may be readily differentiated based on size. The viruses may also be separated away from helper virus based on affinity for a heparin substrate (Zolotukhin et al. (1999) Gene Therapy 6:973). Preferably, deleted replication-defective helper viruses are used so that any contaminating helper virus is not replication competent. As a further alternative, an adenovirus helper lacking late gene expression may be employed, as only adenovirus early gene expression is required to mediate packaging of the duplexed virus. Adenovirus mutants defective for late gene expression are known in the art (e.g., ts100K and ts149 adenovirus mutants).

One method for providing helper functions employs a non-infectious adenovirus miniplasmid that carries all of the helper genes required for efficient AAV production (Ferrari et al., (1997) Nature Med. 3:1295; Xiao et al., (1998) J. Virology 72:2224). The rAAV titers obtained with adenovirus miniplasmids are forty-fold higher than those obtained with conventional methods of wild-type adenovirus infection (Xiao et al., (1998) J. Virology 72:2224). This approach obviates the need to perform co-transfections with adenovirus (Holscher et al., (1994), J. Virology 68:7169; Clark et al., (1995) Hum. Gene Ther. 6:1329; Trempe and Yang, (1993), in, Fifth Parvovirus Workshop, Crystal River, Fla.).

Other methods of producing rAAV stocks have been described, including but not limited to, methods that split the rep and cap genes onto separate expression cassettes to prevent the generation of replication-competent AAV (see, e.g., Allen et al., (1997) J. Virol. 71:6816), methods employing packaging cell lines (see, e.g., Gao et al., (1998) Human Gene Therapy 9:2353; Inoue et al., (1998) J. Virol. 72:7024; U.S. Pat. No. 5,837,484; WO 98/27207; U.S. Pat. No. 5,658,785; WO 96/17947), and other helper virus free systems (see, e.g., U.S. Pat. No. 5,945,335 to Colosi).

Herpesvirus may also be used as a helper virus in AAV packaging methods. Hybrid herpesviruses encoding the AAV Rep protein(s) may advantageously facilitate for more scalable AAV vector production schemes. A hybrid herpes simplex virus type I (HSV-1) vector expressing the AAV-2 rep and cap genes has been described (Conway et al., (1999) Gene Therapy 6:986 and WO 00/17377).

In summary, the gene cassette to be replicated and packaged, parvovirus cap genes, appropriate parvovirus rep genes, and (preferably) helper functions are provided to a cell (e.g., a permissive or packaging cell) to produce rAAV particles carrying the vector genome. The combined expression of the rep and cap genes encoded by the gene cassette and/or the packaging vector(s) and/or the stably transformed packaging cell results in the production of a viral vector particle in which a viral vector capsid packages a viral vector genome according to the invention. The single stranded or self-complementary viral vectors are allowed to assemble within the cell, and may then be recovered by any method known by those of skill in the art and described in the examples. For example, viral vectors may be purified by standard CsCl centrifugation methods (Grieger J C et al 2006) or by various methods of column chromatography known to the skilled artisan (see: Lock M et al (2010), Smith R H et al (2009) and Vadenberghe L H et al (2010)).

The reagents and methods disclosed herein may be employed to produce high-titer stocks of the inventive viral vectors, preferably at essentially wild-type titers. It is also preferred that the parvovirus stock has a titer of at least about $10^5$ transducing units (tu)/ml, more preferably at least about $10^6$ to/ml, more preferably at least about $10^7$ to/ml, yet more preferably at least about $10^8$ to/ml, yet more preferably at least about $10^9$ to/ml, still yet more preferably at least about $10^{10}$ to/ml, still more preferably at least about $10"$ to/ml, or more.

Further, the RLBP1 viral vectors of the invention, may have an improved transducing unit/particle ratio over conventional AAV vectors. Preferably, the tu/particle ratio is less than about 1:50, less than about 1:20, less than about 1:15, less than about 1:10, less than about 1:8, less than about 1:7, less than about 1:6, less than about 1:5, less than about 1:4, or lower. Typically, the tu/particle ratio will be greater than about 1:1, 1:2, 1:3 or 1:4.

2. Nucleic Acids for Use in Generating the Viral Vector

The invention also relates to nucleic acids useful for the generation of viral vectors. In certain aspects of the invention, the nucleic acids useful for the generation of viral vectors may be in the form of plasmids. Plasmids useful for the generation of viral vectors, also referred to as a viral vector plasmid, may contain a gene cassette. At a minimum, a gene cassette of a viral vector plasmid contains: a heterologous gene and its regulatory elements (e.g.: promoter, enhancer, and/or introns, etc.), and 5' and 3' AAV inverted terminal repeats (ITRs).

The composition of the heterologous gene and its regulatory elements will depend upon the use to which the resulting vector will be put. For example, one type of heterologous gene sequence includes a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc. For example, where the reporter sequence is the LacZ gene, the presence of the vector carrying the signal is detected by assays for beta-galactosidase activity. Where the reporter sequence is green fluorescent protein or luciferase, the vector carrying the signal may be measured visually by color or light production in a luminometer.

The heterologous gene sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry.

The heterologous gene may also be a non-marker sequence encoding a product which is useful in biology and medicine, such as proteins, peptides, RNA, enzymes, dominant negative mutants, or catalytic RNAs. Desirable RNA molecules include tRNA, dsRNA, ribosomal RNA, catalytic RNAs, siRNA, small hairpin RNA, trans-splicing RNA, and antisense RNAs. One example of a useful RNA sequence is a sequence which inhibits or extinguishes expression of a targeted nucleic acid sequence in the treated animal.

The heterologous gene may also be used to correct or ameliorate gene deficiencies, which may include deficiencies in which normal genes are expressed at less than normal levels or deficiencies in which the functional gene product is not expressed. It is contemplated in the present invention that the heterologous gene sequence may be an RLBP1 coding sequence. Examples of RLBP1 coding sequences are provided in Table 1: SEQ ID NOs: 6, 37, 39, 41, 43, 45 or 47.

In addition to the heterologous gene, the gene cassette may include regulatory elements operably linked to the heterologous gene. These regulatory elements may include appropriate transcription initiation, termination, promoter and enhancer sequences, efficient RNA processing signals such as splicing and polyadenylation (polyA) signals; sequences that stabilize cytoplasmic mRNA; sequences that enhance translation efficiency; sequences that enhance protein stability; and when desired, sequences that enhance secretion of the encoded product. A great number of regulatory sequences, including promoters which are native, constitutive, inducible and/or tissue-specific, are known in the art and may be utilized. Regulatory element sequences of the invention include those described in Table 1, for example SEQ ID NO: 3, 4, 5, 8, 10, 11, 12 and 22.

The gene cassette may include an RLBP1 promoter with a nucleic acid sequence of SEQ ID NO: 3 or 10 operably linked to a heterologous gene. In particular, the RLBP1 short promoter (SEQ ID NO: 3) is operably linked to an RLBP1 coding sequence (SEQ ID NO: 6, 37, 39, 41, 43, 45 or 47). Alternatively, the RLBP1 long promoter (SEQ ID NO: 10) is operably linked to an RLBP1 coding sequence (SEQ ID NO: 6, 37, 39, 41, 43, 45 or 47).

It is contemplated that the ITRs of AAV serotype 2 may be used (e.g.: SEQ ID NO: 2, 9, 16, 17, 36). However, ITRs from other suitable serotypes may be selected from among any AAV serotype known in the art, as described herein. These ITRs or other AAV components may be readily isolated using techniques available to those of skill in the art from any AAV serotype known, or yet to be identified serotypes, for example, the AAV sequences may be obtained through synthetic or other suitable means by reference to published sequences such as are available in the literature or in databases such as, e.g., GenBank, PubMed, or the like. Alternatively, such AAV components may also be isolated or obtained from academic, commercial, or public sources (e.g., the American Type Culture Collection, Manassas, Va.).

It is contemplated that in certain aspects of the invention, one ITR of the gene cassette may be a modified ITR, or non-resolvable ITR, sequence without the terminal resolution site (TRS). During replication of a gene cassette comprising a non-resolvable ITR, the inability of Rep protein to resolve the non-resolvable ITRs will result in a dimeric inverted repeat sequence (i.e.: self-complementary) with a non-resolvable ITR (e.g.: ΔITR) in the middle and a wild-type ITR at each end. The resulting sequence is a self-complementary viral genome sequence such that the genome is capable of forming a hairpin structure upon release from the capsid (see also: U.S. Pat. No. 7,465,583 and McCarty (2008)) A non-resolvable ITR may be produced by any method known in the art. For example, insertion into the ITR will displace the TRS and result in a non-resolvable ITR. Preferably, the insertion is in the region of the TRS site. Alternatively, the ITR may be rendered non-resolvable by deletion of the TRS site, a specific example includes ΔITR (SEQ ID NO: 1).

The invention relates to nucleic acids that comprise a gene cassette comprising in the 5' to 3' direction nucleic acid sequences selected from the following: a) SEQ ID NOs: 2, 10, 5, 6, 8, and 9; b) SEQ ID NOs: 2, 11, 5, 6, 8, 14 and 9; c) SEQ ID NOs: 2, 22, 5, 6, 8, 23 and 9; d) SEQ ID NOs: 2, 3, 4, 5, 6, 8, 23 and 9; e) SEQ ID NOs: 2, 10, 5, 24, 8, and 9; f) SEQ ID NOs: 2, 11, 24, 8, 14, and 9; and g) SEQ ID NOs: 2, 12, 24, 8, 14, and 9. In certain aspects the nucleic acid comprising the gene cassette may be a plasmid. In particular, the sequence of the plasmid may have a sequence selected from SEQ ID NOs: 27, 28, 29, 30, 32, 33, 34 and 35.

The invention also relates to nucleic acids that comprise a gene cassette comprising in the 5' to 3' direction nucleic acid sequences selected from the following: a) SEQ ID NOs: 1, 3, 4, 5, 6, 8, and 9; and b) SEQ ID NOs: 1, 3, 4, 5, 24, 8 and 9. In certain aspects the nucleic acid comprising the gene cassette may be a plasmid. In particular, the sequence of the plasmid may have a sequence selected from SEQ ID NOs: 26, 31 and 50.

Methods for incorporating the elements in Table 2 are well known in the art and would allow for the skilled artisan to generate the nucleic acids and plasmids of the invention using the methods outlined in Table 3 and the Examples.

3 Pharmaceutical Compositions

The invention provides pharmaceutical compositions comprising the viral vectors of the invention formulated together with a pharmaceutically acceptable carrier. The compositions can additionally contain one or more other therapeutic agents that are suitable for treating or preventing, for example, RLBP1-associated retinal dystrophy, and/or retinal pigmentosa (RP). Pharmaceutically acceptable carriers enhance or stabilize the composition, or can be used to facilitate preparation of the composition. Pharmaceutically acceptable carriers include solvents, surfactants, dispersion media, coatings, antibacterial and antifungal agents, isotonic and absorption delaying agents, and the like that are physiologically compatible.

A pharmaceutical composition of the present invention can be administered by a variety of methods known in the art. The route and/or mode of administration vary depending upon the desired results. It is preferred that administration be subretinal. The pharmaceutically acceptable carrier should be suitable for subretinal, intravitreal, intravenous, sub-cutaneous or topical administration.

The composition should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition.

Pharmaceutical compositions of the invention can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the viral vector is employed in the pharmaceutical compositions of the invention. The viral vectors may be formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician or veterinarian can start doses of the viral vectors of the invention employed in the pharmaceutical composition at levels lower than that required to achieve the desired therapeutic effect and gradually increase the dosage until the desired effect is achieved. In general, effective doses of the compositions of the present invention, for the treatment of RLBP1-associated retinal dystrophy as described herein vary depending upon many different factors, including means of administration, target site, physiological state of the patient, whether the patient is human or an animal, other medications administered, and whether treatment is prophylactic or therapeutic. Treatment dosages need to be titrated to optimize safety and efficacy. For subretinal administration with a viral vector, the dosage may range from $1 \times 10^8$ vector genomes (vg)/eye to $1 \times 10^{12}$ vg/eye. For example the dosage may be, $1 \times 10^8$ vg/eye, $2.5 \times 10^8$ vg/eye, $5 \times 10^8$ vg/eye, $7.5 \times 10^8$ vg/eye, $1 \times 10^9$ vg/eye, $2.5 \times 10^9$ vg/eye, $5 \times 10^9$ vg/eye, $7.5 \times 10^9$ vg/eye, $1 \times 10^{10}$ vg/eye, $2.5 \times 10^{10}$ vg/eye, $5 \times 10^{10}$ vg/eye, $7.5 \times 10^{10}$ vg/eye, $1 \times 10^{11}$ vg/eye, $2.5 \times 10^{11}$ vg/eye, $5 \times 10^{11}$ vg/eye, $7.5 \times 10^{11}$ vg/eye, $1 \times 10^{12}$ vg/eye.

The viral vectors described herein are mainly used as one time doses per eye, with the possibility of repeat dosing to treat regions of the retina that are not covered in the previous dosing. The dosage of administration may vary depending on whether the treatment is prophylactic or therapeutic.

The various features and embodiments of the present invention, referred to in individual sections and embodiments above apply, as appropriate, to other sections and embodiments, mutatis mutandis. Consequently features specified in one section or embodiment may be combined with features specified in other sections or embodiments, as appropriate.

4. Therapeutic Uses

Viral vectors as described herein, can be used at a therapeutically useful concentration for the treatment of eye related diseases, by administering to a subject in need thereof, an effective amount of the viral vectors of the invention. More specifically, the present invention provides a method of treating RLBP1-associated retinal dystrophy, by administering to a subject in need thereof an effective amount of a viral vector comprising an RLBP1 coding sequence.

The present invention provides a viral vector comprising an RLBP1 coding sequence for use in treating RLBP1-associated retinal dystrophy in a subject.

Table A: RLBP1 Mutations and Associated Phenotypes of RLBP1-Associated Retinal Dystrophy. Disease phenotypes of RLBP1-associated retinal dystrophy include: Autosomal recessive retinitis pigmentosa (AARP), Bothnia dystrophy (BD), Newfoundland rod-cone dystrophy (NFRCD), Retinitis punctata albescens (RPA) and Fundus albipunctatus (FA).

TABLE A

| # pts | Mutation | Region | Disease | Night Blind | Yellow Dots | Pigment Deposits | Atrophy | Reference |
|---|---|---|---|---|---|---|---|---|
| Missense Mutations |||||||||
| 67 | R234W | Sweden | BD | Yes | Perifoveal, midperiphery | In advanced | Advanced | Burstedt et al 2001; Golovleva et al 2010; Golovleva et al 2012 |
| 10 | R234W/M226K | Sweden | BD | Yes | Perifoveal, midperiphery | In advanced | Advanced | Köhn et al 2008; Golovleva et al 2010; Golovleva et al 2012 |
| 2 | M226K | Sweden | BD | Yes | Perifoveal, midperiphery | In advanced | Advanced | Golovleva et al 2010; Golovleva et al 2012 |
| 4 | G116R | Pakistan | FA | Yes | Midperiphery | No | No | Naz et al 2011 |
| 4 | R151Q | Saudi Arabia | FA | Yes | Whole fundus | No | No | Katsaris et al 2001 |
| 4 | R151Q | India | ARRP | Yes | Whole fundus | Yes | Yes | Maw et al 1997 |
| 1 | R234W | Japan | BD | Yes | Perifoveal, midperiphery | In advanced | Advanced | Nojima et al 2011 |
| 1 | R103W R234W | Japan | RPA | Yes | Perifoveal, midperiphery | In advanced | Yes | Nakamura et al 2011 |
| 1 | G146D I201T | USA | RPA | No | Midperiphery | No | No | Demirci et al 2004 |
| 1 | R103W | USA | RPA | Yes | Midperiphery | No | Yes | Demirci et al 2004 |
| Truncating Mutations |||||||||
| 26 | 324G_A IVS3_2T 3 C | Canada | NFRCD | Yes | Perifoveal, midperiphery | No | Yes | Eichers et al 2002 |
| 6 | R156X | Pakistan | FA | Yes | Midperiphery | No | No | Naz et al 2011 |
| 4 | R151W Gly31 (2-bp del) | USA | RPA | Yes | Midperiphery | Few, peripheral | No | Fishman et al 2004 |
| 6 | Exons 7_9 del | Morocco | RPA | Yes | Perifoveal, midperiphery | No | No | Humbert et al 2006; Littink et al 2012 |

TABLE A-continued

| # pts | Mutation | Region | Disease | Night Blind | Yellow Dots | Pigment Deposits | Atrophy | Reference |
|---|---|---|---|---|---|---|---|---|
| 1 | IVS3_2T 3 C M226K | USA | RPA | Yes | Perifoveal, midperiphery | No | No | Morimura et al 1999 |
| 1 | Q278(1-bp del) | USA | RPA | Yes | Perifoveal | Few, peripheral | Yes | Morimura et al 1999 |

Use of recombinant AAV has been shown to be feasible and safe for the treatment of retinal disease (See, e.g., Bainbridge et al. 2008, Houswirth et al 2008, Maguire et al 2008). The viral vectors of the invention can be used, inter alia, to treat and prevent progression of RLBP1-associated retinal dystrophy and improve vision loss. Viral vectors of the invention can also be used in patients where other retinal dystrophy is caused by other loss of function mutations in the RLBP1 gene, for example, Autosomal recessive retinitis pigmentosa, Retinitis punctata albescens and Fundus albipunctatus.

The present invention is also relates to a method of expressing an RLBP1 coding sequence in RPE and Müller cells of the retina, by administering viral vectors of the invention to a subject in need thereof. The present invention also relates to viral vectors of the invention for use in expressing an RLBP1 coding sequence in RPE and/or Müller cells of the retina of the subject in need thereof. The invention also contemplates a method of delivering an RLBP1 coding sequence to the retina, specifically to RPE and/or Müller cells in the retina, of a subject having RLBP1-associated retinal dystrophy. It is contemplated that the an RLBP1 coding sequence is delivered to the subject in need thereof by contacting the retina, RPE and/or Müller cells of the subject with a viral vector as described herein. Alternatively, an RLBP1 coding sequence is delivered to a subject by administering to the subject a viral vector as described herein.

The present invention further includes methods of expressing an RLBP1 coding sequence in RPE and/or Müller cells in the retina of a subject having RLBP1-associated retinal dystrophy, by contacting the retina of the subject with viral vectors of the invention. In certain aspects RPE and/or Müller cells of the retina of the subject are contacted with viral vectors of the invention.

It is further contemplated that the viral vectors used in the methods described herein comprise an AAV2 or AAV8 capsid, and the vector genome comprises an RLBP1 coding sequence operably linked to an RLBP1 promoter with a nucleotide sequence selected from SEQ ID NO: 3 or 10. It is further contemplated that the vector genome can be self-complementary.

In one aspect the viral vectors described herein can be administered subretinally or intravitreally using methods known to those of skill in the art.

Treatment and/or prevention of ocular disease such as RLBP1-associated retinal dystrophy can be determined by an ophthalmologist or health care professional using clinically relevant measurements of visual function and/or retinal anatomy. Treatment of RLBP1-associated retinal dystrophy means any action (e.g., administration of a viral vector described herein) contemplated to improve or preserve visual function and/or retinal anatomy. In addition, prevention as it relates to RLBP1-associated retinal dystrophy means any action (e.g., administration of a viral vector described herein) that prevents or slows a worsening in visual function, retinal anatomy, and/or RLBP1-associated retinal dystrophy disease phenotype, as defined herein, in a patient at risk for said worsening.

Visual function may include, for example, visual acuity, visual acuity with low illumination, visual field, central visual field, peripheral vision, contrast sensitivity, dark adaptation, photostress recovery, color discrimination, reading speed, dependence on assistive devices (e.g., large typeface, magnifying devices, telescopes), facial recognition, proficiency at operating a motor vehicle, ability to perform one or more activities of daily living, and/or patient-reported satisfaction related to visual function. Thus, treatment of retinitis pigmentosa (RP), specifically RLBP1-associated retinal dystrophy, can be said to occur where a subject has an at least 10% decrease or lack of a 10% or more increase in time to a pre-specified degree of dark adaptation. In addition, treatment of RLBP1-associated retinal dystrophy can be said to occur where a subject exhibits early severe night blindness and slow dark adaptation in young age, followed by progressive loss of visual acuity, visual fields and color vision, leading to legal blindness, determined by a qualified health care professional (i.e., ophthalmologist) (Burstedt and Mönestam, 2010).

Exemplary measures of visual function include Snellen visual acuity, ETDRS visual acuity, low-luminance visual acuity, Amsler grid, Goldmann visual field, standard automated perimetry, microperimetry, Pelli-Robson charts, SKILL card, Ishihara color plates, Farnsworth D15 or D100 color test, standard electroretinography, multifocal electroretinography, validated tests for reading speed, facial recognition, driving simulations, and patient reported satisfaction. Thus, treatment of RLBP1-associated retinal dystrophy can be said to be achieved upon a gain of or failure to lose 2 or more lines (or 10 letters) of vision on an ETDRS scale. In addition, treatment of RLBP1-associated retinal dystrophy can be said to occur where a subject exhibits at least a 10% increase or lack of 10% decrease in reading speed (words per minute). In addition, treatment of RLBP1-associated retinal dystrophy can be said to occur where a subject exhibits at least a 20% increase or lack of a 20% decrease in the proportion of correctly identified plates on an Ishihara test or correctly sequenced disks on a Farnsworth test. Thus, treatment of, for example, RLBP1-associated retinal dystrophy can be determined by, for example, improvement of rate of dark adaptation, or an improvement in, or slowing of the rate of, visual acuity loss.

Undesirable aspects of retinal anatomy that may be treated or prevented include, for example, retinal atrophy, retinal pigment epithelium atrophy, narrowing of retinal vessels, pigmentary clumping, retinal yellow/white spots, subretinal fluid.

Exemplary means of assessing retinal anatomy include fundoscopy, fundus photography, fluorescein angiography, indocyanine green angiography, optical coherence tomography (OCT), spectral domain optical coherence tomography, scanning laser ophthalmoscopy, confocal microscopy, adaptive optics, fundus autofluorescence, biopsy, necropsy, and immunohistochemistry. Thus, RLBP1-associated retinal dystrophy can be said to be treated in a subject as determined by, for example, a reduction in the rate of development of retinal atrophy.

Subjects to be treated with therapeutic agents of the present invention can also be administered other therapeutic agents or devices with known efficacy for treating retinal dystrophy such as vitamin and mineral preparations, low-vision aids, guide dogs, or other devices known to assist patients with low vision.

Currently there are no other approved therapeutic agents for the treatment of RLBP1-associated retinal dystrophy. As other new therapies emerge, the two can be administered sequentially in either order or simultaneously as clinically indicated.

EXAMPLES

The following examples are provided to further illustrate the invention but not to limit its scope. Other variants of the invention will be readily apparent to one of ordinary skill in the art and are encompassed by the appended claims.

Example 1

Construction of AAV-ITR Plasmids 1.1 Cloning of AAV-ITR Plasmids:

The nucleic acid sequences of the individual plasmid elements are described in Table 1. The sequences were either synthesized or purchased commercially. Table 2 describes the elements that exist in each plasmid that was constructed. Standard molecular biology cloning techniques were used in generating the plasmids as described in Table 3. The plasmid backbone pAAV-MCS (Stratagene®) with Ampicillin resistance or pUC57 with Kanamycin resistance was used as the backbone and starting material. The individual sequence elements were cloned in at restriction enzyme sites or using blunt end cloning.

Because the antibiotic resistance gene cassette contained in the plasmid backbone does not play a role in the production of the AAV vectors, one of skill in the art could use alternate plasmid backbones and/or antibiotic resistance gene cassettes and yield the same viral vectors. We have demonstrated that functionally equivalent NVS2 vectors can be generated using plasmids with different backbones. For example, plasmid sequences SEQ ID NO: 26 and SEQ ID NO: 50 produce functionally equivalent NVS2 vectors.

1.2. Triple Plasmid Transfection to Produce rAAV Vectors:

Recombinant AAV (rAAV) viral vectors were generated by triple transfection methods. Methods for triple transfection are known in the art (Ferrari F K et al 1997). Briefly, AAV-ITR-containing plasmids (described in Table 2), AAV-Rep-Cap containing plasmid (carrying Rep2 and Cap2 or Cap8) and Adeno-helper plasmid (carrying genes that assist in completing AAV replication cycle) were co-transfected into 293 cells. Cells were cultured for 4 days. At the end of the culture period the cells were lysed and the vectors in the culture supernatant and in the cell lysate were purified by a standard CsCl gradient centrifugation method (method modified based on Grieger J C et al 2006). The purified viral vectors are described in Table 4.

Alternatively, GMP-like rAAV vectors were generated by the cell transfection and culture methods described above. The harvested cell culture material was then processed by column chromatography based on methods described by Lock M et al (2010), Smith R H et al (2009) and Vadenberghe L H et al (2010).

1.3. Variation of 5' ITR Sequences:

As described previously (Samulski et al, 1983; Muzyczka et al, 1984), mutations within the terminal repeat sequences of AAV plasmids are well tolerated in generating functional AAV vectors. Even plasmids with one of the two ITRs deleted, the AAV sequences could be rescued, replicated, and infectious virions be produced, as long as the existing ITR in the construct contains the full AAV ITR sequence (Samulski et al, 1983; Muzyczka et al, 1984). Therefore, even though SEQ. ID. NO. 2 is used as the 5' ITR sequence of all single-stranded AAV vectors described in this document, it is expected that any 5'ITR sequence that carries the terminal resolution site (i.e.: SEQ. ID. NOS. 2, 16 and 17) would produce vectors with the same functionality.

TABLE 1

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:) AND SEQUENCE |
|---|---|
| ΔITR | 1<br>cgcgctcgctcgctcactgaggccgcccgggcaaagcccgggcg<br>tcgggcgacctttggtcgcccggcctcagtgagcgagcgagcgc<br>gcagagagggagtgg |
| 5' ITR | 2<br>ctgcgcgctcgctcgctcactgaggccgcccgggcgtcgggcga<br>cctttggtcgcccggcctcagtgagcgagcgagcgcgcagagag<br>ggagtggccaactccatcactagggttcct |
| Human RLBP1 Promoter (short) (NT_010274.17) | 3<br>ttgtcctctccctgcttggccttaaccagccacatttctcaact<br>gacccccactcactgcagaggtgaaaactaccatgccaggtcctg<br>ctggctggggagggggtgggcaataggcctggatttgccagagc<br>tgccactgtagatgtagtcatatttacgatttcccttcacctct<br>tattacctggtggtggtggtgggggggggggggtgctctctca<br>gcaaccccaccccgggatcttgaggagaaagagggcagagaaaa<br>gagggaatgggactggcccagatcccagccccacagccgggctt<br>ccacatggccgagcaggaactccagagcaggagcacacaaagga<br>gggctttgatgcgcctccagccaggcccaggcctctcccctctc<br>ccctttctctctgggtcttcctttgccccactgagggcctcctg<br>tgagcccgatttaacggaaactgtgggcggtgagaagttcctta<br>tgacacactaatcccaacctgctgaccggaccacgcctccagcg |

TABLE 1-continued

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:) AND SEQUENCE |
|---|---|
| | gagggaacctctagagctccaggacattcaggtaccaggtagcc<br>ccaaggaggagctgccga |
| MODIFIED SV40INTRON (MODIFIED EF579804) | 4<br>aactgaaaaaccagaaagttaactggtaagtttagtcttttttgt<br>cttttatttcaggtcccggatccggtggtggtgcaaatcaaaga<br>actgctcctcagtggatgttgcctttacttctaggcctgtacgg<br>aagtgttacttctgctctaaaagctgcggaattgtacccgcccc<br>gggatcc |
| ADDED-KOZAK | 5<br>gccacc |
| HUMAN RLBP1 GENE CDS NM_000326.4 | 6<br>atgtcagaagggtgggcacgttccgcatggtacctgaagagga<br>acaggagctccgtgcccaactggagcagctcacaaccaaggacc<br>atggacctgtctttggcccgtgcagccagctgccccgccacacc<br>ttgcagaaggccaaggatgagctgaacgagagagaggagacccg<br>ggaggaggcagtgcgagagctgcaggagatggtgcaggcgcagg<br>cggcctcgggggaggagctggcggtggccgtggcggagagggtg<br>caagagaaggacagcggcttcttcctgcgcttcatccgcgcacg<br>gaagttcaacgtgggccgtgcctatgagctgctcagaggctatg<br>tgaatttccggctgcagtaccctgagctctttgacagcctgtcc<br>ccagaggctgtccgctgcaccattgaagctggctaccctggtgt<br>cctctctagtcgggacaagtatggccgagtggtcatgctcttca<br>acattgagaactggcaaagtcaagaaatcacctttgatgagatc<br>ttgcaggcatattgcttcatcctggagaagctgctggagaatga<br>ggaaactcaaatcaatggcttctgcatcattgagaacttcaagg<br>gctttaccatgcagcaggctgctagtctccggacttcagatctc<br>aggaagatggtggacatgctccaggattccttcccagcccggtt<br>caaagccatccacttcatccaccagccatggtacttcaccacga<br>cctacaatgtggtcaagcccttcttgaagagcaagctgcttgag<br>agggtctttgtccacggggatgacctttctggttttctaccagga<br>gatcgatgagaacatcctgccctctgacttcggggggcacgctgc<br>ccaagtatgatggcaaggccgttgctgagcagctctttggcccc<br>caggcccaagctgagaacacagccttctga |
| HUMAN RLBP1 GENE PRODUCT (CELLULAR RETINALDEHYDE BINDING PROTEIN - CRALBP) | 7<br>MSEGVGTFRMVPEEEQELRAQLEQLTTKDHGPVFGPCSQLPRHT<br>LQKAKDELNEREETREEAVRELQEMVQAQAASGEELAVAVAERV<br>QEKDSGFFLRFIRARKFNVGRAYELLRGYVNFRLQYPELFDSLS<br>PEAVRCTIEAGYPGVLSSRDKYGRVVMLFNIENWQSQEITFDEI<br>LQAYCFILEKLLENEETQINGFCIIENFKGFTMQQAASLRTSDL<br>RKMVDMLQDSFPARFKAIHFIHQPWYFTTTYNVVKPFLKSKLLE<br>RVFVHGDDLSGFYQEIDENILPSDFGGTLPKYDGKAVAEQLFGP<br>QAQAENTAF |
| SV40 POLYA (EF579804) | 8<br>gatcataatcagccataccacatttgtagaggttttacttgctt<br>taaaaaacctcccacacctccccctgaacctgaaacataaaatg<br>aatgcaattgttgttgttaacttgtttattgcagcttataatgg<br>ttacaaataaagcaatagcatcacaaatttcacaaataaagcat<br>ttttttcactgcattctagttgtggtttgtccaaactcatcaat<br>gtatcttatcatgtct |
| 3' ITR (AF043303) | 9<br>aggaacccctagtgatggagttggccactccctctctgcgcgct<br>cgctcgctcactgaggccgggcgaccaaaggtcgcccgacgccc<br>gggctttgcccgggcggcctcagtgagcgagcgagcgcgcag |
| Human RLBP1 Promoter(long) (NT_010274.17) | 10<br>ttgtcctctccctgcttggccttaaccagccacatttctcaact<br>gaccccactcactgcagaggtgaaaactaccatgccaggtcctg<br>ctggctgggggagggtgggcaataggcctggatttgccagagc<br>tgccactgtagatgtagtcatatttacgatttcccttcacctct<br>tattaccctggtggtggtggtggggggggggggggtgctctctca<br>gcaaccccaccccgggatcttgaggagaaagagggcagagaaaa<br>gagggaatgggactggcccagatcccagcccacagccgggctt<br>ccacatgccgagcaggaactccagagcaggagcacacaaagga<br>gggctttgatgcgcctccagccaggcccaggcctctcccctctc<br>cccttttctctctgggtcttcctttgcccactgagggcctcctg<br>tgagcccgatttaacggaaactgtgggcggtgagaagttcctta<br>tgacacactaatcccaacctgctgaccggaccacgcctccagcg<br>gagggaacctctagagctccaggacattcaggtaccaggtagcc |

TABLE 1-continued

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:) AND SEQUENCE |
|---|---|
| | ccaaggaggagctgccgacctggcaggtaagtcaatacctgggg |
| | cttgcctgggccagggagcccaggactggggtgaggactcaggg |
| | gagcagggagaccacgtcccaagatgcctgtaaaactgaaacca |
| | cctggccattctccaggttgagccagaccaatttgatggcagat |
| | ttagcaaataaaaatacaggacacccagttaaatgtgaatttca |
| | gatgaacagcaaatactttttagtattaaaaaagttcacatttt |
| | aggctcacgcctgtaatcccagcactttgggaggccgaggcagg |
| | cagatcacctgaggtcaggagttcgagaccagcctggccaacat |
| | ggtgaaaccccatctccactaaaaataccaaaaattagccaggc |
| | gtgctggtgggcacctgtagttccagctactcaggaggctaagg |
| | caggagaattgcttgaacctgggaggcagaggttgcagtgagct |
| | gagatcgcaccattgcactctagcctgggcgacaagaacaaaac |
| | tccatctcaaaaaaaaaaaaaaaaaaaagttcacatttaactg |
| | ggcattctgtatttaattggtaatctgagatggcagggaacagc |
| | atcagcatggtgtgagggataggcattttttcattgtgtacagc |
| | ttgtaaatcagtatttttaaaactcaaagttaatggcttgggca |
| | tatttagaaaagagttgccgcacggacttgaaccctgtattcct |
| | aaaatctaggatcttgttctgatggtctgcacaactggctgggg |
| | gtgtccagccactgtccctcttgcctgggctccccagggcagtt |
| | ctgtcagcctctccatttccattcctgttccagcaaaacccaac |
| | tgatagcacagcagcatttcagcctgtctacctctgtgcccaca |
| | tacctggatgtctaccagccagaaaggtggcttagatttggttc |
| | ctgtgggtggattatggcccccagaacttccctgtgcttgctgg |
| | gggtgtggagtggaaagagcaggaaatgggggaccctccgatac |
| | tctatgggggtcctccaagtctctttgtgcaagttagggtaata |
| | atcaatatggagctaagaaagagaaggggaactatgctttagaa |
| | caggacactgtgccaggagcattgcagaaattatatggttttca |
| | cgacagttcttttggtaggtactgttattatcctcagtttgca |
| | gatgaggaaactgagacccagaaaggttaaataacttgctaggg |
| | tcacacaagtcataactgacaaagcctgattcaaacccaggtct |
| | ccctaacctttaaggtttctatgacgccagctctcctagggagt |
| | ttgtcttcagatgtcttggctctaggtgtcaaaaaaagacttgg |
| | tgtcaggcaggcataggttcaagtcccaactctgtcacttacca |
| | actgtgactaggtgattgaactgaccatggaacctggtcacatg |
| | caggagcaggatggtgaagggttcttgaaggcacttaggcagga |
| | catttaggcaggagagaaaacctggaaacagaagagctgtctcc |
| | aaaaatacccactggggaagcaggttgtcatgtgggccatgaat |
| | gggacctgttctggtaaccaagcattgcttatgtgtccattaca |
| | tttcataacacttccatcctactttacagggaacaaccaagact |
| | ggggttaaatctcacagcctgcaagtggaagagaagaacttgaa |
| | cccaggtccaacttttgcgccacagcaggctgcctcttggtcct |
| | gacaggaagtcacaacttgggtctgagtactgatccctggctat |
| | ttttggctgtgttaccttggacaagtcacttattcctcctccc |
| | gtttcctcctatgtaaaatggaaataataatgttgaccctgggt |
| | ctgagagagtggatttgaaagtacttagtgcatcacaaagcaca |
| | gaacacacttccagtctcgtgattatgtacttatgtaactggtc |
| | atcacccatcttgagaatgaatgcattggggaaagggccatcca |
| | ctaggctgcgaagtttctgagggactccttcgggctggagaagg |
| | atggccacaggagggaggagagattgccttatcctgcagtgatc |
| | atgtcattgagaacagagccagattcttttttttcctggcagggc |
| | caacttgttttaacatctaaggactgagctatttgtgtctgtgc |
| | cctttgtccaagcagtgtttcccaaagtgtagcccaagaaccat |
| | ctccctcagagccaccaggaagtgctttaaattgcaggttccta |
| | ggccacagcctgcacctgcagagtcagaatcatggaggttggga |
| | cccaggcacctgcgtttctaacaaatgcctcgggtgattctgat |
| | gcaattgaaagtttgagatccacagttctgagacaataacagaa |
| | tggtttttctaaccccctgcagccctgacttcctatcctagggaa |
| | ggggccggctggagaggccaggacagagaaagcagatcccttct |
| | ttttccaaggactctgtgtcttccataggcaac |
| HUMAN RPE65 PROMOTER | 11 |
| | tacgtaatatttattgaagtttaatattgtgtttgtgatacaga |
| | agtatttgctttaattctaaataaaaattttatgcttttattgc |
| | tggtttaagaagatttggattatccttgtactttgaggagaagt |
| | ttcttatttgaaatattttggaaacaggtcttttaatgtggaaa |
| | gatagatattaatctcctcttctattactctccaagatccaaca |
| | aaagtgattataccccccaaaatatgatggtagtatcttatact |
| | accatcattttataggcatagggctcttagctgcaaataatgga |
| | actaactctaataaagcagaacgcaaatattgtaaatattagag |
| | agctaacaatctctgggatggctaaaggatggagcttggaggct |
| | acccagccagtaacaatattccgggctccactgttgaatggaga |
| | cactacaactgccttggatgggcagagatattatggatgctaag |
| | ccccaggtgctaccattaggacttctaccactgtccctaacggg |
| | tggagcccatcacatgcctatgccctcactgtaaggaaatgaag |

TABLE 1-continued

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:) AND SEQUENCE |
|---|---|
| | ctactgttgtatatcttgggaagcacttggattaattgttatac |
| | agttttgttgaagaagaccccctagggtaagtagccataactgca |
| | cactaaatttaaaattgttaatgagtttctcaaaaaaaatgtta |
| | aggttgttagctggtatagtatatatcttgcctgttttccaagg |
| | acttctttgggcagtaccttgtctgtgctggcaagcaactgaga |
| | cttaatgaaagagtattggagatatgaatgaattgatgctgtat |
| | actctcagagtgccaaacatataccaatggacaagaaggtgagg |
| | cagagagcagacaggcattagtgacaagcaaagatatgcagaat |
| | ttcattctcagcaaatcaaaagtcctcaacctggttggaagaat |
| | attggcactgaatggtatcaataaggttgctagagagggttaga |
| | ggtgcacaatgtgcttccataacatttatacttctccaatctt |
| | agcactaatcaaacatggttgaatactttgtttactataactct |
| | tacagagttataagatctgtgaagacagggacagggacaatacc |
| | catctctgtctggttcataggtggtatgtaatagatatttttaa |
| | aaataagtgagttaatgaatgagggtgagaatgaaggcacagag |
| | gtattaggggggaggtgggccccagagaatggtgccaaggtccag |
| | tggggtgactgggatcagctcaggcctgacgctggccactccca |
| | cctagctcctttctttctaatctgttctcattctccttgggaag |
| | gattgaggtctctggaaaacagccaaacaactgttatgggaaca |
| | gcaagcccaaataaagccaagcatcaggggatctgagagctga |
| | aagcaacttctgttccccctccctcagctgaaggggtggggaag |
| | ggctcccaaagccataactccttttaagggatttagaaggcata |
| | aaaaggcccctggctgagaacttccttcttcattctgcagttggt |
| HUMAN VMD2 PROMOTER | 12 |
| | tacgtaattctgtcattttactagggtgatgaaattcccaagca |
| | acaccatcctttcagataagggcactgaggctgagagaggagc |
| | tgaaacctacccggcgtcaccacacacaggtggcaaggctggga |
| | ccagaaaccaggactgttgactgcagcccggtattcattctttc |
| | catagcccacagggctgtcaaagaccccagggcctagtcagagg |
| | ctcctccttcctggagagttcctggcacagaagttgaagctcag |
| | cacagcccctaaccccaactctctgcaaggcctcaggggt |
| | cagaacactggtggagcagatccttagcctctggattttaggg |
| | ccatggtagagggggtgttgccctaaattccagccctggtctca |
| | gcccaacaccctccaagaagaaattagaggggccatggccaggc |
| | tgtgctagccgttgcttctgagcagattacaagaagggactaag |
| | acaaggactcctttgtggaggtcctggcttagggagtcaagtga |
| | cggcggctcagcactcacgtgggcagtgccagcctctaagagtg |
| | ggcaggggcactggccacagagtcccagggagtcccaccagcct |
| | agtcgccagacc |
| SYNUCLEIN INTRONIC SEQUENCE AS STUFFER SEQUENCE | 13 |
| | gggcccccggtgttatctcattctttttctcctctgtaagttga |
| | catgtgatgtgggaacaaagggggataaagtcattattttgtgct |
| | aaaatcgtaattggagaggacctcctgttagctgggctttcttc |
| | tatttattgtggtggttactggagttccttcttctagttttagg |
| | atatatatatatattttttttttctttccctgaagatataat |
| | aatatatatacttctgaagattgagattttttaaattagttgtat |
| | tgaaaactagctaatcagcaatttaaggctagcttgagacttat |
| | gtcttgaatttgtttttgtaggctccaaaaccaaggagggagtg |
| | gtgcatggtgtggcaacaggtaagctccattgtgcttatatcca |
| | aagatgatatttaaagtatctagtgattagtgtggcccagtatt |
| | caagattcctatgaaattgtaaaacaatcactgagcattctaag |
| | aacatatcagtcttattgaaactgaattcttataaagtatttt |
| | taaaaaggtaaatattgattataaataaaaaatatacttgccaa |
| | gaataatgagggctttgaattgataagctatgtttaatttatag |
| | taagtgggcatttaaatattctgaccaaaaatgtattgacaaac |
| | tgctgacaaaaatataaaatgtgaatattgccataattttaaaaaa |
| | agagtaaaatttctgttgattacagtaaaatattttgaccttaa |
| | attatgttgattacaatattcctttgataattcagagtgcattt |
| | caggaaacacccttggacagtcagtaaattgtttattgtattta |
| | tctttgtattgttatggtatagctatttgtacaaatattattgt |
| | gcaattattacatttctgattatattattcattggcctaaatt |
| | taccaagaatttgaacaagtcaattaggtttacaatcaagaaat |
| | atcaaaaatgatgaaaggatgataatcatcatcagatgttgag |
| | gaagatgacgatgagagtgccagaaatagagaaatcaaaggaga |
| | accaaaatttaacaaattaaaagcccacagacttgctgtaatta |
| | agttttctgttgtaagtactccacgtttcctggcagatgtggtg |
| | aagcaaaagatataatcagaaatataatttatatgatcggaaag |
| | cattaaacacaatagtgcctatacaaataaaatgttcctatcac |
| | tgacttctaaaatggaaatgaggacaatgatatgggaatcttaa |
| | tacagtgttgtggataggactaaaaacacaggagtcagatcttc |
| | ttggttcaacttcctgcttactccttaccagctgtgtgttttt |
| | gcaaggttcttcacctctatgtgatttagcttcctcatctataa |

TABLE 1-continued

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:) AND SEQUENCE |
|---|---|
| | aataattcagtgaattaatgtacacaaaacatctggaaaacaaa<br>agcaaacaatatgtattttataagtgttacttatagttttatag<br>tgaacttctcttgtgcaacattttacaactagtgggagaaaata<br>tttctttaaatgaatacttttgatttaaaaatcagagtgtaaaa<br>ataaaacagactcctttgaaactagttctgttagaagttaattg<br>tgcacctttaatgggctctgttgcaatccaacagagaagtagtt<br>aagtaagtggactatgatggcttctagggacctcctataaatat<br>gatattgtgaagcatgattataataagaactagataacagacag<br>gtggagactccactatctgaagagggtcaacctagatgaatggt<br>gttccatttagtagttgaggaagaacccatgaggtttagaaagc<br>agacaagcatgtggcaagttctggagtcagtggtaaaaattaaa<br>gaacccaactattactgtcacctaatgatctaatggagactgtg<br>gagatgggctgcattttttttaatcttctccagaatgccaaaatg<br>taaacacatatctgtgtgtgtgtgtgtgtgtgtgtgtgtgtg<br>agagagagagagagagagagagagactgaagtttgtacaattag<br>acatttataaaatgttttctgaaggacagtggctcacaatctt<br>aagtttctaacattgtacaatgttgggagactttgtatacttta<br>ttttctctttagcatattaaggaatctgagatgtcctacagtaa<br>agaaatttgcattacatagttaaaatcagggttattcaaactt<br>ttgattattgaaaccttctcttcattagttactagggttgaatga<br>aactagtgttccacagaaaactatgggaaatgttgctaggcagt<br>aaggacatggtgatttcagcatgtgcaatatttacagcgattgc<br>acccatggaccaccctggcagtagtgaaataaccaaaaatgctg<br>tcataactagtatggctatgagaaacacattggg |
| RLBP1 INTRONIC SEQUENCE AS STUFFER SEQUENCE (NT_010274.17) | 14<br>ATTCTCCAGGTTGAGCCAGACCAATTTGATGGTAGATTTAGCAA<br>ATAAAAATACAGGACACCCAGTTAAATGTGAATTTCCGATGAAC<br>AGCAAATACTTTTTTAGTATTAAAAAAGTTCACATTTAGGCTCA<br>CGCCTGTAATCCCAGCACTTTGGGAGGCCGAGGCAGGCAGATCA<br>CCTGAGGTCAGGAGTTCGAGACCAGCCTGGCCAACATGGTGAAA<br>CCCCATCTCCACTAAAAATACCAAAAATTAGCCAGGCGTGCTGG<br>TGGGCACCTGTAGTTCCAGCTACTCAGGAGGCTAAGGCAGGAGA<br>ATTGCTTGAACCTGGGAGGCAGAGGTTGCAGTGAGCTGAGATCG<br>CACCATTGCACTCTAGCCTGGGCGACAAGAACAAAACTCCATCT<br>CAAAAAAAAAAAAAAAAAAAAAGTTCACATTTAACTGGGCATTC<br>TGTATTTAATTGGTAATCTGAGATGGCAGGGAACAGCATCAGCA<br>TGGTGTGAGGGATAGGCATTTTTTCATTGTGTACAGCTTGTAAA<br>TCAGTATTTTTAAAACTCAAAGTTAATGGCTTGGGCATATTTAG<br>AAAAGAGTTGCCGCACGGACTTGAACCCTGTATTCCTAAAATCT<br>AGGATCTTGTTCTGATGGTCTGCACAACTGGCTGGGGGTGTCCA<br>GCCACTGTCCCTCTTGCCTGGGCTCCCCAGGGCAGTTCTGTCAG<br>CCTCTCCATTTCCATTCCTGTTCCAGCAAAACCCAACTGATAGC<br>ACAGCAGCATTTCAGCCTGTCTACCTCTGTGCCCACATACCTGG<br>ATGTCTACCAGCCAGAAAGGTGGCTTAGATTTGGTTCCTGTGGG<br>TGGATTATGGCCCCCAGAACTTCCCTGTGCTTGCTGGGGGTGTG<br>GAGTGGAAAGAGCAGGAAATGGGGGACCCTCCGATACTCTATGG<br>GGGTCCTCCAAGTCTCTTTGTGCAAGTTAGGGTAATAATCAATA<br>TGGAGCTAAGAAAGAGAAGGGGAACTATGCTTTAGAACAGGACA<br>CTGTGCCAGGAGCATTGCAGAAATTATATGGTTTTCACGACAGT<br>TCTTTTTGGTAGGTACTGTTATTATCCTCAGTTTGCAGATGAGG<br>AAACTGAGACCCAGAAAGGTTAAATAACTTGCTAGGGTCACACA<br>AGTCATAACTGACAAAGCCTGATTCAAACCCAGGTCTCCCTAAC<br>CTTTAAGGTTTCTATGACGCCAGCTCTCCTAGGGAGTTTGTCTT<br>CAGATGTCTTGGCTCTAGGTGTCAAAAAAAGACTTGGTGTCAGG<br>CAGGCATAGGTTCAAGTCCCAACTCTGTCACTTACCAACTGTGA<br>CTAGGTGATTGAACTGACCATGGAACCTGGTCACATGCAGGAGC<br>AGGATGGTGAAGGGTTCTTGAAGGCACTTAGGCAGGACATTTAG<br>GCAGGAGAGAAAACCTGGAAACAGAAGAGCTGTCTCCAAAAATA<br>CCCACTGGGGAAGCAGGTTGTCATGTGGGCCATGAATGGGACCT<br>GTTCTGG |
| AMP BACTERIAL BACKBONE | 15<br>ctgcctgcaggggcgcctgatgcggtattttctccttacgcatc<br>tgtgcggtatttcacaccgcatacgtcaaagcaaccatagtacg<br>cgccctgtagcggcgcattaagcgcggcgggtgtggtggttacg<br>cgcagcgtgaccgctacacttgccagcgccttagcgcccgctcc<br>tttcgctttcttcccttcctttctcgccacgttcgccggctttc<br>cccgtcaagctctaaatcgggggctcccttagggttccgattt<br>agtgctttacggcacctcgaccccaaaaaacttgatttgggtga<br>tggttcacgtagtgggccatcgccctgatagacggtttttcgcc<br>ctttgacgttggagtccacgttctttaatagtggactcttgttc<br>caaactggaacaacactcaactctatctcgggctattctttga<br>tttataagggattttgccgatttcggtctattggttaaaaaatg |

TABLE 1-continued

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:) AND SEQUENCE |
|---|---|
| | agctgatttaacaaaaatttaacgcgaattttaacaaaatatta |
| | acgtttacaattttatggtgcactctcagtacaatctgctctga |
| | tgccgcatagttaagccagccccgacacccgccaacacccgctg |
| | acgcgccctgacgggcttgtctgctcccggcatccgcttacaga |
| | caagctgtgaccgtctccgggagctgcatgtgtcagaggttttc |
| | accgtcatcaccgaaacgcgcgagacgaaagggcctcgtgatac |
| | gcctatttttataggttaatgtcatgataataatggtttcttag |
| | acgtcaggtggcacttttcggggaaatgtgcgcggaacccctat |
| | ttgtttatttttctaaatacattcaaatatgtatccgctcatga |
| | gacaataaccctgataaatgcttcaataatattgaaaaaggaag |
| | agtatgagtattcaacatttccgtgtcgcccttattccctttt |
| | tgcggcattttgccttcctgtttttgctcacccagaaacgctgg |
| | tgaaagtaaaagatgctgaagatcagttgggtgcacgagtgggt |
| | tacatcgaactggatctcaacagcggtaagatccttgagagttt |
| | tcgccccgaagaacgttttccaatgatgagcacttttaaagttc |
| | tgctatgtggcgcggtattatcccgtattgacgccgggcaagag |
| | caactcggtcgccgcatacactattctcagaatgacttggttga |
| | gtactcaccagtcacagaaaagcatcttacggatggcatgacag |
| | taagagaattatgcagtgctgccataaccatgagtgataacact |
| | gcggccaacttacttctgacaacgatcggaggaccgaaggagct |
| | aaccgcttttttgcacaacatgggggatcatgtaactcgccttg |
| | atcgttgggaaccggagctgaatgaagccataccaaacgacgag |
| | cgtgacaccacgatgcctgtagcaatggcaacaacgttgcgcaa |
| | actattaactggcgaactacttactctagcttcccggcaacaat |
| | taatagactggatggaggcggataaagttgcaggaccacttctg |
| | cgctcggcccttccggctggctggtttattgctgataaatctgg |
| | agccggtgagcgtgggtctcgcggtatcattgcagcactggggc |
| | cagatggtaagccctcccgtatcgtagttatctacacgacgggg |
| | agtcaggcaactatggatgaacgaaatagacagatcgctgagat |
| | aggtgcctcactgattaagcattggtaactgtcagaccaagttt |
| | actcatatactttagattgatttaaaacttcatttttaattt |
| | aaaaggatctaggtgaagatcctttttgataatctcatgaccaa |
| | aatcccttaacgtgagttttcgttccactgagcgtcagacccg |
| | tagaaaagatcaaaggatcttcttgaaatcctttttttctgcgc |
| | gtaatctgctgcttgcaaacaaaaaaaccaccgctaccagcggt |
| | ggtttgtttgccggatcaagagctaccaactctttttccgaagg |
| | taactggcttcagcagagcgcagataccaaatactgttcttcta |
| | gtgtagccgtagttaggccaccacttcaagaactctgtagcacc |
| | gcctacatacctcgctctgctaatcctgttaccagtggctgctg |
| | ccagtggcgataagtcgtgtcttaccgggttggactcaagacga |
| | tagttaccggataaggcgcagcggtcgggctgaacggggggttc |
| | gtgcacacagcccagcttggagcgaacgacctacaccgaactga |
| | gatacctacagcgtgagctatgagaaagcgccacgcttcccgaa |
| | gggagaaaggcggacaggtatccggtaagcggcagggtcggaac |
| | aggagagcgcacgagggagcttccaggggaaacgcctggtatc |
| | tttatagtcctgtcgggtttcgccacctctgacttgagcgtcga |
| | tttttgtgatgctcgtcaggggggcggagcctatggaaaaacgc |
| | cagcaacgcggcctttttacggttcctggccttttgctggcctt |
| | ttgctcacatgtcctgcaggcag |
| 5' ITR - STRATAGENE | 16<br>Ctgcgcgctcgctcgctcactgaggccgcccgggcaaagcccgg<br>gcgtcgggcgacctttggtcgcccggcctcagtgagcgagcgag<br>cgcgcagagagggagtggccaactccatcactaggggttcct |
| 5' ITR - NCBI (AF043303) | 17<br>Ttggccactccctctctgcgcgctcgctcgctcactgaggccgg<br>gcgaccaaaggtcgcccgacgcccgggctttgcccgggcggcct<br>cagtgagcgagcgagcgcgcagagagggagtggccaactccatc<br>actaggggttcct |
| AAV2 CAPSID CODING SEQUENCE | 18<br>atggctgccgatggttatcttccagattggctcgaggacactct<br>ctctgaaggaataagacagtggtggaagctcaaacctggcccac<br>caccaaaagcccgcagagcggcataaggacgacagcaggggt<br>cttgtgcttcctgggtacaagtacctcggacccttcaacggact<br>cgacaagggagagccggtcaacgaggcagacgccgcggccctcg<br>agcacgacaaagcctacgaccggcagctcgacagcggagacaac<br>ccgtacctcaagtacaaccacgccgacgcggagtttcaggacg<br>cctaaagaagatacgtcttttgggggcaacctcggacgagcag<br>tcttccaggcgaaaaagagggttcttgaacctctgggcctggtt<br>gaggaacctgttaagacggctccgggaaaaaagaggccggtaga<br>gcactctcctgtggagccagactcctcctcgggaaccggaaagg<br>cgggccagcagcctgcaagaaaaagattgaattttggtcagact |

TABLE 1-continued

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:) AND SEQUENCE |
|---|---|
| | ggagacgcagactcagtacctgacccccagcctctcggacagcc<br>accagcagcccctctggtctgggaactaatacgatggctacag<br>gcagtggcgccaccaatggcagacaataacgagggcgccgacgga<br>gtgggtaattcctcgggaaattggcattgcgattccacatggat<br>gggcgacagagtcatcaccaccagcacccgaacctgggccctgc<br>ccacctacaacaaccacctctacaaacaaatttccagccaatca<br>ggagcctcgaacgacaatcactactttggctacagcacccctg<br>ggggtattttgacttcaacagattccactgccacttttcaccac<br>gtgactggcaaagactcatcaacaacaactggggattccgaccc<br>aagagactcaacttcaagctctttaacattcaagtcaaagaggt<br>cacgcagaatgacggtacgacgacgattgccaataaccttacca<br>gcacggttcaggtgtttactgactcggagtaccagctcccgtac<br>gtcctcggctcggcgcatcaaggatgcctcccgccgttcccagc<br>agacgtcttcatggtgccacagtatggatacctcaccctgaaca<br>acgggagtcaggcagtaggacgctcttcattttactgcctggag<br>tactttccttctcagatgctgcgtaccggaaacaactttaccttt<br>cagctacacttttgaggacgttcctttccacagcagctacgctc<br>acagccagagtctggaccgtctcatgaatcctctcatcgaccag<br>tacctgtattacttgagcagaacaaacactccaagtggaaccac<br>cacgcagtcaaggcttcagtttttctcaggccggagcgagtgaca<br>ttcgggaccagtctaggaactggcttcctggaccctgttaccgc<br>cagcagcgagtatcaaagacatctgcggataacaacaacagtga<br>atactcgtggactggagctaccaagtaccacctcaatggcagag<br>actctctggtgaatccgggcccggccatggcaagccacaaggac<br>gatgaagaaaagttttttcctcagagcggggttctcatctttgg<br>gaagcaaggctcagagaaaacaaatgtggacattgaaaaggtca<br>tgattacagacgaagaggaaatcaggacaaccaatcccgtggct<br>acggagcagtatggttctgtatctaccaacctccagagaggcaa<br>cagacaagcagctaccgcagatgtcaacacacaaggcgttcttc<br>caggcatggtctggcaggacagagatgtgtaccttcaggggccc<br>atctgggcaaagattccacacacggacggacattttcaccctc<br>tcccctcatgggtggattcggacttaaacaccctcctccacaga<br>ttctcatcaagaacaccccggtacctgcgaatccttcgaccacc<br>ttcagtgcggcaaagtttgcttccttcatcacacagtactccac<br>gggacaggtcagcgtggagatcgagtgggagctgcagaaggaaa<br>acagcaaacgctggaatcccgaaattcagtacacttccaactac<br>aacaagtctgttaatgtggactttactgtggacactaatggcgt<br>gtattcagagcctcgcccattggcaccagatacctgactcgta<br>atctgtaa |
| AAV2 CAPSID SEQUENCE (VP1) | 19<br>maadgylpdwledtlsegirqwwklkpgppppkpaerhkddsrg<br>lvlpgykylgpfngldkgepvneadaaalehdkaydrqldsgdn<br>pylkynhadaefqerlkedtsfggnlgravfqakkrvleplglv<br>eepvktapgkkrpvehspvepdsssgtgkagqqparkrlnfgqt<br>gdadsvpdpqplgqppaapsglgtntmatgsgapmadnnegadg<br>vgnssgnwhcdstwmgdrvittstrtwalptynnhlykqissqs<br>gasndnhyfgystpwgyfdfnrfhchfsprdwqrlinnnwgfrp<br>krlnfklfniqvkevtqndgtttiannltstvqvftdseyqlpy<br>vlgsahqgclppfpadvfmvpqygyltlnngsqavgrssfycle<br>yfpsqmlrtgnnftfsytfedvpfhssyahsqsldrlmnplidq<br>ylyylsrtntpsgtttqsrlqfsqagasdirdqsrnwlpgpcyr<br>qqrvsktsadnnnseyswtgatkyhlngrdslvnpgpamashkd<br>deekffpqsgvlifgkqgsektnvdiekvmitdeeeirttnpva<br>teqygsvstnlqrgnrqaatadvntqgvlpgmvwqdrdvylqgp<br>iwakiphtdghfhpsplmggfglkhpppqilikntpvpanpstt<br>fsaakfasfitqystgqvsveiewelqkenskrwnpeiqytsny<br>nksvnvdftvdtngvyseprpigtryltrnl |
| AAV2 CAPSID SEQUENCE (VP2) | 68<br>mapgkkrpvehspvepdsssgtgkagqqparkrlnfgqtgdads<br>vpdpqplgqppaapsglgtntmatgsgapmadnnegadgvgnss<br>gnwhcdstwmgdrvittstrtwalptynnhlykqissqsgasnd<br>nhyfgystpwgyfdfnrfhchfsprdwqrlinnnwgfrpkrlnf<br>klfniqvkevtqndgtttiannltstvqvftdseyqlpyvlgsa<br>hqgclppfpadvfmvpqygyltlnngsqavgrssfycleyfpsq<br>mlrtgnnftfsytfedvpfhssyahsqsldrlmnplidqylyyl<br>srtntpsgtttqsrlqfsqagasdirdqsrnwlpgpcyrqqrvs<br>ktsadnnnseyswtgatkyhlngrdslvnpgpamashkddeekf<br>fpqsgvlifgkqgsektnvdiekvmitdeeeirttnpvateqyg<br>svstnlqrgnrqaatadvntqgvlpgmvwqdrdvylqgpiwaki<br>phtdghfhpsplmggfglkhpppqilikntpvpanpsttfsaak |

TABLE 1-continued

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:) AND SEQUENCE |
|---|---|
|  | fasfitqystgqvsveiewelqkenskrwnpeiqytsnynksvn<br>vdftvdtngvyseprpigtryltrnl |
| AAV2 CAPSID SEQUENCE (VP3) | 69<br>matgsgapmadnnegadgvgnssgnwhcdstwmgdrvittstrt<br>walptynnhlykqissqsgasndnhyfgystpwgyfdfnrfhch<br>fsprdwqrlinnnwgfrpkrlnfklfniqvkevtqndgtttian<br>nltstvqvftdseyqlpyvlgsahqgclppfpadvfmvpqygyl<br>tlnngsqavgrssfycleyfpsqmlrtgnnftfsytfedvpfhs<br>syahsqsldrlmnplidqylyylsrtntpsgtttqsrlqfsqag<br>asdirdqsrnwlpgpcyrqqrvsktsadnnnseyswtgatkyhl<br>ngrdslvnpgpamashkddeekffpqsgvlifgkqgsektnvdi<br>ekvmitdeeeirttnpvateqygsvstnlqrgnrqaatadvntq<br>gvlpgmvwqdrdvylqgpiwakiphtdghfhpsplmggfglkhp<br>ppqiliknt pvpanpsttfsaakfasfitqystgqvsveiewel<br>qkenskrwnpeiqytsnynksvnvdftvdtngvyseprpigtry<br>ltrnl |
| AAV8 CAPSID CODING SEQUENCE | 20<br>atggctgccgatggttatcttccagattggctcgaggacaacct<br>ctctgagggcattcgcgagtggtgggcgctgaaacctggagccc<br>cgaagcccaaagccaaccagcaaaagcaggacgacggccggggt<br>ctggtgcttcctggctacaagtacctcggacccttcaacggact<br>cgacaaggggagcccgtcaacgcggcggacgcagcggccctcg<br>agcacgacaaggcctacgaccagcagctgcaggcgggtgacaat<br>ccgtacctgcggtataaccacgccgacgccgagtttcaggagcg<br>tctgcaagaagatacgtcttttgggggcaacctcggcgagcag<br>tcttccaggccaagaagcgggttctcgaacctctcggtctggtt<br>gaggaaggcgctaagacggcctctggaaagaagagaccggtaga<br>gccatcaccccagcgttctccagactcctctacgggcatcggca<br>agaaaggccaacagcccgccagaaaaagactcaatttggtcag<br>actggcgactcagagtcagttccagaccctcaacctctcggaga<br>acctccagcagcgccctctggtgtgggacctaatacaatggctg<br>caggcggtggcgcaccaatggcagacaataacgaaggcgccgac<br>ggagtgggtagttcctcgggaaattggcattgcgattccacatg<br>gctgggcgacagagtcatcaccaccagcacccgaacctgggccc<br>tgcccacctacaacaaccacctctacaagcaaatctccaacggg<br>acatcgggaggagccaccaacgacaacacctacttcggctacag<br>cacccctgggggtattttgactttaacagattccactgccact<br>tttcaccacgtgactggcagcgactcatcaacaacaactgggga<br>ttccggcccaagagactcagcttcaagctcttcaacatccaggt<br>caaggaggtcacgcagaatgaaggcaccaagaccatcgccaata<br>acctcaccagcaccatccaggtgtttacggactcggagtaccag<br>ctgccgtacgttctcggctctgcccaccagggctgctgcctcc<br>gttccggcggacgtgttcatgattcccagtacggctacctaa<br>cactcaacaacggtagtcaggccgtgggacgctcctcctttctac<br>tgcctggaatactttccttcgcagatgctgagaaccggcaacaa<br>cttccagtttacttacaccttcgaggacgtgccttt ccacagca<br>gctacgccacagccagagcttggaccggctgatgaatcctctg<br>attgaccagtacctgtactacttgtctcggactcaaacaacagg<br>aggcacggcaaatacgcagactctgggcttcagccaaggtgggc<br>ctaatacaatggccaatcaggcaaagaactggctgccaggaccc<br>tgttaccgccaacaacgcgtctcaacgacaaccgggcaaaacaa<br>caatagcaactttgcctggactgctgggaccaaataccatctga<br>atgaagaaattcattggctaatcctggcatcgctatggcaaca<br>cacaaagacgacgaggagcgttttttcccagtaacgggatcct<br>gatttttggcaaacaaaatgctgccagagacaatgcggattaca<br>gcgatgtcatgctcaccagcgaggaagaaatcaaaaccactaac<br>cctgtggctacagaggaatacggtatcgtggcagataacttgca<br>gcagcaaaacacggctcctcaaattggaactgtcaacagccagg<br>gggccttacccggtatggtctggcagaaccgggacgtgtacctg<br>cagggtcccatctgggccaagattcctcacacgacggcaactt<br>ccacccgtctccgctgatgggcggctttggcctgaaacatcctc<br>cgcctcagatcctgatcaagaacacgcctgtacctgcggatcct<br>ccgaccaccttcaaccagtcaaagctgaactctttcatcacgca<br>atacagcaccggacaggtcagctggaaattgaatgggagctgc<br>agaaggaaaacagcaagcgctggaaccccgagatccagtacacc<br>tccaactactacaaatctacaagtgtggactttgctgttaatac<br>agaaggcgtgtactctgaaccccgcccattggcacccgttacc<br>tcacccgtaatctgtaa |
| AAV8 CAPSID SEQUENCE (VP1) | 21<br>maadgylpdwlednlsegirewwalkpgapkpkanqqkqddgrg<br>lvlpgykylgpfngldkgepvnaadaaalehdkaydqqlqagdn |

TABLE 1-continued

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:) AND SEQUENCE |
|---|---|
| | pylrynhadaefqerlqedtsfggnlgravfqakkrvleplglv eegaktapgkkrpvepspqrspdsstgigkkgqqparkrlnfgq tgdsesvpdpqplgeppaapsgvgpntmaagggapmadnnegad gvgsssgnwhcdstwlgdrvittstrtwalptynnhlykqisng tsggatndntyfgystpwgyfdfnrfhchfsprdwqrlinnnwg frpkrlsfklfniqvkevtqnegtktiannltstiqvftdseyq lpyvlgsahqgclppfpadvfmipqygyltlnngsqavgrssfy cleyfpsqmlrtgnnfqftytfedvpfhssyahsqsldrlmnpl idqylyylsrtqttggtantqtlgfsqggpntmanqaknwlpgp cyrqqrvstttgqnnnsnfawtagtkyhlngrnslanpgiamat hkddeerffpsngilifgkqnaardnadysdvmltseeeikttn pvateeygivadnlqqqntapqigtvnsqgalpgmvwqnrdvyl qgpiwakiphtdgnfhpsplmggfglkhpppqiliknrpvpadp pttfnqsklnsfitqystgqvsveiewelqkenskrwnpeiqyt snyykstsvdfavntegvyseprpigtryltrnl |
| AAV8 CAPSID SEQUENCE (VP2) | 70<br>mapgkkrpvepspqrspdsstgigkkgqqparkrlnfgqtgdse svpdpqplgeppaapsgvgpntmaagggapmadnnegadgvgss sgnwhcdstwlgdrvittstrtwalptynnhlykqisngtsgga tndntyfgystpwgyfdfnrfhchfsprdwqrlinnnwgfrpkr lsfklfniqvkevtqnegtktiannltstiqvftdseyqlpyvl gsahqgclppfpadvfmipqygyltlnngsqavgrssfycleyf psqmlrtgnnfqftytfedvpfhssyahsqsldrlmnplidqyl yylsrtqttggtantqtlgfsqggpntmanqaknwlpgpcyrqq rvstttgqnnnsnfawtagtkyhlngrnslanpgiamathkdde erffpsngilifgkqnaardnadysdvmltseeeikttnpvate eygivadnlqqqntapqigtvnsqgalpgmvwqnrdvylqgpiw akiphtdgnfhpsplmggfglkhpppqiliknrpvpadppttfn qsklnsfitqystgqvsveiewelqkenskrwnpeiqytsnyyk stsvdfavntegvyseprpigtryltrnl |
| AAV8 CAPSID SEQUENCE (VP3) | 71<br>maagggapmadnnegadgvgsssgnwhcdstwlgdrvittstrt walptynnhlykqisngtsggatndntyfgystpwgyfdfnrfh chfsprdwqrlinnnwgfrpkrlsfklfniqvkevtqnegtkt annltstiqvftdseyqlpyvlgsahqgclppfpadvfmipqyg yltlnngsqavgrssfycleyfpsqmlrtgnnfqftytfedvpf hssyahsqsldrlmnplidqylyylsrtqttggtantqtlgfsq ggpntmanqaknwlpgpcyrqqrvstttgqnnnsnfawtagtky hlngrnslanpgiamathkddeerffpsngilifgkqnaardna dysdvmltseeeikttnpvateeygivadnlqqqntapqigtvn sqgalpgmvwqnrdvylqgpiwakiphtdgnfhpsplmggfglk hpppqiliknrpvpadppttfnqsklnsfitqystgqvsveiew elqkenskrwnpeiqytsnyykstsvdfavntegvyseprpigt ryltrnl |
| CVM ENHANCER AND CBA PROMOTER (GENBANK ACCESSION DD215332 FROM BP 1-BP 1616) | 22<br>ACTAGTTATTAATAGTAATCAATTACGGGGTCATTAGTTCATAG CCCATATATGGAGTTCCGCGTTACATAACTTACGGTAAATGGCC CGCCTGGCTGACCGCCCAACGACCCCCGCCCATTGACGTCAATA ATGACGTATGTTCCCATAGTAACGCCAATAGGGACTTTCCATTG ACGTCAATGGGTGGAGTATTTACGGTAAACTGCCCACTTGGCAG TACATCAAGTGTATCATATGCCAAGTACGCCCCCTATTGACGTC AATGACGGTAAATGGCCCGCCTGGCATTATGCCCAGTACATGAC CTTATGGGACTTTCCTACTTGGCAGTACATCTACGTATTAGTCA TCGCTATTACCATGGTCGAGGTGAGCCCCACGTTCTGCTTCACT CTCCCCATCTCCCCCCCCTCCCCACCCCCAATTTTGTATTTATT TATTTTTTAATTATTTTGTGCAGCGATGGGGGCGGGGGGGGGGG GGGGGCGCGCGCCAGGCGGGGCGGGGCGGGGCGAGGGGCGGGGC GGGGCGAGGCGGAGAGGTGCGGCGGCAGCCAATCAGAGCGGCGC GCTCCGAAAGTTTCCTTTTATGGCGAGGCGGCGGCGGCGGCGGC CCTATAAAAAGCGAAGCGCGCGGCGGGCGGGAGTCGCTGCGAC GCTGCCTTCGCCCCGTGCCCCGCTCCGCCGCCGCCTCGCGCCGC CCGCCCCGGCTCTGACTGACCGCGTTACTCCCACAGGTGAGCGG GCGGGACGGCCCTTCTCCTCCGGGCTGTAATTAGCGCTTGGTTT AATGACGGCTTGTTTCTTTTCTGTGGCTGCGTGAAAGCCTTGAG GGGCTCCGGGAGGGCCCTTTGTGCGGGGGGAGCGGCTCGGGGGG TGCGTGCGTGTGTGTGTGCGTGGGGAGCGCCGCGTGCGGCCCCC CGCTGCCCGGCGGCTGTGAGCGCTGCGGGCGCGGCGCGGGGCTT TGTGCGCTCCGCAGTGTGCGCGAGGGGAGCGCGGCCGGGGGCGG TGCCCCGCGGTGCGGGGGGGGCTGCGAGGGGAACAAAGGCTGCG TGCGGGGTGTGTGCGTGGGGGGGTGAGCAGGGGGTGTGGGCGCG TCGGTCGGGCTGCAACCCCCCCTGCACCCCCCTCCCCGAGTTGC |

TABLE 1-continued

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:) AND SEQUENCE |
|---|---|
| | TGAGCACGGCCCGGCTTCGGGTGCGGGGCTCCGTACGGGGCGTG GCGCGGGGCTCGCCGTGCCGGGCGGGGGGTGGCGGCAGGTGGGG GTGCCGGGCGGGGCGGGGCCGCCTCGGGCCGGGGAGGGCTCGGG GGAGGGGCGCGGCGGCCCCCGGAGCGCCGGCGGCTGTCGAGGCG CGGCGAGCCGCAGCCATTGCCTTTTATGGTAATCGTGCGAGAGG GCGCAGGGACTTCCTTTGTCCCAAATCTGTGCGGAGCCGAAATC TGGGAGGCGCCGCCGCACCCCCTCTAGCGGGCGCGGGGCGAAGC GGTGCGGCGCCGGCAGGAAGGAAATGGGCGGGGAGGGCCTTCGT GCGTCGCCGCGCCGCCGTCCCCTTCTCCCTCTCCAGCCTCGGGG CTGTCCGCGGGGGACGGCTGCCTTCGGGGGGACGGGGCAGGG CGGGGTTCGGCTTCTGGCGTGTGACCGGCGGC |
| REVERSE COMPLEMENT OF RLBP1 INTRONIC SEQUENCE AS STUFFER SEQUENCE (NT_010274.17) | 23 CCAGAACAGGTCCCATTCATGGCCCACATGACAACCTGCTTCCC CAGTGGGTATTTTTGGAGACAGCTCTTCTGTTTCCAGGTTTTCT CTCCTGCCTAAATGTCCTGCCTAAGTGCCTTCAAGAACCCTTCA CCATCCTGCTCCTGCATGTGACCAGGTTCCATGGTCAGTTCAAT CACCTAGTCACAGTTGGTAAGTGACAGAGTTGGGACTTGAACCT ATGCCTGCCTGACACCAAGTCTTTTTTTGACACCTAGAGCCAAG ACATCTGAAGACAAACTCCCTAGGAGAGCTGGCGTCATAGAAAC CTTAAAGGTTAGGGAGACCTGGGTTTGAATCAGGCTTTGTCAGT TATGACTTGTGTGACCCTAGCAAGTTATTTAACCTTTCTGGGTC TCAGTTTCCTCATCTGCAAACTGAGGATAATAACAGTACCTACC AAAAAGAACTGTCGTGAAAACCATATAATTTCTGCAATGCTCCT GGCACAGTGTCCTGTTCTAAAGCATAGTTCCCCTTCTCTTTCTT AGCTCCATATTGATTATTACCCTAACTTGCACAAAGAGACTTGG AGGACCCCCATAGAGTATCGGAGGGTCCCCCATTTCCTGCTCTT TCCACTCCACACCCCCAGCAAGCACAGGGAAGTTCTGGGGGCCA TAATCCACCCACAGGAACCAAATCTAAGCCACCTTTCTGGCTGG TAGACATCCAGGTATGTGGGCACAGAGGTAGACAGGCTGAAATG CTGCTGTGCTATCAGTTGGGTTTTGCTGGAACAGGAATGGAAAT GGAGAGGCTGACAGAACTGCCCTGGGGAGCCCAGGCAAGAGGGA CAGTGGCTGGACACCCCCAGCCAGTTGTGCAGACCATCAGAACA AGATCCTAGATTTTAGGAATACAGGGTTCAAGTCCGTGCGGCAA CTCTTTTCTAAATATGCCCAAGCCATTAACTTTGAGTTTTAAAA ATACTGATTTACAAGCTGTACACAATGAAAAAATGCCTATCCCT CACACCATGCTGATGCTGTTCCCTGCCATCTCAGATTACCAATT AAATACAGAATGCCCAGTTAAATGTGAACTTTTTTTTTTTTTTT TTTTTTGAGATGGAGTTTTGTTCTTGTCGCCCAGGCTAGAGTGC AATGGTGCGATCTCAGCTCACTGCAACCTCTGCCTCCCAGGTTC AAGCAATTCTCCTGCCTTAGCCTCCTGAGTAGCTGGAACTACAG GTGCCCACCAGCACGCCTGGCTAATTTTTGGTATTTTTAGTGGA GATGGGGTTTCACCATGTTGGCCAGGCTGGTCTCGAACTCCTGA CCTCAGGTGATCTGCCTGCCTCGGCCTCCCAAAGTGCTGGGATT ACAGGCGTGAGCCTAAATGTGAACTTTTTTAATACTAAAAAAGT ATTTGCTGTTCATCGGAAATTCACATTTAACTGGGTGTCCTGTA TTTTTATTTGCTAAATCTACCATCAAATTGGTCTGGCTCAACCT GGAGAAT |
| EGFP SEQUENCE | 24 ATGGTGAGCAAGGGCGAGGAGCTGTTCACCGGGGTGGTGCCCAT CCTGGTCGAGCTGGACGGCGACGTAAACGGCCACAAGTTCAGCG TGTCCGGCGAGGGCGAGGGCGATGCCACCTACGGCAAGCTGACC CTGAAGTTCATCTGCACCACCGGCAAGCTGCCCGTGCCCTGGCC CACCCTCGTGACCACCCTGACCTACGGCGTGCAGTGCTTCAGCC GCTACCCCGACCACATGAAGCAGCACGACTTCTTCAAGTCCGCC ATGCCCGAAGGCTACGTCCAGGAGCGCACCATCTTCTTCAAGGA CGACGGCAACTACAAGACCCGCGCCGAGGTGAAGTTCGAGGGCG ACACCCTGGTGAACCGCATCGAGCTGAAGGGCATCGACTTCAAG GAGGACGGCAACATCCTGGGGCACAAGCTGGAGTACAACTACAA CAGCCACAACGTCTATATCATGGCCGACAAGCAGAAGAACGGCA TCAAGGTGAACTTCAAGATCCGCCACAACATCGAGGACGGCAGC GTGCAGCTCGCCGACCACTACCAGCAGAACACCCCCATCGGCGA CGGCCCCGTGCTGCTGCCCGACAACCACTACCTGAGCACCCAGT CCGCCCTGAGCAAAGACCCCAACGAGAAGCGCGATCACATGGTC CTGCTGGAGTTCGTGACCGCCGCCGGGATCACTCTCGGCATGGA CGAGCTGTACAAGTAA |

TABLE 1-continued

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:) AND SEQUENCE |
|---|---|
| GFP AMINO ACID SEQUENCE | 25<br>MVSKGEELFTGVVPILVELDGDVNGHKFSVSGEGEGDATYGKLT<br>LKFICT<br>TGKLPVPWPTLVTTLTYGVQCFSRYPDHMKQHDFFKSAMPEGYV<br>QERTIF<br>FKDDGNYKTRAEVKFEGDTLVNRIELKGIDFKEDGNILGHKLEY<br>NYNSHN<br>VYIMADKQKNGIKVNFKIRHNIEDGSVQLADHYQQNTPIGDGPV<br>LLPDNH<br>YLSTQSALSKDPNEKRDHMVLLEFVTAAGITLGMDELYK |
| SC5'ITR | 36<br>CTGCGCGCTCGCTCGCTCACTGAGGCCGCCCGGGCAAAGCCCGG<br>GCGTCGGGCGACCTTTGGTCGCCCGGCCTCAGTGAGCGAGCGAG<br>CGCGCAGAGAGGGAGTGGCCAACTCCATCACTAGGGGTTCCT |
| *MACACA MULATTA* (RHESUS MONKEY) RLBP1 CDS XM_001091538 | 37<br>ATGTCAGAAGGGGTGGGCACGTTCCGCATGGTACCTGAAGAGGA<br>ACAGGAGCTCCGTGCCCAACTGGAGCAGCTCACAACCAAGGACC<br>ATGGACCTGTCTTTGGCCCGTGCAGCCAGCTGCCCCGCCACACC<br>TTGCAGAAGGCCAAAGATGAGCTGAATGAGAGAGAGGAGACCCG<br>GGAGGAGGCAGTGCGAGAGCTGCAGGAGATGGTGCAGGCGCAGG<br>CGGCCTCGGGGGAGGAGCTGGCCGTGGCCGTGGCGGAGAGGGTG<br>CAAGAGAAGGACAGCGGCTTCTTCCTGCGCTTCATCCGCGCGCG<br>AAAGTTCAACGTGGGCCGTGCCTATGAGCTGCTCAGAGGCTATG<br>TGAATTTCCGGCTGCAGTACCCTGAGCTCTTTGACAGCCTGTCC<br>CCAGAGGCTGTCCGCTGTACCATTGAAGCTGGCTACCCTGGTGT<br>CCTCTCTAGTCGGGACAAGTATGGCCGAGTGGTCATGCTCTTCA<br>ACATTGAGAACTGGCAAAGTCAAGAAATCACCTTCGATGAGATC<br>TTGCAGGCATATTGCTTCATCCTGGAGAAGCTGCTGGAGAATGA<br>GGAAACTCAAATTAATGGATTCTGCATCATTGAGAACTTCAAGG<br>GCTTTACCATGCAGCAGGCTGCTAGTCTCCGCACTTCAGATCTC<br>AGGAAGATGGTGGACATGCTCCAGGATTCCTTCCCAGCCCGGTT<br>CAAAGCCATCCACTTCATCCACCAGCCATGGTACTTCACCACGA<br>CCTACAATGTGGTCAAGCCCTTCTTGAAGAGCAAGCTGCTTGAG<br>AGGGTCTTTGTCCACGGGGAGGACCTCTCTGGTTTCTACCAGGA<br>GATTGATGAGAACATCCTGCCCTCTGACTTTGGGGGCACGCTGC<br>CCAAGTATGATGGCAAAGCTGTTGCTGAGCAGCTCTTTGGCCCC<br>CGGGGCCCAAGCTGAGAACACAGCCTTCTGA |
| *MACACA MULATTA* (RHESUS MONKEY) RLBP1 GENE PRODUCT (CELLULAR RETINALDEHYDE BINDING PROTEIN - CRALBP) | 38<br>MSEGVGTFRMVPEEEQELRAQLEQLTTKDHGPVFGPCSQLPRHT<br>LQKAKDELNEREETREEAVRELQEMVQAQAASGEELAVAVAERV<br>QEKDSGFFLRFIRARKFNVGRAYELLRGYVNFRLQYPELFDSLS<br>PEAVRCTIEAGYPGVLSSRDKYGRVVMLFNIENWQSQEITFDEI<br>LQAYCFILEKLLENEETQINGFCIIENFKGFTMQQAASLRTSDL<br>RKMVDMLQDSFPARFKAIHFIHQPWYFTTTYNVVKPFLKSKLLE<br>RVFVHGEDLSGFYQEIDENILPSDFGGTLPKYDGKAVAEQLFGP<br>RAQAENTAF |
| *BOS TAURUS* RLBP1 CDS NM_174451 | 39<br>ATGTCAGAGGGGGCGGGCACGTTCCGCATGGTCCCTGAAGAGGA<br>ACAGGAGCTCCGTGCCCAACTGGAGAGGCTTACGACCAAAGACC<br>ATGGACCTGTCTTTGGCCCGTGCAGCCAGCTGCCCCGCCACACC<br>TTGCAGAAGGCCAAGGACGAGCTGAATGAAAAGGAAGAGACCCG<br>GGAAGAGGCAGTGCGGGAGCTACAGGAGCTGGTGCAGGCGGAGG<br>CCGCCTCGGGGCAGGAGCTGGCCGTGGCCGTGGCGGAGAGGGTG<br>CAGGGAAAAGACAGTGCCTTCTTCCTGCGCTTCATCCGCGCGCG<br>CAAGTTCCACGTGGGGCGCGCCTACGAGCTGCTCAGAGGCTACG<br>TGAACTTCCGGCTGCAGTACCCAGAGCTCTTCGACAGCCTGTCC<br>CCAGAGGCTGTCCGCTGCACCGTTGAGGCTGGCTACCCTGGTGT<br>CCTCTCCACGCGGGACAAGTATGGCCGAGTGGTCATGCTCTTCA<br>ATATTGAGAACTGGGACTCTGAAGAAATCACCTTTGATGAGATC<br>TTGCAGGCATACTGCGTCATCCTGGAGAAGCTACTGGAGAATGA<br>GGAGACTCAAATTAATGGCTTTTGCATCATTGAGAACTTCAAGG<br>GCTTCACCATGCAGCAGGCTGCCGGACTTCGGCCTTCCGATC<br>TCAGAAAGATGGTGGACATGCTCCAGGATTCCTTCCCAGCTCGG<br>TTCAAAGCCATCCACTTCATCTACCAGCCCTGGTACTTCACCAC<br>CACCTACAACGTGGTCAAGCCCTTCTTGAAGAGCAAATTGCTCC<br>AGAGGGTATTTGTCCATGGAGAAGACCTCTCCAGCTTCTACCAG<br>GAGTTTGACGAGGACATCCTGCCCTCCGACTTTGGGGGTACACT<br>GCCCAAGTATGATGGCAAGGCCGTTGCTGAGCAGCTCTTTGGTC<br>CTCGGGACCAAACTGAGAACACAGCCTTCTGA |

TABLE 1-continued

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:) AND SEQUENCE |
|---|---|
| BOS TAURUS RLBP1 GENE PRODUCT (CELLULAR RETINALDEHYDE BINDING PROTEIN - CRALBP) | 40<br>MSEGAGTFRMVPEEEQELRAQLERLTTKDHGPVFGPCSQLPRHT<br>LQKAKDELNEKEETREEAVRELQELVQAEAASGQELAVAVAERV<br>QGKDSAFFLRFIRARKFHVGRAYELLRGYVNFRLQYPELFDSLS<br>PEAVRCTVEAGYPGVLSTRDKYGRVVMLFNIENWDSEEITFDEI<br>LQAYCVILEKLLENEETQINGFCIIENFKGFTMQQAAGLRPSDL<br>RKMVDMLQDSFPARFKAIHFIYQPWYFTTTYNVVKPFLKSKLLQ<br>RVFVHGEDLSSFYQEFDEDILPSDFGGTLPKYDGKAVAEQLFGP<br>RDQTENTAF |
| CANIS LUPUS FAMILIARIS RLBP1 CDS XM_549634 | 41<br>ATGTCAGAAGGCGTGGGCACATTCCGTGTGGTCCCTGAAGAGGA<br>ACAGGAGCTCCGTGCCCAGCTGGAGCGGCTTACAACCAAGGACC<br>ATGGGCCTGTCTTTGGCCCTTGCAGCCAGCTCCCTCGTCATACC<br>TTACAGAAGGCCAAGGACGAGCTGAACGAGAGGGAGGAGACCCG<br>GGAGGAGGTGGTGCGAGAGCTGCAGGAGCTGGTGCAGGCACAGG<br>CTGCCACCGGGCAGGAGCTGGCCAGGGCGGTGGCTGAGAGGGTG<br>CAGGGAAGGGACAGTGCCTTCTTCCTGCGCTTCATCCGCGCGCG<br>GAAGTTCCATGTGGGGCGTGCCTACGAGCTGCTTCGAGGCTACG<br>TGAACTTCCGGCTGCAGTACCCAGAGCTCTTCGACAGCCTGTCC<br>CTGGAGGCTGTCCGTTGCACCGTCGAGGCCGGCTATCCTGGGGT<br>CCTCCCCAGTCGGGACAAGTATGGCCGAGTGGTCATGCTCTTCA<br>ACATCGAGAACTGGGACTCCGAAGAAATCACCTTCGATGAGATC<br>TTGCAGGCATATTGTTTCATCCTGGAGAAGCTACTAGAGAATGA<br>GGAAACTCAAATTAATGGCTTCTGCATTATTGAGAACTTTAAGG<br>GCTTTACCATGCAGCAGGCTGCTGGACTTCGGGCTTCCGATCTC<br>AGGAAGATGGTGGACATGCTCCAGGATTCCTTCCCAGCGCGGTT<br>CAAAGCCATCCACTTCATTCACCAACCATGGTACTTCACCACCA<br>CCTACAACATGGTCAAGCCCCTCCTGAAGAACAAGCTGCTCCAA<br>AGAGTCTTTGTCCATGGAGATGACCTCTCTGGCTTCTTCCAGGA<br>GATTGATGAAGACATACTGCCCGCTGACTTTGGGGGCACACTGC<br>CCAAGTATGATGGCAAGGTGGTTGCTGAGCAGCTCTTTGGCCCC<br>CGGGCCCAAGCTGAGAACACAGCCTTCTGA |
| CANIS LUPUS FAMILIARIS RLBP1 GENE PRODUCT (CELLULAR RETINALDEHYDE BINDING PROTEIN - CRALBP) | 42<br>MSEGVGTFRVVPEEEQELRAQLERLTTKDHGPVFGPCSQLPRHT<br>LQKAKDELNEREETREEVVRELQELVQAQAATGQELARAVAERV<br>QGRDSAFFLRFIRARKFHVGRAYELLRGYVNFRLQYPELFDSLS<br>LEAVRCTVEAGYPGVLPSRDKYGRVVMLFNIENWDSEEITFDEI<br>LQAYCFILEKLLENEETQINGFCIIENFKGFTMQQAAGLRASDL<br>RKMVDMLQDSFPARFKAIHFIHQPWYFTTTYNMVKPLLKNKLLQ<br>RVFVHGDDLSGFFQEIDEDILPADFGGTLPKYDGKVVAEQLFGP<br>RAQAENTAF |
| RATTUS NORVEGICUS RLBP1 CDS NM_001106274.1 | 43<br>ATGTCAGAGGGGGTGGGCACATTCCGAATGGTCCCTGAAGAGGA<br>GCAGGAGCTCCGGGCACAGCTAGAACAGCTCACAACCAAGGATC<br>ATGGTCCTGTCTTTGGCCCATGCAGCCAGCTGCCCCGCCACACT<br>TTGCAGAAGGCTAAGGATGAGCTGAATGAAAGGGAGGAAACCCG<br>GGATGAGGCGGTGAGGGAGCTACAGGAGCTGGTCCAGGCACAGG<br>CAGCTTCTGGGGAAGAGTTGGCCGTGGCAGTGGCTGAGAGGGTG<br>CAGGCAAGAGACAGCGCCTTCCTCCTGCGCTTCATCCGTGCCCG<br>AAAGTTTGATGTGGGCCGGGCTTATGAGCTGCTCAAAGGCTATG<br>TGAACTTCCGGCTCCAGTACCCTGAACTCTTCGATAGCCTATC<br>TATGGAGGCTCTCCGCTGCACTATCGAGGCCGGTTACCCTGGTG<br>TCCTTTCCAGTCGGGACAAGTATGGTCGAGTGGTTATGCTCTTC<br>AACATTGAAAACTGGCACTGTGAAGAAGTCACCTTTGATGAGAT<br>CTTACAGGCATATTGTTTCATTCTGGAGAAACTGCTGGAGAACG<br>AGGAAACCCAAATCAACGGCTTCTGTATTGTGGAGAACTTCAAG<br>GGCTTCACCATGCAGCAGGCCGCGGGACTCCGCCCCTCCGATCT<br>CAAGAAGATGGTGGACATGCTCCAGGATTCATTCCCAGCCAGGT<br>TCAAAGCTATCCACTTCATCCACCAACCATGGTACTTCACCACC<br>ACTTACAATGTGGTCAAGCCCTTCTTGAAGAACAAGTTGCTACA<br>GAGGGTCTTCGTTCATGGAGATGACCTGGACGGCTTCTTCCAGG<br>AGATTGATGAGAATATCTTGCCTGCTGACTTTGGGGGTACACTG<br>CCCAAGTATGACGGCAAAGTTGTCGCTGAGCAGCTCTTCGGTCC<br>CCGGGTTGAGGTTGAGAACACAGCCTTGTGA |
| RATTUS NORVEGICUS RLBP1 GENE PRODUCT (CELLULAR | 44<br>MSEGVGTFRMVPEEEQELRAQLEQLTTKDHGPVFGPCSQLPRHT<br>LQKAKDELNEREETRDEAVRELQELVQAQAASGEELAVAVAERV<br>QARDSAFLLRFIRARKFDVGRAYELLKGYVNFRLQYPELFDSLS<br>MEALRCTIEAGYPGVLSSRDKYGRVVMLFNIENWHCEEVTFDEI |

TABLE 1-continued

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:) AND SEQUENCE |
|---|---|
| RETINALDEHYDE BINDING PROTEIN - CRALBP) | LQAYCFILEKLLENEETQINGFCIVENFKGFTMQQAAGLRPS DLKKMVDMLQDSFPARFKAIHFIHQPWYFTTTYNVVKPFLKNKL LQRVFVHGDDLDGFFQEIDENILPADFGGTLPKYDGKVVAEQLF GPRVEVENTAL |
| MUS MUSCULUS RLBP1 CDS NM_020599.2 | 45<br>ATGTCAGACGGGGTGGGCACTTTCCGCATGGTTCCTGAAGAGGA GCAGGAGCTCCGAGCACAACTGGAGCAGCTCACAACCAAGGATC ATGGTCCTGTCTTTGGCCCATGCAGCCAGCTGCCCCGCACACT TTGCAGAAGGCCAAGGATGAGCTGAATGAAAAGGAGGAGACCCG GGAGGAAGCGGTGAGGGAGCTACAGGAGCTGGTACAGGCACAGG CAGCTTCTGGCGAGGAATTGGCCCTGGCAGTGGCTGAGAGGGTG CAGGCAAGAGACAGCGCCTTCCTCCTGCGCTTCATCCGTGCCCG CAAGTTCGATGTGGGTCGTGCTTATGAGCTGCTCAAAGGCTATG TGAACTTCCGCCTCCAGTACCCTGAACTCTTCGATAGTCTCTCC ATGGAGGCTCTCCGCTGCACTATCGAGGCCGGATACCCTGGTGT CCTTTCCAGTCGGGACAAGTATGGTCGAGTGGTTATGCTCTTCA ACATCGAAAACTGGCACTGTGAAGAAGTGACCTTTGATGAGATC TTACAGGCATATTGTTTCATTTTGGAGAAACTGCTGGAAAATGA GGAAACCCAAATCAACGGCTTCTGTATTGTTGAGAACTTCAAGG GCTTCACCATGCAGCAGGCAGCAGGGCTCCGCCCCTCGGATCTC AAGAAGATGGTGGACATGCTCCAGGATTCATTCCCAGCCAGGTT CAAAGCTATCCACTTCATCCACCAGCCATGGTACTTCACCACCA CCTATAATGTGGTCAAGCCCTTCTTGAAGAACAAGCTGCTACAG AGGGTCTTTGTTCACGGAGATGACCTGGATGGCTTCTTCCAGGA GATTGATGAGAACATCCTGCCTGCTGACTTTGGGGGTACACTGC CCAAGTACGACGGCAAAGTTGTTGCTGAGCAGCTCTTTGGTCCC CGGGCTGAAGTTGAGAACACAGCCTTATGA |
| MUS MUSCULUS RLBP1 GENE PRODUCT (CELLULAR RETINALDEHYDE BINDING PROTEIN - CRALBP) | 46<br>MSDGVGTFRMVPEEEQELRAQLEQLTTKDHGPVFGPCSQLPRHT LQKAKDELNEKEETREEAVRELQELVQAQAASGEELALAVAERV QARDSAFLLRFIRARKFDVGRAYELLKGYVNFRLQYPELFDSLS MEALRCTIEAGYPGVLSSRDKYGRVVMLFNIENWHCEEVTFDEI LQAYCFILEKLLENEETQINGFCIVENFKGFTMQQAAGLRPSDL KKMVDMLQDSFPARFKAIHFIHQPWYFTTTYNVVKPFLKNKLLQ RVFVHGDDLDGFFQEIDENILPADFGGTLPKYDGKVVAEQLFGP RAEVENTAL |
| GALLUS GALLUS RLBP1 CDS NM_001024694.1 | 47<br>ATGTCTGCTGTTACGGGCACCTTCCGCATTGTCTCGGAAGAGGA GCAGGCGCTGCGCACCAAACTGGAGCGCCTCACCACCAAGGACC ACGGCCCTGTTTTTGGGAGGTGCCAGCAGATCCCCCCTCACACC CTGCAGAAGGCAAAGATGAGCTGAATGAGACGGAGGAGCAGAG GGAGGCAGCGGTCAAAGCGCTGCGGGAGCTGGTGCAGGAGCGGG CCGGCAGCGAGGATGTCTGCAAGGCAGTGGCAGAGAAGATGCAG GGGAAGGACGATTCCTTCTTCCTCCGCTTCATCCGTGCCCGCAA GTTTGACGTGCACAGGGCCTACGACCTGCTGAAAGGCTATGTGA ACTTTCGCCAGCAATACCCTGAACTCTTTGACAACCTGACCCCC GAGGCCGTGCGCAGCACCATCGAGGCGGGCTACCCCGGCATCCT GGCCAGCAGGGACAAATACGGGCGGGTAGTGATGCTCTTCAACA TCGAGAACTGGGACTACGAGGAGATCACCTTTGATGAGATCCTT CGTGCCTACTGCGTTATCTTGGAGAAGCTGCTGGAAAACGAAGA GACCCAGATCAATGGGTTCTGCATCATTGAGAACTTCAAGGGCT TCACCATGCAGCAGGCATCAGGGATCAAACCCTCCGAGCTCAAG AAGATGGTGGACATGCTCAGGACTCCTTCCCAGCGCGGTTCAA AGCTGTCCACTTCATCCACCAGCCCTGGTACTTCACCACTACCT ACAACGTGGTCAAACCGTTCCTGAAGAGCAAGCTGCTGGAGAGG GTGTTTGTGCACGGCGAGGAGCTGGAGTCCTTCTACCAGGAG ATCGATGCTGACATACTGCCAGCAGACTTCGGTGGCAACCTGCC CAAGTACGACGGCAAAGCAACTGCAGAGCAGCTCTTTGGGCCCC GCATTGAGGCTGAAGACACGGCACTTTAA |
| GALLUS GALLUS RLBP1 GENE PRODUCT (CELLULAR RETINALDEHYDE BINDING PROTEIN - CRALBP) NP_001019865.1 | 48<br>MSAVTGTFRIVSEEEQALRTKLERLTTKDHGPVFGRCQQIPPHT LQKAKDELNETEEQREAAVKALRELVQERAGSEDVCKAVAEKMQ GKDDSFFLRFIRARKFDVHRAYDLLKGYVNFRQQYPELFDNLTP EAVRSTIEAGYPGILASRDKYGRVVMLFNIENWDYEEITFDEIL RAYCVILEKLLENEETQINGFCIIENFKGFTMQQASGIKPSELK KMVDMLQDSFPARFKAVHFIHQPWYFTTTYNVVKPFLKSKLLER VFVHGEELESFYQEIDADILPADFGGNLPKYDGKATAEQLFGPR IEAEDTAL |

TABLE 1-continued

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:) AND SEQUENCE |
|---|---|
| KAN-R BACTERIAL BACKBONE | 49<br>CTGCCTGCAGGGTTCCATCCCAATGGCGCGTCAATTCACTGGCC<br>GTCGTTTTACAACGTCGTGACTGGGAAAACCCTGGCGTTACCCA<br>ACTTAATCGCCTTGCAGCACATCCCCCTTTCGCCAGCTGGCGTA<br>ATAGCGAAGAGGCCCGCACCGATCGCCCTTCCCAACAGTTGCGC<br>AGCCTGAATGGCGAATGGCGCCTGATGCGGTATTTTCTCCTTAC<br>GCATCTGTGCGGTATTTCACACCGCATATGGTGCACTCTCAGTA<br>CAATCTGCTCTGATGCCGCATAGTTAAGCCAGCCCCGACACCCG<br>CCAACACCCGCTGACGCGCCCTGACGGGCTTGTCTGCTCCCGGC<br>ATCCGCTTACAGACAAGCTGTGACCGTCTCCGGGAGCTGCATGT<br>GTCAGAGGTTTTCACCGTCATCACCGAAACGCGCGAGACGAAAG<br>GGCCTCGTGATACGCCTATTTTTATAGGTTAATGTCATGATAAT<br>AATGGTTTCTTAGACGTCAGGTGGCACTTTTCGGGGAAATGTGC<br>GCGGAACCCCTATTTGTTTATTTTTCTAAATACATTCAAATATG<br>TATCCGCTCATGAGACAATAACCCTGATAAATGCTTCAATAATA<br>TTGAAAAAGGAAGAGTATGAGCCATATTCAACGGGAAACGTCTT<br>GCTCTAGGCCGCGATTAAATTCCAACATGGATGCTGATTTATAT<br>GGGTATAAATGGGCTCGCGATAATGTCGGGCAATCAGGTGCGAC<br>AATCTATCGATTGTATGGGAAGCCCGATGCGCCAGAGTTGTTTC<br>TGAAACATGGCAAAGGTAGCGTTGCCAATGATGTTACAGATGAG<br>ATGGTCAGACTAAACTGGCTGACGGAATTTATGCCTCTTCCGAC<br>CATCAAGCATTTTATCCGTACTCCTGATGATGCATGGTTACTCA<br>CCACTGCGATCCCTGGGAAAACAGCATTCCAGGTATTAGAAGAA<br>TATCCTGATTCAGGTGAAAATATTGTTGATGCGCTGGCAGTGTT<br>CCTGCGCCGGTTGCATTCGATTCCTGTTTGTAATTGTCCTTTTA<br>ACAGCGATCGCGTATTTCGTCTCGCTCAGGCGCAATCACGAATG<br>AATAACGGTTTGGTTGATGCGAGTGATTTTGATGACGAGCGTAA<br>TGGCTGGCCTGTTGAACAAGTCTGGAAAGAAATGCATAAACTTT<br>TGCCATTCTCACCGGATTCAGTCGTCACTCATGGTGATTTCTCA<br>CTTGATAACCTTATTTTTGACGAGGGGAAATTAATAGGTTGTAT<br>TGATGTTGGACGAGTCGGAATCGCAGACCGATACCAGGATCTTG<br>CCATCCTATGGAACTGCCTCGGTGAGTTTTCTCCTTCATTACAG<br>AAACGGCTTTTTCAAAAATATGGTATTGATAATCCTGATATGAA<br>TAAATTGCAGTTTCATTTGATGCTCGATGAGTTTTTCTAACTGT<br>CAGACCAAGTTTACTCATATATACTTTAGATTGATTTAAAACTT<br>CATTTTTAATTTAAAAGGATCTAGGTGAAGATCCTTTTTGATAA<br>TCTCATGACCAAAATCCCTTAACGTGAGTTTTCGTTCCACTGAG<br>CGTCAGACCCCGTAGAAAAGATCAAAGGATCTTCTTGAGATCCT<br>TTTTTTCTGCGCGTAATCTGCTGCTTGCAAACAAAAAAACCACC<br>GCTACCAGCGGTGGTTTGTTTGCCGGATCAAGAGCTACCAACTC<br>TTTTTCCGAAGGTAACTGGCTTCAGCAGAGCGCAGATACCAAAT<br>ACTGTTCTTCTAGTGTAGCCGTAGTTAGGCCACCACTTCAAGAA<br>CTCTGTAGCACCGCCTACATACCTCGCTCTGCTAATCCTGTTAC<br>CAGTGGCTGCTGCCAGTGGCGATAAGTCGTGTCTTACCGGGTTG<br>GACTCAAGACGATAGTTACCGGATAAGGCGCAGCGGTCGGGCTG<br>AACGGGGGGTTCGTGCACACAGCCCAGCTTGGAGCGAACGACCT<br>ACACCGAACTGAGATACCTACAGCGTGAGCTATGAGAAAGCGCC<br>ACGCTTCCCGAAGGGAGAAAGGCGGACAGGTATCCGGTAAGCGG<br>CAGGGTCGGAACAGGAGAGCGCACGAGGGAGCTTCCAGGGGGAA<br>ACGCCTGGTATCTTTATAGTCCTGTCGGGTTTCGCCACCTCTGA<br>CTTGAGCGTCGATTTTTGTGATGCTCGTCAGGGGGGCGGAGCCT<br>ATGGAAAAACGCCAGCAACGCGGCCTTTTTACGGTTCCTGGCCT<br>TTTGCTGGCCTTTTGCTCACATGTTCTTTCCTGCGTTATCCCCT<br>GATTCTGTGGATAACCGTATTACCGCCTTTGAGTGAGCTGATAC<br>CGCTCGCCGCAGCCGAACGACCGAGCGCAGCGAGTCAGTGAGCG<br>AGGAAGCGGAAGAGCGCCCAATACGCAAACCGCCTCTCCCCGCG<br>CGTTGGCCGATTCATTAATGCAGCTGGCACGACAGGTTTCCCGA<br>CTGGAAAGCGGGCAGTGAGCGCAACGCAATTAATGTGAGTTAGC<br>TCACTCATTAGGCACCCCAGGCTTTACACTTTATGCTTCCGGCT<br>CGTATGTTGTGTGGAATTGTGAGCGGATAACAATTTCACACAGG<br>AAACAGCTATGACCATGATTACGCCAAGCTCGGCGCGCCATTGG<br>GATGGAACCCTGCAGGCAG |
| Reverse Complementary sequence of SV40polyA (SEQ ID NO: 8) | 62<br>AGACATGATAAGATACATTGATGAGTTTGGACAAACCACAACTA<br>GAATGCAGTGAAAAAAATGCTTTATTTGTGAAATTTGTGATGCT<br>ATTGCTTTATTTGTAACCATTATAAGCTGCAATAAACAAGTTAA<br>CAACAACAATTGCATTCATTTTATGTTTCAGGTTCAGGGGGAGG<br>TGTGGGAGGTTTTTTAAAGCAAGTAAAACCTCTACAAATGTGGT<br>ATGGCTGATTATGATC |

TABLE 1-continued

Sequence of viral vector and plasmid elements
AMINO ACID SEQUENCE OR POLYNUCLEOTIDE (PN)

| SEQUENCE ELEMENTS | SEQUENCE IDENTIFIER (SEQ. ID. NO:) AND SEQUENCE |
|---|---|
| Reverse Complementary sequence of HUMAN RLBP1 GENE CDS (SEQ ID NO: 7) | 63<br>TCAGAAGGCTGTGTTCTCAGCTTGGGCCTGGGGGCCAAAGAGCT<br>GCTCAGCAACGGCCTTGCCATCATACTTGGGCAGCGTGCCCCCG<br>AAGTCAGAGGGCAGGATGTTCTCATCGATCTCCTGGTAGAAACC<br>AGAAAGGTCATCCCCGTGGACAAAGACCCTCTCAAGCAGCTTGC<br>TCTTCAAGAAGGGCTTGACCACATTGTAGGTCGTGGTGAAGTAC<br>CATGGCTGGTGGATGAAGTGGATGGCTTTGAACCGGGCTGGGAA<br>GGAATCCTGGAGCATGTCCACCATCTTCCTGAGATCTGAAGTCC<br>GGAGACTAGCAGCCTGCTGCATGGTAAAGCCCTTGAAGTTCTCA<br>ATGATGCAGAAGCCATTGATTTGAGTTTCCTCATTCTCCAGCAG<br>CTTCTCCAGGATGAAGCAATATGCCTGCAAGATCTCATCAAAGG<br>TGATTTCTTGACTTTGCCAGTTCTCAATGTTGAAGAGCATGACC<br>ACTCGGCCATACTTGTCCCGACTAGAGAGGACACCAGGGTAGCC<br>AGCTTCAATGGTGCAGCGGACAGCCTCTGGGGACAGGCTGTCAA<br>AGAGCTCAGGGTACTGCAGCCGGAAATTCACATAGCCTCTGAGC<br>AGCTCATAGGCACGGCCCACGTTGAACTTCCGTGCGCGGATGAA<br>GCGCAGGAAGAAGCCGCTGTCCTTCTCTTGCACCCTCTCCGCCA<br>CGGCCACCGCCAGCTCCTCCCCCGAGGCCGCCTGCGCCTGCACC<br>ATCTCCTGCAGCTCTCGCACTGCCTCCTCCCGGGTCTCCTCTCT<br>CTCGTTCAGCTCATCCTTGGCCTTCTGCAAGGTGTGGCGGGGCA<br>GCTGGCTGCACGGGCCAAAGACAGGTCCATGGTCCTTGGTTGTG<br>AGCTGCTCCAGTTGGGCACGGAGCTCCTGTTCCTCTTCAGGTAC<br>CATGCGGAACGTGCCCACCCCTTCTGACAT |
| Reverse Complementary sequence of Added KOZAK (SEQ ID NO: 5) | 64<br>GGTGGC |
| Reverse Complementary sequence of Modified SV40INTRON (SEQ ID NO: 4) | 65<br>GGATCCCGGGGCGGGTACAATTCCGCAGCTTTTAGAGCAGAAGT<br>AACACTTCCGTACAGGCCTAGAAGTAAAGGCAACATCCACTGAG<br>GAGCAGTTCTTTGATTTGCACCACCACCGGATCCGGGACCTGAA<br>ATAAAAGACAAAAAGACTAAACTTACCAGTTAACTTTCTGGTTT<br>TTCAGTT |
| Reverse Complementary sequence of Human RLBP1 PROMOTER (short) (SEQ ID NO: 3) | 66<br>TCGGCAGCTCCTCCTTGGGGCTACCTGGTACCTGAATGTCCTGG<br>AGCTCTAGAGGTTCCCTCCGCTGGAGGCGTGGTCCGGTCAGCAG<br>GTTGGGATTAGTGTGTCATAAGGAACTTCTCACCGCCCACAGTT<br>TCCGTTAAATCGGGCTCACAGGAGGCCCTCAGTGGGGCAAAGGA<br>AGACCCAGAGAGAAAGGGGAGAGGGGAGAGGCCTGGGCCTGGCT<br>GGAGGCGCATCAAAGCCCTCCTTTGTGTGCTCCTGCTCTGGAGT<br>TCCTGCTCGGCCATGTGGAAGCCCGGCTGTGGGGCTGGGATCTG<br>GGCCAGTCCCATTCCCTCTTTTCTCTGCCCTCTTTCTCCTCAAG<br>ATCCCGGGGTGGGGTTGCTGAGAGAGCACCCCCCCCCCCCACC<br>ACCACCACCAGGGTAATAAGAGGTGAAGGGAAATCGTAAATATG<br>ACTACATCTACAGTGGCAGCTCTGGCAAATCCAGGCCTATTGCC<br>CACCCCTCCCCCAGCCAGCAGGACCTGGCATGGTAGTTTTCACC<br>TCTGCAGTGAGTGGGGTCAGTTGAGAAATGTGGCTGGTTAAGGC<br>CAAGCAGGGAGAGGACAA |
| Reverse Complementary sequence of eGFP (SEQ ID NO: 24) | 67<br>TTACTTGTACAGCTCGTCCATGCCGAGAGTGATCCCGGCGGCGG<br>TCACGAACTCCAGCAGGACCATGTGATCGCGCTTCTCGTTGGGG<br>TCTTTGCTCAGGGCGGACTGGGTGCTCAGGTAGTGGTTGTCGGG<br>CAGCAGCACGGGGCCGTCGCCGATGGGGGTGTTCTGCTGGTAGT<br>GGTCGGCGAGCTGCACGCTGCCGTCCTCGATGTTGTGGCGGATC<br>TTGAAGTTCACCTTGATGCCGTTCTTCTGCTTGTCGGCCATGAT<br>ATAGACGTTGTGGCTGTTGTAGTTGTACTCCAGCTTGTGCCCCA<br>GGATGTTGCCGTCCTCCTTGAAGTCGATGCCCTTCAGCTCGATG<br>CGGTTCACCAGGGTGTCGCCCTCGAACTTCACCTCGGCGCGGGT<br>CTTGTAGTTGCCGTCGTCCTTGAAGAAGATGGTGCGCTCCTGGA<br>CGTAGCCTTCGGGCATGGCGGACTTGAAGAAGTCGTGCTGCTTC<br>ATGTGGTCGGGGTAGCGGCTGAAGCACTGCACGCCGTAGGTCAG<br>GGTGGTCACGAGGGTGGGCCAGGGCACGGGCAGCTTGCCGGTGG<br>TGCAGATGAACTTCAGGGTCAGCTTGCCGTAGGTGGCATCGCCC<br>TCGCCCTCGCCGGACACGCTGAACTTGTGGCCGTTTACGTCGCC<br>GTCCAGCTCGACCAGGATGGGCACCACCCCGGTGAACAGCTCCT<br>CGCCCTTGCTCACCAT |

TABLE 2

Plasmid Composition

| Elements | SEQUENCE IDENTIFIER (SEQ. ID. NO:) AND SEQUENCE INFORMATION |
|---|---|
| Plasmid TM017 Composition | |
| ΔITR | 1<br>occurs at bp 4 through bp 106 of SEQ ID NO: 26 |
| Human RLBP1 Promoter(short) | 3<br>Occurs at bp 119 through bp 708 of SEQ ID NO: 26 |
| MODIFIED SV40INTRON | 4<br>occurs at bp 723 through bp 905 of SEQ ID NO: 26 |
| Added Kozak | 5<br>occurs at bp 919 through bp 924 of SEQ ID NO: 26 |
| HUMAN RLBP1 GENE CDS | 6<br>occurs at bp 925 through bp 1878 of SEQ ID NO: 26 |
| SV40 POLYA | 8<br>occurs at bp 1937 through bp 2172 of SEQ ID NO: 26 |
| 3' ITR | 9<br>occurs at bp 2201 through bp 2330 of SEQ ID NO: 26 |
| AMP BACTERIAL BACKBONE | 15<br>occurs at bp 2331 through bp 4949 of SEQ ID NO: 26 |
| TM017 PLASMID SEQUENCE | 26<br>ctgcgcgctcgctcgctcactgaggccgcccgggcaaagccc<br>gggcgtcgggcgaccttggtcgcccggcctcagtgagcgag<br>cgagcgcgcagagagggagtggggtaccacgcgtttgtcctc<br>tccctgcttggccttaaccagccacatttctcaactgacccc<br>actcactgcagaggtgaaaactaccatgccaggtcctgctgg<br>ctgggggaggggtgggcaataggcctggatttgccagagctg<br>ccactgtagatgtagtcatatttacgatttcccttcacctct<br>tattaccctggtggtggtggtgggggggggggggtgctctct<br>cagcaaccccaccccgggatcttgaggagaaagagggcagag<br>aaaagagggaatgggactggcccagatcccagccccacagcc<br>gggcttccacatggccgagcaggaactccagagcaggagcac<br>acaaaggagggctttgatgcgcctccagccaggcccaggcct<br>ctcccctctccccttttctctctgggtcttcctttgccccact<br>gagggcctcctgtgagcccgatttaacggaaactgtgggcgg<br>tgagaagttccttatgacacactaatcccaacctgctgaccg<br>gaccacgcctccagcggagggaacctctagagctccaggaca<br>ttcaggtaccaggtagccccaaggaggagctgccgaatcgat<br>ggatcgggaactgaaaaaccagaaagttaactggtaagttta<br>gtcttttttgtcttttatttcaggtcccggatccggtggtggt<br>gcaaatcaaagaactgctcctcagtggatgttgcctttactt<br>ctaggcctgtacggaagtgttacttctgctctaaaagctgcg<br>gaattgtaccgccccgggatccatcgattgaattcgccacc<br>atgtcagaagggtgggcacgttccgcatggtacctgaagag<br>gaacaggagctccgtgcccaactggagcagctcacaaccaag<br>gaccatgacctgtctttggcccgtgcagccagctgccccgc<br>cacaccttgcagaaggccaaggatgagctgaacgagagagag<br>gagacccgggaggaggcagtgcgagagctgcaggagatggtg<br>caggcgcaggcggcctcggggagagctggcggtggccgtg<br>gcggagagggtgcaagagaaggacagcggcttcttcctgcgc<br>ttcatccgcgcacggaagttcaacgtgggccgtgcctatgag<br>ctgctcagaggctatgtgaatttccggctgcagtaccctgag<br>ctctttgacagcctgtccccagaggctgtccgctgcaccatt<br>gaagctggctaccctggtgtcctctctagtcgggacaagtat<br>ggccgagtggtcatgctcttcaacattgagaactggcaaagt<br>caagaaatcaccttttgatgagatcttgcaggcatattgcttc<br>atcctggagaagctgctggagaatgaggaaactcaaatcaat<br>ggcttctgcatcattgagaacttcaagggcttttaccatgcag<br>caggctgctagtctccggacttcagatctcaggaagatggtg<br>gacatgctccaggattccttcccagcccggttcaaagccatc |

TABLE 2-continued

Plasmid Composition
Plasmid Composition

| Elements | SEQUENCE IDENTIFIER (SEQ. ID. NO:) AND SEQUENCE INFORMATION |
|---|---|
| | cacttcatccaccagccatggtacttcaccacgacctacaat |
| | gtggtcaagcccttcttgaagagcaagctgcttgagagggtc |
| | tttgtccacggggatgacctttctggtttctaccaggagatc |
| | gatgagaacatcctgccctctgacttcgggggcacgctgccc |
| | aagtatgatggcaaggccgttgctgagcagctctttggcccc |
| | caggcccaagctgagaacacagccttctgaggatcgtaccgg |
| | tcgacctgcagaagcttgcctcgagcagcgctgctcgagaga |
| | tctggatcataatcagccataccacatttgtagaggttttac |
| | ttgctttaaaaaacctcccacacctcccccctgaacctgaaac |
| | ataaaatgaatgcaattgttgttgttaacttgtttattgcag |
| | cttataatggttacaaataaagcaatagcatcacaaatttca |
| | caaataaagcatttttttcactgcattctagttgtggtttgt |
| | ccaaactcatcaatgtatcttatcatgtctggtaaccacgtg |
| | cggaccgagcggccgcaggaaccctagtgatggagttggcc |
| | actccctctctgcgcgctcgctcgctcactgaggccgggcga |
| | ccaaaggtcgcccgacgcccgggctttgcccgggcggcctca |
| | gtgagcgagcgagcgcgcagctgcctgcaggggcgcctgatg |
| | cggtattttctccttacgcatctgtgcggtatttcacaccgc |
| | atacgtcaaagcaaccatagtacgcgccctgtagcggcgcat |
| | taagcgcggcgggtgtggtggttacgcgcagcgtgaccgcta |
| | cacttgccagcgccttagcgcccgctcctttcgctttcttcc |
| | cttcctttctcgccacgttcgccggctttccccgtcaagctc |
| | taaatcgggggctcccttaggttccgatttagtgctttac |
| | ggcacctcgaccccaaaaaacttgatttgggtgatggttcac |
| | gtagtgggccatcgccctgatagacggtttttcgccctttga |
| | cgttggagtccacgttctttaatagtggactcttgttccaaa |
| | ctggaacaacactcaactctatctcgggctattcttttgatt |
| | tataagggattttgccgatttcggtctattggttaaaaatg |
| | agctgatttaacaaaaatttaacgcgaattttaacaaaatat |
| | taacgtttacaattttatggtgcactctcagtacaatctgct |
| | ctgatgccgcatagttaagccagccccgacacccgccaacac |
| | ccgctgacgcgccctgacgggcttgtctgctcccggcatccg |
| | cttacagacaagctgtgaccgtctccgggagctgcatgtgtc |
| | agaggttttcaccgtcatcaccgaaacgcgcgagacgaaagg |
| | gcctcgtgatacgcctatttttataggttaatgtcatgataa |
| | taatggtttcttagacgtcaggtggcacttttcggggaaatg |
| | tgcgcggaacccctatttgttattttctaaatacattcaa |
| | atatgtatccgctcatgagacaataaccctgataaatgcttc |
| | aataatattgaaaaaggaagagtatgagtattcaacatttcc |
| | gtgtcgcccttattcccttttttgcggcattttgccttcctg |
| | tttttgctcacccagaaacgctggtgaaagtaaaagatgctg |
| | aagatcagttgggtgcacgagtgggttacatcgaactggatc |
| | tcaacagcggtaagatccttgagagttttcgccccgaagaac |
| | gttttccaatgatgagcacttttaaagttctgctatgtggcg |
| | cggtattatcccgtattgacgccgggcaagagcaactcggtc |
| | gccgcatacactattctcagaatgacttggttgagtactcac |
| | cagtcacagaaaagcatcttacggatggcatgacagtaagag |
| | aattatgcagtgctgccataaccatgagtgataacactgcgg |
| | ccaacttacttctgacaacgatcggaggaccgaaggagctaa |
| | ccgctttttgcacaacatgggggatcatgtaactcgccttg |
| | atcgttgggaaccggagctgaatgaagccataccaaacgacg |
| | agcgtgacaccacgatgcctgtagcaatggcaacaacgttgc |
| | gcaaactattaactggcgaactacttactctagcttcccggc |
| | aacaattaatagactggatggaggcggataaagttgcaggac |
| | cacttctgcgctcggcccttccggctggctggtttattgctg |
| | ataaatctggagccggtgagcgtgggtctcgcggtatcattg |
| | cagcactggggccagatggtaagccctcccgtatcgtagtta |
| | tctacacgacggggagtcaggcaactatggatgaacgaaata |
| | gacagatcgctgagataggtgcctcactgattaagcattggt |
| | aactgtcagaccaagtttactcatatatactttagattgatt |
| | taaaacttcattttaattaaaaggatctaggtgaagatcc |
| | ttttttgataatctcatgaccaaaatcccttaacgtgagtttt |
| | cgttccactgagcgtcagacccctagaaaagatcaaaggat |
| | cttcttgaaatccttttttctcgcgcgtaatctgctgcttgc |
| | aaacaaaaaaaccaccgctaccagcggtggtttgtttgccgg |
| | atcaagagctaccaactctttttccgaaggtaactggcttca |
| | gcagagcgcagataccaaatactgttcttctagtgtagccgt |
| | agttaggccaccacttcaagaactctgtagcaccgcctacat |
| | acctcgctctgctaatcctgttaccagtggctgctgccagtg |
| | gcgataagtcgtgtcttaccgggttggactcaagacgatagt |
| | taccggataaggcgcagcggtcgggctgaacggggggttcgt |
| | gcacacagcccagcttggagcgaacgacctacaccgaactga |
| | gatacctacagcgtgagctatgagaaagcgccacgcttcccg |
| | aagggagaaaggcggacaggtatccggtaagcggcagggtcg |

TABLE 2-continued

Plasmid Composition
Plasmid Composition

| Elements | SEQUENCE IDENTIFIER (SEQ. ID. NO:) AND SEQUENCE INFORMATION |
|---|---|
| | gaacaggagagcgcacgagggagcttccagggggaaacgcct ggtatctttatagtcctgtcgggtttcgccacctctgacttg agcgtcgattttttgtgatgctcgtcagggggcggagcctat ggaaaaacgccagcaacgcggccttttttacggttcctggcct tttgctggccttttgctcacatgtcctgcaggcag |
| GENE CASSETTE OF PLASMID TM017 OCCURS AT BP 4 THROUGH 2330 OF SEQ ID NO: 26 | 51<br>cgcgctcgctcgctcactgaggccgcccggcaaagcccggg cgtcgggcgacctttggtcgcccggcctcagtgagcgagcga gcgcgcagagagggagtggggtaccacgcgtttgtcctctcc ctgcttggccttaaccagccacatttctcaactgaccccact cactgcagaggtgaaaactaccatgccaggtcctgctggctg ggggaggggtgggcaataggcctggatttgccagagctgcca ctgtagatgtagtcatatttacgatttcccttcacctcttat taccctggtggtggtggtggggggggggggggtgctctctcag caacccccaccccgggatcttgaggagaaagagggcagagaaa agagggaatgggactggcccagatcccagccccacagccggg cttccacatggccgagcaggaactccagagcaggagcacaca aaggagggctttgatgcgcctccagccaggcccaggcctctc ccctctcccctttctctctgggtcttcctttgccccactgag ggcctcctgtgagcccgatttaacggaaactgtgggcggtga gaagttccttatgacacactaatcccaacctgctgaccggac cacgcctccagcggagggaacctctagagctccaggacattc aggtaccaggtagcccaaggaggagctgccgaatcgatgga tcgggaactgaaaaaccagaaagttaactggtaagtttagtc ttttttgtcttttatttcaggtcccggatccggtggtggtgca aatcaaagaactgctcctcagtggatgttgcctttacttcta ggcctgtacggaagtgttacttctgctctaaaagctgcggaa ttgtacccgccccgggatccatcgattgaattcgccaccatg tcagaaggggtgggcacgttccgcatggtacctgaagaggaa caggagctccgtgcccaactggagcagctcacaaccaaggac catggacctgtctttggccgtgcagccagctgccccgccac accttgcagaaggccaaggatgagctgaacgagagagaggag acccgggaggaggcagtgcgagagctgcaggagatggtgcag gcgcaggcggcctcggggagggagctggcggtggccgtggcg gagagggtgcaagagaaggacagcggcttcttcctgcgcttc atccgcgcacggaagttcaacgtgggccgtgcctatgagctg ctcagaggctatgtgaatttccggctgcagtaccctgagctc tttgacagcctgtccccagaggctgtccgctgcaccattgaa gctggctaccctggtgtcctctctagtcgggacaagtatggc cgagtggtcatgctcttcaacattgagaactggcaaagtcaa gaaatcacctttgatgagatcttgcaggcatattgcttcatc ctggagaagctgctggagaatgaggaaactcaaatcaatggc ttctgcatcattgagaacttcaagggctttaccatgcagcag gctgctagtctccggacttcagatctcaggaagatggtggac atgctccaggattccttcccagcccggttcaaagccatccac ttcatccaccagccatggtacttcaccacgacctacaatgtg gtcaagcccttcttgaagagcaagctgcttgagagggtcttt gtccacggggatgacctttctggtttctaccaggagatcgat gagaacatcctgccctctgacttcgggggcacgctgcccaag tatgatggcaaggccgttgctgagcagctctttggcccccag gcccaagctgagaacacagccttctgaggatcgtaccggtcg acctgcagaagcttgcctcgagcagcgctgctcgagagatct ggatcataatcagccataccacatttgtagaggtttttacttg ctttaaaaaacctcccacacctcccccctgaacctgaaacata aaatgaatgcaattgttgttgttaacttgtttattgcagctt ataatggttacaaataaagcaatagcatcacaaatttcacaa ataaagcattttttcactgcattctagttgtggtttgtcca aactcatcaatgtatcttatcatgtctggtaaccacgtgcgg accgagcggccgcaggaacccctagtgatggagttggccact ccctctctgcgcgctcgctcgctcactgaggccgggcgacca aaggtcgcccgacgcccgggctttgcccgggcggcctcagtg agcgagcgagcgcgcag |
| Plasmid TM037 Composition | |
| 5' ITR | 2<br>occurs @ bp 1 through bp 119 of SEQ ID NO: 27 |
| Human RLBP1 Promoter(long) | 10<br>occurs @ bp 137 through bp 3293 of SEQ ID NO: 27 |

TABLE 2-continued

Plasmid Composition
Plasmid Composition

| Elements | SEQUENCE IDENTIFIER (SEQ. ID. NO:) AND SEQUENCE INFORMATION |
|---|---|
| Added Kozak | 5<br>occurs at bp 3300 through bp 3305 of SEQ ID NO: 27 |
| HUMAN RLBP1 GENE CDS | 6<br>occurs at bp 3306 through bp 4259 of SEQ ID NO: 27 |
| SV40 POLYA | 8<br>occurs at bp 4318 through bp 4553 of SEQ ID NO: 27 |
| 3' ITR | 9<br>occurs at bp 4582 through bp 4711 of SEQ ID NO: 27 |
| AMP BACTERIAL BACKBONE | 15<br>occurs at bp 4712 through bp 7330 of SEQ ID NO: 27 |
| Plasmid TM037 sequence | 27<br>CTGCGCGCTCGCTCGCTCACTGAGGCCGCCCGGGCGTCGGGC<br>GACCTTTGGTCGCCCGGCCTCAGTGAGCGAGCGAGCGCGCAG<br>AGAGGGAGTGGCCAACTCCATCACTAGGGGTTCCTGCGGCCG<br>CACGCAGCTTTTGTCCTCTCCCTGCTTGGCCTTAACCAGCCA<br>CATTTCTCAACTGACCCCACTCACTGCAGAGGTGAAAACTAC<br>CATGCCAGGTCCTGCTGGCTGGGGGAGGGGTGGGCAATAGGC<br>CTGGATTTGCCAGAGCTGCCACTGTAGATGTAGTCATATTTA<br>CGATTTCCCTTCACCTCTTATTACCCTGGTGGTGGTGGTGGG<br>GGGGGGGGGGTGCTCTCTCAGCAACCCCACCCCGGGATCTTG<br>AGGAGAAAGAGGGCAGAGAAAAGAGGGAATGGGACTGGCCCA<br>GATCCCAGCCCCACAGCCGGGCTTCCACATGGCCGAGCAGGA<br>ACTCCAGAGCAGGAGCACACAAAGGAGGGCTTTGATGCGCCT<br>CCAGCCAGGCCCAGGCCTCTCCCCTCTCCCCTTTCTCTCTGG<br>GTCTTCCTTTGCCCCACTGAGGGCCTCCTGTGAGCCCGATTT<br>AACGGAAACTGTGGGCGGTGAGAAGTTCCTTATGACACACTA<br>ATCCCAACCTGCTGACCGGACCACGCCTCCAGCGGAGGGAAC<br>CTCTAGAGCTCCAGGACATTCAGGTACCAGGTAGCCCCAAGG<br>AGGAGCTGCCGACCTGGCAGGTAAGTCAATACCTGGGGCTTG<br>CCTGGGCCAGGGAGCCCAGGACTGGGGTGAGGACTCAGGGGA<br>GCAGGGAGACCACGTCCCAAGATGCCTGTAAAACTGAAACCA<br>CCTGGCCATTCTCCAGGTTGAGCCAGACCAATTTGATGGCAG<br>ATTTAGCAAATAAAAATACAGGACACCCAGTTAAATGTGAAT<br>TTCAGATGAACAGCAAATACTTTTTTAGTATTAAAAAAGTTC<br>ACATTTAGGCTCACGCCTGTAATCCCAGCACTTTGGGAGGCC<br>GAGGCAGGCAGATCACCTGAGGTCAGGAGTTCGAGACCAGCC<br>TGGCCAACATGGTGAAACCCCATCTCCACTAAAAATACCAAA<br>AATTAGCCAGGCGTGCTGGTGGGCACCTGTAGTTCCAGCTAC<br>TCAGGAGGCTAAGGCAGGAGAATTGCTTGAACCTGGGAGGCA<br>GAGGTTGCAGTGAGCTGAGATCGCACCATTGCACTCTAGCCT<br>GGGCGACAAGAACAAAACTCCATCTCAAAAAAAAAAAAAAAA<br>AAAAAGTTCACATTTAACTGGGCATTCTGTATTTAATTGGTA<br>ATCTGAGATGGCAGGGAACAGCATCAGCATGGTGTGAGGGAT<br>AGGCATTTTTCATTGTGTACAGCTTGTAAATCAGTATTTTT<br>AAAACTCAAAGTTAATGGCTTGGGCATATTTAGAAAAGAGTT<br>GCCGCACGGACTTGAACCCTGTATTCCTAAAATCTAGGATCT<br>TGTTCTGATGGTCTGCACAACTGGCTGGGGGTGTCCAGCCAC<br>TGTCCCTCTTGCCTGGGCTCCCCAGGGCAGTTCTGTCAGCCT<br>CTCCATTTCCATTCCTGTTCCAGCAAAACCCAACTGATAGCA<br>CAGCAGCATTTCAGCCTGTCTACCTCTGTGCCCACATACCTG<br>GATGTCTACCAGCCAGAAAGGTGGCTTAGATTTGGTTCCTGT<br>GGGTGGATTATGGCCCCCAGAACTTCCCTGTGCTTGCTGGGG<br>GTGTGGAGTGGAAAGAGCAGGAAATGGGGACCCTCCGATAC<br>TCTATGGGGGTCCTCCAAGTCTCTTTGTGCAAGTTAGGGTAA<br>TAATCAATATGGAGCTAAGAAAGAGAAGGGGAACTATGCTTT<br>AGAACAGGACACTGTGCCAGGAGCATTGCAGAAATTATATGG<br>TTTTCACGACAGTTCTTTTTGGTAGGTACTGTTATTATCCTC<br>AGTTTGCAGATGAGGAAACTGAGACCCAGAAAGGTTAAATAA<br>CTTGCTAGGGTCACACAAGTCATAACTGACAAAGCCTGATTC<br>AAACCCAGGTCTCCCTAACCTTTAAGGTTTCTATGACGCCAG<br>CTCCCTAGGGAGTTTGTCTTCAGATGTCTTGGCTCTAGGTG<br>TCAAAAAAAGACTTGGTGTCAGGCAGGCATAGGTTCAAGTCC<br>CAACTCTGTCACTTACCAACTGTGACTAGGTGATTGAACTGA<br>CCATGGAACCTGGTCACATGCAGGAGCAGGATGGTGAAGGGT |

TABLE 2-continued

Plasmid Composition
Plasmid Composition

| Elements | SEQUENCE IDENTIFIER (SEQ. ID. NO:) AND SEQUENCE INFORMATION |
|---|---|
| | TCTTGAAGGCACTTAGGCAGGACATTTAGGCAGGAGAGAAAA |
| | CCTGGAAACAGAAGAGCTGTCTCCAAAAATACCCACTGGGGA |
| | AGCAGGTTGTCATGTGGGCCATGAATGGGACCTGTTCTGGTA |
| | ACCAAGCATTGCTTATGTGTCCATTACATTTCATAACACTTC |
| | CATCCTACTTTACAGGGAACAACCAAGACTGGGGTTAAATCT |
| | CACAGCCTGCAAGTGGAAGAGAAGAACTTGAACCCAGGTCCA |
| | ACTTTTGCGCCACAGCAGGCTGCCTCTTGGTCCTGACAGGAA |
| | GTCACAACTTGGGTCTGAGTACTGATCCCTGGCTATTTTTTG |
| | GCTGTGTTACCTTGGACAAGTCACTTATTCCTCCTCCCGTTT |
| | CCTCCTATGTAAAATGGAAATAATAATGTTGACCCTGGGTCT |
| | GAGAGAGTGGATTTGAAAGTACTTAGTGCATCACAAAGCACA |
| | GAACACACTTCCAGTCTCGTGATTATGTACTTATGTAACTGG |
| | TCATCACCCATCTTGAGAATGAATGCATTGGGGAAAGGGCCA |
| | TCCACTAGGCTGCGAAGTTTCTGAGGGACTCCTTCGGGCTGG |
| | AGAAGGATGGCCACAGGAGGGAGGAGAGATTGCCTTATCCTG |
| | CAGTGATCATGTCATTGAGAACAGAGCCAGATTCTTTTTTTC |
| | CTGGCAGGGCCAACTTGTTTTAACATCTAAGGACTGAGCTAT |
| | TTGTGTCTGTGCCCTTTGTCCAAGCAGTGTTTCCCAAAGTGT |
| | AGCCCAAGAACCATCTCCCTCAGAGCCACCAGGAAGTGCTTT |
| | AAATTGCAGGTTCCTAGGCCACAGCCTGCACCTGCAGAGTCA |
| | GAATCATGGAGGTTGGGACCCAGGCACCTGCGTTTCTAACAA |
| | ATGCCTCGGGTGATTCTGATGCAATTGAAAGTTTGAGATCCA |
| | CAGTTCTGAGACAATAACAGAATGGTTTTTCTAACCCCTGCA |
| | GCCCTGACTTCCTATCCTAGGGAAGGGGCCGGCTGGAGAGGC |
| | CAGGACAGAGAAAGCAGATCCCTTCTTTTTCCAAGGACTCTG |
| | TGTCTTCCATAGGCAACGAATTCGCCACCATGTCAGAAGGGG |
| | TGGGCACGTTCCGCATGGTACCTGAAGAGGAACAGGAGCTCC |
| | GTGCCCAACTGGAGCAGCTCACAACCAAGGACCATGGACCTG |
| | TCTTTGGCCCGTGCAGCCAGCTGCCCCGCCACACCTTGCAGA |
| | AGGCCAAGGATGAGCTGAACGAGAGAGAGGAGACCCGGGAGG |
| | AGGCAGTGCGAGAGCTGCAGGAGATGGTGCAGGCGCAGGCGG |
| | CCTCGGGGGAGGAGCTGGCGGTGGCCGTGGCGGAGAGGGTGC |
| | AAGAGAAGGACAGCGGCTTCTTCCTGCGCTTCATCCGCGCAC |
| | GGAAGTTCAACGTGGGCCGTGCCTATGAGCTGCTCAGAGGCT |
| | ATGTGAATTTCCGGCTGCAGTACCCTGAGCTCTTTGACAGCC |
| | TGTCCCCAGAGGCTGTCCGCTGCACCATTGAAGCTGGCTACC |
| | CTGGTGTCCTCTCTAGTCGGGACAAGTATGGCCGAGTGGTCA |
| | TGCTCTTCAACATTGAGAACTGGCAAAGTCAAGAAATCACCT |
| | TTGATGAGATCTTGCAGGCATATTGCTTCATCCTGGAGAAGC |
| | TGCTGGAGAATGAGGAAACTCAAATCAATGGCTTCTGCATCA |
| | TTGAGAACTTCAAGGGCTTTACCATGCAGCAGGCTGCTAGTC |
| | TCCGGACTTCAGATCTCAGGAAGATGGTGGACATGCTCCAGG |
| | ATTCCTTCCCAGCCCGGTTCAAAGCCATCCACTTCATCCACC |
| | AGCCATGGTACTTCACCACGACCTACAATGTGGTCAAGCCCT |
| | TCTTGAAGAGCAAGCTGCTTGAGAGGGTCTTTGTCCACGGGG |
| | ATGACCTTTCTGGTTTCTACCAGGAGATCGATGAGAACATCC |
| | TGCCCTCTGACTTCGGGGGCACGCTGCCCAAGTATGATGGCA |
| | AGGCCGTTGCTGAGCAGCTCTTTGGCCCCCAGGCCCAAGCTG |
| | AGAACACAGCCTTCTGAGGATCGTACCGGTCGACCTGCAGAA |
| | GCTTGCCTCGAGCAGCGCTGCTCGAGAGATCTGGATCATAAT |
| | CAGCCATACCACATTTGTAGAGGTTTTACTTGCTTTAAAAAA |
| | CCTCCCACACCTCCCCCTGAACCTGAAACATAAAATGAATGC |
| | AATTGTTGTTGTTAACTTGTTTATTGCAGCTTATAATGGTTA |
| | CAAATAAAGCAATAGCATCACAAATTTCACAAATAAAGCATT |
| | TTTTTCACTGCATTCTAGTTGTGGTTTGTCCAAACTCATCAA |
| | TGTATCTTATCATGTCTGGTAACCACGTGCGGACCGAGCGGC |
| | CGCAGGAACCCCTAGTGATGGAGTTGGCCACTCCCTCTCTGC |
| | GCGCTCGCTCGCTCACTGAGGCCGGGCGACCAAAGGTCGCCC |
| | GACGCCCGGGCTTTGCCCGGGCGGCCTCAGTGAGCGAGCGAG |
| | CGCGCAGCTGCCTGCAGGGGCGCCTGATGCGGTATTTTCTCC |
| | TTACGCATCTGTGCGGTATTTCACACCGCATACGTCAAAGCA |
| | ACCATAGTACGCGCCCTGTAGCGGCGCATTAAGCGCGGCGGG |
| | TGTGGTGGTTACGCGCAGCGTGACCGCTACACTTGCCAGCGC |
| | CTTAGCGCCCGCTCCTTTCGCTTTCTTCCCTTCCTTTCTCGC |
| | CACGTTCGCCGGCTTTCCCCGTCAAGCTCTAAATCGGGGGCT |
| | CCCTTTAGGGTTCCGATTTAGTGCTTTACGGCACCTCGACCC |
| | CAAAAAACTTGATTTGGGTGATGGTTCACGTAGTGGGCCATC |
| | GCCCTGATAGACGGTTTTTCGCCCTTTGACGTTGGAGTCCAC |
| | GTTCTTTAATAGTGGACTCTTGTTCCAAACTGGAACAACACT |
| | CAACTCTATCTCGGGCTATTCTTTTGATTTATAAGGGATTTT |
| | GCCGATTTCGGTCTATTGGTTAAAAAATGAGCTGATTTAACA |
| | AAAATTTAACGCGAATTTTAACAAAATATTAACGTTTACAAT |
| | TTTATGGTGCACTCTCAGTACAATCTGCTCTGATGCCGCATA |
| | GTTAAGCCAGCCCCGACACCCGCCAACACCCGCTGACGCGCC |

TABLE 2-continued

Plasmid Composition

| Elements | SEQUENCE IDENTIFIER (SEQ. ID. NO:) AND SEQUENCE INFORMATION |
|---|---|
| | CTGACGGGCTTGTCTGCTCCCGGCATCCGCTTACAGACAAGC
TGTGACCGTCTCCGGGAGCTGCATGTGTCAGAGGTTTTCACC
GTCATCACCGAAACGCGCGAGACGAAAGGGCCTCGTGATACG
CCTATTTTTATAGGTTAATGTCATGATAATAATGGTTTCTTA
GACGTCAGGTGGCACTTTTCGGGGAAATGTGCGCGGAACCCC
TATTTGTTTATTTTTCTAAATACATTCAAATATGTATCCGCT
CATGAGACAATAACCCTGATAAATGCTTCAATAATATTGAAA
AAGGAAGAGTATGAGTATTCAACATTTCCGTGTCGCCCTTAT
TCCCTTTTTTGCGGCATTTTGCCTTCCTGTTTTTGCTCACCC
AGAAACGCTGGTGAAAGTAAAAGATGCTGAAGATCAGTTGGG
TGCACGAGTGGGTTACATCGAACTGGATCTCAACAGCGGTAA
GATCCTTGAGAGTTTTCGCCCCGAAGAACGTTTTCCAATGAT
GAGCACTTTTAAAGTTCTGCTATGTGGCGCGGTATTATCCCG
TATTGACGCCGGGCAAGAGCAACTCGGTCGCCGCATACACTA
TTCTCAGAATGACTTGGTTGAGTACTCACCAGTCACAGAAAA
GCATCTTACGGATGGCATGACAGTAAGAGAATTATGCAGTGC
TGCCATAACCATGAGTGATAACACTGCGGCCAACTTACTTCT
GACAACGATCGGAGGACCGAAGGAGCTAACCGCTTTTTTGCA
CAACATGGGGGATCATGTAACTCGCCTTGATCGTTGGGAACC
GGAGCTGAATGAAGCCATACCAAACGACGAGCGTGACACCAC
GATGCCTGTAGCAATGGCAACAACGTTGCGCAAACTATTAAC
TGGCGAACTACTTACTCTAGCTTCCCGGCAACAATTAATAGA
CTGGATGGAGGCGGATAAAGTTGCAGGACCACTTCTGCGCTC
GGCCCTTCCGGCTGGCTGGTTTATTGCTGATAAATCTGGAGC
CGGTGAGCGTGGGTCTCGCGGTATCATTGCAGCACTGGGGCC
AGATGGTAAGCCCTCCCGTATCGTAGTTATCTACACGACGGG
GAGTCAGGCAACTATGGATGAACGAAATAGACAGATCGCTGA
GATAGGTGCCTCACTGATTAAGCATTGGTAACTGTCAGACCA
AGTTTACTCATATATACTTTAGATTGATTTAAAACTTCATTT
TTAATTTAAAAGGATCTAGGTGAAGATCCTTTTTGATAATCT
CATGACCAAAATCCCTTAACGTGAGTTTTCGTTCCACTGAGC
GTCAGACCCCGTAGAAAAGATCAAAGGATCTTCTTGAAATCC
TTTTTTTCTGCGCGTAATCTGCTGCTTGCAAACAAAAAAACC
ACCGCTACCAGCGGTGGTTTGTTTGCCGGATCAAGAGCTACC
AACTCTTTTTCCGAAGGTAACTGGCTTCAGCAGAGCGCAGAT
ACCAAATACTGTTCTTCTAGTGTAGCCGTAGTTAGGCCACCA
CTTCAAGAACTCTGTAGCACCGCCTACATACCTCGCTCTGCT
AATCCTGTTACCAGTGGCTGCTGCCAGTGGCGATAAGTCGTG
TCTTACCGGGTTGGACTCAAGACGATAGTTACCGGATAAGGC
GCAGCGGTCGGGCTGAACGGGGGGTTCGTGCACACAGCCCAG
CTTGGAGCGAACGACCTACACCGAACTGAGATACCTACAGCG
TGAGCTATGAGAAAGCGCCACGCTTCCCGAAGGGAGAAAGGC
GGACAGGTATCCGGTAAGCGGCAGGGTCGGAACAGGAGAGCG
CACGAGGGAGCTTCCAGGGGGAAACGCCTGGTATCTTTATAG
TCCTGTCGGGTTTCGCCACCTCTGACTTGAGCGTCGATTTTT
GTGATGCTCGTCAGGGGGCGGAGCCTATGGAAAAACGCCAG
CAACGCGGCCTTTTTACGGTTCCTGGCCTTTTGCTGGCCTTT
TGCTCACATGTCCTGCAGGCAG |
| GENE CASSETTE
OF PLASMID
TM037 OCCURS AT
BP 1 THROUGH
4711 OF SEQ ID
NO: 27 | 52
ctgcgcgctcgctcgctcactgaggccgcccgggcgtcgggc
gacctttggtcgcccggcctcagtgagcgagcgagcgcgcag
agagggagtggccaactccatcactaggggttcctgcggccg
cacgcagcttttgtcctctccctgcttggccttaaccagcca
catttctcaactgacccactcactgcagaggtgaaaactac
catgccaggtcctgctggctggggagggtgggcaataggc
ctggatttgccagagctgccactgtagatgtagtcatattta
cgatttccttcacctcttattaccctggtggtggtggtggg
gggggggggtgctctctcagcaacccaccccgggatcttg
aggagaaagagggcagagaaaagagggaatgggactggccca
gatcccagccccacagccgggcttccacatggccgagcagga
actccagagcaggagcacacaaaggagggctttgatgcgcct
ccagccaggcccaggcctctcccctctcccttttctctctgg
gtcttcctttgcccactgagggcctcctgtgagcccgattt
aacggaaactgtgggcggtgagaagttccttatgacacacta
atcccaacctgctgaccggaccacgcctccagcggagggaac
ctctagagctccaggacattcaggtaccaggtagccccaagg
aggagctgccgacctggcaggtaagtcaatacctgggcttg
cctgggccagggagcccaggactggggtgaggactcagggga
gcagggagaccacgtcccaagatgcctgtaaaactgaaacca
cctggccattctccaggttgagccagaccaatttgatggcag
atttagcaaataaaaatacaggacacccagttaaatgtgaat
ttcagatgaacagcaaatactttttagtattaaaaaagttc
acatttaggctcacgcctgtaatcccagcactttgggaggcc |

TABLE 2-continued

Plasmid Composition
Plasmid Composition

| Elements | SEQUENCE IDENTIFIER (SEQ. ID. NO:) AND SEQUENCE INFORMATION |
|---|---|
| | gaggcaggcagatcacctgaggtcaggagttcgagaccagcc |
| | tggccaacatggtgaaaccccatctccactaaaaataccaaa |
| | aattagccaggcgtgctggtgggcacctgtagttccagctac |
| | tcaggaggctaaggcaggagaattgcttgaacctgggaggca |
| | gaggttgcagtgagctgagatcgcaccattgcactctagcct |
| | gggcgacaagaacaaaactccatctcaaaaaaaaaaaaaaaa |
| | aaaaagttcacatttaactgggcattctgtatttaattggta |
| | atctgagatggcagggaacagcatcagcatggtgtgagggat |
| | aggcattttttcattgtgtacagcttgtaaatcagtattttt |
| | aaaactcaaagttaatggcttgggcatatttagaaaagagtt |
| | gccgcacggacttgaaccctgtattcctaaaatctaggatct |
| | tgttctgatggtctgcacaactggctgggggtgtccagccac |
| | tgtccctcttgcctgggctcccagggcagttctgtcagcct |
| | ctccatttccattcctgttccagcaaaacccaactgatagca |
| | cagcagcatttcagcctgtctacctctgtgcccacatacctg |
| | gatgtctaccagccagaaaggtggcttagatttggttcctgt |
| | gggtggattatggcccccagaacttccctgtgcttgctggg |
| | gtgtggagtggaaagagcaggaaatgggggaccctccgatac |
| | tctatggggtcctccaagtctctttgtgcaagttagggtaa |
| | taatcaatatggagctaagaaagagaaggggaactatgcttt |
| | agaacaggacactgtgccaggagcattgcagaaattatatgg |
| | ttttcacgacagttcttttttggtaggtactgttattatcctc |
| | agtttgcagatgaggaaactgagacccagaaaggttaaataa |
| | cttgctagggtcacacaagtcataactgacaaagcctgattc |
| | aaacccaggtctccctaacctttaaggtttctatgacgccag |
| | ctctcctaggagtttgtcttcagatgtcttggctctaggtg |
| | tcaaaaaaagacttggtgtcaggcaggcataggttcaagtcc |
| | caactctgtcacttaccaactgtgactaggtgattgaactga |
| | ccatggaacctggtcacatgcaggagcaggatggtgaagggt |
| | tcttgaaggcacttaggcaggacatttaggcaggagagaaaa |
| | cctggaaacagaagagctgtctccaaaaatacccactgggga |
| | agcaggttgtcatgtgggccatgaatgggacctgttctggta |
| | accaagcattgcttatgtgtccattacatttcataacacttc |
| | catcctactttacagggaacaaccaagactggggttaaatct |
| | cacagcctgcaagtggaagagaagaacttgaacccaggtcca |
| | acttttgcgccacagcaggctgcctcttggtcctgacaggaa |
| | gtcacaacttgggtctgagtactgatccctggctatttttg |
| | gctgtgttaccttggacaagtcacttattcctcctcccgttt |
| | cctcctatgtaaaatggaaataataatgttgaccctgggtct |
| | gagagagtggatttgaaagtacttagtgcatcacaaagcaca |
| | gaacacacttccagtctcgtgattatgtacttatgtaactgg |
| | tcatcacccatcttgagaatgaatgcattggggaaagggcca |
| | tccactaggctgcgaagtttctgagggactccttcgggctgg |
| | agaaggatggccacaggagggaggagagattgccttatcctg |
| | cagtgatcatgtcattgagaacagagccagattcttttttc |
| | ctggcagggccaacttgttttaacatctaaggactgagctat |
| | ttgtgtctgtgccctttgtccaagcagtgtttcccaaagtgt |
| | agcccaagaaccatctccctcagagccaccaggaagtgcttt |
| | aaattgcaggttcctaggccacagcctgcacctgcagagtca |
| | gaatcatggaggttgggacccaggcacctgcgtttctaacaa |
| | atgcctcgggtgattctgatgcaattgaaagtttgagatcca |
| | cagttctgagacaataacagaatggttttttctaaccctgca |
| | gccctgacttcctatcctagggaaggggccggctggagaggc |
| | caggacagagaaagcagatcccttctttttccaaggactctg |
| | tgtcttccataggcaacgaattcgccaccatgtcagaagggg |
| | tgggcacgttccgcatggtacctgaagaggaacaggagctcc |
| | gtgcccaactggagcagctcacaaccaaggaccatggacctg |
| | tctttggcccgtgcagccagctgccccgccacaccttgcaga |
| | aggccaaggatgagctgaacgagagagaggagacccgggagg |
| | aggcagtgcgagagctgcaggagatggtgcaggcgcaggcgg |
| | cctcgggggaggagctggcggttggccgtggcggagagggtgc |
| | aagagaaggacagcggcttcttcctgcgcttcatccgcgcac |
| | ggaagttcaacgtgggccgtgcctatgagctgctcagaggct |
| | atgtgaatttccggctgcagtaccctgagctctttgacagcc |
| | tgtcccagaggctgtccgctgcaccattgaagctggctacc |
| | ctggtgtcctctctagtcgggacaagtatggccgagtggtca |
| | tgctcttcaacattgagaactggcaaagtcaagaaatcacct |
| | ttgatgagatcttgcaggcatattgcttcatcctggagaagc |
| | tgctggagaatgaggaaactcaaatcaatggcttctgtcatca |
| | ttgagaacttcaaggggctttaccatgcagcaggctgctagtc |
| | tccggacttcagatctcaggaagatggtggacatgctccagg |
| | attccttcccagcccggttcaaagccatccacttcatccacc |
| | agccatggtacttcaccacgacctacaatgtggtcaagccct |
| | tcttgaagagcaagctgcttgagagggtctttgtccacgggg |

TABLE 2-continued

Plasmid Composition
Plasmid Composition

| Elements | SEQUENCE IDENTIFIER (SEQ. ID. NO:) AND SEQUENCE INFORMATION |
|---|---|
| | atgacctttctggtttctaccaggagatcgatgagaacatcc<br>tgccctctgacttcgggggcacgctgcccaagtatgatggca<br>aggccgttgctgagcagctcttttggccccccaggcccaagctg<br>agaacacagccttctgaggatcgtaccggtcgacctgcagaa<br>gcttgcctcgagcagcgctgctcgagagatctggatcataat<br>cagccataccacatttgtagaggttttacttgctttaaaaaa<br>cctcccacacctcccccctgaacctgaaacataaaatgaatgc<br>aattgttgttgttaacttgtttattgcagcttataatggtta<br>caaataaagcaatagcatcacaaatttcacaaataaagcatt<br>tttttcactgcattctagttgtggtttgtccaaactcatcaa<br>tgtatcttatcatgtctggtaaccacgtgcggaccgagcggc<br>cgcaggaaccccctagtgatggagttggccactccctctctgc<br>gcgctcgctcgctcactgaggccgggcgaccaaaggtcgccc<br>gacgcccgggctttgcccgggcggcctcagtgagcgagcgag<br>cgcgcag |

Plasmid AG007 Composition

| 5' ITR | 2<br>occurs @ bp 1 through bp 119 of SEQ ID NO: 28 |
|---|---|
| Human RPE65 Promoter | 11<br>occurs @ bp 134 through bp 1718 of SEQ ID NO: 28 |
| ADDED-KOZAK | 5<br>occurs @ bp 1725 through bp 1730 of SEQ ID NO: 28 |
| HUMAN RLBP1 GENE CDS | 6<br>occurs at bp 1731 through bp 2684 of SEQ ID NO: 28 |
| SV40 POLYA | 8<br>occurs at bp 2742 through bp 2977 of SEQ ID NO: 28 |
| RLBP1 INTRONIC SEQUENCE AS STUFFER SEQUENCE | 14<br>occurs at bp 2985 through bp 4487 of SEQ ID NO: 28 |
| 3' ITR | 9<br>occurs at bp 4516 through bp 4645 of SEQ ID NO: 28 |
| AMP BACTERIAL BACKBONE | 15<br>occurs at bp 4646 through bp 7264 of SEQ ID NO: 28 |
| AG007 Plasmid Sequence | 28<br>ctgcgcgctcgctcgctcactgaggccgccgggcgtcgggc<br>gacctttggtcgcccggcctcagtgagcgagcgagcgcgcag<br>agagggagtggccaactccatcactagggggttcctgcggccg<br>cacgcgttacgtaatatttattgaagtttaatattgtgtttg<br>tgatacagaagtatttgctttaattctaaataaaaattttat<br>gcttttattgctggtttaagaagatttggattatccttgtac<br>tttgaggagaagtttcttatttgaaatattttggaaacaggt<br>cttttaatgtggaaagatagatattaatctcctcttctatta<br>ctctccaagatccaacaaaagtgattataccccccaaaatat<br>gatggtagtatcttatactaccatcattttataggcataggg<br>ctcttagctgcaaataatggaactaactctaataaagcagaa<br>cgcaaatattgtaaatattagagagctaacaatctctgggat<br>ggctaaaggatggagcttggaggctacccagccagtaacaat<br>attccgggctccactgttgaatggagacactacaactgcctt<br>ggatgggcagagatattatggatgctaagcccccaggtgctac<br>cattaggacttctaccactgtccctaacgggtggagcccatc<br>acatgcctatgccctcactgtaaggaaatgaagctactgttg<br>tatatcttgggaagcacttggattaattgttatacagttttg<br>ttgaagaagacccctagggtaagtagccataactgcacacta<br>aatttaaaattgttaatgagtttctcaaaaaaaatgttaagg<br>ttgttagctggtatagtatatatcttgcctgttttccaagga<br>cttctttgggcagtaccttgtctgtgctggcaagcaactgag |

TABLE 2-continued

Plasmid Composition
Plasmid Composition

| Elements | SEQUENCE IDENTIFIER (SEQ. ID. NO:) AND SEQUENCE INFORMATION |
|---|---|
| | acttaatgaaagagtattggagatatgaatgaattgatgctg |
| | tatactctcagagtgccaaacatataccaatggacaagaagg |
| | tgaggcagagagcagacaggcattagtgacaagcaaagatat |
| | gcagaatttcattctcagcaaatcaaaagtcctcaacctggt |
| | tggaagaatattggcactgaatggtatcaataaggttgctag |
| | agagggttagaggtgcacaatgtgcttccataacattttata |
| | cttctccaatcttagcactaatcaaacatggttgaatacttt |
| | gtttactataactcttacagagtttataagatctgtgaagaca |
| | gggacagggacaatacccatctctgtctggttcataggtggt |
| | atgtaatagatattttttaaaaataagtgagttaatgaatgag |
| | ggtgagaatgaaggcacagaggtattaggggggaggtgggccc |
| | cagagaatggtgccaaggtccagtgggtgactgggatcagc |
| | tcaggcctgacgctggccactcccacctagctcctttctttc |
| | taatctgttctcattctccttgggaaggattgaggtctctgg |
| | aaaacagccaaacaactgttatgggaacagcaagcccaaata |
| | aagccaagcatcaggggatctgagagctgaaagcaacttct |
| | gttcccctccctcagctgaaggggtgggaagggctcccaa |
| | agccataactccttttaagggattagaaggcataaaaaggc |
| | ccctggctgagaacttccttcttcattctgcagttggtgaat |
| | tcgccaccatgtcagaagggtgggcacgttccgcatggtac |
| | ctgaagaggaacaggagccgtgcccaactggagcagctca |
| | caaccaaggaccatggacctgtctttggcccgtgcagccagc |
| | tgccccgccacaccttgcagaaggccaaggatgagctgaacg |
| | agagagaggagacccggaggaggcagtgcgagagctgcagg |
| | agatggtgcaggcgcaggcggcctcgggggaggagctggcgg |
| | tggccgtggcggagagggtgcaagagaaggacagcggcttct |
| | tcctgcgcttcatccgcgcacggaagttcaacgtgggccgtg |
| | cctatgagctgctcagaggctatgtgaatttccggctgcagt |
| | accctgagctctttgacagcctgtcccagaggctgtccgct |
| | gcaccattgaagctggctacctggtgtcctctctagtcggg |
| | acaagtatggccgagtggtcatgctcttcaacattgagaact |
| | ggcaaagtcaagaaatcacctttgatgagatcttgcaggcat |
| | attgcttcatcctggagaagctgctggagaatgaggaaactc |
| | aaaatcaatggcttctgcatcattgagaacttcaagggctttta |
| | ccatgcagcaggctgctagtctccggacttcagatctcagga |
| | agatggtggacatgctccaggattccttcccagcccggttca |
| | aagccatccacttcatccaccagccatggtacttcaccacga |
| | cctacaatgtggtcaagcccttcttgaagagcaagctgcttg |
| | agagggtctttgtccacggggatgacctttctggtttctacc |
| | aggagatcgatgagaacatcctgccctctgacttcgggggca |
| | cgctgcccaagtatgatggcaaggccgttgctgagcagctct |
| | ttggccccaggcccaagctgagaacacagccttctgaggat |
| | ctaccggtcgacctgcagaagcttgcctcgagcagcgctgct |
| | cgagagatctggatcataatcagccataccacatttgtagag |
| | gttttacttgctttaaaaaacctcccacacctcccctgaac |
| | ctgaaacataaaatgaatgcaattgttgttgttaacttgttt |
| | attgcagcttataatggttacaaataaagcaatagcatcaca |
| | aatttcacaaataaagcatttttttcactgcattctagttgt |
| | ggtttgtccaaactcatcaatgtatcttatcatgtctggtaa |
| | ccattctccaggttgagccagaccaatttgatggtagattta |
| | gcaaataaaaatacaggacacccagttaaatgtgaatttccg |
| | atgaacagcaaatactttttagtattaaaaaagttcacatt |
| | taggctcacgcctgtaatcccagcactttgggaggccgagc |
| | aggcagatcacctgaggtcaggagttcgagaccagcctggcc |
| | aacatggtgaaacccatctccactaaaaataccaaaaatta |
| | gccaggcgtgctggtgggcacctgtagttccagctactcagg |
| | aggctaaggcaggagaattgcttgaacctggaggcagaggt |
| | tgcagtgagctgagatcgcaccattgcactctagcctgggcg |
| | acaagaacaaaactccatctcaaaaaaaaaaaaaaaaaaaaa |
| | gttcacatttaactgggcattctgtatttaattggtaatctg |
| | agatggcagggaacagcatcagcatggtgtgagggataggca |
| | tttttttcattgtgtacagcttgtaaatcagtatttttaaaac |
| | tcaaagttaatggcttgggcatatttagaaaagagttgccgc |
| | acggacttgaaccctgtattcctaaaatctaggatcttgttc |
| | tgatggtctgcacaactggctgggggtgtccagccactgtcc |
| | ctcttgcctgggctcccagggcagttctgtcagcctctcca |
| | tttccattcctgttccagcaaaacccaactgatagcacagca |
| | gcatttcagcctgtctacctctgtcccacatacctggatgt |
| | ctaccagccagaaaggtggcttagatttggttcctgtgggtg |
| | gattatgccccccagaacttccctgtgcttgctgggggtgtg |
| | gagtggaaagagcaggaaatgggggaccctccgatactctat |
| | gggggtcctccaagtctctttgtgcaagttagggtaataatc |
| | aatatggagctaagaaagagaaggggaactatgctttagaac |
| | aggacactgtgccaggagcattgcagaaattatatggttttc |

TABLE 2-continued

Plasmid Composition
Plasmid Composition

| Elements | SEQUENCE IDENTIFIER (SEQ. ID. NO:) AND SEQUENCE INFORMATION |
|---|---|
|  | acgacagttcttttggtaggtactgttattatcctcagttt<br>gcagatgaggaaactgagacccagaaaggttaaataacttgc<br>tagggtcacacaagtcataactgacaaagcctgattcaaacc<br>caggtctccctaacctttaaggtttctatgacgccagctctc<br>ctagggagtttgtcttcagatgtcttggctctaggtgtcaaa<br>aaaagacttggtgtcaggcaggcataggttcaagtcccaact<br>ctgtcacttaccaactgtgactaggtgattgaactgaccatg<br>gaacctggtcacatgcaggagcaggatggtgaagggttcttg<br>aaggcacttaggcaggacatttaggcaggagagaaaacctgg<br>aaacagaagagctgtctccaaaaatacccactggggaagcag<br>gttgtcatgtgggccatgaatgggacctgttctggggtaacc<br>acgtgcggaccgagcggccgcaggaaccccctagtgatggagt<br>tggccactccctctctgcgcgctcgctcgctcactgaggccg<br>ggcgaccaaaggtcgcccgacgcccgggctttgcccgggcgg<br>cctcagtgagcgagcgagcgcgcagctgcctgcaggggcgcc<br>tgatgcggtattttctccttacgcatctgtgcggtatttcac<br>accgcatacgtcaaagcaaccatagtacgcgccctgtagcgg<br>cgcattaagcgcggcgggtgtggtggttacgcgcagcgtgac<br>cgctacacttgccagcgccttagcgcccgctcctttcgcttt<br>cttcccttcctttctcgccacgttcgccggctttccccgtca<br>agctctaaatcggggctccctttaggttccgatttagtgc<br>tttacggcacctcgaccccaaaaaacttgatttgggtgatgg<br>ttcacgtagtgggccatcgcccttgatagacggttttcgccc<br>tttgacgttggagtccacgttctttaatagtggactcttgtt<br>ccaaactggaacaacactcaactctatctcgggctattcttt<br>tgatttataagggattttgccgatttcggtctattggttaaa<br>aaatgagctgatttaacaaaaatttaacgcgaattttaacaa<br>aatattaacgtttacaattttatggtgcactctcagtacaat<br>ctgctctgatgccgcatagttaagccagccccgacacccgcc<br>aacacccgctgacgcgccctgacgggcttgtctgctcccggc<br>atccgcttacagacaagctgtgaccgtctccgggagctgcat<br>gtgtcagaggttttcaccgtcatcaccgaaacgcgcgagacg<br>aaagggcctcgtgatacgcctatttttataggttaatgtcat<br>gataataatggtttcttagacgtcaggtggcacttttcgggg<br>aaatgtgcgcggaacccctatttgttattttctaaataca<br>ttcaaatatgtatccgctcatgagacaataaccctgataaat<br>gcttcaataatattgaaaaaggaagagtatgagtattcaaca<br>tttccgtgtcgcccttattccctttttgcggcattttgcct<br>tcctgtttttgctcacccagaaacgctggtgaaagtaaaaga<br>tgctgaagatcagttgggtgcacgagtgggttacatcgaact<br>ggatctcaacagcggtaagatccttgagagttttcgccccga<br>agaacgttttccaatgatgagcacttttaaagttctgctatg<br>tggcgcggtattatcccgtattgacgccgggcaagagcaact<br>cggtcgccgcatacactattctcagaatgacttggttgagta<br>ctcaccagtcacagaaaagcatcttacggatggcatgacagt<br>aagagaattatgcagtgctgccataaccatgagtgataacac<br>tgcggccaacttacttctgacaacgatcggaggaccgaagga<br>gctaaccgcttttttgcacaacatgggggatcatgtaactcg<br>ccttgatcgttgggaaccggagctgaatgaagccataccaaa<br>cgacgagcgtgacaccacgatgcctgtagcaatggcaacaac<br>gttgcgcaaactattaactggcgaactacttactctagcttc<br>ccggcaacaattaatagactggatggaggcggataaagttgc<br>aggaccacttctgcgctcggcccttccggctggctggtttat<br>tgctgataaatctggagccggtgagcgtgggtctcgcggtat<br>cattgcagcactggggccagatggtaagccctcccgtatcgt<br>agttatctacacgacggggagtcaggcaactatggatgaacg<br>aaatagacagatcgctgagataggtgcctcactgattaagca<br>ttggtaactgtcagaccaagtttactcatatatactttagat<br>tgatttaaaacttcattttaatttaaaaggatctaggtgaa<br>gatcctttttgataatctcatgaccaaaatcccttaacgtga<br>gttttcgttccactgagcgtcagaccccgtagaaaagatcaa<br>aggatcttcttgaaatccttttttctgcgcgtaatctgctg<br>cttgcaaacaaaaaaaccaccgctaccagcggtggtttgttt<br>gccggatcaagagctaccaactctttttccgaaggtaactgg<br>cttcagcagagcgcagataccaaatactgttcttctagtgta<br>gccgtagttaggccaccacttcaagaactctgtagcaccgcc<br>tacatacctcgctctgctaatcctgttaccagtggctgctgc<br>cagtggcgataagtcgtgtcttaccgggttggactcaagacg<br>atagttaccggataaggcgcagcggtcgggctgaacggggggg<br>ttcgtgcacacagcccagcttggagcgaacgacctacaccga<br>actgagatacctacagcgtgagctatgagaaagcgccacgct<br>tcccgaagggagaaaggcggacaggtatccggtaagcggcag<br>ggtcggaacaggagagcgcacgagggagcttccaggggaaa<br>cgcctggtatctttatagtcctgtcgggtttcgccacctctg |

TABLE 2-continued

Plasmid Composition
Plasmid Composition

| Elements | SEQUENCE IDENTIFIER (SEQ. ID. NO:) AND SEQUENCE INFORMATION |
|---|---|
|  | acttgagcgtcgattttttgtgatgctcgtcaggggggcggag<br>cctatggaaaaacgccagcaacgcggccttttttacggttcct<br>ggccttttgctggccttttgctcacatgtcctgcaggcag |
| GENE CASSETTE OF PLASMID AG007 OCCURS AT BP 1 THROUGH 4645 OF SEQ ID NO: 28 | 53<br>ctgcgcgctcgctcgctcactgaggccgcccgggcgtcgggc<br>gacctttggtcgcccggcctcagtgagcgagcgagcgcgcag<br>agagggagtggccaactccatcactaggggttcctgcggccg<br>cacgcgttacgtaatatttattgaagtttaatattgtgtttg<br>tgatacagaagtatttgctttaattctaaataaaaattttat<br>gcttttattgctggtttaagaagatttggattatccttgtac<br>tttgaggagaagtttcttatttgaaatattttggaaacaggt<br>cttttaatgtggaaagatagatattaatctcctcttctatta<br>ctctccaagatccaacaaaagtgattataccccccaaaatat<br>gatggtagtatcttatactaccatcattttataggcataggg<br>ctcttagctgcaaataatggaactaactctaataaagcagaa<br>cgcaaatattgtaaatattagagagctaacaatctctgggat<br>ggctaaaggatggagcttggaggctacccagccagtaacaat<br>attccgggctccactgttgaatggagacactacaactgcctt<br>ggatgggcagagatattatggatgctaagcccaggtgctac<br>cattaggacttctaccactgtccctaacgggtggagcccatc<br>acatgcctatgccctcactgtaaggaaatgaagctactgttg<br>tatatcttgggaagcacttggattaattgttatacagttttg<br>ttgaagaaccccctagggtaagtagccataactgcacacta<br>aatttaaaattgttaatgagtttctcaaaaaaaatgttaagg<br>ttgttagctggtatagtatatatcttgcctgttttccaagga<br>cttctttgggcagtaccttgtctgtgctggcaagcaactgag<br>acttaatgaaagagtattggagatatgaatgaattgatgctg<br>tatactctcagagtgccaaacatataccaatggacaagaagg<br>tgaggcagagagcagacaggcattagtgacaagcaaagatat<br>gcagaatttcattctcagcaaatcaaaagtcctcaacctggt<br>tggaagaatattggcactgaatggtatcaataaggttgctag<br>agagggttagaggtgcacaatgtgcttccataacattttata<br>cttctccaatcttagcactaatcaaacatggttgaatacttt<br>gtttactataactcttacagagttataagatctgtgaagaca<br>gggacagggacaataccatctctgtctggttcataggtggt<br>atgtaatagatattttaaaaataagtgagttaatgaatgag<br>ggtgagaatgaaggcacagaggtattagggggaggtgggccc<br>cagagaatggtgccaaggtccagtggggtgactgggatcagc<br>tcaggcctgacgctggccactcccacctagctcctttcttc<br>taatctgttctcattctccttgggaaggattgaggtctctgg<br>aaaacagccaaacaactgttatgggaacagcaagcccaaata<br>aagccaagcatcaggggatctgagagctgaaagcaacttct<br>gttcccctccctcagctgaagggtggggaagggctcccaa<br>agccataactccttttaagggattagaaggcataaaaaggc<br>ccctggctgagaacttccttcttcattctgcagttggtgaat<br>tcgccaccatgtcagaagggtgggcacgttccgcatggtac<br>ctgaagaggaacaggagctccgtgcccaactggagcagctca<br>caaccaaggaccatggacctgtctttggcccgtgcagccagc<br>tgcccgccacaccttgcagaaggccaaggatgagctgaacg<br>agagagaggagacccgggaggaggcagtgcgagagctgcagg<br>agatggtgcaggcgcaggcggcctcgggggaggagctggcgg<br>tggccgtggcggagagggtgcaagagaaggacagcggcttct<br>tcctgcgcttcatccgcgcacggaagttcaacgtgggccgtg<br>cctatgagctgctcagaggctatgtgaatttccggctgcagt<br>accctgagctcttttgacagcctgtccccagaggctgtccgct<br>gcaccattgaagctggctaccctggtgtcctctctagtcggg<br>acaagtatggccgagtggtcatgctcttcaacattgagaact<br>ggcaaagtcaagaaatcacctttgatgagatcttgcaggcat<br>attgcttcatcctggagaagctgctggagaatgaggaaactc<br>aaatcaatggcttctgcatcattgagaacttcaagggcttta<br>ccatgcagcaggctgctagtctccggacttcagatctcagga<br>agatggtggacatgctccaggattccttcccagcccggttca<br>aagccatccacttcatccaccagccatggtacttcaccacga<br>cctacaatgtggtcaagcccttcttgaagagcaagctgcttg<br>agagggtcttttgtccacggggatgacctttctggtttctacc<br>aggagatcgatgagaacatcctgccctctgacttcgggggca<br>cgctgcccaagtatgatggcaaggccgttgctgagcagctct<br>ttggcccccaggcccaagctgagaacacagccttctgaggat<br>ctaccggtcgacctgcagaagcttgcctcgagcagcgctgct<br>cgagagatctggatcataatcagccataccacatttgtagag<br>gttttacttgctttaaaaaacctcccacacctccccctgaac<br>ctgaaacataaaatgaatgcaattgttgttgttaacttgttt<br>attgcagcttataatggttacaaataaagcaatagcatcaca |

TABLE 2-continued

Plasmid Composition
Plasmid Composition

| Elements | SEQUENCE IDENTIFIER (SEQ. ID. NO:) AND SEQUENCE INFORMATION |
|---|---|
| | aatttcacaaataaagcattttttcactgcattctagttgt<br>ggtttgtccaaactcatcaatgtatcttatcatgtctggtaa<br>ccattctccaggttgagccagaccaatttgatggtagattta<br>gcaaataaaaatacaggacacccagttaaatgtgaatttccg<br>atgaacagcaaatactttttagtattaaaaaagttcacatt<br>taggctcacgcctgtaatcccagcactttgggaggccgaggc<br>aggcagatcacctgaggtcaggagttcgagaccagcctggcc<br>aacatggtgaaaccccatctccactaaaaataccaaaaatta<br>gccaggcgtgctggtgggcacctgtagttccagctactcagg<br>aggctaaggcaggagaattgcttgaacctgggaggcagaggt<br>tgcagtgagctgagatcgcaccattgcactctagcctgggcg<br>acaagaacaaaactccatctcaaaaaaaaaaaaaaaaaaaa<br>gttcacatttaactgggcattctgtatttaattggtaatctg<br>agatggcagggaacagcatcagcatggtgtgagggataggca<br>ttttttcattgtgtacagcttgtaaatcagtattttttaaaac<br>tcaaagttaatggcttgggcatatttagaaaagagttgccgc<br>acggacttgaaccctgtattcctaaaatctaggatcttgttc<br>tgatggtctgcacaactggctgggggtgtccagccactgtcc<br>ctcttgcctgggctccccagggcagttctgtcagcctctcca<br>tttccattcctgttccagcaaaacccaactgatagcacagca<br>gcatttcagcctgtctacctctgtgcccacatacctggatgt<br>ctaccagccagaaaggtggcttagatttggttcctgtgggtg<br>gattatggccccagaacttccctgtgcttgctgggggtgtg<br>gagtggaaagagcaggaaatgggggaccctccgatactctat<br>gggggtcctccaagtctctttgtgcaagttagggtaataatc<br>aatatggagctaagaaagagaagggaactatgctttagaac<br>aggacactgtgccaggagcattgcagaaattatatggttttc<br>acgacagttcttttggtaggtactgttattatcctcagttt<br>gcagatgaggaaactgagacccagaaaggttaaataacttgc<br>tagggtcacacaagtcataactgacaaagcctgattcaaacc<br>caggtctccctaacctttaaggtttctatgacgccagctctc<br>ctagggagtttgtcttcagatgtcttggctctaggtgtcaaa<br>aaaagacttggtgtcaggcaggcataggttcaagtcccaact<br>ctgtcacttaccaactgtgactaggtgattgaactgaccatg<br>gaacctggtcacatgcaggagcaggatggtgaagggttcttg<br>aaggcacttaggcaggacatttaggcaggagagaaaacctgg<br>aaacagaagagctgtctccaaaaatacccactggggaagcag<br>gttgtcatgtgggccatgaatgggacctgttctggggtaacc<br>acgtgcggaccgagcggccgcaggaacccctagtgatggagt<br>tggccactccctctctgcgcgctcgctcgctcactgaggccg<br>ggcgaccaaaggtcgcccgacgcccgggctttgcccggcgg<br>cctcagtgagcgagcgagcgcgcag |

Plasmid TM039 Composition

| 5' ITR | 2<br>occurs at bp 1 through bp 119 of SEQ ID NO: 29 |
|---|---|
| CVM ENHANCER AND CBA PROMOTER GENBANK ACCESSION DD215332 FROM BP 1-BP 1616) | 22<br>occurs at bp 134 through bp 1749 of SEQ ID NO: 29 |
| Added Kozak | 5<br>occurs at bp 1763 through bp 1768 of SEQ ID NO: 29 |
| HUMAN RLBP1 GENE CDS | 6<br>occurs at bp 1769 through bp 2722 of SEQ ID NO: 29 |
| SV40 POLYA | 8<br>occurs at bp 2781 through bp 3016 of SEQ ID NO: 29 |
| REVERSE COMPLEMENT OF RLBP1 INTRONIC SEQUENCE AS STUFFER | 23<br>occurs at bp 3032 through bp 4534 of SEQ ID NO: 29 |

TABLE 2-continued

Plasmid Composition
Plasmid Composition

| Elements | SEQUENCE IDENTIFIER (SEQ. ID. NO:) AND SEQUENCE INFORMATION |
|---|---|
| SEQUENCE (NT 010274.17) | |
| 3' ITR | 9<br>occurs at bp 4573 through bp 4702 of SEQ ID NO: 29 |
| AMP BACTERIAL BACKBONE | 15<br>occurs at bp 4703 through bp 7321 of SEQ ID NO: 29 |
| PLASMID TM039 SEQUENCE | 29<br>ctgcgcgctcgctcgctcactgaggccgcccgggcgtcgggc<br>gacctttggtcgcccggcctcagtgagcgagcgagcgcgcag<br>agagggagtggccaactccatcactaggggttcctgcggccg<br>cacgcgtactagttattaatagtaatcaattacggggtcatt<br>agttcatagcccatatatggagttccgcgttacataacttac<br>ggtaaatggcccgcctggctgaccgcccaacgacccccgccc<br>attgacgtcaataatgacgtatgttcccatagtaacgccaat<br>agggactttccattgacgtcaatgggtggagtatttacggta<br>aactgcccacttggcagtacatcaagtgtatcatatgccaag<br>tacgccccctattgacgtcaatgacggtaaatggcccgcctg<br>gcattatgcccagtacatgaccttatgggactttcctacttg<br>gcagtacatctacgtattagtcatcgctattaccatggtcga<br>ggtgagccccacgttctgcttcactctccccatctcccccc<br>ctccccacccccaatttgtatttatttattttttaattatt<br>ttgtgcagcgatgggggcgggggggggggggggcgcgcgcc<br>aggcggggcggggcggggcgaggggcggggcggggcgaggcg<br>gagaggtgcggcggcagccaatcagagcggcgcgctccgaaa<br>gtttccttttatggcgaggcggcggcggcggcggccctataa<br>aaagcgaagcgcgcggcgggcggggagtcgctgcgacgctgc<br>cttcgccccgtgccccgctccgccgccgcctcgcgccgcccg<br>ccccggctctgactgaccgcgttactcccacaggtgagcggg<br>cgggacggcccttctcctccgggctgtaattagcgcttggtt<br>taatgacggcttgtttcttttctgtggctgcgtgaaagcctt<br>gaggggctccgggagggcccttttgtgcgggggagcggctcg<br>gggggtgcgtgcgtgtgtgtgtgcgtggggagcgccgcgtgc<br>ggctccgcgctgcccggcggctgtgagcgctgcgggcgcggc<br>gcggggctttgtgcgctccgcagtgtgcgcgaggggagcgcg<br>gccggggcggtgccccgcggtgcggggggggctgcgagggg<br>aacaaaggctgcgtgcggggtgtgtgcgtggggggtgagca<br>gggggtgtgggcgcgtcggtcgggctgcaacccccccctgcac<br>cccctccccgagttgctgagcacggcccggcttcgggtgcg<br>gggctccgtacggggcgtggcgcggggctcgccgtgccgggc<br>gggggtggcggcaggtgggggtgccgggcggggcggggccg<br>cctcgggccggggagggctcggggagggggcgcggcggcccc<br>cggagcgccggcggctgtcgaggcgcggcgagccgcagccat<br>tgcctttttatggtaatcgtgcgagagggcgcagggacttcct<br>ttgtcccaaatctgtgcggagccgaaatctgggaggcgccgc<br>cgcaccccctctagcgggcgcggggcgaagcggtgcggcgcc<br>ggcaggaaggaaatgggcggggagggccttcgtgcgtcgccg<br>cgccgccgtcccttctccctctccagcctcggggctgtccg<br>cgggggggacggctgccttcgggggggacggggcagggcgggg<br>ttcggcttctggcgtgtgaccggcggcatcgattgaattcgc<br>caccatgtcagaagggggtgggcacgttccgcatggtacctga<br>agaggaacaggagctccgtgcccaactggagcagctcacaac<br>caaggaccatggacctgtctttggcccgtgcagccagctgcc<br>ccgccacaccttgcagaaggccaaggatgagctgaacgagag<br>agaggagaccccgggaggaggcagtgcgagagctgcaggagat<br>ggtgcaggcgcaggcggcctcggggaggagctggcggtggc<br>cgtggcggagagggtgcaagagaaggacagcggcttcttcct<br>gcgcttcatccgcgcacggaagttcaacgtgggccgtgccta<br>tgagctgctcagaggctatgtgaatttccggctgcagtaccc<br>tgagctctttgacagcctgtccccagaggctgtccgctgcac<br>cattgaagctggctaccctggtgtcctctctagtcgggacaa<br>gtatggccgagtggtcatgctcttcaacattgagaactggca<br>aagtcaagaaatcacctttgatgagatcttgcaggcatattg<br>cttcatcctggagaagctgctggagaatgaggaaactcaaat<br>caatggcttctgcatcattgagaacttcaagggcttaccat<br>gcagcaggctgctagtctccggacttcagatctcaggaagat<br>ggtggacatgctccaggattccttcccagcccggttcaaagc<br>catccacttcatccaccagccatggtacttcaccacgaccta<br>caatgtggtcaagcccttcttgaagagcaagctgcttgagag<br>ggtctttgtccacggggatgacctttctggtttctaccagga |

TABLE 2-continued

Plasmid Composition

| Elements | SEQUENCE IDENTIFIER (SEQ. ID. NO:) AND SEQUENCE INFORMATION |
|---|---|
| | gatcgatgagaacatcctgccctctgacttcgggggcacgct |
| | gcccaagtatgatggcaaggccgttgctgagcagctctttgg |
| | cccccaggcccaagctgagaacacagccttctgaggatcgta |
| | ccggtcgacctgcagaagcttgcctcgagcagcgctgctcga |
| | gagatctggatcataatcagccataccacatttgtagaggtt |
| | ttacttgctttaaaaaacctcccacacctcccctgaacctg |
| | aaacataaaatgaatgcaattgttgttgttaacttgtttatt |
| | gcagcttataatggttacaaataaagcaatagcatcacaaat |
| | ttcacaaataaagcattttttcactgcattctagttgtggt |
| | ttgtccaaactcatcaatgtatcttatcatgtctggtactag |
| | ggttacccagaacaggtcccattcatggcccacatgacaac |
| | ctgcttcccagtgggtattttggagacagctcttctgttt |
| | ccaggttttctctcctgcctaaatgtcctgcctaagtgcctt |
| | caagaacccttcaccatcctgctcctgcatgtgaccaggttc |
| | catggtcagttcaatcacctagtcacagttggtaagtgacag |
| | agttgggacttgaacctatgcctgcctgacaccaagtctttt |
| | tttgacacctagagccaagacatctgaagacaaactccctag |
| | gagagctggcgtcatagaaaccttaaaggttagggagacctg |
| | ggtttgaatcaggctttgtcagttatgacttgtgtgaccta |
| | gcaagttatttaacctttctgggtctcagtttcctcatctgc |
| | aaactgaggataataacagtacctaccaaaaagaactgtcgt |
| | gaaaaccatataatttctgcaatgctcctggcacagtgtcct |
| | gttctaaagcatagttccccttctctttcttagctccatatt |
| | gattattaccctaacttgcacaaagagacttggaggaccccc |
| | atagagtatcggagggtcccccatttcctgctctttccactc |
| | cacaccccagcaagcacagggaagttctgggggccataatc |
| | cacccacaggaaccaaatctaagccaccttctggctggtag |
| | acatccaggtatgtgggcacagaggtagacaggctgaaatgc |
| | tgctgtgctatcagttgggttttgctggaacaggaatggaaa |
| | tggagaggctgacagaactgccctggggagcccaggcaagag |
| | ggacagtggctggacaccccagccagttgtgcagaccatca |
| | gaacaagatcctagattttaggaatacaggttcaagtccgt |
| | gcggcaactctttctaaatatgcccaagccattaactttga |
| | gttttaaaaatactgatttacaagctgtacacaatgaaaaaa |
| | tgcctatccctcacaccatgctgatgctgttccctgccatct |
| | cagattaccaattaaatacagaatgcccagttaaatgtgaac |
| | tttttttttttttttttttttgagatggagttttgttcttgt |
| | cgcccaggctagagtgcaatggtgcgatctcagctcactgca |
| | acctctgcctcccaggttcaagcaattctcctgccttagcct |
| | cctgagtagctggaactacaggtgcccaccagcacgcctggc |
| | taatttttggtatttttagtggagatggggtttcaccatgtt |
| | ggccaggctggtctcgaactcctgacctcaggtgatctgcct |
| | gcctcggcctcccaaagtgctgggattacaggcgtgagccta |
| | aatgtgaacttttttaatactaaaaaagtatttgctgttcat |
| | cggaaattcacatttaactgggtgtcctgtattttatttgc |
| | taaatctaccatcaaattggtctggctcaacctggagaatgg |
| | ttaccctaggtaaccacgtgcggaccgagcggccgcaggaac |
| | ccctagtgatggagttggccactccctctctgcgcgctcgct |
| | cgctcactgaggccgggcgaccaaaggtcgcccgacgcccgg |
| | gctttgcccgggcggcctcagtgagcgagcgagcgcgcagct |
| | gcctgcaggggcgcctgatgcggtattttctccttacgcatc |
| | tgtgcggtatttcacaccgcatacgtcaaagcaaccatagta |
| | cgcgccctgtagcggcgcattaagcgcggcgggtgtggtggt |
| | tacgcgcagcgtgaccgctacacttgccagcgccttagcgcc |
| | cgctcctttcgctttcttcccttcctttctcgccacgttcgc |
| | cggctttccccgtcaagctctaaatcggggctccctttagg |
| | gttccgatttagtgctttacggcacctcgaccccaaaaaact |
| | tgatttgggtgatggttcacgtagtgggccatcgccctgata |
| | gacggttttcgccctttgacgttggagtccacgttctttaa |
| | tagtggactcttgttccaaactggaacaacactcaactctat |
| | ctcgggctattcttttgatttataagggattttgccgatttc |
| | ggtctattggttaaaaaatgagctgatttaacaaaaatttaa |
| | cgcgaattttaacaaaatattaacgtttacaattttatggtg |
| | cactctcagtacaatctgctctgatgccgcatagttaagcca |
| | gccccgacacccgccaacacccgctgacgcgccctgacgggc |
| | ttgtctgctcccggcatccgcttacagacaagctgtgaccgt |
| | ctccgggagctgcatgtgtcagaggttttcaccgtcatcacc |
| | gaaacgcgcgagacgaaagggcctcgtgatacgcctatttt |
| | ataggttaatgtcatgataataatggtttcttagacgtcagg |
| | tggcacttttcggggaaatgtgcgcggaacccctatttgttt |
| | atttttctaaatacattcaaatatgtatccgctcatgagaca |
| | ataaccctgataaatgcttcaataatattgaaaaaggaagag |
| | tatgagtattcaacatttccgtgtcgcccttattcccttttt |
| | tgcggcattttgccttcctgtttttgctcacccagaaacgct |

TABLE 2-continued

Plasmid Composition
Plasmid Composition

| Elements | SEQUENCE IDENTIFIER (SEQ. ID. NO:) AND SEQUENCE INFORMATION |
|---|---|
| | ggtgaaagtaaaagatgctgaagatcagttgggtgcacgagt<br>gggttacatcgaactggatctcaacagcggtaagatccttga<br>gagttttcgccccgaagaacgttttccaatgatgagcacttt<br>taaagttctgctatgtggcgcggtattatcccgtattgacgc<br>cgggcaagagcaactcggtcgccgcatacactattctcagaa<br>tgacttggttgagtactcaccagtcacagaaaagcatcttac<br>ggatggcatgacagtaagagaattatgcagtgctgccataac<br>catgagtgataacactgcggccaacttacttctgacaacgat<br>cggaggaccgaaggagctaaccgcttttttgcacaacatggg<br>ggatcatgtaactcgccttgatcgttgggaaccggagctgaa<br>tgaagccataccaaacgacgagcgtgacaccacgatgcctgt<br>agcaatggcaacaacgttgcgcaaactattaactggcgaact<br>acttactctagcttcccggcaacaattaatagactggatgga<br>ggcggataaagttgcaggaccacttctgcgctcggcccttcc<br>ggctggctggtttattgctgataaatctggagccggtgagcg<br>tgggtctcgcggtatcattgcagcactggggccagatggtaa<br>gccctcccgtatcgtagttatctacacgacggggagtcaggc<br>aactatggatgaacgaaatagacagatcgctgagataggtgc<br>ctcactgattaagcattggtaactgtcagaccaagtttactc<br>atatatactttagattgatttaaaacttcattttttaatttaa<br>aaggatctaggtgaagatcctttttgataatctcatgaccaa<br>aatcccttaacgtgagttttcgttccactgagcgtcagaccc<br>cgtagaaaagatcaaaggatcttcttgaaatcctttttttct<br>gcgcgtaatctgctgcttgcaaacaaaaaaaccaccgctacc<br>agcggtggtttgtttgccggatcaagagctaccaactctttt<br>tccgaaggtaactggcttcagcagagcgcagataccaaatac<br>tgttcttctagtgtagccgtagttaggccaccacttcaagaa<br>ctctgtagcaccgcctacatacctcgctctgctaatcctgtt<br>accagtggctgctgccagtggcgataagtcgtgtcttaccgg<br>gttggactcaagacgatagttaccggataaggcgcagcggtc<br>gggctgaacggggggttcgtgcacacagcccagcttggagcg<br>aacgacctacaccgaactgagatacctacagcgtgagctatg<br>agaaagcgccacgcttcccgaagggagaaaggcggacaggta<br>tccggtaagcggcagggtcggaacaggagagcgcacgaggga<br>gcttccaggggaaacgcctggtatctttatagtcctgtcgg<br>gtttcgccacctctgacttgagcgtcgatttttgtgatgctc<br>gtcaggggggcggagcctatggaaaaacgccagcaacgcggc<br>cttttacggttcctggccttttgctggccttttgctcacat<br>gtcctgcaggcag |
| GENE CASSETTE<br>OF PLASMID<br>TM039 OCCURS AT<br>BP 1 THROUGH<br>4702 OF SEQ ID<br>NO: 29 | 54<br>ctgcgcgctcgctcgctcactgaggccgcccgggcgtcggc<br>gacctttggtcgcccggcctcagtgagcgagcgagcgcgcag<br>agagggagtggccaactccatcactaggggttcctgcggccg<br>cacgcgtactagttattaatagtaatcaattacgggtcatt<br>agttcatagcccatatatggagttccgcgttacataacttac<br>ggtaaatggcccgcctggctgaccgcccaacgacccccgccc<br>attgacgtcaataatgacgtatgttcccatagtaacgccaat<br>agggactttccattgacgtcaatgggtggagtatttacggta<br>aactgcccacttggcagtacatcaagtgtatcatatgccaag<br>tacgccccctattgacgtcaatgacggtaaatggcccgcctg<br>gcattatgcccagtacatgacccttatgggactttcctacttg<br>gcagtacatctacgtattagtcatcgctattaccatggtcga<br>ggtgagccccacgttctgcttcactctccccatctccccccc<br>ctccccacccccaatttgtatttattttttttttaattatt<br>ttgtgcagcgatggggcgggggggggggggggggcgcgcgcc<br>aggcggggcgggcggggcgagggcgggcgggcgaggcg<br>gagaggtgcggcggcagccaatcagagcggcgcgctccgaaa<br>gtttccttttatggcgaggcggcggcggcggcggccctataa<br>aaagcgaagcgcgcggcgggcggggagtcgctgcgacgctgc<br>cttcgccccgtgccccgctccgccgccgcctcgcgccgcccg<br>ccccggctctgactgaccgcgttactcccacaggtgagcggg<br>cgggacggcccttctcctccgggctgtaattagcgcttggtt<br>taatgacggcttgtttcttttctgtggctgcgtgaaagcctt<br>gaggggctccggagggcccttgtgcggggggagcggctcg<br>gggggtgcgtgcgtgtgtgtgcgtggggagcgccgcgtgc<br>ggctccgcgctgcccggcggctgtgagcgctgcgggcgcggc<br>gcggggctttgtgcgctccgcagtgtgcgcgaggggagcgcg<br>gccgggggcggtgccccgcggtgcgggggggctgcgaggggg<br>aacaaaggctgcgtgcggggtgtgtgcgtgggggggtgagca<br>gggggtgtgggcgcgtcggtcggctgcaaccccccctgcac<br>ccccctccccgagttgctgagcacggcccggcttcgggtgcg<br>gggctccgtacggggcgtggcgcggggctcgccgtgccggc<br>gggggggtggcggcaggtggggggtgccgggcggggcggggccg |

TABLE 2-continued

Plasmid Composition
Plasmid Composition

| Elements | SEQUENCE IDENTIFIER (SEQ. ID. NO:) AND SEQUENCE INFORMATION |
|---|---|
| | cctcggggccggggagggctcggggagggcgcggcggcccc |
| | cggagcgccggcggctgtcgaggcgcggcgagccgcagccat |
| | tgcctttatggtaatcgtgcgagagggcgcagggacttcct |
| | ttgtcccaaatctgtgcggagccgaaatctgggaggcgccgc |
| | cgcacccctctagcgggcgcggggcgaagcggtgcggcgcc |
| | ggcaggaaggaaatgggcggggagggccttcgtgcgtcgccg |
| | cgccgccgtcccccttctccctctccagcctcggggctgtccg |
| | cgggggacggctgccttcgggggggacggggcagggcgggg |
| | ttcggcttctggcgtgtgaccggcggcatcgattgaattcgc |
| | caccatgtcagaagggggtgggcacgttccgcatggtacctga |
| | agaggaacaggagctccgtgcccaactggagcagctcacaac |
| | caaggaccatggacctgtctttggcccgtgcagccagctgcc |
| | ccgccacaccttgcagaaggccaaggatgagctgaacgagag |
| | agaggagacccgggaggaggcagtgcgagagctgcaggagat |
| | ggtgcaggcgcaggcggcctcgggggaggagctggcggtggc |
| | cgtggcgagagggtgcaagagaaggacagcggcttcttcct |
| | gcgcttcatccgcgcacggaagttcaacgtgggccgtgccta |
| | tgagctgctcagaggctatgtgaatttccggctgcagtaccc |
| | tgagctctttgacagcctgtccccagaggctgtccgctgcac |
| | cattgaagctggctaccctggtgtcctctctagtcgggacaa |
| | gtatggccgagtggtcatgctcttcaacattgagaactggca |
| | aagtcaagaaatcacctttgatgagatcttgcaggcatattg |
| | cttcatcctggagaagctgctggagaatgaggaaactcaaat |
| | caatggcttctgcatcattgagaacttcaagggctttaccat |
| | gcagcaggctgctagtctccggacttcagatctcaggaagat |
| | ggtggacatgctccaggattccttcccagcccggttcaaagc |
| | catccacttcatccaccagccatggtacttcaccacgaccta |
| | caatgtggtcaagcccttcttgaagagcaagctgcttgagag |
| | ggtctttgtccacggggatgacctttctggtttctaccagga |
| | gatcgatgagaacatcctgccctctgacttcggggggcacgct |
| | gcccaagtatgatggcaaggccgttgctgagcagctctttgg |
| | ccccaggcccaagctgagaacacagccttctgaggatcgta |
| | ccggtcgacctgcagaagcttgcctcgagcagcgctgctcga |
| | gagatctggatcataatcagccataccacatttgtagaggtt |
| | ttacttgctttaaaaaacctcccacacctcccctgaacctg |
| | aaacataaaatgaatgcaattgttgttgttaacttgtttatt |
| | gcagcttataatggttacaaataaagcaatagcatcacaaat |
| | ttcacaaataaagcattttttttcactgcattctagttgtggt |
| | ttgtccaaactcatcaatgtatcttatcatgtctggtactag |
| | ggttaccccagaacaggtcccattcatggcccacatgacaac |
| | ctgcttcccagtgggtattttttggagacagctcttctgttt |
| | ccaggttttctctcctgcctaaatgtcctgcctaagtgcctt |
| | caagaaccctcaccatcctgctcctgcatgtgaccaggttc |
| | catggtcagttcaatcacctagtcacagttggtaagtgacag |
| | agttgggacttgaacctatgcctgcctgacaccaagtcttt |
| | tttgacacctagagccaagacatctgaagacaaactccctag |
| | gagagctggcgtcatagaaacctaaaggttagggagacctg |
| | ggtttgaatcaggctttgtcagttatgacttgtgtgacccta |
| | gcaagttattaacctttctgggtctcagtttcctcatctgc |
| | aaactgaggataataacagtacctaccaaaaagaactgtcgt |
| | gaaaaccatataatttctgcaatgctcctggcacagtgtcct |
| | gttctaaagcatagttccccttctctttcttagctccatatt |
| | gattattaccctaacttgcacaaagagacttggaggaccccc |
| | atagagtatcggagggtcccccatttcctgctctttccactc |
| | cacaccccagcaagcacagggaagttctgggggccataatc |
| | cacccacaggaaccaaatctaagccacctttctggctggtag |
| | acatccaggtatgtgggcacagaggtagacaggctgaaatgc |
| | tgctgtgctatcagttgggttttgctggaacaggaatggaaa |
| | tggagaggctgacagaactgccctggggagcccaggcaagag |
| | ggacagtggctggacacccccagccagttgtgcagaccatca |
| | gaacaagatcctagattttaggaatacagggttcaagtccgt |
| | gcggcaactctttctaaatatgcccaagccattaactttga |
| | gttttaaaaatactgatttacaagctgtacacaatgaaaaaa |
| | tgcctatccctcacaccatgctgatgctgttccctgccatct |
| | cagattaccaattaaatacagaatgcccagttaaatgtgaac |
| | tttttttttttttttttttgagatggagttttgttcttgt |
| | cgcccaggctagagtgcaatggtgcgatctcagctcactgca |
| | acctctgcctcccaggttcaagcaattctcctgccttagcct |
| | cctgagtagctggaactacaggtgcccaccagcacgcctggc |
| | taattttttgtattttagtgggagatggggtttcaccatgtt |
| | ggccaggctggtctcgaactcctgacctcaggtgatctgcct |
| | gcctcggcctcccaaagtgctgggattacaggcgtgagccta |
| | aatgtgaactttttaatactaaaaaagtatttgctgttcat |
| | cggaaattcacatttaactgggtgtcctgtattttatttgc |

TABLE 2-continued

Plasmid Composition
Plasmid Composition

| Elements | SEQUENCE IDENTIFIER (SEQ. ID. NO:) AND SEQUENCE INFORMATION |
|---|---|
| | taaatctaccatcaaattggtctggctcaacctggagaatgg<br>ttaccctaggtaaccacgtgcggaccgagcggccgcaggaac<br>ccctagtgatggagttggccactccctctctgcgcgctcgct<br>cgctcactgaggccgggcgaccaaaggtcgcccgacgcccgg<br>gctttgcccgggcggcctcagtgagcgagcgagcgcgcag |

Plasmid TM040 Composition

| 5' ITR | 2<br>occurs at bp 1 through bp 119 of SEQ ID NO: 30 |
|---|---|
| Human RLBP1 Promoter(short) | 3<br>occurs at bp 134 through bp 723 of SEQ ID NO: 30 |
| Modified SV40 intron | 4<br>occurs at bp 738 through bp 920 of SEQ ID NO: 30 |
| Added Kozak | 5<br>occurs at bp 934 through bp 939 of SEQ ID NO: 30 |
| HUMAN RLBP1 GENE CDS | 6<br>occurs at bp 940 through bp 1893 of SEQ ID NO: 30 |
| SV40 POLYA | 8<br>occurs at bp 1952 through bp 2187 of SEQ ID NO: 30 |
| REVERSE COMPLEMENT OF RLBP1 INTRONIC SEQUENCE AS STUFFER SEQUENCE (NT 010274.17) | 23<br>occurs at bp 2203 through bp 3705 of SEQ ID NO: 30 |
| 3' ITR | 9<br>occurs at bp 3744 through bp 3873 of SEQ ID NO: 30 |
| AMP BACTERIAL BACKBONE | 15<br>occurs at bp 3874 through bp 6492 of SEQ ID NO: 30 |
| TM040 plasmid sequence | 30<br>ctgcgcgctcgctcgctcactgaggccgccgggcgtcgggc<br>gacctttggtcgcccggcctcagtgagcgagcgagcgcgcag<br>agagggagtggccaactccatcactaggggttcctgcggccg<br>cacgcgtttgtcctctccctgcttggccttaaccagccacat<br>ttctcaactgaccccactcactgcagaggtgaaaactaccat<br>gccaggtcctgctggctgggggaggggtgggcaataggcctg<br>gatttgccagagctgccactgtagatgtagtcatatttacga<br>tttcccttcacctcttattaccctggtggtggtggtgggggg<br>gggggggtgctctctcagcaaccccaccccgggatcttgagg<br>agaaagagggcagagaaaagagggaatgggactggcccagat<br>cccagccccacagccgggcttccacatggccgagcaggaact<br>ccagagcaggagcacacaaaggagggctttgatgcgcctcca<br>gccaggcccaggcctctcccctctccccttctctctgggtc<br>ttcctttgccccactgagggcctcctgtgagcccgatttaac<br>ggaaactgtgggcggtgagaagttccttatgacacactaatc<br>ccaacctgctgaccggaccacgcctccagcggagggaacctc<br>tagagctccaggacattcaggtaccaggtagccccaaggagg<br>agctgccgaatcgatggatcgggaactgaaaaaccagaaagt<br>taactggtaagtttagtcttttgtcttttatttcaggtccc<br>ggatccggtggtggtgcaaatcaaagaactgctcctcagtgg<br>atgttgcctttacttctaggcctgtacggaagtgttacttct<br>gctctaaaagctgcggaattgtaccgcccgggatccatcg<br>attgaattcgccaccatgtcagaaggggtgggcacgttccgc<br>atggtacctgaagaggaacaggagctccgtgcccaactggag<br>cagctcacaaccaaggaccatggacctgtctcttggcccgtgc TABLE 2-continued Plasmid Composition

| Elements | SEQUENCE IDENTIFIER (SEQ. ID. NO:) AND SEQUENCE INFORMATION |
|---|---|
| | agccagctgccccgccacaccttgcagaaggccaaggatgag |
| | ctgaacgagagagaggagacccgggaggaggcagtgcgagag |
| | ctgcaggagatggtgcaggcgcaggcggcctcggggaggag |
| | ctggcggtggccgtggcggagagggtgcaagagaaggacagc |
| | ggcttcttcctgcgcttcatccgcgcacggaagttcaacgtg |
| | ggccgtgcctatgagctgctcagaggctatgtgaatttccgg |
| | ctgcagtaccctgagctctttgacagcctgtccccagaggct |
| | gtccgctgcaccattgaagctggctaccctggtgtcctctct |
| | agtcgggacaagtatggccgagtggtcatgctcttcaacatt |
| | gagaactggcaaagtcaagaaatcacctttgatgagatcttg |
| | caggcatattgcttcatcctggagaagctgctggagaatgag |
| | gaaactcaaatcaatggcttctgcatcattgagaacttcaag |
| | ggctttaccatgcagcaggctgctagtctccggacttcagat |
| | ctcaggaagatggtggacatgctccaggattccttcccagcc |
| | cggttcaaagccatccacttcatccaccagccatggtacttc |
| | accacgacctacaatgtggtcaagcccttcttgaagagcaag |
| | ctgcttgagagggtctttgtccacggggatgacctttctggt |
| | ttctaccaggagatcgatgagaacatcctgccctctgacttc |
| | gggggcacgctgcccaagtatgatggcaaggccgttgctgag |
| | cagctctttggcccccaggcccaagctgagaacacagccttc |
| | tgaggatcgtaccggtcgacctgcagaagcttgcctcgagca |
| | gcgctgctcgagagatctggatcataatcagccataccacat |
| | ttgtagaggttttacttgctttaaaaaaacctcccacacctcc |
| | ccctgaacctgaaacataaaatgaatgcaattgttgttgtta |
| | acttgtttattgcagcttataatggttacaaataaagcaata |
| | gcatcacaaatttcacaaataaagcatttttttcactgcatt |
| | ctagttgtggtttgtccaaactcatcaatgtatcttatcatg |
| | tctggtactagggttaccccagaacaggtcccattcatgcc |
| | cacatgacaacctgcttccccagtgggtattttttggagacag |
| | ctcttctgtttccaggttttctctcctgcctaaatgtcctgc |
| | ctaagtgccttcaagaacccttcaccatcctgctcctgcatg |
| | tgaccaggttccatggtcagttcaatcacctagtcacagttg |
| | gtaagtgacagagttgggacttgaacctatgcctgcctgaca |
| | ccaagtctttttttgacacctagagccaagacatctgaagac |
| | aaactccctaggagagctggcgtcatagaaaccttaaaggtt |
| | agggagacctgggtttgaatcaggctttgtcagttatgactt |
| | gtgtgaccctagcaagttatttaaccttctgggtctcagtt |
| | tcctcatctgcaaactgaggataataacagtacctaccaaaa |
| | agaactgtcgtgaaaaccatataatttctgcaatgctcctgg |
| | cacagtgtcctgttctaaagcatagttcccctctcttttctt |
| | agctccatattgattattaccctaacttgcacaaagagactt |
| | ggaggaccccatagagtatcggagggtccccccatttcctgc |
| | tctttccactccacaccccagcaagcacagggaagttctgg |
| | gggccataatccacccacaggaaccaaatctaagccacctt |
| | ctggctggtagacatccaggtatgtgggcacagaggtagaca |
| | ggctgaaatgctgctgtgctatcagttgggttttgctggaac |
| | aggaatggaaatggagaggctgacagaactgccctggggagc |
| | ccaggcaagagggacagtggctggacaccccccagccagttgt |
| | gcagaccatcagaacaagatcctagattttaggaatacaggg |
| | ttcaagtccgtgcggcaactcttttctaaatatgcccaagcc |
| | attaactttgagttttaaaaatactgatttacaagctgtaca |
| | caatgaaaaaatgcctatccctcacaccatgctgatgctgtt |
| | ccctgccatctcagattaccaattaaatacagaatgcccagt |
| | taaatgtgaacttttttttttttttttttttgagatggagt |
| | tttgttcttgtcgcccaggctagagtgcaatggtgcgatctc |
| | agctcactgcaacctctgcctcccaggttcaagcaattctcc |
| | tgccttagcctcctgagtagctggaactacaggtgcccacca |
| | gcacgcctggctaattttttgtattttagtggagatggggt |
| | ttcaccatgttggccaggctggtctcgaactcctgacctcag |
| | gtgatctgcctgcctcggcctcccaaagtgctgggattacag |
| | gcgtgagcctaaatgtgaactttttaatactaaaaaagtat |
| | ttgctgttcatcggaaattcacatttaactgggtgtcctgta |
| | ttttttatttgctaaatctaccatcaaattggtctggctcaac |
| | ctggagaatggttaccctaggtaaccacgtgcggaccgagcg |
| | gccgcaggaaccctagtgatggagttggccactccctctct |
| | gcgcgctcgctcgctcactgaggccgggcgaccaaaggtcgc |
| | ccgacgcccgggctttgcccgggcggcctcagtgagcgagcg |
| | agcgcgcagctgcctgcaggggcgcctgatgcggtatttct |
| | ccttacgcatctgtgcggtatttcacaccgcatacgtcaaag |
| | caaccatagtacgcgccctgtagcggcgcattaagcgcggcg |
| | ggtgtggtggttacgcgcagcgtgaccgctacacttgccagc |
| | gccttagcgcccgctcctttcgctttcttcccttcctttctc |
| | gccacgttcgccggctttccccgtcaagctctaaatcggggg |
| | ctccctttagggttccgatttagtgctttacggcacctcgac |

TABLE 2-continued

Plasmid Composition

| Elements | SEQUENCE IDENTIFIER (SEQ. ID. NO:) AND SEQUENCE INFORMATION |
|---|---|
| | cccaaaaaacttgatttgggtgatggttcacgtagtgggcca<br>tcgccctgatagacggttttccgcccttttgacgttggagtcc<br>acgttctttaatagtggactcttgttccaaactggaacaaca<br>ctcaactctatctcgggctattcttttgatttataagggatt<br>ttgccgatttcggtctattggttaaaaaatgagctgatttaa<br>caaaaatttaacgcgaattttaacaaaatattaacgtttaca<br>attttatggtgcactctcagtacaatctgctctgatgccgca<br>tagttaagccagccccgacacccgccaacacccgctgacgcg<br>ccctgacgggcttgtctgctcccggcatccgcttacagacaa<br>gctgtgaccgtctccgggagctgcatgtgtcagaggttttca<br>ccgtcatcaccgaaacgcgcgagacgaaagggcctcgtgata<br>cgcctattttttataggttaatgtcatgataataatggtttct<br>tagacgtcaggtggcacttttcggggaaatgtgcgcggaacc<br>cctatttgtttattttctaaatacattcaaatatgtatccg<br>ctcatgagacaataaccctgataaatgcttcaataatattga<br>aaaaggaagagtatgagtattcaacatttccgtgtcgcccttt<br>attccctttttgcggcattttgccttcctgttttttgctcac<br>ccagaaacgctggtgaaagtaaaagatgctgaagatcagttg<br>ggtgcacgagtgggttacatcgaactggatctcaacagcggt<br>aagatccttgagagttttcgccccgaagaacgttttccaatg<br>atgagcacttttaaagttctgctatgtggcgcggtattatcc<br>cgtattgacgccgggcaagagcaactcggtcgccgcatacac<br>tattctcagaatgacttggttgagtactcaccagtcacagaa<br>aagcatcttacggatggcatgacagtaagagaattatgcagt<br>gctgccataaccatgagtgataacactgcggccaacttactt<br>ctgacaacgatcggaggaccgaaggagctaaccgcttttttg<br>cacaacatgggggatcatgtaactcgccttgatcgttgggaa<br>ccggagctgaatgaagccataccaaacgacgagcgtgacacc<br>acgatgcctgtagcaatggcaacaacgttgcgcaaactatta<br>actggcgaactacttactctagcttcccggcaacaattaata<br>gactggatggaggcggataaagttgcaggaccacttctgcgc<br>tcggcccttccggctggctggttttattgctgataaatctgga<br>gccggtgagcgtgggtctcgcggtatcattgcagcactgggg<br>ccagatggtaagccctcccgtatcgtagttatctacacgacg<br>gggagtcaggcaactatggatgaacgaaatagacagatcgct<br>gagataggtgcctcactgattaagcattggtaactgtcagac<br>caagtttactcatatatactttagattgatttaaaacttcat<br>ttttaatttaaaaggatctaggtgaagatcctttttgataat<br>ctcatgaccaaaatcccttaacgtgagttttcgttccactga<br>gcgtcagaccccgtagaaaagatcaaaggatcttcttgaaat<br>cctttttttctgcgcgtaatctgctgcttgcaaacaaaaaaa<br>ccaccgctaccagcggtggtttgtttgccggatcaagagcta<br>ccaactctttttccgaaggtaactggcttcagcagagcgcag<br>ataccaaatactgttcttctagtgtagccgtagttaggccac<br>cacttcaagaactctgtagcaccgcctacatacctcgctctg<br>ctaatcctgttaccagtggctgctgccagtggcgataagtcg<br>tgtcttaccgggttggactcaagacgatagttaccggataag<br>gcgcagcggtcgggctgaacggggggttcgtgcacacagccc<br>agcttggagcgaacgacctacaccgaactgagatacctacag<br>cgtgagctatgagaaagcgccacgcttcccgaagggagaaag<br>gcggacaggtatccggtaagcggcagggtcggaacaggagag<br>cgcacgagggagcttccaggggaaacgcctggtatctttat<br>agtcctgtcgggtttcgccacctctgacttgagcgtcgattt<br>ttgtgatgctcgtcaggggggcggagcctatggaaaaacgcc<br>agcaacgcggcctttttacggttcctggccttttgctggcct<br>tttgctcacatgtcctgcaggcag |
| GENE CASSETTE OF PLASMID TM040 OCCURS AT BP 1 THROUGH 3873 OF SEQ ID NO: 30 | 55<br>ctgcgcgctcgctcgctcactgaggccgcccgggcgtcgggc<br>gacctttggtcgcccggcctcagtgagcgagcgagcgcgcag<br>agagggagtggccaactccatccataggggttcctgcggccg<br>cacgcgtttgtcctctccctgcttggccttaaccagccacat<br>ttctcaactgaccccactcactgcagaggtgaaaactaccat<br>gccaggtcctgctggctgggggaggggtgggcaataggcctg<br>gatttgccagagctgccactgtagatgtagtcatatttacga<br>tttcccttcacctcttattaccctggtggtggtggtgggggg<br>ggggggtgctctctcagcaaccccaccccgggatcttgagg<br>agaaagagggcagagaaaagagggaatgggactggcccagat<br>cccagccccacagccgggcttccacatggccgagcaggaact<br>ccagagcaggagcacacaaaggagggctttgatgcgcctcca<br>gccaggcccaggcctctcccctctcccttttctctctgggtc<br>ttcctttgccccactgagggcctcctgtgagcccgatttaac<br>ggaaactgtgggcggtgagaagttccttatgacacactaatc<br>ccaacctgctgaccggaccacgcctccagcggagggaacctc |

TABLE 2-continued

Plasmid Composition
Plasmid Composition

| Elements | SEQUENCE IDENTIFIER (SEQ. ID. NO:) AND SEQUENCE INFORMATION |
|---|---|
| | tagagctccaggacattcaggtaccaggtagccccaaggagg |
| | agctgccgaatcgatggatcgggaactgaaaaaccagaaagt |
| | taactggtaagtttagtcttttgtcttttatttcaggtccc |
| | ggatccggtggtggtgcaaatcaaagaactgctcctcagtgg |
| | atgttgcctttacttctaggcctgtacggaagtgttacttct |
| | gctctaaaagctgcggaattgtacccgccccgggatccatcg |
| | attgaattcgccaccatgtcagaagggggtgggcacgttccgc |
| | atggtacctgaagaggaacaggagctccgtgcccaactggag |
| | cagctcacaaccaaggaccatggacctgtctttggcccgtgc |
| | agccagctgccccgccacaccttgcagaaggccaaggatgag |
| | ctgaacgagagagaggagacccgggaggaggcagtgcgagag |
| | ctgcaggagatggtgcaggcgcaggcggcctcggggaggag |
| | ctggcggtggccgtggcggagagggtgcaagagaaggacagc |
| | ggcttcttcctgcgcttcatccgcgcacggaagttcaacgtg |
| | ggccgtgcctatgagctgctcagaggctatgtgaatttccgg |
| | ctgcagtaccctgagctctttgacagcctgtccccagaggct |
| | gtccgctgcaccattgaagctggctaccctggtgtcctctct |
| | agtcgggacaagtatggccgagtggtcatgctcttcaacatt |
| | gagaactggcaaagtcaagaaatcacctttgatgagatcttg |
| | caggcatattgcttcatcctggagaagctgctggagaatgag |
| | gaaactcaaatcaatggcttctgcatcattgagaacttcaag |
| | ggctttaccatgcagcaggctgctagtctccggacttcagat |
| | ctcaggaagatggtggacatgctccaggattccttcccagcc |
| | cggttcaaagccatccacttcatccaccagccatggtacttc |
| | accacgacctacaatgtggtcaagcccttcttgaagagcaag |
| | ctgcttgagagggtctttgtccacggggatgacctttctggt |
| | ttctaccaggagatcgatgagaacatcctgccctctgacttc |
| | gggggcacgctgcccaagtatgatggcaaggccgttgctgag |
| | cagctcttttggccccaggcccaagctgagaacacagccttc |
| | tgaggatcgtaccggtcgacctgcagaagcttgcctcgagca |
| | gcgctgctcgagagatctggatcataatcagccataccacat |
| | ttgtagaggttttacttgctttaaaaaacctcccacacctcc |
| | ccctgaacctgaaacataaaatgaatgcaattgttgttgtta |
| | acttgtttattgcagcttataatggttacaaataaagcaata |
| | gcatcacaaatttcacaaataaagcattttttttcactgcatt |
| | ctagttgtggtttgtccaaactcatcaatgtatcttatcatg |
| | tctggtactagggttaccccagaacaggtcccattcatggcc |
| | cacatgacaacctgcttccccagtgggtattttggagacag |
| | ctcttctgtttccaggttttctctcctgcctaaatgtcctgc |
| | ctaagtgccttcaagaacccttcaccatcctgctcctgcatg |
| | tgaccaggttccatggtcagttcaatcacctagtcacagttg |
| | gtaagtgacagagttgggacttgaacctatgcctgcctgaca |
| | ccaagtctttttttgacacctagagccaagacatctgaagac |
| | aaactccctaggagagctggcgtcatagaaaaccttaaaggtt |
| | agggagacctgggtttgaatcaggctttgtcagttatgactt |
| | gtgtgaccctagcaagttatttaaccttctgggtctcagtt |
| | tcctcatctgcaaactgaggataataacagtacctaccaaaa |
| | agaactgtcgtgaaaaccatataatttctgcaatgctcctgg |
| | cacagtgtcctgttctaaagcatagttcccttctcttttctt |
| | agctccatattgattattaccctaacttgcacaaagagactt |
| | ggaggaccccatagagtatcggagggtcccccatttcctgc |
| | tctttccactccacaccccagcaagcacagggaagttctgg |
| | gggccataatccacccacaggaaccaaatctaagccacctt |
| | ctggctggtagacatccaggtatgtgggcacagaggtagaca |
| | ggctgaaatgctgctgtgctatcagttgggttttgctggaac |
| | aggaatggaaatggagaggctgacagaactgccctggggagc |
| | ccaggcaagagggacagtggctggacacccccagccagttgt |
| | gcagaccatcagaacaagatcctagattttaggaatacaggg |
| | ttcaagtccgtgcggcaactcttttctaaatatgcccaagcc |
| | attaactttgagttttaaaaatactgatttacaagctgtaca |
| | caatgaaaaaatgcctatccctcacaccatgctgatgctgtt |
| | ccctgccatctcagattaccaattaaatacagaatgcccagt |
| | taaatgtgaactttttttttttttttttttgagatggagt |
| | tttgttcttgtcgcccaggctagagtgcaatggtgcgatctc |
| | agctcactgcaacctctgcctcccaggttcaagcaattctcc |
| | tgccttagcctcctgagtagctggaactacaggtgcccacca |
| | gcacgcctggctaattttttgtattttagtggagatggggt |
| | ttcaccatgttggccaggctggtctcgaactcctgacctcag |
| | gtgatctgcctgcctcggcctcccaaagtgctgggattacag |
| | gcgtgagcctaaatgtgaacttttttaatactaaaaaagtat |
| | ttgctgttcatcggaaattcacatttaactgggtgtcctgta |
| | ttttatttgctaaatctaccatcaaattggtctggctcaac |
| | ctggagaatggttaccctaggtaaccacgtgcggaccgagcg |
| | gccgcaggaaccctagtgatggagttggccactccctctct |

TABLE 2-continued

Plasmid Composition
Plasmid Composition

| Elements | SEQUENCE IDENTIFIER (SEQ. ID. NO:) AND SEQUENCE INFORMATION |
|---|---|
| | gcgcgctcgctcgctcactgaggccgggcgaccaaaggtcgc<br>ccgacgcccgggctttgcccgggcggcctcagtgagcgagcg<br>agcgcgcag |

Plasmid TM016 Composition

| Elements | SEQUENCE IDENTIFIER (SEQ. ID. NO:) AND SEQUENCE INFORMATION |
|---|---|
| Δ5' ITR | 1<br>occurs at bp 1 through bp 103 of SEQ ID NO: 31 |
| Human RLBP1 Promoter (short) | 3<br>occurs at bp 116 through bp 705 of SEQ ID NO: 31 |
| Modified SV40 intron | 4<br>occurs at bp 720 through bp 902 of SEQ ID NO: 31 |
| Added Kozak | 5<br>occurs at bp 943 through bp 948 of SEQ ID NO: 31 |
| E_GFP | 24<br>occurs at bp 949 through bp 1668 of SEQ ID NO: 31 |
| SV40 POLYA | 8<br>occurs at bp 1726 through bp 1961 of SEQ ID NO: 31 |
| 3' ITR | 9<br>occurs at bp 1990 through bp 2119 of SEQ ID NO: 31 |
| AMP BACTERIAL BACKBONE | 15<br>occurs at bp 2120 through bp 4738 of SEQ ID NO: 31 |
| Sequence of TM016 Plasmid | 31<br>cgcgctcgctcgctcactgaggccgccgggcaaagcccggg<br>cgtcgggcgacctttggtcgcccggcctcagtgagcgagcga<br>gcgcgcagagagggagtgggggtaccacgcgtttgtcctctcc<br>ctgcttggccttaaccagccacatttctcaactgaccccact<br>cactgcagaggtgaaaactaccatgccaggtcctgctggctg<br>ggggaggggtgggcaataggcctggatttgccagagctgcca<br>ctgtagatgtagtcatatttacgatttcccttcacctcttat<br>taccctggtggtggtggtgggggggggggggtgctctctcag<br>caaccccaccccgggatcttgaggagaaagagggcagagaaa<br>agagggaatgggactggcccagatcccagccccacagccggg<br>cttccacatggccgagcaggaactccagagcaggagcacaca<br>aaggagggctttgatgcgcctccagccaggcccaggcctctc<br>ccctctccccttctctctgggtcttcctttgccccactgag<br>ggcctcctgtgagcccgatttaacggaaactgtgggcggtga<br>gaagttccttatgacacactaatcccaacctgctgaccggac<br>cacgcctccagcggagggaacctctagagctccaggacattc<br>aggtaccaggtagccccaaggaggagctgccgaatcgatgga<br>tcgggaactgaaaaaccagaaagttaactggtaagtttagtc<br>ttttgtcttttatttcaggtcccggatccggtggtggtgca<br>aatcaaagaactgctcctcagtggatgttgcctttacttcta<br>ggcctgtacggaagtgttacttctgctctaaaagctgcggaa<br>ttgtacccgcccgggatccatcgattgaattccccgggat<br>cctctagagtcgaaattcgccaccatggtgagcaagggcgag<br>gagctgttcaccggggtggtgcccatcctggtcgagctggac<br>ggcgacgtaaacggccacaagttcagcgtgtccggcgagggc<br>gagggcgatgccacctacggcaagctgaccctgaagttcatc<br>tgcaccaccggcaagctgcccgtgcctggccccaccctcgtg<br>accaccctgacctacggcgtgcagtgcttcagccgctacccc<br>gaccacatgaagcagcacgacttcttcaagtccgccatgccc<br>gaaggctacgtccaggagcgcaccatcttcttcaaggacgac<br>ggcaactacaagacccgcgccgaggtgaagttcgagggcgac<br>accctggtgaaccgcatcgagctgaagggcatcgacttcaag<br>gaggacggcaacatcctggggcacaagctggagtacaactac<br>aacagccacaacgtctatatcatggccgacaagcagaagaac<br>ggcatcaaggtgaacttcaagatccgccacaacatcgaggac |

TABLE 2-continued

Plasmid Composition
Plasmid Composition

| Elements | SEQUENCE IDENTIFIER (SEQ. ID. NO:) AND SEQUENCE INFORMATION |
|---|---|
| | ggcagcgtgcagctcgccgaccactaccagcagaacacccccc
atcggcgacggccccgtgctgctgcccgacaaccactacctg
agcacccagtccgccctgagcaaagaccccaacgagaagcgc
gatcacatggtcctgctggagttcgtgaccgccgccgggatc
actctcggcatggacgagctgtacaagtaatagggtaccggt
cgacctgcagaagcttgcctcgagcagcgctgctcgagagat
ctggatcataatcagccataccacctttgtagaggttttact
tgcttttaaaaaacctcccacacctcccctgaacctgaaaca
taaaatgaatgcaattgttgttgttaacttgtttattgcagc
ttataatggttacaaataaagcaatagcatcacaaatttcac
aaataaagcattttttcactgcattctagttgtggtttgtc
caaactcatcaatgtatcttatcatgtctggtaaccacgtgc
ggaccgagcggccgcaggaaccctagtgatggagttggcca
ctccctctctgcgcgctcgctcgctcactgaggccgggcgac
caaaggtcgcccgacgcccgggctttgcccgggcggcctcag
tgagcgagcgagcgcgcagctgcctgcaggggcgcctgatgc
ggtattttctccttacgcatctgtgcggtatttcacaccgca
tacgtcaaagcaaccatagtacgcgccctgtagcggcgcatt
aagcgcggcgggtgtggtggttacgcgcagcgtgaccgctac
acttgccagcgccttagcgccgctccttcgctttcttccc
ttcctttctcgccacgttcgccggctttccccgtcaagctct
aaatcgggggctccctttagggttccgatttagtgctttacg
gcacctcgaccccaaaaaacttgatttgggtgatggttcacg
tagtgggccatcgccctgatagacggttttcgccctttgac
gttggagtccacgttctttaatagtggactcttgttccaaac
tggaacaacactcaactctatctcgggctattctttgattt
ataaggattttgccgatttcggtctattggttaaaaaatga
gctgatttaacaaaaatttaacgcgaattttaacaaaatatt
aacgtttacaattttatggtgcactctcagtacaatctgctc
tgatgccgcatagttaagccagccccgacacccgccaacacc
cgctgacgcgccctgacgggcttgtctgctcccggcatccgc
ttacagacaagctgtgaccgtctccgggagctgcatgtgtca
gaggttttcaccgtcatcaccgaaacgcgcgagacgaaaggg
cctcgtgatacgcctatttttataggttaatgtcatgataat
aatggtttcttagacgtcaggtggcacttttcggggaaatgt
gcgcggaacccctatttgtttatttttctaaatacattcaaa
tatgtatccgctcatgagacaataaccctgataaatgcttca
ataatattgaaaaaggaagagtatgagtattcaacatttccg
tgtcgcccttattccctttttgcggcattttgccttcctgt
ttttgctcacccagaaacgctggtgaaagtaaaagatgctga
agatcagttgggtgcacgagtgggttacatcgaactggatct
caacagcggtaagatccttgagagttttcgccccgaagaacg
ttttccaatgatgagcacttttaaagttctgctatgtggcgc
ggtattatcccgtattgacgccgggcaagagcaactcggtcg
ccgcatacactattctcagaatgacttggttgagtactcacc
agtcacagaaaagcatcttacggatggcatgacagtaagaga
attatgcagtgctgccataaccatgagtgataacactgcggc
caacttacttctgacaacgatcggaggaccgaaggagctaac
cgcttttttgcacaacatgggggatcatgtaactcgccttga
tcgttgggaaccggagctgaatgaagccataccaaacgacga
gcgtgacaccacgatgcctgtagcaatggcaacaacgttgcg
caaactattaactggcgaactacttactctagcttcccggca
acaattaatagactggatggaggcggataaagttgcaggacc
acttctgcgctcggcccttccggctggctggtttattgctga
taaatctggagccggtgagcgtgggtctcgcggtatcattgc
agcactggggccagatggtaagccctcccgtatcgtagttat
ctacacgacggggagtcaggcaactatggatgaacgaaatag
acagatcgctgagataggtgcctcactgattaagcattggta
actgtcagaccaagtttactcatatatactttagattgattt
aaaacttcattttaatttaaaaggatctaggtgaagatcct
ttttgataatctcatgaccaaaatcccttaacgtgagttttc
gttccactgagcgtcagacccctgtagaaaagatcaaaggatc
ttcttgaaatccttttttctgcgcgtaatctgctgcttgca
aacaaaaaaaccaccgctaccagcggtggtttgtttgccgga
tcaagagctaccaactcttttccgaaggtaactggcttcag
cagagcgcagataccaaatactgttcttctagtgtagccgta
gttaggccaccacttcaagaactctgtagcaccgcctacata
cctcgctctgctaatcctgttaccagtggctgctgccagtgg
cgataagtcgtgtcttaccgggttggactcaagacgatagtt
accggataaggcgcagcggtcgggctgaacggggggttcgt
cacacagcccagcttggagcgaacgacctacaccgaactgag
atacctacagcgtgagctatgagaaagcgccacgcttcccga
agggagaaaggcggacaggtatccggtaagcggcagggtcgg
aacaggagagcgcacgagggagcttccaggggaaacgcctg |

TABLE 2-continued

Plasmid Composition
Plasmid Composition

| Elements | SEQUENCE IDENTIFIER (SEQ. ID. NO:) AND SEQUENCE INFORMATION |
|---|---|
| | gtatctttatagtcctgtcgggtttcgccacctctgacttga gcgtcgatttttgtgatgctcgtcagggggcggagcctatg gaaaaacgccagcaacgcggccttttacggttcctggccttt tgctggccttttgctcacatgtcctgcaggcagctg |
| GENE CASSETTE OF PLASMID TM016 OCCURS AT BP 1 THROUGH 2119 OF SEQ ID NO: 31 | 56<br>cgcgctcgctcgctcactgaggccgccgggcaaagcccggg cgtcgggcgaccctttggtcgcccggcctcagtgagcgagcga gcgcgcagagagggagtggggtaccacgcgtttgtcctctcc ctgcttggccttaaccagccacatttctcaactgaccccact cactgcagaggtgaaaactaccatgccaggtcctgctggctg ggggaggggtgggcaataggcctggatttgccagagctgcca ctgtagatgtagtcatatttacgatttcccttcacctcttat taccctggtggtggtggtgggggggggggggtgctctctcag caaccccaccccgggatcttgaggagaaagagggcagagaaa agagggaatgggactggcccagatcccagccccacagccggg cttccacatggccgagcaggaactccagagcaggagcacaca aaggagggctttgatgcgcctccagccaggcccaggcctctc ccctctcccctttctctctgggtcttcctttgccccactgag ggcctcctgtgagcccgatttaacggaaactgtgggcggtga gaagttccttatgacacactaatcccaacctgctgaccggac cacgcctccagcggagggaacctctagagctccaggacattc aggtaccaggtagccccaaggaggagctgccgaatcgatgga tcgggaactgaaaaaccagaaagttaactggtaagtttagtc ttttgtctttattttcaggtcccggatccggtggtggtgca aatcaaagaactgctcctcagtggatgttgcctttacttcta ggcctgtacggaagtgttacttctgctctaaaagctgcggaa ttgtacccgccccgggatccatcgattgaattccccggggat cctctagagtcgaaattcgccaccatggtgagcaagggcgag gagctgttcaccggggtggtgcccatcctggtcgagctggac ggcgacgtaaacggccacaagttcagcgtgtccggcgagggc gagggcgatgccacctacggcaagctgaccctgaagttcatc tgcaccaccggcaagctgcccgtgccctggcccaccctcgtg accaccctgacctacggcgtgcagtgcttcagccgctacccc gaccacatgaagcagcacgacttcttcaagtccgccatgccc gaaggctacgtccaggagcgcaccatcttcttcaaggacgac ggcaactacaagacccgcgccgaggtgaagttcgagggcgac accctggtgaaccgcatcgagctgaagggcatcgacttcaag gaggacggcaacatcctggggcacaagctggagtacaactac aacagccacaacgtctatatcatggccgacaagcagaagaac ggcatcaaggtgaacttcaagatccgccacaacatcgaggac ggcagcgtgcagctcgccgaccactaccagcagaacacccc atcggcgacggccccgtgctgctgcccgacaaccactacctg agcacccagtccgccctgagcaaagaccccaacgagaagcgc gatcacatggtcctgctggagttcgtgaccgccgccgggatc actctcggcatggacgagctgtacaagtaatagggtaccggt cgacctgcagaagcttgcctcgagcagcgctgctcgagagat ctggatcataatcagccataccacatttgtagaggttttact tgctttaaaaaacctcccacacctcccctgaacctgaaaca taaaatgaatgcaattgttgttgttaacttgtttattgcagc ttataatggttacaaataaagcaatagcatcacaaatttcac aaataaagcatttttttcactgcattctagttgtggtttgtc caaactcatcaatgtatcttatcatgtctggtaaccacgtgc ggaccgagcggccgcaggaacccctagtgatggagttggcca ctccctctctgcgcgctcgctcgctcactgaggccgggcgac caaaggtcgcccgacgcccgggctttgcccgggcggcctcag tgagcgagcgagcgcag |
| Plasmid TM035 Composition |
| 5' ITR | 2<br>occurs at bp 1 through bp 119 of SEQ ID NO: 32 |
| Human RLBP1 Promoter (long) | 10<br>occurs at bp 137 through bp 3293 of SEQ ID NO: 32 |
| Added Kozak | 5<br>occurs at bp 3327 through bp 3332 of SEQ ID NO: 32 |

TABLE 2-continued

Plasmid Composition
Plasmid Composition

| Elements | SEQUENCE IDENTIFIER (SEQ. ID. NO:) AND SEQUENCE INFORMATION |
|---|---|
| E_GFP | 24<br>occurs at bp 3333 through bp 4052 of SEQ ID NO: 32 |
| SV40 POLYA | 8<br>occurs at bp 4110 through bp 4345 of SEQ ID NO: 32 |
| 3' ITR | 9<br>occurs at bp 4374 through bp 4503 of SEQ ID NO: 32 |
| AMP BACTERIAL BACKBONE | 15<br>occurs at bp 4504 through bp 7122 of SEQ ID NO: 32 |
| Sequence of TM035 Plasmid | 32<br>ctgcgcgctcgctcgctcactgaggccgcccgggcgtcgggc<br>gacctttggtcgcccggcctcagtgagcgagcgagcgcgcag<br>agagggagtggccaactccatcactaggggttcctgcggccg<br>cacgcagcttttgtcctctccctgcttggccttaaccagcca<br>catttctcaactgaccccactcactgcagaggtgaaaactac<br>catgccaggtcctgctggctgggggaggggtgggcaataggc<br>ctggatttgccagagctgccactgtagatgtagtcatattta<br>cgatttcccttcacctcttattaccctggtggtggtggtggg<br>gggggggggtgctctctcagcaaccccaccccgggatcttg<br>aggagaaagagggcagagaaaagagggaatgggactggccca<br>gatcccagccccacagccgggcttccacatggccgagcagga<br>actccagagcaggagcacacaaaggagggctttgatgcgcct<br>ccagccaggcccaggcctctcccctctccccttctctctgg<br>gtcttcctttgccccactgagggcctcctgtgagcccgattt<br>aacggaaactgtgggcggtgagaagttccttatgacacacta<br>atcccaacctgctgaccggaccacgcctccagcggagggaac<br>ctctagagctccaggacattcaggtaccaggtagccccaagg<br>aggagctgccgacctggcaggtaagtcaatacctgggcttg<br>cctgggccagggagcccaggactggggtgaggactcagggga<br>gcagggagaccacgtcccaagatgcctgtaaaactgaaacca<br>cctggccattctccaggttgagccagaccaatttgatggcag<br>atttagcaaataaaaatacaggacacccagttaaatgtgaat<br>ttcagatgaacagcaaatacttttttagtattaaaaaagttc<br>acatttaggctcacgcctgtaatcccagcactttgggaggcc<br>gaggcaggcagatcacctgaggtcaggagttcgagaccagcc<br>tggccaacatggtgaaaccccatctccactaaaaatccaaa<br>aattagccaggcgtgctggtgggcacctgtagttccagctac<br>tcaggaggctaaggcaggagaattgcttgaacctgggaggca<br>gaggttgcagtgagctgagatcgcaccattgcactctagcct<br>gggcgacaagaacaaaactccatctcaaaaaaaaaaaaaaa<br>aaaaagttcacatttaactgggcattctgtatttaattggta<br>atctgagatggcagggaacagcatcagcatggtgtgagggat<br>aggcattttttcattgtgtacagcttgtaaatcagtattttt<br>aaaactcaaagttaatggcttgggcatatttagaaaagagtt<br>gccgcacggacttgaaccctgtattcctaaaatctaggatct<br>tgttctgatggtctgcacaactggctgggggtgtccagccac<br>tgtccctcttgcctgggctccccagggcagttctgtcagcct<br>ctccatttccattcctgttccagcaaaacccaactgatagca<br>cagcagcatttcagcctgtctacctctgtgcccacatacctg<br>gatgtctaccagccagaaaggtggcttagatttggttcctgt<br>gggtggattatgccccccagaacttccctgtgcttgctgggg<br>gtgtggagtggaaagagcaggaaatgggggaccctccgatac<br>tctatggggtcctccaagtctctttgtgcaagttagggtaa<br>taatcaatatggagctaagaaagagaaggggaactatgcttt<br>agaacaggacactgtgccaggagcattgcagaaattatatgg<br>ttttcacgacagttcttttggtaggtactgttattatcctc<br>agtttgcagatgaggaaactgagacccagaaaggttaaataa<br>cttgctagggtcacacaagtcataactgacaaagcctgattc<br>aaacccaggtctccctaacctttaaggtttctatgacgccag<br>ctctcctagggagtttgtcttcagatgtcttggctctaggtg<br>tcaaaaaagacttggtgtcaggcaggcataggttcaagtcc<br>caactctgtcacttaccaactgtgactaggtgattgaactga<br>ccatggaacctggtcacatgcaggagcaggatggtgaagggt<br>tcttgaaggcacttaggcaggacatttaggcaggagagaaaa<br>cctggaaacagaagagctgtctccaaaaataccccactgggga<br>agcaggttgtcatgtgggccatgaatgggacctgttctggta |

TABLE 2-continued

Plasmid Composition

| Elements | SEQUENCE IDENTIFIER (SEQ. ID. NO:) AND SEQUENCE INFORMATION |
|---|---|
| | accaagcattgcttatgtgtccattacatttcataacacttc |
| | catcctactttacagggaacaaccaagactggggttaaatct |
| | cacagcctgcaagtggaagagaagaacttgaacccaggtcca |
| | acttttgcgccacagcaggctgcctcttggtcctgacaggaa |
| | gtcacaacttgggtctgagtactgatccctggctattttttg |
| | gctgtgttaccttggacaagtcacttattcctcctcccgttt |
| | cctcctatgtaaaatggaaataataatgttgaccctgggtct |
| | gagagagtggatttgaaagtacttagtgcatcacaaagcaca |
| | gaacacacttccagtctcgtgattatgtacttatgtaactgg |
| | tcatcacccatcttgagaatgaatgcattgggaaagggcca |
| | tccactaggctgcgaagtttctgagggactccttcgggctgg |
| | agaaggatggccacaggagggaggagagattgccttatcctg |
| | cagtgatcatgtcattgagaacagagccagattcttttttc |
| | ctggcagggccaacttgttttaacatctaaggactgagctat |
| | ttgtgtctgtgccctttgtccaagcagtgtttcccaaagtgt |
| | agcccaagaaccatctccctcagagccaccaggaagtgcttt |
| | aaattgcaggttcctaggccacagcctgcacctgcagagtca |
| | gaatcatggaggttgggacccaggcacctgcgtttctaacaa |
| | atgcctcgggtgattctgatgcaattgaaagtttgagatcca |
| | cagttctgagacaataacagaatggttttctaacccctgca |
| | gccctgacttcctatcctagggaaggggccggctggagaggc |
| | caggacagagaaagcagatcccttcttttccaaggactctg |
| | tgtcttccataggcaacgaattccccggggatcctctagagt |
| | cgaaattcgccaccatggtgagcaagggcgaggagctgttca |
| | ccggggtggtgcccatcctggtcgagctggacggcgacgtaa |
| | acggccacaagttcagcgtgtccggcgagggcgagggcgatg |
| | ccacctacggcaagctgaccctgaagttcatctgcaccaccg |
| | gcaagctgcccgtgccctggcccaccctcgtgaccaccctga |
| | cctacggcgtgcagtgcttcagccgctaccccgaccacatga |
| | agcagcacgacttcttcaagtccgccatgcccgaaggctacg |
| | tccaggagcgcaccatcttcttcaaggacgacggcaactaca |
| | agacccgcgccgaggtgaagttcgagggcgacaccctggtga |
| | accgcatcgagctgaagggcatcgacttcaaggaggacggca |
| | acatcctggggcacaagctggagtacaactacaacagccaca |
| | acgtctatatcatggccgacaagcagaagaacggcatcaagg |
| | tgaacttcaagatccgccacaacatcgaggacggcagcgtgc |
| | agctcgccgaccactaccagcagaacacccccatcggcgacg |
| | gccccgtgctgctgcccgacaaccactacctgagcacccagt |
| | ccgccctgagcaaagaccccaacgagaagcgcgatcacatgg |
| | tcctgctggagttcgtgaccgccgccgggatcactctcggca |
| | tggacgagctgtacaagtaatagggtaccggtcgacctgcag |
| | aagcttgcctcgagcagcgctgctcgagagatctggatcata |
| | atcagccataccacatttgtagaggttttacttgctttaaaa |
| | aacctcccacacctcccctgaacctgaaacataaaatgaat |
| | gcaattgttgttgttaacttgtttattgcagcttataatggt |
| | tacaaataaagcaatagcatcacaaatttcacaaataaagca |
| | ttttttttcactgcattctagttgtggtttgtccaaactcatc |
| | aatgtatcttatcatgtctggtaaccacgtgcggaccgagcg |
| | gccgcaggaaccccctagtgatggagttggccactccctctct |
| | gcgcgctcgctcgctcactgaggccgggcgaccaaaggtcgc |
| | ccgacgcccgggctttgcccgggcggcctcagtgagcgagcg |
| | agcgcgcagctgcctgcaggggcgcctgatgcggtattttct |
| | ccttacgcatctgtgcggtatttcacaccgcatacgtcaaag |
| | caaccatagtacgcgccctgtagcggcgcattaagcgcggcg |
| | ggtgtggtggttacgcgcagcgtgaccgctacacttgccagc |
| | gccttagcgcccgctcctttcgctttcttcccttcctttctc |
| | gccacgttcgccggctttccccgtcaagctctaaatcggggg |
| | ctccctttagggttccgatttagtgctttacggcacctcgac |
| | cccaaaaaacttgatttgggtgatggttcacgtagtgggcca |
| | tcgccctgatagacggttttcgccctttgacgttggagtcc |
| | acgttctttaatagtggactcttgttccaaactggaacaaca |
| | ctcaactctatctcgggctattcttttgatttataagggatt |
| | ttgccgatttcggtctattggttaaaaaatgagctgatttaa |
| | caaaaatttaacgcgaattttaacaaaatattaacgtttaca |
| | attttatggtgcactctcagtacaatctgctctgatgccgca |
| | tagttaagccagccccgacacccgccaacacccgctgacgcg |
| | ccctgacgggcttgtctgctcccggcatccgcttacagacaa |
| | gctgtgaccgtctccgggagctgcatgtgtcagaggttttca |
| | ccgtcatcaccgaaacgcgcgagacgaaagggcctcgtgata |
| | cgcctatttttataggttaatgtcatgataataatggtttct |
| | tagacgtcaggtggcacttttcggggaaatgtgcgcggaacc |
| | cctatttgtttatttttctaaatacattcaaatatgtatccg |
| | ctcatgagacaataaccctgataaatgcttcaataatattga |
| | aaaaggaagagtatgagtattcaacatttccgtgtcgccctt |

TABLE 2-continued

Plasmid Composition
Plasmid Composition

| Elements | SEQUENCE IDENTIFIER (SEQ. ID. NO:) AND SEQUENCE INFORMATION |
|---|---|
| | attccctttttgcggcattttgccttcctgttttgctcac ccagaaacgctggtgaaagtaaaagatgctgaagatcagttg ggtgcacgagtgggttacatcgaactggatctcaacagcggt aagatccttgagagttttcgccccgaagaacgttttccaatg atgagcacttttaaagttctgctatgtggcgcggtattatcc cgtattgacgccgggcaagagcaactcggtcgccgcatacac tattctcagaatgacttggttgagtactcaccagtcacagaa aagcatcttacggatggcatgacagtaagagaattatgcagt gctgccataaccatgagtgataacactgcggccaacttactt ctgacaacgatcggaggaccgaaggagctaaccgcttttttg cacaacatggggatcatgtaactcgccttgatcgttgggaa ccggagctgaatgaagccataccaaacgacgagcgtgacacc acgatgcctgtagcaatggcaacaacgttgcgcaaactatta actggcgaactacttactctagcttcccggcaacaattaata gactggatggaggcggataaagttgcaggaccacttctgcgc tcggcccttccggctggctggtttattgctgataaatctgga gccggtgagcgtgggtctcgcggtatcattgcagcactgggg ccagatggtaagccctcccgtatcgtagttatctacacgacg gggagtcaggcaactatggatgaacgaaatagacagatcgct gagataggtgcctcactgattaagcattggtaactgtcagac caagtttactcatatatactttagattgatttaaaacttcat ttttaatttaaaaggatctaggtgaagatcctttttgataat ctcatgaccaaaatcccttaacgtgagttttcgttccactga gcgtcagaccccgtagaaaagatcaaaggatcttcttgaaat cctttttttctgcgcgtaatctgctgcttgcaaacaaaaaaa ccaccgctaccagcggtggtttgtttgccggatcaagagcta ccaactctttttccgaaggtaactggcttcagcagagcgcag ataccaaatactgttcttctagtgtagccgtagttaggccac cacttcaagaactctgtagcaccgcctacatacctcgctctg ctaatcctgttaccagtggctgctgccagtggcgataagtcg tgtcttaccgggttggactcaagacgatagttaccggataag gcgcagcggtcgggctgaacggggggttcgtgcacacagccc agcttggagcgaacgacctacaccgaactgagatacctacag cgtgagctatgagaaagcgccacgcttcccgaagggagaaag gcggacaggtatccggtaagcggcagggtcggaacaggagag cgcacgagggagcttccaggggaaacgcctggtatctttat agtcctgtcgggtttcgccacctctgacttgagcgtcgattt ttgtgatgctcgtcaggggcggagcctatggaaaaacgcc agcaacgcggcctttttacggttcctggccttttgctggcct tttgctcacatgtcctgcaggcag |
| GENE CASSETTE OF PLASMID TM035 OCCURS AT BP 1 THROUGH 4503 OF SEQ ID NO: 32 | 57 ctgcgcgctcgctcgctcactgaggccgcccgggcgtcgggc gacctttggtcgcccggcctcagtgagcgagcgagcgcgcag agagggagtggccaactccatcactaggggttcctgcggccg cacgcagcttttgtcctctccctgcttggccttaaccagcca catttctcaactgaccccactcactgcagaggtgaaaactac catgccaggtcctgctggctggggagggtgggcaataggc ctggatttgccagagctgccactgtagatgtagtcatattta cgatttcccttcacctcttattaccctggtggtggtggtggg ggggggggtgctctctcagcaacccaccccgggatcttg aggagaaagagggcagagaaaagagggaatgggactggccca gatcccagccccacagccgggcttccacatggccgagcagga actccagagcaggagcacacaaaggagggctttgatgcgcct ccagccaggcccaggcctctcccctctcccctttctctctgg gtcttcctttgccccactgagggcctcctgtgagcccgattt aacggaaactgtgggcggtgagaagttccttatgacacacta atcccaacctgctgaccggaccacgcctccagcggagggaac ctctagagctccaggacattcaggtaccaggtagccccaagg aggagctgccgacctggcaggtaagtcaatacctgggcttg cctgggccagggagcccaggactggggtgaggactcagggga gcaggagaccacgtcccaagatgcctgtaaaactgaaacca cctggccattctccaggttgagccagaccaatttgatggcag atttagcaaataaaaatacaggacacccagttaaatgtgaat ttcagatgaacagcaaatactttttttagtattaaaaaagttc acatttaggctcacgcctgtaatcccagcactttgggaggcc gaggcaggcagatcacctgaggtcaggagttcgagaccagcc tggccaacatggtgaaaccccatctccactaaaaataccaaa aattagccaggcgtgctggtgggcacctgtagttccagctac tcaggaggctaaggcaggagaattgcttgaacctgggaggcg gaggttgcagtgagctgagatcgcaccattgcactctagcct gggcgacaagaacaaaactccatctcaaaaaaaaaaaaaaa aaaagttcacatttaactgggcattctgtatttaattggta atctgagatggcagggaacagcatcagcatggtgtgagggat |

TABLE 2-continued

Plasmid Composition
Plasmid Composition

| Elements | SEQUENCE IDENTIFIER (SEQ. ID. NO:) AND SEQUENCE INFORMATION |
|---|---|
| | aggcattttttcattgtgtacagcttgtaaatcagtattttt<br>aaaactcaaagttaatggcttgggcatatttagaaaagagtt<br>gccgcacggacttgaaccctgtattcctaaaatctaggatct<br>tgttctgatggtctgcacaactggctggggtgtccagccac<br>tgtccctcttgcctgggctcccagggcagttctgtcagcct<br>ctccatttccattcctgttccagcaaaacccaactgatagca<br>cagcagcatttcagcctgtctacctctgtgcccacatacctg<br>gatgtctaccagccagaaaggtggcttagatttggttcctgt<br>gggtggattatggcccccagaacttccctgtgcttgctgggg<br>gtgtggagtggaaagagcaggaaatgggggaccctccgatac<br>tctatggggtcctccaagtctctttgtgcaagttagggtaa<br>taatcaatatggagctaagaaagagaaggggaactatgcttt<br>agaacaggacactgtgccaggagcattgcagaaattatatgg<br>ttttcacgacagttcttttggtaggtactgttattatcctc<br>agtttgcagatgaggaaactgagacccagaaaggttaaataa<br>cttgctagggtcacacaagtcataactgacaaagcctgattc<br>aaacccaggtctccctaacctttaaggtttctatgacgccag<br>ctctcctagggagtttgtcttcagatgtcttggctctaggtg<br>tcaaaaaagacttggtgtcaggcaggcataggttcaagtcc<br>caactctgtcacttaccaactgtgactaggtgattgaactga<br>ccatggaacctggtcacatgcaggagcaggatggtgaagggt<br>tcttgaaggcacttaggcaggacatttaggcaggagagaaaa<br>cctggaaacagaagagctgtctccaaaaatacccactgggga<br>agcaggttgtcatgtgggccatgaatgggacctgttctggta<br>accaagcattgcttatgtgtccattacatttcataacacttc<br>catcctactttacagggaacaaccaagactggggttaaatct<br>cacagcctgcaagtggaagagaagaacttgaacccaggtcca<br>acttttgcgccacagcaggctgcctcttggtcctgacaggaa<br>gtcacaacttgggtctgagtactgatccctggctattttttg<br>gctgtgttaccttggacaagtcacttattcctcctcccgttt<br>cctcctatgtaaaatggaaataataatgttgaccctgggtct<br>gagagagtggatttgaaagtacttagtgcatcacaaagcaca<br>gaacacacttccagtctcgtgattatgtacttatgtaactgg<br>tcatcacccatcttgagaatgaatgcattggggaaagggcca<br>tccactaggctgcgaagtttctgagggactccttcgggctgg<br>agaaggatggccacaggagggaggagagattgccttatcctg<br>cagtgatcatgtcattgagaacagagccagattcttttttc<br>ctggcagggccaacttgttttaacatctaaggactgagctat<br>ttgtgtctgtgcccttttgtccaagcagtgtttcccaaagtgt<br>agcccaagaaccatctccctcagagccaccaggaagtgcttt<br>aaattgcaggttcctaggccacagcctgcacctgcagagtca<br>gaatcatggaggttgggacccaggcacctgcgtttctaacaa<br>atgcctcgggtgattctgatgcaattgaaagtttgagatcca<br>cagttctgagacaataacagaatggtttttctaaccctga<br>gccctgacttcctatcctagggaaggggccggctggagaggc<br>caggacagagaaagcagatcccttcttttttccaaggactctg<br>tgtcttccataggcaacgaattccccggggatcctctagagt<br>cgaaattcgccaccatggtgagcaagggcgaggagctgttca<br>ccggggtggtgcccatcctggtcgagctggacggcgacgtaa<br>acggccacaagttcagcgtgtccggcgagggcgagggcgatg<br>ccacctacggcaagctgaccctgaagttcatctgcaccaccg<br>gcaagctgcccgtgccctggcccaccctcgtgaccaccctga<br>cctacggcgtgcagtgcttcagccgctaccccgaccacatga<br>agcagcacgacttcttcaagtccgccatgcccgaaggctacg<br>tccaggagcgcaccatcttcttcaaggacgacggcaactaca<br>agacccgcgccgaggtgaagttcgagggcgacaccctggtga<br>accgcatcgagctgaagggcatcgacttcaaggaggacggca<br>acatcctggggcacaagctggagtacaactacaacagccaca<br>acgtctatatcatggccgacaagcagaagaacggcatcaagg<br>tgaacttcaagatccgccacaacatcgaggacggcagcgtgc<br>agctcgccgaccactaccagcagaacacccccatcggcgacg<br>gccccgtgctgctgcccgacaaccactacctgagcacccagt<br>ccgccctgagcaaagaccccaacgagaagcgcgatcacatgg<br>tcctgctggagttcgtgaccgccgccgggatcactctcggca<br>tggacgagctgtacaagtaatagggtaccggtcgacctgcag<br>aagcttgcctcgagcagcgctgctcgagagatctggatcata<br>atcagccataccacatttgtagaggttttacttgctttaaaa<br>aacctcccacacctcccctgaacctgaaacataaaatgaat<br>gcaattgttgttgttaacttgtttattgcagcttataatggt<br>tacaaataaagcaatagcatcacaaatttcacaaataaagca<br>ttttttcactgcattctagttgtggtttgtccaaactcatc<br>aatgtatcttatcatgtctggtaaccacgtgcggaccgagcg<br>gccgcaggaaccctagtgatggagttggccactccctctct<br>gcgcgctcgctcgctcactgaggccgggcgaccaaaggtcgc |

TABLE 2-continued

Plasmid Composition
Plasmid Composition

| Elements | SEQUENCE IDENTIFIER (SEQ. ID. NO:) AND SEQUENCE INFORMATION |
|---|---|
| | ccgacgcccgggctttgcccgggcggcctcagtgagcgagcg agcgcgcag |

Plasmid AG012 Composition

| | |
|---|---|
| 5' ITR | 2<br>occurs @ bp 1 through bp 119 of SEQ ID NO: 33 |
| SYNUCLEIN INTRONIC SEQUENCE AS STUFFER SEQUENCE | 13<br>occurs @ bp 148 through bp 2601 of SEQ ID NO: 33 |
| SV40 POLYA | 8<br>occurs @ bp 2640 through bp 2875 of SEQ ID NO: 33 |
| RLBP1 INTRONIC SEQUENCE AS STUFFER SEQUENCE | 14<br>occurs at bp 2883 through bp 4385 of SEQ ID NO: 33 |
| 3' ITR | 9<br>occurs at bp 4414 through bp 4543 of SEQ ID NO: 33 |
| AMP BACTERIAL BACKBONE | 15<br>occurs at bp 4544 through bp 7162 of SEQ ID NO: 33 |
| Sequence of AG012 Plasmid | 33<br>ctgcgcgctcgctcgctcactgaggccgcccgggcgtcgggc gacctttggtcgcccggcctcagtgagcgagcgagcgcgcag agagggagtggccaactccatcactaggggttcctgcggccg cacgcgtgacgtcgtttaaacgggccccggtgttatctcatt cttttttctcctctgtaagttgacatgtgatgtgggaacaaa ggggataaagtcattattttgtgctaaaatcgtaattggaga ggacctcctgttagctgggctttcttctatttattgtggtgg ttactggagttccttcttctagttttaggatatatatatata ttttttttttttctttccctgaagatataataatatatatac ttctgaagattgagattttttaaattagttgtattgaaaacta gctaatcagcaatttaaggctagcttgagacttatgtcttga atttgtttttgtaggctccaaaaccaaggagggagtggtgca tggtgtggcaacaggtaagctccattgtgcttatatccaaag atgatatttaaagtatctagtgattagtgtggcccagtattc aagattcctatgaaattgtaaaacaatcactgagcattctaa gaacatatcagtcttattgaaactgaattcttttataaagtat ttttaaaaaggtaaatattgattataaataaaaaatatactt gccaagaataatgagggctttgaattgataagctatgtttaa tttatagtaagtgggcatttaaatattctgaccaaaaatgta ttgacaaactgctgacaaaaataaaatgtgaatattgccata atttttaaaaaaagagtaaaatttctgttgattacagtaaaat attttgaccttaaattatgttgattacaatattcctttgata attcagagtgcatttcaggaaacacccttggacagtcagtaa attgtttattgtatttatctttgtattgttatggtatagctc tttgtacaaatattattgtgcaattattacatttctgattat attattcatttggcctaaatttaccaagaatttgaacaagtc aattaggtttacaatcaagaaatatcaaaaatgatgaaaagg atgataatcatcatcagatgttgaggaagatgacgatgagag tgccagaaatagagaaatcaaaggagaaccaaaatttaacaa attaaaagcccacagacttgctgtaattaagttttctgttgt aagtactccacgtttcctggcagatgtggtgaagcaaaagat ataatcagaaatataatttatatgatcggaaagcattaaaca caatagtgcctatacaaataaaatgttcctatcactgacttc taaaatggaaatgaggacaatgatatgggaatcttaatacag tgttgtggataggactaaaaacacaggagtcagatcttcttg gttcaacttcctgcttactccttaccagctgtgtgttttttg caaggttcttcacctctatgtgatttagcttcctcatctata aaataattcagtgaattaatgtacacaaaacatctggaaaac aaaagcaaacaatatgtatttttataagtgttacttatagttt tatagtgaactttcttgtgcaacattttttacaactagtggag aaaaatatttctttaaatgaatacttttgatttaaaaatcag |

TABLE 2-continued

Plasmid Composition
Plasmid Composition

| Elements | SEQUENCE IDENTIFIER (SEQ. ID. NO:) AND SEQUENCE INFORMATION |
|---|---|
| | agtgtaaaaataaaacagactcctttgaaactagttctgtta
gaagttaattgtgcacctttaatgggctctgttgcaatccaa
cagagaagtagttaagtaagtggactatgatggcttctaggg
acctcctataaatatgatattgtgaagcatgattataataag
aactagataacagacaggtggagactccactatctgaagagg
gtcaacctagatgaatggtgttccatttagtagttgaggaag
aacccatgaggtttagaaagcagacaagcatgtggcaagttc
tggagtcagtggtaaaaattaaagaacccaactattactgtc
acctaatgatctaatggagactgtggagatgggctgcatttt
tttaatcttctccagaatgccaaaatgtaaacacatatctgt
gtgtgtgtgtgtgtgtgtgtgtgtgtgtgagagagagagaga
gagagagagagactgaagtttgtacaattagacattttataa
aatgttttctgaaggacagtggctcacaatcttaagtttcta
acattgtacaatgtgggactttgtatactttattttctc
tttagcatattaaggaatctgagatgtcctacagtaaagaaa
tttgcattacatagttaaaatcagggttattcaaactttttg
attattgaaacctttcttcattagttactagggttgaatgaa
actagtgttccacagaaaactatgggaaatgttgctaggcag
taaggacatggtgatttcagcatgtgcaatatttacagcgat
tgcacccatggaccaccctggcagtagtgaaataaccaaaaa
tgctgtcataactagtatggctatgagaaacacattgggcag
aagcttgcctcgagcagcgctgctcgagagatctggatcata
atcagccataccacatttgtagaggttttacttgctttaaaa
aacctcccacacctcccctgaacctgaaacataaaatgaat
gcaattgttgttgttaacttgtttattgcagcttataatggt
tacaaataaagcaatagcatcacaaatttcacaaatgaagca
tttttttcactgcattctagttgtggtttgtccaaactcatc
aatgtatcttatcatgtctggtaaccattctccaggttgagc
cagaccaatttgatggtagatttagcaaataaaaatacagga
cacccagttaaatgtgaatttccgatgaacagcaaatacttt
tttagtattaaaaaagttcacatttaggctcacgcctgtaat
cccagcactttgggaggccgaggcaggcagatcacctgaggt
caggagttcgagaccagcctggccaacatggtgaaacccccat
ctccactaaaaataccaaaaattagccaggcgtgctggtggg
cacctgtagttccagctactcaggaggctaaggcaggagaat
tgcttgaacctgggaggcagaggttgcagtgagctgagatcg
caccattgcactctagcctgggcgacaagaacaaaactccat
ctcaaaaaaaaaaaaaaaaaaaagttcacatttaactgggc
attctgtatttaattggtaatctgagatggcagggaacagca
tcagcatggtgtgagggataggcattttttcattgtgtacag
cttgtaaatcagtatttttaaaactcaaagttaatggcttgg
gcatatttagaaaagagttgccgcacggacttgaaccctgta
ttcctaaaatctaggatcttgttctgatggtctgcacaactg
gctggggtgtccagccactgtccctcttgcctgggctcccc
agggcagttctgtcagcctctccatttccattcctgttccag
caaaacccaactgatagcacagcagcatttcagcctgtctac
ctctgtgcccacatacctggatgtctaccagccagaaaggtg
gcttagatttggttcctgtgggtggattatggcccccagaac
ttccctgtgcttgctgggggtgtggagtggaaagagcaggaa
atgggggacccctccgatactctatgggggtcctccaagtctc
tttgtgcaagttagggtaataatcaatatggagctaagaaag
agaaggggaactatgctcttagaacaggacactgtgccaggag
cattgcagaaattatatggttttcacgacagttcttttttgt
aggtactgttattatcctcagttttgcagatgaggaaactgag
acccagaaaggttaaataacttgctagggtcacacaagtcat
aactgacaaagcctgattcaaacccaggtctccctaaccttt
aaggtttctatgacgccagctctcctagggagtttgtcttca
gatgtcttggctctaggtgtcaaaaaaagacttggtgtcagg
caggcataggttcaagtcccaactctgtcacttaccaactgt
gactaggtgattgaactgaccatggaacctggtcacatgcag
gagcaggatggtgaagggttcttgaaggcacttaggcaggac
atttaggcaggagagaaaacctggaaacagaagagctgtctc
caaaaatacccactggggaagcaggttgtcatgtgggccatg
aatgggacctgttctggggtaaccacgtgcggaccgagcggc
cgcaggaaccccctagtgatggagttggccactccctctctgc
gcgctcgctcgctcactgaggccgggcgaccaaaggtcgccc
gacgcccgggctttgcccgggcggcctcagtgagcgagcgag
cgcgcagctgcctgcaggggcgcctgatgcggtattttctcc
ttacgcatctgtgcggtatttcacaccgcatacgtcaaagca
accatagtacgcgccctgtagcggcgcattaagcgcggcggg
tgtggtggttacgcgcagcgtgaccgctacacttgccagcgc
cttagcgcccgctcctttcgctttcttcccttcctttctcgc
cacgttcgccggctttccccgtcaagctctaaatcgggggct
ccctttagggttccgatttagtgctttacggcacctcgaccc |

TABLE 2-continued

Plasmid Composition
Plasmid Composition

| Elements | SEQUENCE IDENTIFIER (SEQ. ID. NO:) AND SEQUENCE INFORMATION |
|---|---|
| | caaaaaacttgatttgggtgatggttcacgtagtgggccatc<br>gccctgatagacggttttttcgcccctttgacgttggagtccac<br>gttctttaatagtggactcttgttccaaactggaacaacact<br>caactctatctcgggctattcttttgatttataagggatttt<br>gccgatttcggtctattggttaaaaaatgagctgatttaaca<br>aaaatttaacgcgaattttaacaaaatattaacgtttacaat<br>tttatggtgcactctcagtacaatctgctctgatgccgcata<br>gttaagccagccccgacacccgccaacacccgctgacgcgcc<br>ctgacgggcttgtctgctcccggcatccgcttacagacaagc<br>tgtgaccgtctccgggagctgcatgtgtcagaggttttcacc<br>gtcatcaccgaaacgcgcgagacgaaagggcctcgtgatacg<br>cctattttataggttaatgtcatgataataatggtttctta<br>gacgtcaggtggcacttttcggggaaatgtgcgcggaacccc<br>tatttgtttattttctaaatacattcaaatatgtatccgct<br>catgagacaataaccctgataaatgcttcaataatattgaaa<br>aaggaagagtatgagtattcaacatttccgtgtcgcccttat<br>tccctttttgcggcatttgccttcctgttttgctcaccc<br>agaaacgctggtgaaagtaaaagatgctgaagatcagttggg<br>tgcacgagtgggttacatcgaactggatctcaacagcggtaa<br>gatccttgagagttttcgccccgaagaacgttttccaatgat<br>gagcacttttaaagttctgctatgtggcgcggtattatcccg<br>tattgacgccgggcaagagcaactcggtcgccgcatacacta<br>ttctcagaatgacttggttgagtactcaccagtcacagaaaa<br>gcatcttacggatggcatgacagtaagagaattatgcagtgc<br>tgccataaccatgagtgataacactgcggccaacttacttct<br>gacaacgatcggaggaccgaaggagctaaccgcttttttgca<br>caacatggggatcatgtaactcgccttgatcgttgggaacc<br>ggagctgaatgaagccataccaaacgacgagcgtgacaccac<br>gatgcctgtagcaatggcaacaacgttgcgcaaactattaac<br>tggcgaactacttactctagcttcccggcaacaattaataga<br>ctggatggaggcggataaagttgcaggaccacttctgcgctc<br>ggcccttccggctggctggtttattgctgataaatctggagc<br>cggtgagcgtgggtctcgcggtatcattgcagcactggggcc<br>agatggtaagccctcccgtatcgtagttatctacacgacggg<br>gagtcaggcaactatggatgaacgaaatagacagatcgctga<br>gataggtgcctcactgattaagcattggtaactgtcagacca<br>agtttactcatatatactttagattgatttaaaacttcattt<br>ttaatttaaaaggatctaggtgaagatcctttttgataatct<br>catgaccaaaatcccttaacgtgagttttcgttccactgagc<br>gtcagaccccgtagaaaagatcaaaggatcttcttgaaatcc<br>ttttttctgcgcgtaatctgctgcttgcaaacaaaaaaacc<br>accgctaccagcggtggtttgtttgccggatcaagagctacc<br>aactctttttccgaaggtaactggcttcagcagagcgcagat<br>accaaatactgttcttctagtgtagccgtagttaggccacca<br>cttcaagaactctgtagcaccgcctacatacctcgctctgct<br>aatcctgttaccagtggctgctgccagtggcgataagtcgtg<br>tcttaccgggttggactcaagacgatagttaccggataaggc<br>gcagcggtcgggctgaacggggggttcgtgcacacagcccag<br>cttggagcgaacgacctacaccgaactgagatacctacagcg<br>tgagctatgagaaagcgccacgcttcccgaagggagaaaggc<br>ggacaggtatccggtaagcggcagggtcggaacaggagagcg<br>cacgagggagcttccaggggggaaacgcctggtatctttatag<br>tcctgtcgggtttcgccacctctgacttgagcgtcgatttt<br>gtgatgctcgtcaggggggcggagcctatggaaaaacgccag<br>caacgcggccttttacggttcctggccttttgctggccttt<br>tgctcacatgtcctgcaggcag |
| INSERT OF PLASMID AG012 OCCURS AT BP 1 THROUGH 4543 OF SEQ ID NO: 33 (USED AS NEGATIVE CONTROL FOR GENE CASSETTE) | 58<br>ctgcgcgctcgctcgctcactgaggccgcccgggcgtcgggc<br>gacctttggtcgcccggcctcagtgagcgagcgagcgcgcag<br>agagggagtggccaactccatcactaggggttcctgcggccg<br>cacgcgtgacgtcgtttaaacgggcccccggtgttatctcatt<br>cttttttctcctctgtaagttgacatgtgatgtgggaacaaa<br>ggggataaagtcattattttgtgctaaaatcgtaattggaga<br>ggacctcctgttagctgggcttcttctatttattgtggtgg<br>ttactggagttccttcttctagttttaggatatatatatata<br>tttttttttttttcttccctgaagataataatatatatac<br>ttctgaagattgagattttaaattagttgtattgaaaacta<br>gctaatcagcaatttaaggctagcttgagacttatgtcttga<br>atttgtttttgtaggctccaaaaccaaggagggagtggtgca<br>tggtgtggcaacaggtaagctccattgtgcttatatccaaag<br>atgatatttaaagtatctagtgattagtgtggcccagtattc<br>aagattcctatgaaattgtaaaacaatcactgagcattctaa<br>gaacatatcagtcttattgaaactgaattctttataaagtat |

TABLE 2-continued

Plasmid Composition
Plasmid Composition

| Elements | SEQUENCE IDENTIFIER (SEQ. ID. NO:) AND SEQUENCE INFORMATION |
|---|---|
| | ttttaaaaaggtaaatattgattataaataaaaaatatactt |
| | gccaagaataatgagggctttgaattgataagctatgtttaa |
| | tttatagtaagtgggcatttaaatattctgaccaaaaatgta |
| | ttgacaaactgctgacaaaaataaaatgtgaatattgccata |
| | attttaaaaaagagtaaaatttctgttgattacagtaaaat |
| | attttgaccttaaattatgttgattacaatattcctttgata |
| | attcagagtgcatttcaggaaacacccttggacagtcagtaa |
| | attgtttattgtatttatctttgtattgttatggtatagcta |
| | tttgtacaaatattattgtgcaattattacatttctgattat |
| | attattcatttggcctaaatttaccaagaatttgaacaagtc |
| | aattaggtttacaatcaagaaatatcaaaaatgatgaaaagg |
| | atgataatcatcatcagatgttgaggaagatgacgatgagag |
| | tgccagaaatagagaaatcaaaggagaaccaaaatttaacaa |
| | attaaaagcccacagacttgctgtaattaagttttctgttgt |
| | aagtactccacgtttcctggcagatgtggtgaagcaaaagat |
| | ataatcagaaatataatttatatgatcggaaagcattaaaca |
| | caatagtgcctatacaaataaaatgttcctatcactgacttc |
| | taaaatggaaatgaggacaatgatatgggaatcttaatacag |
| | tgttgtggataggactaaaaacacaggagtcagatcttcttg |
| | gttcaacttcctgcttactccttaccagctgtgtgttttttg |
| | caaggttcttcacctctatgtgatttagcttcctcatctata |
| | aaataattcagtgaattaatgtacacaaaacatctggaaaac |
| | aaaagcaaacaatatgtattttataagtgttacttatagttt |
| | tatagtgaactttcttgtgcaacattttttacaactagtggag |
| | aaaaatatttctttaaatgaatacttttgatttaaaaatcag |
| | agtgtaaaaataaaacagactcctttgaaactagttctgtta |
| | gaagttaattgtgcacctttaatgggctctgttgcaatccaa |
| | cagagaagtagttaagtaagtggactatgatggcttctaggg |
| | acctcctataaatatgatattgtgaagcatgattataataag |
| | aactagataacagacaggtggagactccactatctgaagagg |
| | gtcaacctagatgaatggtgttccatttagtagttgaggaag |
| | aacccatgaggtttagaaagcagacaagcatgtggcaagttc |
| | tggagtcagtggtaaaaattaaagaacccaactattactgtc |
| | acctaatgatctaatggagactgtggagatgggctgcatttt |
| | tttaatcttctccagaatgccaaaatgtaaacacatatctgt |
| | gtgtgtgtgtgtgtgtgtgtgtgtgagagagagaga |
| | gagagagagagactgaagtttgtacaattagacattttataa |
| | aatgttttctgaaggacagtggctcacaatcttaagtttcta |
| | acattgtacaatgttgggagactttgtatactttattttctc |
| | tttagcatattaaggaatctgagatgtcctacagtaaagaaa |
| | tttgcattacatagttaaaatcagggttattcaaactttttg |
| | attattgaaacctttcttcattagttactagggttgaatgaa |
| | actagtgttccacagaaaactatgggaaatgttgctaggcag |
| | taaggacatggtgatttcagcatgtgcaatatttacagcgat |
| | tgcacccatggaccaccctggcagtagtgaaataaccaaaaa |
| | tgctgtcataactagtatggctatgagaaacacattgggcag |
| | aagcttgcctcgagcagcgctgctcgagagatctggatcata |
| | atcagccataccacatttgtagaggttttacttgcttaaaa |
| | aacctcccacacctcccctgaacctgaaacataaaatgaat |
| | gcaattgttgttgttaacttgtttattgcagcttataatggt |
| | tacaaataaagcaatagcatcacaaatttcacaaatataagca |
| | ttttttttcactgcattctagttgtggtttgtccaaactcatc |
| | aatgtatcttatcatgtctggtaaccattctccaggttgagc |
| | cagaccaatttgatggtagatttagcaaataaaaatacagga |
| | cacccagttaaatgtgaatttccgatgaacagcaaatactt |
| | tttagtattaaaaaagttcacatttaggctcacgcctgtaat |
| | cccagcactttgggaggccgaggcaggcagatcacctgaggt |
| | caggagttcgagaccagcctggccaacatggtgaaacccat |
| | ctccactaaaaataccaaaaattagccaggcgtgctggtggg |
| | cacctgtagttccagctactcaggaggctaaggcaggagaat |
| | tgcttgaacctgggaggcagaggttgcagtgagctgagatcg |
| | caccattgcactctagcctgggcgacaagaacaaaactccat |
| | ctcaaaaaaaaaaaaaaaaaaagttcacatttaactgggc |
| | attctgtatttaattggtaatctgagatggcagggaacagca |
| | tcagcatggtgtgagggataggcattttttcattgtgtacag |
| | cttgtaaatcagtattttaaaactcaaagttaatggcttgg |
| | gcatatttagaaaagagttgccgcacggacttgaaccctgta |
| | ttcctaaaatctaggatcttgttctgatggtctgcacaactg |
| | gctggggtgtccagccactgtccctcttgcctgggctcccc |
| | agggcagttctgtcagcctctccatttccattcctgttccag |
| | caaaacccaactgatagcacagcagcatttcagcctgtctac |
| | ctctgtgcccacatacctggatgtctaccagccagaaaggtg |
| | gcttagatttggttcctgtgggtggattatggcccccagaac |
| | ttccctgtgcttgctgggggtgtggagtggaaagagcaggaa |

TABLE 2-continued

Plasmid Composition
Plasmid Composition

| Elements | SEQUENCE IDENTIFIER (SEQ. ID. NO:) AND SEQUENCE INFORMATION |
|---|---|
| | atgggggaccctccgatactctatgggggtcctccaagtctc<br>tttgtgcaagttagggtaataatcaatatggagctaagaaag<br>agaaggggaactatgctttagaacaggacactgtgccaggag<br>cattgcagaaattatatggttttcacgacagttcttttttggt<br>aggtactgttattatcctcagtttgcagatgagggaaactgag<br>acccagaaaggttaaataacttgctagggtcacacaagtcat<br>aactgacaaagcctgattcaaacccaggtctccctaaccttt<br>aaggtttctatgacgccagctctcctagggagtttgtcttca<br>gatgtcttggctctaggtgtcaaaaaaagacttggtgtcagg<br>caggcataggttcaagtcccaactctgtcacttaccaactgt<br>gactaggtgattgaactgaccatggaacctggtcacatgcag<br>gagcaggatggtgaagggttcttgaaggcacttaggcaggac<br>atttaggcaggagagaaaacctggaaacagaagagctgtctc<br>caaaaatacccactggggaagcaggttgtcatgtgggccatg<br>aatgggacctgttctggggtaaccacgtgcggaccgagcggc<br>cgcaggaaccctagtgatggagttggccactccctctctgc<br>gcgctcgctcgctcactgaggccgggcgaccaaaggtcgccc<br>gacgcccgggctttgcccgggcggcctcagtgagcgagcgag<br>cgcgcag |
| | Plasmid AG004 Composition |
| 5' ITR | 2<br>occurs @ bp 1 through bp 119 of SEQ ID NO: 34 |
| Human RPE65 Promoter | 11<br>occurs @ bp 134 through bp 1718 of SEQ ID NO: 34 |
| Added Kozak | 5<br>occurs @ bp 1752 through 1757 of of SEQ ID NO: 34 |
| E-GFP | 24<br>occurs @ bp 1758 through bp 2477 of SEQ ID NO: 34 |
| SV40 POLYA | 8<br>occurs at bp 2535 through bp 2770 of SEQ ID NO: 34 |
| RLBP1 INTRONIC SEQUENCE AS STUFFER SEQUENCE | 14<br>occurs at bp 2778 through bp 4280 of SEQ ID NO: 34 |
| 3' ITR | 9<br>occurs at bp 4309 through bp 4438 of SEQ ID NO: 34 |
| AMP BACTERIAL BACKBONE | 15<br>occurs at bp 4439 through bp 7057 of SEQ ID NO: 34 |
| Sequence of plasmid AG004 | 34<br>ctgcgcgctcgctcgctcactgaggccgcccgggcgtcgggc<br>gacctttggtcgcccggcctcagtgagcgagcgagcgcgcag<br>agagggagtggccaactccatcactaggggttcctgcggccg<br>cacgcgttacgtaatatttattgaagtttaatattgtgtttg<br>tgatacagaagtatttgctttaattctaaataaaaattttat<br>gcttttattgctggtttaagaagatttggattatccttgtac<br>tttgaggagaagtttcttatttgaaatattttggaaacaggt<br>cttttaatgtggaaagatagatattaatctcctcttctatta<br>ctctccaagatccaacaaaagtgattataccccccaaaatat<br>gatggtagtatcttatactaccatcatttataggcataggg<br>ctcttagctgcaaataatggaactaactctaataaagcagaa<br>cgcaaatattgtaaatattagagagctaacaatctctgggat<br>ggctaaaggatggagcttggaggctacccagccagtaacaat<br>attccgggctccactgttgaatggagacactacaactgcttt<br>ggatgggcagagatattatggatgctaagcccaggtgctac<br>cattaggacttctaccactgtccctaacgggtggagcccatc<br>acatgcctatgccctcactgtaaggaaatgaagctactgttg<br>tatatcttgggaagcacttggattaattgttatacagttttg |

TABLE 2-continued

Plasmid Composition
Plasmid Composition

| Elements | SEQUENCE IDENTIFIER (SEQ. ID. NO:) AND SEQUENCE INFORMATION |
|---|---|
| | ttgaagaagacccctagggtaagtagccataactgcacacta |
| | aatttaaaattgttaatgagtttctcaaaaaaaatgttaagg |
| | ttgttagctggtatagtatatatcttgcctgttttccaagga |
| | cttctttgggcagtaccttgtctgtgctggcaagcaactgag |
| | acttaatgaaagagtattggagatatgaatgaattgatgctg |
| | tatactctcagagtgccaaacatataccaatggacaagaagg |
| | tgaggcagagagcagacaggcattagtgacaagcaaagatat |
| | gcagaatttcattctcagcaaatcaaaagtcctcaacctggt |
| | tggaagaatattggcactgaatggtatcaataaggttgctag |
| | agagggttagaggtgcacaatgtgcttccataacattttata |
| | cttctccaatcttagcactaatcaaacatggttgaatacttt |
| | gtttactataactcttacagagtttataagatctgtgaagaca |
| | gggacagggacaatacccatctctgtctggttcataggtggt |
| | atgtaatagatatttttaaaaataagtgagttaatgaatgag |
| | ggtgagaatgaaggcacagaggtattaggggggaggtgggccc |
| | cagagaatggtgccaaggtccagtggggtgactgggatcagc |
| | tcaggcctgacgctggccactcccacctagctcctttctttc |
| | taatctgttctcattctccttgggaaggattgaggtctctgg |
| | aaaacagccaaacaactgttatgggaacagcaagcccaaata |
| | aagccaagcatcaggggggatctgagagctgaaagcaacttct |
| | gttccccctccctcagctgaaggggtggggaagggctcccaa |
| | agccataactccttttaagggatttagaaggcataaaaaggc |
| | ccctggctgagaacttccttcttcattctgcagttggtgaat |
| | tccccggggatcctctagagtcgaaattcgccaccatggtga |
| | gcaagggcgaggagctgttcaccgggggtggtgcccatcctgg |
| | tcgagctggacggcgacgtaaacggccacaagttcagcgtgt |
| | ccggcgagggcgagggcgatgccacctacggcaagctgaccc |
| | tgaagttcatctgcaccaccggcaagctgcccgtgccctgc |
| | ccaccctcgtgaccaccctgacctacggcgtgcagtgcttca |
| | gccgctaccccgaccacatgaagcagcacgacttcttcaagt |
| | ccgccatgcccgaaggctacgtccaggagcgcaccatcttct |
| | tcaaggacgacggcaactacaagaccccgcgccgaggtgaagt |
| | tcgagggcgacaccctggtgaaccgcatcgagctgaagggca |
| | tcgacttcaaggaggacggcaacatcctggggcacaagctgg |
| | agtacaactacaacagccacaacgtctatatcatggccgaca |
| | agcagaagaacggcatcaaggtgaacttcaagatccgccaca |
| | acatcgaggacggcagcgtgcagctcgccgaccactaccagc |
| | agaacacccccatcggcgacggccccgtgctgctgcccgaca |
| | accactacctgagcacccagtccgccctgagcaaagacccca |
| | acgagaagcgcgatcacatggtcctgctggagttcgtgaccg |
| | ccgccgggatcactctcggcatggacgagctgtacaagtaat |
| | agggtaccggtcgacctgcagaagcttgcctcgagcagcgct |
| | gctcgagagatctggatcataatcagccataccacatttgta |
| | gaggttttacttgctttaaaaaacctcccacacctccccctg |
| | aacctgaaacataaaatgaatgcaattgttgttgttaacttg |
| | tttattgcagcttataatggttacaaataaagcaatagcatc |
| | acaaatttcacaaataaagcattttttttcactgcattctagt |
| | tgtggtttgtccaaactcatcaatgtatcttatcatgtctgg |
| | taaccattctccaggttgagccagaccaatttgatggtagat |
| | ttagcaaataaaaatacaggacacccagttaaatgtgaattt |
| | ccgatgaacagcaaatactttttagtattaaaaaagttcac |
| | atttaggctcacgcctgtaatcccagcactttgggaggccga |
| | ggcaggcagatcacctgaggtcaggagttcgagaccagcctg |
| | gccaacatggtgaaaccccatctctactaaaaatccaaaaa |
| | ttagccaggcgtgctggtgggcacctgtagttccagctactc |
| | aggaggctaaggcaggagaattgcttgaacctggggaggcaga |
| | ggttgcagtgagctgagatcgcaccattgcactctagcctgg |
| | gcgacaagaacaaaactccatctcaaaaaaaaaaaaaaaaa |
| | aaagttcacatttaactgggcattctgtatttaattggtaat |
| | ctgagatggcagggaacagcatcagcatggtgtgagggatag |
| | gcattttttcattgtgtacagcttgtaaatcagtattttaa |
| | aactcaaagttaatggcttgggcatatttagaaaagagttgc |
| | cgcacggacttgaaccctgtattcctaaaatctaggatcttg |
| | ttctgatggtctgcacaactggctgggggtgtccagccactg |
| | tccctcttgcctgggctccccagggcagttctgtcagcctct |
| | ccatttccattcctgttccagcaaaacccaactgatagcaca |
| | gcagcatttcagcctgtctacctctgtgcccacatacctgga |
| | tgtctaccagccagaaaggtggcttagatttggttcctgtgg |
| | gtggattatgccccccagaacttccctgtgcttgctgggggt |
| | gtggagtggaaagagcaggaaatggggggaccctccgatactc |
| | tatggggggtcctccaagtctcttttgtgcaagttagggtaata |
| | atcaatatggagctaagaaagagaagggggaactatgctttag |
| | aacaggacactgtgccaggagcattgcagaaattatatggtt |
| | ttcacgacagttcttttggtaggtactgttattatcctcag |

TABLE 2-continued

Plasmid Composition
Plasmid Composition

| Elements | SEQUENCE IDENTIFIER (SEQ. ID. NO:) AND SEQUENCE INFORMATION |
|---|---|
| | tttgcagatgaggaaactgagacccagaaaggttaaataact |
| | tgctagggtcacacaagtcataactgacaaagcctgattcaa |
| | acccaggtctccctaacctttaaggtttctatgacgccagct |
| | ctcctagggagtttgtcttcagatgtcttggctctaggtgtc |
| | aaaaaaagacttggtgtcaggcaggcataggttcaagtccca |
| | actctgtcacttaccaactgtgactaggtgattgaactgacc |
| | atggaacctggtcacatgcaggagcaggatggtgaagggttc |
| | ttgaaggcacttaggcaggacatttaggcaggagagaaaacc |
| | tggaaacagaagagctgtctccaaaaatacccactggggaag |
| | caggttgtcatgtgggccatgaatgggacctgttctgggta |
| | accacgtgcggaccgagcggccgcaggaaccccctagtgatgg |
| | agttggccactccctctctgcgcgctcgctcgctcactgagg |
| | ccgggcgaccaaaggtcgcccgacgcccgggctttgcccggg |
| | cggcctcagtgagcgagcgagcgcgcagctgcctgcagggggc |
| | gcctgatgcggtattttctccttacgcatctgtgcggtattt |
| | cacaccgcatacgtcaaagcaaccatagtacgcgccctgtag |
| | cggcgcattaagcgcggcgggtgtggtggttacgcgcagcgt |
| | gaccgctacacttgccagcgccttagcgcccgctcctttcgc |
| | tttcttcccttcctttctcgccacgttcgccggctttccccg |
| | tcaagctctaaatcgggggctccctttagggttccgatttag |
| | tgctttacggcacctcgaccccaaaaaacttgatttgggtga |
| | tggttcacgtagtgggccatcgccctgatagacggttttttcg |
| | ccctttgacgttggagtccacgttctttaatagtggactctt |
| | gttccaaactggaacaacactcaactctatctcgggctattc |
| | ttttgatttataagggattttgccgatttcggtctattggtt |
| | aaaaaatgagctgatttaacaaaaatttaacgcgaatttttaa |
| | caaaatattaacgtttacaattttatggtgcactctcagtac |
| | aatctgctctgatgccgcatagttaagccagccccgacaccc |
| | gccaacacccgctgacgcgccctgacgggcttgtctgctccc |
| | ggcatccgcttacagacaagctgtgaccgtctccgggagctg |
| | catgtgtcagaggttttcaccgtcatcaccgaaacgcgcgag |
| | acgaaagggcctcgtgatacgcctatttttataggttaatgt |
| | catgataataatggtttcttagacgtcaggtggcacttttcg |
| | gggaaatgtgcgcggaacccctatttgtttatttttctaaat |
| | acattcaaatatgtatccgctcatgagacaataaccctgata |
| | aatgcttcaataatattgaaaaaggaagagtatgagtattca |
| | acatttccgtgtcgcccttattccctttttttgcggcatttttg |
| | ccttcctgtttttgctcacccagaaacgctggtgaaagtaaa |
| | agatgctgaagatcagttgggtgcacgagtgggttacatcga |
| | actggatctcaacagcggtaagatccttgagagttttcgccc |
| | cgaagaacgttttccaatgatgagcacttttaaagttctgct |
| | atgtggcgcggtattatcccgtattgacgccgggcaagagca |
| | actcggtcgccgcatacactattctcagaatgacttggttga |
| | gtactcaccagtcacagaaaagcatcttacggatggcatgac |
| | agtaagagaattatgcagtgctgccataaccatgagtgataa |
| | cactgcggccaacttacttctgacaacgatcggaggaccgaa |
| | ggagctaaccgcttttttgcacaacatgggggatcatgtaac |
| | tcgccttgatcgttgggaaccggagctgaatgaagccatacc |
| | aaacgacgagcgtgacaccacgatgcctgtagcaatggcaac |
| | aacgttgcgcaaactattaactggcgaactacttactctagc |
| | ttcccggcaacaattaatagactggatggaggcggataaagt |
| | tgcaggaccacttctgcgctcggcccttccggctggctggtt |
| | tattgctgataaatctggagccggtgagcgtgggtctcgcgg |
| | tatcattgcagcactggggccagatggtaagccctcccgtat |
| | cgtagttatctacacgacggggagtcaggcaactatggatga |
| | acgaaatagacagatcgctgagataggtgcctcactgattaa |
| | gcattggtaactgtcagaccaagtttactcatatatacttta |
| | gattgatttaaaacttcattttttaatttaaaaggatctaggt |
| | gaagatcctttttgataatctcatgaccaaaatcccttaacg |
| | tgagttttcgttccactgagcgtcagacccgtagaaaagat |
| | caaaggatcttcttgaaatcctttttttctgcgcgtaatctg |
| | ctgcttgcaaacaaaaaaaccaccgctaccagcggtggtttg |
| | tttgccggatcaagagctaccaactctttttccgaaggtaac |
| | tggcttcagcagagcgcagataccaaatactgttcttctagt |
| | gtagccgtagttaggccaccacttcaagaactctgtagcacc |
| | gcctacatacctcgctctgctaatcctgttaccagtggctgc |
| | tgccagtggcgataagtcgtgtcttaccgggttggactcaag |
| | acgatagttaccggataaggcgcagcggtcgggctgaacggg |
| | gggttcgtgcacacagcccagcttggagcgaacgacctacac |
| | cgaactgagatacctacagcgtgagctatgagaaagcgccac |
| | gcttcccgaagggagaaaggcggacaggtatccggtaagcgg |
| | cagggtcggaacaggagagcgcacgagggagcttccagggg |
| | aaacgcctggtatctttatagtcctgtcgggtttcgccacct |
| | ctgacttgagcgtcgatttttgtgatgctcgtcagggggcg |

TABLE 2-continued

Plasmid Composition
Plasmid Composition

| Elements | SEQUENCE IDENTIFIER (SEQ. ID. NO:) AND SEQUENCE INFORMATION |
|---|---|
| | gagcctatggaaaaacgccagcaacgcggccttttacggtt cctggccttttgctggccttttgctcacatgtcctgcaggcag |
| GENE CASSETTE AG004 OCCURS AT BP 1 THROUGH 4438 OF SEQ ID NO: 34 | 59<br>ctgcgcgctcgctcgctcactgaggccgcccgggcgtcgggc gacctttggtcgcccggcctcagtgagcgagcgagcgcgcag agagggagtggccaactccatcactaggggttcctgcggccg cacgcgttacgtaatatttattgaagtttaatattgtgtttg tgatacagaagtatttgctttaattctaaataaaaattttat gcttttattgctggtttaagaagatttggattatccttgtac tttgaggagaagtttcttatttgaaatattttggaaacaggt cttttaatgtggaaagatagatattaatctcctcttctatta ctctccaagatccaacaaaagtgattataccccccaaaatat gatggtagtatcttatactaccatcattttataggcataggg ctcttagctgcaaataatggaactaactctaataaagcagaa cgcaaatattgtaaatattagagagctaacaatctctgggat ggctaaaggatggagcttggaggctacccagccagtaacaat attccgggctccactgttgaatggagacactacaactgcctt ggatgggcagagatattatggatgctaagcccaggtgctac cattaggacttctaccactgtccctaacgggtggagcccatc acatgcctatgccctcactgtaaggaaatgaagctactgttg tatatcttgggaagcacttggattaattgttatacagttttg ttgaagaagacccctagggtaagtagccataactgcacacta aatttaaaattgttaatgagtttctcaaaaaaaatgttaagg ttgttagctggtatagtatatatcttgcctgttttccaagga cttctttgggcagtaccttgtctgtgctggcaagcaactgag acttaatgaaagagtattggagatatgaatgaattgatgctg tatactctcagagtgccaaacatataccaatggacaagaagg tgaggcagagagcagacaggcattagtgacaagcaaagatat gcagaatttcattctcagcaaatcaaaagtcctcaacctggt tggaagaatattggcactgaatggtatcaataaggttgctag agagggttagaggtgcacaatgtgcttccataacattttata cttctccaatcttagcactaatcaaacatggttgaatacttt gtttactataactcttacagagtttataagatctgtgaagaca gggacagggacaatacccatctctgtctggttcataggtggt atgtaatagatattttaaaaataagtgagttaatgaatgag ggtgagaatgaaggcacagaggtattaggggagtgggccc cagagaatggtgccaaggtccagtgggtgactgggatcagc tcaggcctgacgctggccactcccacctagctcctttctttc taatctgttctcattctccttgggaaggattgaggtctctgg aaaacagccaaacaactgttatgggaacagcaagcccaaata aagccaagcatcagggggatctgagagctgaaagcaacttct gttccccctccctcagctgaaggggtggggaagggctcccaa agccataactccttttaagggatttagaaggcataaaaaggc ccctggctgagaacttccttcttcattctgcagttggtgaat tccccggggatcctctagagtcgaaattcgccaccatggtga gcaagggcgaggagctgttcaccggggtggtgcccatcctgg tcgagctggacggcgacgtaaacggccacaagttcagcgtgt ccggcgagggcgagggcgatgccacctacggcaagctgaccc tgaagttcatctgcaccaccggcaagctgcccgtgccctggc ccaccctcgtgaccaccctgacctacggcgtgcagtgcttca gccgctaccccgaccacatgaagcagcacgacttcttcaagt ccgccatgcccgaaggctacgtccaggagcgcaccatcttct tcaaggacgacggcaactacaagacccgcgccgaggtgaagt tcgagggcgacacccctggtgaaccgcatcgagctgaagggca tcgacttcaaggaggacggcaacatcctggggcacaagctgg agtacaactacaacagccacaacgtctatatcatggccgcaca agcagaagaacggcatcaaggtgaacttcaagatccgccaca acatcgaggacggcagcgtgcagctcgccgaccactaccagc agaacacccccatcggcgacggccccgtgctgctgcccgaca accactacctgagcacccagtccgccctgagcaaagaccccca acgagaagcgcgatcacatggtcctgctggagttcgtgaccg ccgccgggatcactctcggcatggacgagctgtacaagtaat agggtaccggtcgacctgcagaagcttgcctcgagcagcgct gctcgagagatctggatcataatcagccataccacatttgta gaggttttacttgctttaaaaaacctcccacacctccccctg aacctgaaacataaaatgaatgcaattgttgttgttaacttg tttattgcagcttataatggttacaaataaagcaatagcatc acaaatttcacaaataaagcatttttttcactgcattctagt tgtggtttgtccaaactcatcaatgtatcttatcatgtctgg taaccattctccaggttgagccagaccaatttgatggtagat ttagcaaataaaaatacaggacacccagttaaatgtgaattt ccgatgaacagcaaatactttttttagtattaaaaaagttcac atttaggctcacgcctgtaatcccagcactttgggaggccga |

TABLE 2-continued

Plasmid Composition

| Elements | SEQUENCE IDENTIFIER (SEQ. ID. NO:) AND SEQUENCE INFORMATION |
|---|---|
| | ggcaggcagatcacctgaggtcaggagttcgagaccagcctg<br>gccaacatggtgaaaccccatctccactaaaaataccaaaaa<br>ttagccaggcgtgctggtgggcacctgtagttccagctactc<br>aggaggctaaggcaggagaattgcttgaacctgggaggcaga<br>ggttgcagtgagctgagatcgcaccattgcactctagcctgg<br>gcgacaagaacaaaactccatctcaaaaaaaaaaaaaaaaa<br>aaagttcacatttaactgggcattctgtatttaattggtaat<br>ctgagatggcagggaacagcatcagcatggtgtgagggatag<br>gcatttttcattgtgtacagcttgtaaatcagtattttaa<br>aactcaaagttaatggcttgggcatatttagaaaagagttgc<br>cgcacggacttgaaccctgtattcctaaaatctaggatcttg<br>ttctgatggtctgcacaactggctgggggtgtccagccactg<br>tccctcttgcctgggctccccagggcagttctgtcagcctct<br>ccatttccattcctgttccagcaaaacccaactgatagcaca<br>gcagcatttcagcctgtctacctctgtgcccacatacctgga<br>tgtctaccagccagaaaggtggcttagatttggttcctgtgg<br>gtggattatggccccagaacttccctgtgcttgctggggt<br>gtggagtggaaagagcaggaaatgggggaccctccgatactc<br>tatggggtcctccaagtctctttgtgcaagttagggtaata<br>atcaatatggagctaagaaagagaaggggaactatgctttag<br>aacaggacactgtgccaggagcattgcagaaattatatggtt<br>ttcacgacagttctttttggtaggtactgttattatcctcag<br>tttgcagatgaggaaactgagacccagaaaggttaaataact<br>tgctagggtcacacaagtcataactgacaaagcctgattcaa<br>acccaggtctccctaacctttaaggtttctatgacgccagct<br>ctcctagggagtttgtcttcagatgtcttggctctaggtgtc<br>aaaaaaagacttggtgtcaggcaggcataggttcaagtccca<br>actctgtcacttaccaactgtgactaggtgattgaactgacc<br>atggaacctggtcacatgcaggagcaggatggtgaagggttc<br>ttgaaggcacttaggcaggacatttaggcaggagagaaaacc<br>tggaaacagaagagctgtctccaaaaatacccactggggaag<br>caggttgtcatgtgggccatgaatgggacctgttctggggta<br>accacgtgcggaccgagcggccgcaggaaccctagtgatgg<br>agttggccactccctctctgcgcgctcgctcgctcactgagg<br>ccgggcgaccaaaggtcgcccgacgcccgggctttgcccggg<br>cggcctcagtgagcgagcgagcgcgcag |

Plasmid AG006 Composition

| 5' ITR | 2<br>occurs @ bp 1 through bp 119 of SEQ ID NO: 35 |
|---|---|
| Human VMD2 Promoter | 12<br>occurs @ bp 134 through bp 761 of SEQ ID NO: 35 |
| Added Kozak | 5<br>occurs @ bp 795 through 800 of SEQ ID NO: 34 |
| E-GFP | 24<br>occurs @ bp 801 through bp 1520 of SEQ ID NO: 35 |
| SV40 POLYA | 8<br>occurs at bp 1578 through bp 1813 of SEQ ID NO: 35 |
| RLBP1 INTRONIC SEQUENCE AS STUFFER SEQUENCE | 14<br>occurs at bp 1821 through bp 3323 of SEQ ID NO: 35 |
| 3' ITR | 9<br>occurs at bp 3352 through bp 3481 of SEQ ID NO: 35 |
| AMP BACTERIAL BACKBONE | 15<br>occurs at bp 3482 through bp 6100 of SEQ ID NO: 35 |

TABLE 2-continued

Plasmid Composition
Plasmid Composition

| Elements | SEQUENCE IDENTIFIER (SEQ. ID. NO:) AND SEQUENCE INFORMATION |
|---|---|
| Sequence of plasmid AG006 | 35<br>ctgcgcgctcgctcgctcactgaggccgcccgggcgtcgggc<br>gacctttggtcgcccggcctcagtgagcgagcgagcgcgcag<br>agagggagtggccaactccatcactaggggttcctgcggccg<br>cacgcgttacgtaattctgtcattttactagggtgatgaaat<br>tcccaagcaacaccatccttttcagataagggcactgaggct<br>gagagaggagctgaaacctacccggcgtcaccacacacaggt<br>ggcaaggctggaccagaaaccaggactgttgactgcagccc<br>ggtattcattctttccatagcccacagggctgtcaaagaccc<br>cagggcctagtcagaggctcctccttcctggagagttcctgg<br>cacagaagttgaagctcagcacagcccctaaccccaactc<br>tctctgcaaggcctcaggggtcagaacactggtggagcagat<br>cctttagcctctggattttagggccatggtagaggggggtgtt<br>gccctaaattccagccctggtctcagcccaacaccctccaag<br>aagaaattagagggccatggccaggctgtgctagccgttgc<br>ttctgagcagattacaagaagggactaagacaaggactccctt<br>tgtggaggtcctggcttagggagtcaagtgacggcggctcag<br>cactcacgtgggcagtgccagcctctaagagtgggcaggggc<br>actggccacagagtcccaggagtcccaccagcctagtcgcc<br>agaccgaattccccggggatcctctagagtcgaaattcgcca<br>ccatggtgagcaagggcgaggagctgttcaccggggtggtgc<br>ccatcctggtcgagctggacggcgacgtaaacggccacaagt<br>tcagcgtgtccggcgagggcgagggcgatgccacctacggca<br>agctgaccctgaagttcatctgcaccaccggcaagctgcccg<br>tgccctggcccaccctcgtgaccaccctgacctacggcgtgc<br>agtgcttcagccgctaccccgaccacatgaagcagcacgact<br>tcttcaagtccgccatgcccgaaggctacgtccaggagcga<br>ccatcttcttcaaggacgacggcaactacaagacccgcgccg<br>aggtgaagttcgagggcgacaccctggtgaaccgcatcgagc<br>tgaagggcatcgacttcaaggaggacggcaacatcctgggc<br>acaagctggagtacaactacaacagccacaacgtctatatca<br>tggccgacaagcagaagaacggcatcaaggtgaacttcaaga<br>tccgccacaacatcgaggacggcagcgtgcagctcgccgacc<br>actaccagcagaacacccccatcggcgacggccccgtgctgc<br>tgcccgacaaccactacctgagcacccagtccgccctgagca<br>aagacccccaacgagaagcgcgatcacatggtcctgctggagt<br>tcgtgaccgccgccgggatcactctcggcatggacgagctgt<br>acaagtaatagggtaccggtcgacctgcagaagcttgcctcg<br>agcagcgctgctcgagagatctggatcataatcagccatacc<br>acatttgtagaggttttacttgctttaaaaaaacctcccacac<br>ctccccctgaacctgaaacataaaatgaatgcaattgttgtt<br>gttaacttgtttattgcagcttataatggttacaaataaagc<br>aatagcatcacaaatttcacaaataaagcattttttttcactg<br>cattctagttgtggtttgtccaaactcatcaatgtatcttat<br>catgtctggtaaccattctccaggttgagccagaccaatttg<br>atggtagatttagcaaataaaaatacaggacacccagttaaa<br>tgtgaatttccgatgaacagcaaatactttttttagtattaaa<br>aaagttcacatttaggctcacgcctgtaatcccagcactttg<br>ggaggccgaggcaggcagatcacctgaggtcaggagttcgag<br>accagcctggccaacatggtgaaacccatctccactaaaaa<br>taccaaaaattagccaggcgtgctggtgggcacctgtagttc<br>cagctactcaggaggctaaggcaggagaattgcttgaacctg<br>ggaggcagaggttgcagtgagctgagatcgcaccattgcact<br>ctagcctgggcgacaagaacaaaactccatctcaaaaaaaaa<br>aaaaaaaaaaaagttcacatttaactgggcattctgtattta<br>attggtaatctgagatggcagggaacagcatcagcatggtgt<br>gagggataggcatttttttcattgtgtacagcttgtaaatcag<br>tatttttaaaactcaaagttaatggcttgggcatatttagaa<br>aagagttgccgcacggacttgaaccctgtattcctaaaatct<br>aggatcttgttctgatggtctgcacaactggctgggggtgtc<br>cagccactgtccctcttgcctgggctcccagggcagttctg<br>tcagcctctccatttccattcctgttccagcaaaacccaact<br>gatagcacagcagcatttcagcctgtctacctctgtgcccac<br>atacctggatgtctaccagccagaaaggtggcttagatttgg<br>ttcctgtgggtggattatggccccccagaacttccctgtgctt<br>gctgggggtgtgagtggaaagagcaggaaatgggggaccct<br>ccgatactctatgggggtcctccaagtctctttgtgcaagtt<br>agggtaataatcaatatggagctaagaaagagaagggaact<br>atgctttagaacaggacactgtgccaggagcattgcagaaat<br>tatatggttttcacgacagttcttttttggtaggtactgttat<br>tatcctcagtttgcagatgaggaaactgagacccagaaaggt<br>taaataacttgctagggtcacacaagtcataactgacaaagc<br>ctgattcaaacccaggtctccctaacctttaaggtttctatg |

TABLE 2-continued

Plasmid Composition
Plasmid Composition

| Elements | SEQUENCE IDENTIFIER (SEQ. ID. NO:) AND SEQUENCE INFORMATION |
|---|---|
|  | acgccagctctcctagggagtttgtcttcagatgtcttggct ctaggtgtcaaaaaaagacttggtgtcaggcaggcataggtt caagtcccaactctgtcacttaccaactgtgactaggtgatt gaactgaccatggaacctggtcacatgcaggagcaggatggt gaagggttcttgaaggcacttaggcaggacatttaggcagga gagaaaacctggaaacagaagagctgtctccaaaaataccca ctggggaagcaggttgtcatgtgggccatgaatgggacctgt tctggggtaaccacgtgcggaccgagcggccgcaggaacccc tagtgatggagttggccactccctctctgcgcgctcgctcgc tcactgaggccgggcgaccaaaggtcgcccgacgcccgggct ttgcccggccggcctcagtgagcgagcgagcgcgcagctgcc tgcaggggcgcctgatgcggtatttctccttacgcatctgt gcggtatttcacaccgcatacgtcaaagcaaccatagtacgc gccctgtagcggcgcattaagcgcggcgggtgtggtggttac gcgcagcgtgaccgctacacttgccagcgccttagcgcccgc tcctttcgctttcttcccttcctttctcgccacgttcgccgg ctttccccgtcaagctctaaatcgggggctccctttagggtt ccgatttagtgctttacggcacctcgaccccaaaaaacttga tttgggtgatggttcacgtagtgggccatcgccctgatagac ggtttttcgccctttgacgttggagtccacgttctttaatag tggactcttgttccaaactggaacaacactcaactctatctc gggctattcttttgatttataagggattttgccgatttcggt ctattggttaaaaaatgagctgatttaacaaaaatttaacgc gaattttaacaaaatattaacgtttacaattttatggtgcac tctcagtacaatctgctctgatgccgcatagttaagccagcc ccgacacccgccaacacccgctgacgcgccctgacgggcttg tctgctcccggcatccgcttacagacaagctgtgaccgtctc cgggagctgcatgtgtcagaggttttcaccgtcatcaccgaa acgcgcgagacgaaagggcctcgtgatacgcctatttttata ggttaatgtcatgataataatggtttcttagacgtcaggtgg cacttttcggggaaatgtgcgcggaacccctatttgtttatt tttctaaatacattcaaatatgtatccgctcatgagacaata accctgataaatgcttcaataatattgaaaaaggaagagtat gagtattcaacatttccgtgtcgcccttattcccttttttgc ggcattttgccttcctgtttttgctcacccagaaacgctggt gaaagtaaaagatgctgaagatcagttgggtgcacgagtggg ttacatcgaactggatctcaacagcggtaagatccttgagag ttttcgccccgaagaacgttttccaatgatgagcactttaa agttctgctatgtggcgcggtattatcccgtattgacgccgg gcaagagcaactcggtcgccgcatacactattctcagaatga cttggttgagtactcaccagtcacagaaaagcatcttacgga tggcatgacagtaagagaattatgcagtgctgccataaccat gagtgataacactgcggccaacttacttctgacaacgatcgg aggaccgaaggagctaaccgcttttttgcacaacatgggga tcatgtaactcgccttgatcgttgggaaccggagctgaatga agccataccaaacgacgagcgtgacaccacgatgcctgtagc aatggcaacaacgttgcgcaaactattaactggcgaactact tactctagcttcccggcaacaattaatagactggatggaggc ggataaagttgcaggaccacttctgcgctcggcccttccggc tggctggtttattgctgataaatctggagccggtgagcgtgg gtctcgcggtatcattgcagcactggggccagatggtaagcc ctcccgtatcgtagttatctacacgacggggagtcaggcaac tatggatgaacgaaatagacagatcgctgagataggtgcctc actgattaagcattggtaactgtcagaccaagtttactcata tatactttagattgatttaaaacttcattttaatttaaaag gatctaggtgaagatcctttttgataatctcatgaccaaaat cccttaacgtgagttttcgttccactgagcgtcagaccccgt agaaaagatcaaaggatcttcttgaaatcctttttttctgcg cgtaatctgctgcttgcaaacaaaaaaaccaccgctaccagc ggtggtttgtttgccggatcaagagctaccaactctttttcc gaaggtaactggcttcagcagagcgcagataccaaatactgt tcttctagtgtagccgtagttaggccaccacttcaagaactc tgtagcaccgcctacatacctcgctctgctaatcctgttacc agtggctgctgccagtggcgataagtcgtgtcttaccgggtt ggactcaagacgatagttaccggataaggcgcagcggtcggg ctgaacggggggttcgtgcacacagcccagcttggagcgaac gacctacaccgaactgagatacctacagcgtgagctatgaga aagcgccacgcttcccgaagggagaaaggcggacaggtatcc ggtaagcggcagggtcggaacaggagagcgcacgagggagct tccaggggggaaacgcctggtatctttatagtcctgtcgggtt tcgccacctctgacttgagcgtcgatttttgtgatgctcgtc agggggcggagcctatggaaaaacgccagcaacgcggcctt tttacggttcctggccttttgctggccttttgctcacatgtc ctgcaggcag |

TABLE 2-continued

Plasmid Composition
Plasmid Composition

| Elements | SEQUENCE IDENTIFIER (SEQ. ID. NO:) AND SEQUENCE INFORMATION |
|---|---|
| GENE CASSETTE OF PLASMID AG006 OCCURS AT BP 1 THROUGH 3481 OF SEQ ID NO: 35 | 60<br>ctgcgcgctcgctcgctcactgaggccgcccgggcgtcgggc<br>gacctttggtcgcccggcctcagtgagcgagcgagcgcgcag<br>agagggagtggccaactccatcactaggggttcctgcggccg<br>cacgcgttacgtaattctgtcatttactagggtgatgaaat<br>tcccaagcaacaccatccttttcagataagggcactgaggct<br>gagagaggagctgaaacctacccggcgtcaccacacacaggt<br>ggcaaggctggaccagaaaccaggactgttgactgcagccc<br>ggtattcattctttccatagcccacagggctgtcaaagaccc<br>cagggcctagtcagaggctcctccttcctggagagttcctgg<br>cacagaagttgaagctcagcacagcccctaaccccaactc<br>tctctgcaaggcctcaggggtcagaacactggtggagcagat<br>cctttagcctctggattttagggccatggtagagggggtgtt<br>gccctaaattccagccctggtctcagcccaacaccctccaag<br>aagaaattagaggggccatggccaggctgtgctagccgttgc<br>ttctgagcagattacaagaagggactaagacaaggactcctt<br>tgtggaggtcctggcttagggagtcaagtcagcggcggctcag<br>cactcacgtgggcagtgccagcctctaagagtgggcaggggc<br>actggccacagagtcccaggggagtcccaccagcctagtcgcc<br>agaccgaattccccgggggatcctctagagtcgaaattcgcca<br>ccatggtgagcaagggcgaggagctgttcaccggggtggtgc<br>ccatcctggtcgagctggacggcgacgtaaacggccacaagt<br>tcagcgtgtccggcgagggcgagggcgatgccacctacggca<br>agctgaccctgaagttcatctgcaccaccggcaagctgcccg<br>tgccctggcccaccctcgtgaccaccctgacctacggcgtgc<br>agtgcttcagccgctaccccgaccacatgaagcagcacgact<br>tcttcaagtccgccatgcccgaaggctacgtccaggagcga<br>ccatcttcttcaaggacgacggcaactacaagacccgcgccg<br>aggtgaagttcgagggcgacaccctggtgaaccgcatcgagc<br>tgaagggcatcgacttcaaggaggacggcaacatcctgggc<br>acaagctggagtacaactacaacagccacaacgtctatatca<br>tggccgacaagcagaagaacggcatcaaggtgaacttcaaga<br>tccgccacaacatcgaggacggcagcgtgcagctcgccgacc<br>actaccagcagaacacccccatcggcgacggccccgtgctgc<br>tgcccgacaaccactacctgagcacccagtccgccctgagca<br>aagacccaacgagaagcgcgatcacatggtcctgctggagt<br>tcgtgaccgccgcgggatcactctcggcatggacgagctgt<br>acaagtaatagggtaccggtcgacctgcagaagcttgcctcg<br>agcagcgctgctcgagagatctggatcataatcagccatacc<br>acatttgtagaggttttacttgctttaaaaaacctcccacac<br>ctccccctgaacctgaaacataaaatgaatgcaattgttgtt<br>gttaacttgtttattgcagcttataatggttacaaataaagc<br>aatagcatcacaaatttcacaaataaagcattttttttcactg<br>cattctagttgtggtttgtccaaactcatcaatgtatcttat<br>catgtctggtaaccattctccaggttgagccagaccaatttg<br>atggtagatttagcaaataaaaatacaggacacccagttaaa<br>tgtgaatttccgatgaacagcaaatacttttttagtattaaa<br>aaagttcacatttaggctcacgcctgtaatcccagcactttg<br>ggaggccgaggcaggcagatcacctgaggtcaggagttcgag<br>accagcctggccaacatggtgaaacccatctccactaaaaa<br>taccaaaaattagccaggcgtgctggtgggcacctgtagttc<br>cagctactcaggaggctaaggcaggagaattgcttgaacctg<br>ggaggcagaggttgcagtgagctgagatcgcaccattgcact<br>ctagcctgggcgacaagaacaaaactccatctcaaaaaaaaa<br>aaaaaaaaaaagttcacatttaactgggcattctgtattta<br>attggtaatctgagatggcagggaacagcatcagcatggtgt<br>gagggataggcattttttcattgtgtacagcttgtaaatcag<br>tatttttaaaactcaaagttaatggcttgggcatatttagaa<br>aagagttgccgcacggacttgaaccctgtattcctaaaatct<br>aggatcttgttctgatggtctgcacaactggctgggggtgtc<br>cagccactgtccctcttgcctgggctcccagggcagttctg<br>tcagcctctccatttccattcctgttccagcaaaacccaact<br>gatagcacagcagcatttcagcctgtctacctctgtgcccac<br>ataccctggatgtctaccagccagaaaggtggcttagatttgg<br>ttcctgtgggtggattatggcccccagaacttccctgtgcttt<br>gctgggggtgtgagtggaaagagcaggaaatgggggaccct<br>ccgatactctatgggggtcctccaagtctctttgtgcaagtt<br>agggtaataatcaatatggagctaagaaagagaagggaact<br>atgctttagaacaggacactgtgccaggagcattgcagaaat<br>tatatggttttcacgacagttcttttttggtaggtactgttat<br>tatcctcagtttgcagatgaggaaactgagacccagaaaggt<br>taaataacttgctagggtcacacaagtcataactgacaaagc<br>ctgattcaaacccaggtctccctaacctttaaggttttctatg |

TABLE 2-continued

Plasmid Composition
Plasmid Composition

| Elements | SEQUENCE IDENTIFIER (SEQ. ID. NO:) AND SEQUENCE INFORMATION |
|---|---|
| | acgccagctctcctagggagtttgtcttcagatgtcttggct<br>ctaggtgtcaaaaaaagacttggtgtcaggcaggcataggtt<br>caagtcccaactctgtcacttaccaactgtgactaggtgatt<br>gaactgaccatggaacctggtcacatgcaggagcaggatggt<br>gaagggttcttgaaggcacttaggcaggacatttaggcagga<br>gagaaaacctggaaacagaagagctgtctccaaaaatacccca<br>ctggggaagcaggttgtcatgtgggccatgaatgggacctgt<br>tctggggtaaccacgtgcggaccgagcggccgcaggaacccc<br>tagtgatggagttggccactccctctctgcgcgctcgctcgc<br>tcactgaggccgggcgaccaaaggtcgcccgacgcccgggct<br>ttgcccgggcggcctcagtgagcgagcgagcgcgcag |

Plasmid TM042 Composition

| ΔITR | 1<br>occurs at bp 4 through bp 106 of SEQ ID NO: 50 |
|---|---|
| Human RLBP1 Promoter (short) | 3<br>Occurs at bp 119 through bp 708 of SEQ ID NO: 50 |
| MODIFIED SV40INTRON | 4<br>occurs at bp 723 through bp 905 of SEQ ID NO: 50 |
| Added Kozak | 5<br>occurs at bp 919 through bp 924 of SEQ ID NO: 50 |
| HUMAN RLBP1 GENE CDS | 6<br>occurs at bp 925 through bp 1878 of SEQ ID NO: 50 |
| SV40 POLYA | 8<br>occurs at bp 1937 through bp 2172 of SEQ ID NO: 50 |
| 3' ITR | 9<br>occurs at bp 2201 through bp 2330 of SEQ ID NO: 50 |
| KAN-R BACTERIAL BACKBONE | 49<br>occurs at bp 2331 through bp 4989 of SEQ ID NO: 50 |
| Sequence of plasmid TM042 | 50<br>ctgcgcgctcgctcgctcactgaggccgccccgggcaaagccc<br>gggcgtcgggcgaccttttggtcgcccggcctcagtgagcgag<br>cgagcgcgcagagagggagtgggggtaccacgcgtttgtcctc<br>tccctgcttggccttaaccagccacatttctcaactgacccc<br>actcactgcagaggtgaaaactaccatgccaggtcctgctgg<br>ctgggggaggggtgggcaataggcctggatttgccagagctg<br>ccactgtagatgtagtcatatttacgatttccccttcacctct<br>tattaccctggtggtggtggtgggggggggggggtgctctct<br>cagcaaccccaccccgggatcttgaggagaaagagggcagag<br>aaaagagggaatgggactggcccagatcccagccccacagcc<br>gggcttccacatggccgagcaggaactccagagcaggagcac<br>acaaaggagggctttgatgcgcctccagccaggcccaggcct<br>ctcccctctccctttctctctgggtcttcctttgccccact<br>gagggcctcctgtgagcccgatttaacggaaactgtgggcgg<br>tgagaagttccttatgacacactaatcccaacctgctgaccg<br>gaccacgcctccagcggagggaacctctagagctccaggaca<br>ttcaggtaccaggtagccccaaggaggagctgccgaatcgat<br>ggatcgggaactgaaaaaccagaaagttaactggtaagttta<br>gtcttttttgtcttttatttcaggtcccggatccggtggtggt<br>gcaaatcaaagaactgctcctcagtggatgttgcctttactt<br>ctaggcctgtacggaagtgttacttctgctctaaaagctgcg<br>gaattgtaccgccccgggatccatcgattgaattcgccacc<br>atgtcagaaggggtgggcacgttccgcatggtacctgaagag<br>gaacaggagctccgtgcccaactggagcagctcacaaccaag<br>gaccatggacctgtctttggcccgtgcagccagctgccccgc<br>cacaccttgcagaaggccaaggatgagctgaacagagagag<br>gagacccgggaggaggcagtgcgagagctgcaggagatggtg TABLE 2-continued Plasmid Composition
Plasmid Composition

| Elements | SEQUENCE IDENTIFIER (SEQ. ID. NO:) AND SEQUENCE INFORMATION |
|---|---|
| | caggcgcaggcggcctcggggggaggagctggcggtggccgtg |
| | gcggagagggtgcaagagaaggacagcggcttcttcctgcgc |
| | ttcatccgcgcacggaagttcaacgtgggccgtgcctatgag |
| | ctgctcagaggctatgtgaatttccggctgcagtaccctgag |
| | ctctttgacagcctgtcccagaggctgtccgctgcaccatt |
| | gaagctggctaccctggtgtcctctctagtcgggacaagtat |
| | ggccgagtggtcatgtctcttcaacattgagaactggcaaagt |
| | caagaaatcacctttgatgagatcttgcaggcatattgcttc |
| | atcctggagaagctgctggagaatgaggaaactcaaatcaat |
| | ggcttctgcatcattgagaacttcaagggctttaccatgcag |
| | caggctgctagtctccggacttcagatctcaggaagatggtg |
| | gacatgctccaggattccttcccagcccggttcaaagccatc |
| | cacttcatccaccagccatggtacttcaccacgacctacaat |
| | gtggtcaagcccttcttgaagagcaagctgcttgagagggtc |
| | tttgtccacggggatgacctttctggtttctaccaggagata |
| | gatgagaacatcctgccctctgacttcgggggcacgctgccc |
| | aagtatgatggcaaggccgttgctgagcagctctttggcccc |
| | caggcccaagctgagaacacagccttctgaggatcgtaccgg |
| | tcgacctgcagaagcttgcctcgagcagcgctgctcgagaga |
| | tctggatcataatcagccataccacatttgtagaggttttac |
| | ttgctttaaaaaacctcccacacctcccctgaacctgaaac |
| | ataaaatgaatgcaattgttgttgttaacttgtttattgcag |
| | cttataatggttacaaataaagcaatagcatcacaaatttca |
| | caaataaagcattttttcactgcattctagttgtggtttgt |
| | ccaaactcatcaatgtatcttatcatgtctggtaaccacgtg |
| | cggaccgagcggccgcaggaacccctagtgatggagttggcc |
| | actccctctgcgcgctcgctcgctcactgaggccgggcga |
| | ccaaaggtcgcccgacgcccgggctttgcccgggcggcctca |
| | gtgagcgagcgagcgcgcagctgcctgcagggttccatccca |
| | atggcgcgtcaattcactggccgtcgttttacaacgtcgtga |
| | ctgggaaaaccctggcgttacccaacttaatcgccttgcagc |
| | acatccccctttcgccagctggcgtaatagcgaagaggcccg |
| | caccgatcgcccttcccaacagttgcgcagcctgaatggcga |
| | atggcgcctgatgcggtattttctccttacgcatctgtgcgg |
| | tatttcacaccgcatatggtgcactctcagtacaatctgctc |
| | tgatgccgcatagttaagccagccccgacacccgccaacacc |
| | cgctgacgcgccctgacgggcttgtctgctcccggcatccgc |
| | ttacagacaagctgtgaccgtctccgggagctgcatgtgtca |
| | gaggttttcaccgtcatcaccgaaacgcgcgagacgaaaggg |
| | cctcgtgatacgcctatttttataggttaatgtcatgataat |
| | aatgtttcttagacgtcaggtggcacttttcggggaaatgt |
| | gcgcggaacccctatttgtttatttttctaaatacattcaaa |
| | tatgtatccgctcatgagacaataaccctgataaatgcttca |
| | ataatattgaaaaaggaagagtatgagccatattcaacggga |
| | aacgtcttgctctaggccgcgattaaattccaacatggatgc |
| | tgatttatatgggtataaatgggctcgcgataatgtcgggca |
| | atcaggtgcgacaatctatcgattgtatgggaagcccgatgc |
| | gccagagttgtttctgaaacatggcaaaggtagcgttgccaa |
| | tgatgttacagatgagatggtcagactaaactggctgacgga |
| | atttatgcctcttccgaccatcaagcattttatccgtactcc |
| | tgatgatgcatggttactcaccactgcgatccctgggaaaac |
| | agcattccaggtattagaagaatatcctgattcaggtgaaaa |
| | tattgttgatgcgctggcagtgttcctgcgccggttgcattc |
| | gattcctgtttgtaattgtccttttaacagcgatcgcgtatt |
| | tcgtctcgctcaggcgcaatcacgaatgaataacggtttggt |
| | tgatgcgagtgattttgatgacgagcgtaatggctggcctgt |
| | tgaacaagtctggaaagaaatgcataaacttttgccattctc |
| | accggattcagtcgtcactcatggtgatttctcacttgataa |
| | ccttatttttgacgaggggaaattaataggttgtattgatgt |
| | tggacgagtcggaatcgcagaccgataccaggatcttgccat |
| | cctatggaactgcctcggtgagttttctccttcattacagaa |
| | acggcttttcaaaaatatggtattgataatcctgatatgaa |
| | taaattgcagtttcatttgatgctcgatgagttttctaact |
| | gtcagaccaagtttactcatatactttagattgatttaaa |
| | acttcattttaatttaaaaggatctaggtgaagatccttt |
| | tgataatctcatgaccaaaatcccttaacgtgagttttcgtt |
| | ccactgagcgtcagacccccgtagaaaagatcaaaggatcttc |
| | ttgagatcctttttttctgcgcgtaatctgctgcttgcaaac |
| | aaaaaaaccaccgctaccagcggtggtttgtttgccggatca |
| | agagctaccaactctttttccgaaggtaactggcttcagcag |
| | agcgcagataccaaatactgttcttctagtgtagccgtagtt |
| | aggccaccacttcaagaactctgtagcaccgcctacatacct |
| | cgctctgctaatcctgttaccagtggctgctgccagtggcga |
| | taagtcgtgtcttaccgggttggactcaagacgatagttacc |

TABLE 2-continued

Plasmid Composition
Plasmid Composition

| Elements | SEQUENCE IDENTIFIER (SEQ. ID. NO:) AND SEQUENCE INFORMATION |
|---|---|
| | ggataaggcgcagcggtcgggctgaacgggggttcgtgcac<br>acagcccagcttggagcgaacgacctacaccgaactgagata<br>cctacagcgtgagctatgagaaagcgccacgcttcccgaagg<br>gagaaaggcggacaggtatccggtaagcggcagggtcggaac<br>aggagagcgcacgagggagcttccaggggggaaacgcctggta<br>tctttatagtcctgtcgggtttcgccacctctgacttgagcg<br>tcgattttttgtgatgctcgtcagggggggcggagcctatggaa<br>aaacgccagcaacgcggccttttttacggttcctggccttttg<br>ctggccttttgctcacatgttctttcctgcgttatcccctga<br>ttctgtggataaccgtattaccgcctttgagtgagctgatac<br>cgctcgccgcagccgaacgaccgagcgcagcgagtcagtgag<br>cgaggaagcggaagagcgcccaatacgcaaaccgcctctccc<br>cgcgcgttggccgattcattaatgcagctggcacgacaggtt<br>tcccgactggaaagcgggcagtgagcgcaacgcaattaatgt<br>gagttagctcactcattaggcaccccaggctttacactttat<br>gcttccggctcgtatgttgtgtggaattgtgagcggataaca<br>atttcacacaggaaacagctatgaccatgattacgccaagct<br>cggcgcgccattgggatggaaccctgcaggcag |
| GENE CASSETTE<br>TM042 OCCURS AT<br>BP 4 THROUGH<br>2330 OF SEQ ID<br>NO: 50 | 61<br>cgcgctcgctcgctcactgaggccgcccggcaaagcccggg<br>cgtcgggcgacctttggtcgcccggcctcagtgagcgagcga<br>gcgcgcagagagggagtgggtaccacgcgtttgtcctctcc<br>ctgcttggccttaaccagccacatttctcaactgaccccact<br>cactgcagaggtgaaaactaccatgccaggtcctgctggctg<br>ggggagggtgggcaataggcctggatttgccagagctgcca<br>ctgtagatgtagtcatatttacgatttcccttcacctcttat<br>taccctggtggtggtggtgggggggggggtgctctctcag<br>caaccccaccccgggatcttgaggagaaagagggcagagaaa<br>agagggaatgggactggcccagatcccagccccacagccggg<br>cttccacatggccgagcaggaactccagagcaggagcacaca<br>aaggagggctttgatgcgcctccagccaggccaggcctctc<br>ccctctccctttctctctgggtcttccttgccccactgag<br>ggcctcctgtgagcccgatttaacggaaactgtgggcggtga<br>gaagttccttatgacacactaatcccaacctgctgaccggac<br>cacgcctccagcggagggaacctctagagctccaggacattc<br>aggtaccaggtagcccccaaggaggagctgccgaatcgatgga<br>tcgggaactgaaaaaccagaaagttaactggtaagtttagtc<br>ttttttgtcttttatttcaggtcccggatccggtggtggtgca<br>aatcaaagaactgctcctcagtggatgttgcctttacttcta<br>ggcctgtacggaagtgttacttctgctctaaaagctgcggaa<br>ttgtacccgccccgggatccatcgattgaattcgccaccatg<br>tcagaaggggtgggcacgttccgcatggtacctgaagaggaa<br>caggagctccgtgcccaactggagcagctcacaaccaaggac<br>catgacctgtctttggcccgtgcagccagctgccccgccac<br>accttgcagaaggccaaggatgagctgaacgagagagaggag<br>acccgggaggaggcagtgcgagagctgcaggagatggtgcag<br>gcgcaggcggcctcggggagggagctggcggtggccgtggcc<br>gagagggtgcaagagaaggacagcggcttcttcctgcgcttc<br>atccgcgcacggaagttcaacgtgggccgtgcctatgagctg<br>ctcagaggctatgtgaatttccggctgcagtaccctgagctc<br>tttgacagcctgtccccagaggctgtccgctgcaccattgaa<br>gctggctaccctggtgtcctctctagtcgggacaagtatggc<br>cgagtggtcatgctcttcaacattgagaactggcaaagtcaa<br>gaaatcacctttgatgagatcttgcaggcatattgcttcatc<br>ctggagaagctgctggagaatgaggaaactcaaatcaatggc<br>ttctgcatcattgagaacttcaagggctttaccatgcagcag<br>gctgctagtctccggacttcagatctcaggaagatggtggac<br>atgctccaggattccttcccagcccggttcaaagccatccac<br>ttcatccaccagccatggtacttcaccacgacctacaatgtg<br>gtcaagcccttcttgaagagcaagctgcttgagagggtcttt<br>gtccacggggatgacctttctggtttctaccaggagatcgat<br>gagaacatcctgccctctgacttcggggggcacgctgcccaag<br>tatgatggcaaggccgttgctgagcagctctttggcccccag<br>gcccaagctgagaacacagccttctgaggatcgtaccggtcg<br>acctgcagaagcttgcctcgagcagcgctgctcgagagatct<br>ggatcataatcagccataccacatttgtagaggttttacttg<br>ctttaaaaaacctcccacacctcccctgaacctgaaacata<br>aaatgaatgcaattgttgttgttaacttgtttattgcagctt<br>ataatggttacaaataaagcaatagcatcacaaatttcacaa<br>ataaagcattttttcactgcattctagttgtggtttgtcca<br>aactcatcaatgtatcttatcatgtctggtaaccacgtgcgg<br>accgagcggccgcaggaacccctagtgatggagttggccact<br>ccctctctgcgcgctcgctcgctcactgaggccgggcgacca |

TABLE 2-continued

Plasmid Composition

| Elements | SEQUENCE IDENTIFIER (SEQ. ID. NO:) AND SEQUENCE INFORMATION |
|---|---|
| | aaggtcgcccgacgcccgggctttgcccgggcggcctcagtg agcgagcgagcgcgcag |

TABLE 3

Plasmid Construction

| SEQUENCE IDENTIFIER (SEQ. ID. NO:) | Construction summary |
|---|---|
| *Plasmid TM017* | |
| 1 ΔITR | PvuII/MluI restriction fragment of Δ5′ ITR element cloned into PvuII/MluI restriction fragment of plasmid backbone |
| 3 Human RLBP1 Promoter(short) | Blunted BamHI/MluI restriction fragment of human RLBP1 promoter (short) was cloned into blunted SacII/MluI restriction fragment of plasmid backbone |
| 4 MODIFIED SV40INTRON | MluI/ClaI restriction fragment a clone containing an hCMV promoter and modified SV40 intron was cloned into MluI/ClaI restriction fragment of plasmid backbone. The hCMV promoter was removed during subsequent cloning to insert human RLBP1 promoter (short) |
| 5, 6 Added Kozak AND HUMAN RLBP1 GENE CDS | EcoRI/AgeI restriction fragment containing Kozak and human RLBP1 gene CDS was cloned into EcoRI/AgeI restriction fragment of plasmid backbone |
| 8 SV40 POLYA | BglII/BstEII restriction fragment of SV40 polyA was cloned into BglII/BsteII restriction fragment of the plasmid backbone |
| 9 3′ ITR | Present in original Amp resistant backbone, AAV-MCS (Stratagene) |
| *Plasmid TM037 construction summary* | |
| 2 5′ ITR | Present in original Amp resistant backbone, AAV-MCS (Stratagene) |
| 10 Human RLBP1 Promoter(long) | Blunted HindIII/EcoRI restriction fragment of human RLBP1 promoter (long) was cloned into blunted MluI/EcoRI restriction fragment of plasmid backbone |
| 5, 6 Added Kozak AND HUMAN RLBP1 GENE CDS | EcoRI/AgeI restriction fragment containing Kozak and human RLBP1 gene CDS cloned into EcoRI/AgeI restriction fragment of plasmid backbone |
| 8 SV40 POLYA | BglII/BstEII restriction fragment containing SV40 polyA was cloned into BglII/BsteII restriction fragment of the plasmid backbone |
| 9 3′ ITR | Present in original Amp resistant backbone, AAV-MCS (Stratagene) |
| *Plasmid AG007 construction summary* | |
| 2 5′ ITR | Present in original Amp resistant backbone, pAAV-MCS (Stratagene) |
| 11 Human RPE65 Promoter | MluI/EcoRI restriction fragment containing human RPE65 promoter cloned into MluI/EcoRI restriction fragment of the plasmid backbone |
| 5, 6 ADDED-KOZAK and HUMAN RLBP1 GENE CDS | EcoRI/AgeI restriction fragment containing Kozak and human RLBP1 gene CDS cloned into EcoRI/AgeI restriction fragment of plasmid backbone |
| 8 SV40 POLYA | BglII/BstEII restriction fragment containing SV40 polyA was cloned into BglII/BsteII restriction fragment of the plasmid backbone |
| 14 RLBP1 INTRONIC SEQUENCE AS STUFFER SEQUENCE | BstEII restriction fragment containing RLBP1 intron1 stuffer sequence was cloned into BstEII restriction fragment of the plasmid backbone |
| 9 3′ ITR | Present in original Amp resistant backbone, pAAV-MCS (Stratagene) |
| *Plasmid TM039 construction summary* | |
| 2 5′ ITR | Present in original Amp resistant backbone, AAV-MCS purchased from Stratagene |
| 22 CMV-enhancer with CBA promoter | EcoRI/MluI restriction fragment containing CMV-enhancer with CBA promoter was cloned into EcoRI/MluI restriction fragment of plasmid backbone |
| 5, 6 Added Kozak AND HUMAN RLBP1 GENE CDS | EcoRI/SalI restriction fragment containing Kozak and human RLBP1 gene CDS was cloned into EcoRI/SalI restriction fragment of plasmid backbone |
| 8 SV40 POLYA | BglII/BstEII restriction fragment containing SV40 polyA was cloned into BglII/BsteII restriction fragment of the plasmid backbone |
| 23 REVERSE COMPLEMENT OF RLBP1 INTRON STUFFER | Plasmid backbone was cut with BstEII then blunted. The stuffer was PCR amplified from human cell line (HEK293 or ARPE19) genomic DNA, the product was phosphorylated and ligated into backbone. |
| 9 3′ ITR | Present in original Amp resistant backbone, AAV-MCS (Stratagene) |
| *Plasmid TM040 construction summary* | |
| 2 5′ ITR | Present in original Amp resistant backbone, AAV-MCS (Stratagene) |
| 3 Human RLBP1 promoter (short) | Blunted BamHI/MluI restriction fragment of human RLBP1 promoter (short) was cloned into blunted SacII/MluI restriction fragment of plasmid backbone |
| 4 MODIFIED SV40INTRON | MluI/ClaI restriction fragment containing an hCMV promoter and modified SV40 intron was cloned into MluI/ClaI restriction fragment of plasmid backbone. The hCMV promoter was removed during subsequent cloning to insert human RLBP1 promoter (short) |

TABLE 3-continued

Plasmid Construction

| SEQUENCE IDENTIFIER (SEQ. ID. NO:) | Construction summary |
|---|---|
| 5, 6 Added Kozak AND HUMAN RLBP1 GENE CDS | EcoRI/SalI restriction fragment containing Kozak and human RLBP1 gene CDS cloned into EcoRI/SalI restriction fragment of plasmid backbone |
| 8 SV40 POLYA | BglII/BstEII restriction fragment containing SV40 polyA was cloned into BglII/BsteII restriction fragment of the plasmid backbone |
| 23 REVERSE COMPLEMENT OF RLBP1 INTRON STUFFER | Plasmid backbone was cut with BstEII then blunted. The stuffer was PCR amplified from human cell line (HEK293 or ARPE19) genomic DNA, the product was phosphorylated and ligated into backbone. |
| 9 3' ITR | Present in original Amp resistant backbone, AAV-MCS purchased from Stratagene |
| Plasmid TM016 construction summary | |
| 1 Δ5' ITR | PvuII/MluI restriction of Δ5' ITR element cloned into PvuII/MluI restriction fragment of plasmid backbone |
| 3 Human RLBP1 promoter (short) | Blunted BamHI/MluI restriction fragment of human RLBP1 promoter (short) was cloned into blunted SacII/MluI restriction fragment of plasmid backbone |
| 4 MODIFIED SV40INTRON | MluI/ClaI restriction fragment of containing an hCMV promoter and modified SV40 intron was cloned into MluI/ClaI restriction fragment of plasmid backbone. The hCMV promoter was removed during subsequent cloning to insert human RLBP1 promoter (short) |
| 24 E_GFP | EcoRI/Age fragment containing GFP was blunted then cloned into the SalI digested and blunted backbone |
| 8 SV40 POLYA | BglII/BstEII restriction fragment containing SV40 polyA was cloned into BglII/BsteII restriction fragment of the plasmid backbone |
| 9 3' ITR | Present in original Amp resistant backbone, AAV-MCS purchased from Stratagene |
| Plasmid TM035 construction summary | |
| 2 5' ITR | Present in original Amp resistant backbone, AAV-MCS purchased from Stratagene |
| 10 Human RLBP1 promoter (long) | Blunted HindIII/EcoRI restriction fragment of human RLBP1 promoter (long) was cloned into blunted MluI/EcoRI restriction fragment of plasmid backbone |
| 24 E_GFP | EcoRI/Age I digested fragment containing GFP was blunted then cloned into the SalI digested and blunted backbone |
| 8 SV40 POLYA | BglII/BstEII restriction fragment containing SV40 polyA was cloned into BglII/BstEII restriction fragment of the plasmid backbone |
| 9 3' ITR | Present in original Amp resistant backbone, AAV-MCS purchased from Stratagene |
| Plasmid AG012 construction summary | |
| 2 5' ITR | Present in original Amp resistant backbone, AAV-MCS purchased from Stratagene |
| 13 SYNUCLEIN INTRONIC SEQUENCE AS STUFFER SEQUENCE | The plasmid backbone was digested with MluI/AgeI. The synuclein stuffer was PCR amplified from plasmid pBV5, the product was digested with MluI/AgeI, phosphorylated and ligated into the plasmid backbone. |
| 8 SV40 POLYA | BglII/BstEII restriction fragment from GeneArt synthesized clone containing SV40 polyA was cloned into BglII/BstEII restriction fragment of the plasmid backbone |
| 14 RLBP1 INTRONIC SEQUENCE AS STUFFER SEQUENCE | BstEII restriction fragment from intermediary clone containing RLBP1 intron1 stuffer sequence cloned into BstEII restriction fragment of the plasmid backbone |
| 9 3' ITR | Present in original Amp resistant backbone, AAV-MCS purchased from Stratagene |
| Plasmid AG004 construction summary | |
| 2 5' ITR | Present in original Amp resistant backbone, AAV-MCS purchased from Stratagene |
| 11 Human RPE65 Promoter | MluI/EcoRI restriction fragment from GeneArt synthesized clone containing human RPE65 promoter cloned into MluI/EcoRI restriction fragment of the plasmid backbone |
| 24 E_GFP | An EcoRI/AgeI digested fragment from an intermediary clone was blunted then cloned into the SalI digested and blunted backbone |
| 8 SV40 POLYA | BglII/BstEII restriction fragment from GeneArt synthesized clone containing SV40 polyA was cloned into BglII/BstEII restriction fragment of the plasmid backbone |
| 14 RLBP1 INTRONIC SEQUENCE AS STUFFER SEQUENCE | BstEII restriction fragment from intermediary clone containing RLBP1 intron1 stuffer sequence cloned into BstEII restriction fragment of the plasmid backbone |
| 9 3' ITR | Present in original Amp resistant backbone, AAV-MCS purchased from Stratagene |
| Plasmid AG006 construction summary | |
| 2 5' ITR | Present in original Amp resistant backbone, AAV-MCS purchased from Stratagene |
| 12 HUMAN VMD2 PROMOTER | MluI/EcoRI restriction fragment from GeneArt synthesized clone containing human VMD2 promoter cloned into MluI/EcoRI restriction fragment of the plasmid backbone |
| 24 E_GFP | An EcoRI/AgeI digested fragment from an intermediary clone was blunted then cloned into the SalI digested and blunted backbone |
| 8 SV40 POLYA | BglII/BstEII restriction fragment from GeneArt synthesized clone containing SV40 polyA was cloned into BglII/BstEII restriction fragment of the plasmid backbone |
| 14 RLBP1 INTRONIC SEQUENCE AS STUFFER SEQUENCE | BstEII restriction fragment from intermediary clone containing RLBP1 intron1 stuffer sequence cloned into BstEII restriction fragment of the plasmid backbone |
| 9 3' ITR | Present in original Amp resistant backbone, AAV-MCS purchased from Stratagene |

TABLE 3-continued

Plasmid Construction

| SEQUENCE IDENTIFIER (SEQ. ID. NO:) | Construction summary |
|---|---|
| Plasmid TM042 Construction Summary | |
| 1-ΔITR, 3- Human RLBP1 Promoter(short), 4- MODIFIED SV40INTRON, 5, 6- Added Kozak AND HUMAN RLBP1 GENE, 8- SV40 POLYA, and 9- 3' ITR | SbfI restriction fragment of Plamsid pTM017 was cloned into a SbfI restriction fragment of Puc57 with kanamycin resistance gene backbone. |

TABLE 4

Viral Vector Composition: Vector Genome and Caspid

| SEQUENCE ELEMENTS | SEQUENCE IDENTIFIER (SEQ. ID. NO:) |
|---|---|
| Viral Vector NVS1 (Generated from plasmid TM017 or TM042, and AAVRep2/Cap2 plasmid) The viral vector contains a self complementary genome with the following genomic elements in the 5' to 3' direction packaged in the viral capsid AAV2. | |
| SC5' ITR | 36 |
| Reverse Complementary sequence of SV40polyA | 62 |
| Reverse Complementary sequence of HUMAN RLBP1 GENE CDS | 63 |
| Reverse Complementary sequence of Added KOZAK | 64 |
| Reverse Complementary sequence of Modified SV40INTRON | 65 |
| Reverse Complementary sequence of Human RLBP1 PROMOTER (short) | 66 |
| ΔITR | 1 |
| Human RLBP1 PROMOTER (short) | 3 |
| Modified SV40INTRON | 4 |
| Added Kozak | 5 |
| HUMAN RLBP1 GENE CDS | 6 |
| SV40 POLYA | 8 |
| 3' ITR | 9 |

TABLE 4-continued

Viral Vector Composition: Vector Genome and Caspid

| SEQUENCE ELEMENTS | SEQUENCE IDENTIFIER (SEQ. ID. NO:) |
|---|---|
| CAPSID PROTEIN SEQUENCE OF NVS1 | |
| AAV2 CAPSID SEQUENCE | 19, 68 and 69 (Encoded by 18) |
| Viral Vector NVS2 (Generated from plasmid TM017 or TM042, and AAVRep2/Cap8 plasmid) The viral vector contains a self complementary genome with the following genomic elements in the 5' to 3' direction packaged in the viral capsid AAV8. | |
| SC5' ITR | 36 |
| Reverse Complementary sequence of SV40polyA | 62 |
| Reverse Complementary sequence of HUMAN RLBP1 GENE CDS | 63 |
| Reverse Complementary sequence of Added KOZAK | 64 |
| Reverse Complementary sequence of Modified SV40INTRON | 65 |
| Reverse Complementary sequence of Human RLBP1 PROMOTER (short) | 66 |
| ΔITR | 1 |
| Human RLBP1 PROMOTER (short) | 3 |
| Modified SV40INTRON | 4 |
| Added Kozak | 5 |
| HUMAN RLBP1 GENE CDS | 6 |
| SV40 POLYA | 8 |
| 3' ITR | 9 |
| CAPSID PROTEIN SEQUENCE OF NVS2 | |
| AAV8 CAPSID SEQUENCE | 21, 70, and 71 (Encoded by 20) |
| Viral Vector NVS3 (Generated from plasmid TM037 and AAVRep2/Cap2 plasmid) The viral vector genome contains the following genomic elements in the 5' to 3' direction | |
| 5' ITR | 2 |
| HUMAN RLBP1 PROMOTER (long) | 10 |
| ADDED KOZAK | 5 |
| HUMAN RLBP1 GENE CDS | 6 |
| SV40 POLYA | 8 |
| 3' ITR | 9 |
| CAPSID PROTEIN SEQUENCE OF NVS3 | |
| AAV2 CAPSID SEQUENCE | 19, 68 and 69 (Encoded by 18) |
| Viral Vector NVS4 (Generated from plasmid TM037 and AAVRep2/Cap8 plasmid) The viral vector genome contains the following genomic elements in the 5' to 3' direction | |
| 5' ITR | 2 |
| HUMAN RLBP1 PROMOTER (long) | 10 |
| ADDED KOZAK | 5 |
| HUMAN RLBP1 | 6 |

TABLE 4-continued

Viral Vector Composition: Vector Genome and Caspid

| SEQUENCE ELEMENTS | SEQUENCE IDENTIFIER (SEQ. ID. NO:) |
|---|---|
| GENE CDS | |
| SV40 POLYA | 8 |
| 3' ITR | 9 |
| CAPSID PROTEIN SEQUENCE OF NVS4 | |
| AAV8 CAPSID SEQUENCE | 21, 70, and 71 (Encoded by 20) |

Viral Vector NVS5 (Generated from plasmid AG007 and AAVRep2/Cap2 plasmid) The viral vector genome contains the following genomic elements in the 5' to 3' direction

| | |
|---|---|
| 5' ITR | 2 |
| HUMAN RPE65 PROMOTER | 11 |
| ADDED-KOZAK | 5 |
| HUMAN RLBP1 GENE CDS | 6 |
| SV40 POLYA | 8 |
| RLBP1 INTRONIC SEQUENCE AS STUFFER SEQUENCE | 14 |
| 3' ITR | 9 |
| CAPSID PROTEIN SEQUENCE OF NVS5 | |
| AAV2 CAPSID SEQUENCE | 19, 68 and 69 (Encoded by 18) |

Viral Vector NVS6 (Generated from plasmid AG007 and AAVRep2/Cap8 plasmid) The viral vector genome contains the following genomic elements in the 5' to 3' direction

| | |
|---|---|
| 5' ITR | 2 |
| HUMAN RPE65 PROMOTER | 11 |
| ADDED-KOZAK | 5 |
| HUMAN RLBP1 GENE CDS | 6 |
| SV40 POLYA | 8 |
| RLBP1 INTRONIC SEQUENCE AS STUFFER SEQUENCE | 14 |
| 3' ITR | 9 |
| CAPSID PROTEIN SEQUENCE OF NVS6 | |
| AAV8 CAPSID SEQUENCE | 21, 70, and 71 (Encoded by 20) |

Viral Vector NVS7 (Generated from plasmid TM039 and AAVRep2/Cap2 plasmid) The viral vector genome contains the following genomic elements in the 5' to 3' direction

| | |
|---|---|
| 5' ITR | 2 |
| CMV Enhancer and CBA PROMOTER (GENEBANK ACCESSION DD215332 FROM BP 1 to BP 161) | 22 |
| ADDED KOZAK | 5 |
| HUMAN RLBP1 GENE CDS | 6 |
| SV40 POLYA | 8 |
| REVERSE COMPLEMENT OF RLBP1 INTRONIC SEQUENCE AS STUFFER SEQUENCE (NT 010274.17) | 23 |
| 3' ITR | 9 |
| CAPSID PROTEIN SEQUENCE OF NVS7 | |
| AAV2 CAPSID SEQUENCE | 19, 68 and 69 (Encoded by 18) |

TABLE 4-continued

Viral Vector Composition: Vector Genome and Caspid

| SEQUENCE ELEMENTS | SEQUENCE IDENTIFIER (SEQ. ID. NO:) |
|---|---|

Viral Vector NVS8 (Generated from plasmid TM039 and AAVRep2/Cap8 plasmid) The viral vector genome contains the following genomic elements in the 5' to 3' direction

| | |
|---|---|
| 5' ITR | 2 |
| CMV Enhancer and CBA PROMOTER (GENEBANK ACCESSION DD215332 FROM BP 1 to BP 161) | 22 |
| ADDED KOZAK | 5 |
| HUMAN RLBP1 GENE CDS | 6 |
| SV40 POLYA | 8 |
| REVERSE COMPLEMENT OF RLBP1 INTRONIC SEQUENCE AS STUFFER SEQUENCE (NT 010274.17) | 23 |
| 3' ITR | 9 |
| CAPSID PROTEIN SEQUENCE OF NVS8 | |
| AAV8 CAPSID SEQUENCE | 21, 70, and 71 (Encoded by 20) |

Viral Vector NVS9 (Generated from plasmid TM040 and AAVRep2/Cap2 plasmid) The viral vector genome contains the following genomic elements in the 5' to 3' direction

| | |
|---|---|
| 5' ITR | 2 |
| HUMAN RLBP1 PROMOTER (short) | 3 |
| MODIFIED SV40 INTRON | 4 |
| ADDED KOZAK | 5 |
| HUMAN RLBP1 GENE CDS | 6 |
| SV40 POLYA | 8 |
| REVERSE COMPLEMENT OF RLBP1 INTRONIC SEQUENCE AS STUFFER SEQUENCE (NT_010274.17) | 23 |
| 3' ITR | 9 |
| CAPSID PROTEIN SEQUENCE OF NVS9 | |
| AAV2 CAPSID SEQUENCE | 19, 68 and 69 (Encoded by 18) |

Viral Vector NVS10 (Generated from plasmid TM040 and AAVRep2/Cap8 plasmid) The viral vector genome contains the following genomic elements in the 5' to 3' direction

| | |
|---|---|
| 5' ITR | 2 |
| HUMAN RLBP1 PROMOTER (short) | 3 |
| MODIFIED SV40 INTRON | 4 |
| ADDED KOZAK | 5 |
| HUMAN RLBP1 GENE CDS | 6 |
| SV40 POLYA | 8 |
| REVERSE COMPLEMENT OF RLBP1 INTRONIC SEQUENCE AS STUFFER | 23 |

TABLE 4-continued

Viral Vector Composition: Vector Genome and Caspid

| SEQUENCE ELEMENTS | SEQUENCE IDENTIFIER (SEQ. ID. NO:) |
|---|---|
| SEQUENCE (NT_010274.17) | |
| 3' ITR | 9 |
| CAPSID PROTEIN SEQUENCE OF NVS10 | |
| AAV8 CAPSID SEQUENCE | 21, 70, and 71 (Encoded by 20) |
| Viral vector scAAV8-pRLBP1(short)-eGFP (eGFP Reporter viral vector generated from plasmid TM016 and AAVRep2/Cap8 plasmid) The viral vector contains a self complementary genome with the following genomic elements in the 5' to 3' direction packaged in the viral capsid AAV8. | |
| SC5' ITR | 36 |
| Reverse Complementary sequence of SV40polyA | 62 |
| Reverse Complementary sequence of eGFP | 67 |
| Reverse Complementary sequence of Added KOZAK | 64 |
| Reverse Complementary sequence of Modified SV40INTRON | 65 |
| Reverse Complementary sequence of Human RLBP1 PROMOTER (short) | 66 |
| ΔITR | 1 |
| HUMAN RLBP1 PROMOTER (short) | 3 |
| MODIFIED SV40 INTRON | 4 |
| ADDED KOZAK | 5 |
| eGFP | 24 |
| SV40 POLYA | 8 |
| 3' ITR | 9 |
| CAPSID PROTEIN SEQUENCE OF Viral vector scAAV8-pRLBP1(short)-eGFP | |
| AAV8 CAPSID SEQUENCE | 21, 70, and 71 (Encoded by 20) |
| Viral Vector AAV8-pRLBP1(long)-eGFP (eGFP Reporter viral vector generated from plasmid TM035 and AAVRep2/Cap8 plasmid) The viral vector genome contains the following genomic elements in the 5' to 3' direction | |
| 5' ITR | 2 |
| HUMAN RLBP1 PROMOTER (long) | 10 |
| ADDED KOZAK | 5 |
| eGFP | 24 |
| SV40 POLYA | 8 |
| 3' ITR | 9 |
| CAPSID PROTEIN SEQUENCE OF Viral Vector AAV8-pRLBP1(long)-eGFP | |
| AAV8 CAPSID SEQUENCE | 21, 70, and 71 (Encoded by 20) |
| Viral Vector AAV8-pRPE65-eGFP (eGFP Reporter viral vector generated from plasmid AG004 and AAVRep2/Cap8 plasmid) The viral vector genome contains the following genomic elements in the 5' to 3' direction | |
| 5' ITR | 2 |
| HUMAN RPE65 PROMOTER | 11 |
| ADDED KOZAK | 5 |
| eGFP | 24 |
| SV40 POLYA | 8 |
| RLBP1 INTRONIC SEQUENCE AS STUFFER SEQUENCE (NT_010274.17) | 14 |
| 3' ITR | 9 |
| CAPSID PROTEIN SEQUENCE OF Viral Vector AAV8-pRPE65-eGFP | |
| AAV8 CAPSID SEQUENCE | 21, 70, and 71 (Encoded by 20) |
| Viral Vector AAV8-pVMD2-eGFP (eGFP Reporter viral vector generated from plasmid AG006 and AAVRep2/Cap8 plasmid) The viral vector genome contains the following genomic elements in the 5' to 3' direction | |
| 5' ITR | 2 |
| HUMAN VMD2 PROMOTER | 12 |
| ADDED KOZAK | 5 |
| eGFP | 24 |
| SV40 POLYA | 8 |
| RLBP1 INTRONIC SEQUENCE AS STUFFER SEQUENCE (NT_010274.17) | 14 |
| 3' ITR | 9 |
| CAPSID PROTEIN SEQUENCE OF Viral Vector AAV8-pVMD2-eGFP | |
| AAV8 CAPSID SEQUENCE | 21, 70, and 71 (Encoded by 20) |
| Viral Vector NVS11 (Generated from plasmid AG012 and AAVRep2/Cap8 plasmid) The viral vector genome contains the following genomic elements in the 5' to 3' direction | |
| 5' ITR | 2 |
| SYNUCLEIN INTRONIC SEQUENCE AS STUFFER SEQUENCE | 13 |
| SV40 POLYA | 8 |
| RLBP1 INTRONIC SEQUENCE AS STUFFER SEQUENCE (NT_010274.17) | 14 |
| 3' ITR | 9 |
| CAPSID PROTEIN SEQUENCE OF NVS11 | |
| AAV8 CAPSID SEQUENCE | 21, 70, and 71 (Encoded by 20) |

Example 2

Subretinal Injection of rAAV Vectors in Mice

2.1 Subretinal Injection of rAAV Vectors in Mice

Subretinal injection of an rAAV vector can achieve efficient transduction of RPE and other retinal cells because subretinal injection induces a bleb of concentrated virus in intimate contact with RPE cells and the neural retina. In addition, the subretinal space has a relatively high degree of immunoprivilege and typically very little evidence of inflammation is seen in the vicinity of the injection site. Thus, subretinal injection was a preferred route for delivery of rAAV vectors in mouse retina. However, other routes of delivery may be used, for example, intravitreal injection.

Supplies/reagents:
Leica M844 F40 Ophthalmic Surgical Microscope
1% cyclopentolate: Bausch & Lomb Cat#965911
2.5%-10% phenylephrine: Altaire Pharmaceuticals Cat#05626
0.5% Proparacaine: Bausch & Lomb Cat#NDC 54799-500-12
10 µl Hamilton syringe: VWR Cat#89184-476
33G blunt-ended needle: Hamilton Cat#7803-05
Fluorescein sodium salt: Sigma Cat#F6377

Test Articles Used in this Example:
scAAV8-pRLBP1(short)-eGFP viral vector $1\times10^9$ vg/eye
AAV8-pRLBP1(long)-eGFP viral vector $1\times10^9$ vg/eye
AAV8-pRPE-eGFP viral vector $1\times10^9$ vg/eye
AAV8-VMD2-eGFP viral vector $1\times10^9$ vg/eye Protocol:
The subretinal injection was performed either in both eyes or unilaterally in the right eye. All procedures were performed under aseptic conditions, using sterile reagents, syringes and appropriate personal protection equipment.

Subretinal Injection Procedures:
The mouse pupils were dilated by 1 drop of 1% cyclopentolate and followed by 1 drop of 2.5%-10% phenylephrine
The mouse was anesthetized by using Avertin (250 mg/kg) i.p. and a drop of 0.5% Proparacine topically (local anesthetic) in the eye
An approximately 0.5 mm incision was made nasally, posterior to the limbus with a microscalpel
The blunt-ended needle on the 10 µl Hamilton syringe was inserted tangentially through the scleral incision toward the temporal retina. The needle was advanced until resistance was felt. The 1 µl of diluted rAAV vector (containing fluorescein with the concentration of 1:50) was then injected slowly into the subretinal space, and the needle is withdrawn through the incision
The eye was examined and the success of the subretinal injection was confirmed by visualization of a bleb containing fluorescein. The success of injection and the degree of retinal damage (hemorrhage) were scored.
An antibiotic ointment was applied to the eye immediately after the injection

2.2. rAAV Vectors Induced GFP Expression and its Cell-Type Specifics in Mouse Retina To study the rAAV vector-induced gene transduction and cell-type specifics in the mouse retina, the eGFP expression in retinal cross sections and RPE/retina flatmounts were examined. One approach used to identify the eGFP expressing cell types was to co-label eGFP positive cells with retinal cell markers by immunocytochemistry staining in cryosections.

Supplies/Reagents:
Primary Antibodies for Immunocytochemistry Staining:
Anti-CRALBP antibody: Thermo cat#MA1-813
Anti-GFAP antibody: Covance cat#SMI-21
Anti-Opsin Blue antibody: Millipore cat#AB 5407
Anti-Opsin Red antibody: Millipore cat#AB5405
Anti-Vimentin antibody: Santa Cruz cat#sc-7557
Anti-PKC α antibody: C-20 Santa Cruz cat#sc -208
Secondary Antibodies for Immunocytochemistry Staining:
Goat anti-mouse IgG: Invitrogen Cat#A11005
Goat anti-rat IgG: Invitrogen Cat#A11007
Donkey anti-rabbit IgG: Invitrogen Cat#A21207
Other Supplies/Reagents:
Vectashield Mounting Medium with DAPI: Vector Laboratories, Burlingame Cat#H-1200),
Zeiss Imaging system, AxioVision Software
Zeiss LSM 510 confocal microscope, ZEN version of the Zeiss software Protocol:

The mouse eyeball was removed and placed in 4% PFA (paraformaldehyde) for 2 hours at 25° C. and then in PBS buffer for 1-3 days in 4° C. till dissection. The cornea, lens and vitreous were removed from the eye ball and the retinal and RPE/choroid was flatmounted with Vectashield mounting medium on to the slide. The GFP expression in flatmount was captured by Zeiss Imaging system and quantified using AxioVision Software. After imaging, the slides with retinal flatmounts were placed in 0.25% triton buffer at 25° C. for 30 min and then the retinal flatmounts were removed from the slides. The eGFP positive areas of the retina flatmounts were cut and embedded in OCT and then cryosectioned. The immunocytochemistry staining using retinal cell markers was applied in the cryosections. The images were captured by Zeiss LSM 510 confocal microscope and ZEN version of the Zeiss software.

The Immunocytochemistry Staining Procedures:
Day 1.
  air dry sections at room temperature 1 hour.
  place slides in PBS+0.25% Triton 15 min×2
  block in 1% BSA+PBS+0.25% Triton 90 min
  incubate slides with primary antibody in 1% BSA+PBS+ 0.25% Triton at 4° C. overnight
Day 2.
  take out slides from 4° C., leave them at 25° C. for 30 min
  wash slides in PBS+0.25% Triton 15 min×2
  incubate slides with secondary 1:800 at 25° C. for 90 min
  wash slides in PBS+0.25% Triton 15 min×2
  mount slides with Vectashield Mounting Medium with DAPI

TABLE 5

The retinal cell markers and dilutions used in the study

| Cell Type | Cell Marker | Dilutions |
|---|---|---|
| Müller cell | Anti-CRALBP | 1:1000 |
|  | Anti-Vimentin | 1:100 |
|  | Anti-GFAP | 1:1000 |
| Photoreceptor | Anti-Opsin Red/Green | 1:250 |
|  | Anti-Opsin Blue | 1:250 |
| Neuron in INL | Anti-PKCα | 1:200 |
| Astrocytes | Anti-GFAP | 1:1000 |

TABLE 6

Immunohistochemistry results that describe the transduction of cell types by test viral vectors.

| Cell Type | Cell Marker | scAAV8-pRLBP1(short)-eGFP | AAV8-pRLBP1(long)-eGFP | AAV8-pRPE65-eGFP | AAV8 pVMD2-eGFP |
|---|---|---|---|---|---|
| RPE | | + | + | + | + |
| Müller cell | CRALBP | + | + | − | − |
| | Vimentin | + | + | − | − |
| | GFAP | + | + | − | − |
| Photoreceptor | Opsin Red/Green | − | + | + | + |
| | Opsin Blue | − | − | + | + |
| | Recoverin | ND | ND | + | ND |
| Neuron in INL | PKCα | − | − | − | − |
| Ganglion Cell | NeuN | − | ND | ND | ND |
| Astrocytes | GFAP | − | − | − | − |

+, indicates expression of GFP in a given cell type
−, no GFP expression
ND, Not Determined Results:

All tested viral vectors were functional in the mouse retina.

scAAV8-pRLBP1(short)-eGFP vector leads to selective expression of GFP in RPE and the Müller cells in the neural retina.

AAV8-pRLBP1(long)-eGFP leads to expression of GFP in RPE, Müller cells and photoreceptors in the neural retina.

AAV8-pRPE65-eGFP and AAV8-pVMD2-eGFP lead to GFP expression in RPE and photoreceptors in the neural retina.

Conclusion

These results demonstrate that the combination of promoter, AAV genome conformation and AAV capsid sequence can lead to different transduction properties in specific cell types, to achieve the desired effect. Expression of the RLBP1 gene product in RPE and Müller cells of the retina, represents the desired on-target cell type expression. RLBP1 short promoter packaged in a self-complementary genome in conjunction with an AAV8 serotype capsid induces gene expression in RPE and Müller cells in the neural retina without off-target cell expression.

The RLBP1-long promoter packaged in a single-stranded genome in conjunction with an AAV8 serotype capsid induces gene expression in RPE and Müller cells, which are on-target cell types, and also in photoreceptors, which is an off-target cell type.

The RPE65 and VMD2 promoter packaged in a single-stranded genome in conjunction with an AAV8 serotype capsid induces gene expression in RPE cells but also in photoreceptors, which is an off-target cell type.

Example 3 mRNA Based Assay to Measure Vector-Mediated Expression of a Human RLBP1 Transgene Relative to Endogenous Mouse RLBP1 mRNA Expression The expression levels and tissue specificity of an rAAV-transduced transgene will vary depending on the vector serotype, the vector genome, the tissue-specific promoter used and the dose injected. A goal of gene replacement therapy is to achieve a level of expression that is sufficient to compensate for the missing endogenous gene expression while not over expressing the gene to toxic levels.

An assay has been developed to measure the vector-mediated expression of human RLBP1 mRNA relative to the endogenous levels of mouse RLBP1 mRNA following subretinal injections of various AAV vectors at different doses in wild-type mice. This assay utilized Taqman® Gene Expression Assays containing primers and probes for specifically detecting human or mouse RLBP1 cDNA. Prior to performing the experiment the Taqman® Gene Expression Assays were tested for species specificity using plasmid DNA containing either human or mouse RLBP1 cDNA sequences. In brief, Taqman® reagents were used to co-amplify either mouse or human RLBP1 cDNA with mouse GAPDH cDNA as an endogenous control. The levels of the mouse or human RLBP1 were normalized to the internal GAPDH control and then these normalized levels were compared with one another.

Supplies/reagents:
  RNA extraction
    Qiagen RNeasy micro kit (Qiagen cat #74004)
    Qiagen RNase-Free DNase Set (Qiagen cat#79254)
    Beta-Mercaptoethanol (Sigma cat#63689)
    Qiagen Stainless-Steel 5 mm beads (Qiagen cat#69989)
    2.0 ml Seal Rite Microcentrifuge tube (USA Scientific cat#1620-2700)
    Qiagen TissueLyser II (cat#85300)
  cDNA Synthesis
    High Capacity cDNA Reverse Transcription Kit (Applied Biosystems cat#4368814)
    RNase Inhibitor (Applied Biosystems cat#N8080119)
    BioRad Thermal cycler
  Relative Quantitation PCR
    2× TaqMan® Universal PCR Master Mix (Applied Biosystems cat#4304437)
    20× TaqMan® Gene Expression Assay for human RLBP1 (Applied Biosystems cat#4331182: Hs00165632.m1)
    20× TaqMan® Gene Expression Assay for mouse RLBP1 (Applied Biosystems cat#4331182: Mm00445129.m1)
    20× Applied Biosystems® Mouse GAPD (GAPDH) Endogenous Control (VIC®/MGB Probe, Primer Limited) (Applied Biosystems cat#4352339E)
    Applied Biosystems Real-Time PCR machine model 7900HT.

Test articles used in this example:
  NVS8 viral vector
  NVS10 viral vector
  NVS4 viral vector
  NVS2 viral vector
  NVS6 viral vector Protocol:

At the termination of the in vivo experiment neural retina was dissected out of the eyes, placed in a 2 ml microcentrifuge tube and flash frozen on dry ice. The remaining eye cup (minus retina and lens) was frozen in a separate tube. Samples were stored at −80° C. until RNA isolation. Total RNA was extracted using a Qiagen RNeasy micro kit with DNase treatment. For tissue homogenization and lysis, a Qiagen TissueLyzer was used. In particular, a 5 mm stainless-steel bead was added to each tissue-containing tube while on dry ice. Samples were transferred to room temperature and 350 µl of buffer RLT containing 1% beta-mercaptoethanol was added. Samples were processed on the TissueLyzer with a shaking frequency of 30 Hz for two 2 minute cycles. The standard Qiagen RNeasy micro kit protocol for RNA extraction with DNase treatment was then followed with one minor modification. Prior to elution the RNA column was allowed to air dry for >10 minutes to ensure elimination of residual ethanol. Total RNA was stored at −80° C. until ready for cDNA synthesis.

Total RNA concentration was determined using a Nanodrop spectrophotometer. Each sample was adjusted to a final concentration of 50 ng/µl. cDNA was generated using the Applied Biosystems High Capacity cDNA reverse transcriptase kit. A master mix of reagents from the High Capacity cDNA RT kit was prepared such that each 10 µl contained 2 µl of 10× High Capacity RT buffer, 0.8 µl of 25× dNTPs (100 mM), 2 µl of Reverse Transcriptase random primers, 0.4 µl of RNase inhibitor, 1 µl of Multiscribe Reverse transcriptase and 3.8 µl of RNAse-free water. 10 µl of the 50 ng/µl stock of each total RNA was dispensed into a well of a 96-well PCR amplification plate and then 10 µl of the RT master mix was added to each well. The plate was placed in a Bio-Rad thermal cycler and operated using the following parameters: 25° C. for 10 min, 37° C. for 120 min., 85° C. for 5 min then hold at 4 degrees until terminate program. cDNA was stored at −20° C. prior to Relative quantitative PCR reaction set-up.

The cDNA concentration was adjusted to a final concentration of 20 ng/µl by adding 5 µl of RNAse-free water to each well of the cDNA reaction (this is based on the initial total RNA concentration and assuming 100% conversion to cDNA). For each cDNA sample set up two different multiplex qPCR reactions; one using the mouse RLBP1 Taqman Expression Assay probes with the mouse GAPDH endogenous control, and the other using the human RLBP1 Taqman Expression Assay probes with the mouse GAPDH endogenous control. Each of these two reactions were performed in duplicate for each sample. For each sample, 5 µl of the 20 ng/µl cDNA sample was dispensed into a well of a 385-well plate. Two separate master mixes were prepared, one for the mouse RLBP1 Taqman assay and one for the human RLBP1 assay such that each 15 µl of mixture contained 10 µl of 2× TaqMan®Universal PCR Master Mix, 1 µl of 20× TaqMan® Gene Expression Assay for either mouse or human RLBP1, 1 µl of 20× Applied Biosystems® Mouse GAPD (GAPDH) Endogenous Control, and 3 µl of RNAse-free water. 15 µl of the appropriate master mix was dispensed into the well containing the cDNA. The plate was placed in an ABI 7900HT Real Time PCR machine and run using the relative quantitation program with the following parameters: an initial incubation at 50° C. for 2 min then 40 cycles of the following two steps, 15 sec. at 95° C. and 1 min. at 60° C.

The relative quantitation plate results were imported into a RQ study document using the ABI RQ Manager 1.2. The data were analyzed using the automatic threshold setting to generate average and average ΔCt which is the difference in Ct readings of the RLBP1 cDNA (mouse or human) minus the Ct of the internal endogenous GAPDH. The data were exported into Microsoft Excel and used to calculate the ΔΔCt value by subtracting the mouse RLBP1 ΔCt value from the human RLBP1 ΔCt for each sample. The relative expression was calculated using the calculation $2^{-\Delta\Delta Ct}$ this expresses the relative expression of human RLBP1 as a fold change of the mouse endogenous RLBP1 expression. To portray the results as expression of human RLBP1 as a percent of the mouse endogenous expression the relative expression value was multiplied by 100.

Results: mRNA Expression.

FIG. 1A illustrates that NVS8, NVS4, NVS2 and NVS6 successfully transduce both the neural retina cells and the RPE cells in the posterior eyecup. Vector NVS10 transduces the RPE cells but barely at the level of detection limit in the neural retina.

FIG. 1B illustrates that NVS2 is the only vector to show mRNA expression in the neural retina at a lower dose of $1 \times 10^8$ vg/eye.

Conclusion

These surprising results demonstrated that the specific combination of promoter, AAV genome conformation, and AAV capsid sequence can lead to different transduction properties in different cell types in the retina. In general, all tested vectors successfully lead to vector-mediated human RLBP1 mRNA expression. More specifically, NVS2 is the most potent vector in expressing human RLBP1 mRNA in the RPE cells (in the posterior eyecup) and in the neural retina in both doses tested ($1 \times 10^9$ and $1 \times 10^8$ vg/eye), while NVS4 and NVS6 lead to detectable vector-mediated human RLBP1 mRNA expression at the dose of $1 \times 10^9$ vg/eye, and only in the RPE at the dose of $1 \times 10^8$ vg/eye. NVS8 and NVS10 lead to detectable mRNA expression in the RPE and neural retina at the dose of $1 \times 10^9$ vg/eye but almost at the detection limit at the dose of $1 \times 10^8$ vg/eye.

Example 4

Electroretinogram-Based Dark Adaptation Assay

One approach for assessing treatments that modify the visual cycle is to quantify the recovery of visual function in the dark following a bright light exposure (i.e. dark adaptation). Dark adaptation after extensive light exposure is driven largely by the ability of the eye to regenerate photopigment via the visual cycle. Modifications to the visual cycle achieved through treatment will therefore lead to a change in the kinetics of dark adaptation.

An assay has been developed to monitor the recovery of visual function in mice that is based on quantifying dark adaptation using an electroretinogram (ERG). The ERG-based assay typically proceeds over two days with an initial baseline and subsequent follow-up measurement to assess recovery after exposure to light that bleaches a fraction of the photopigment (photobleach). This procedure developed for testing the invention first determines the maximum electrical response of each eye 5 ms after a flash of light during the a-wave portion of the ERG trace. The test subsequently compares the 5 ms a-wave amplitude 4 hours after a photobleach to assess the fraction of maximum amplitude recovered in that time. If the visual cycle is functioning normally, the ERG amplitude will approach baseline values in 4 hours. A delayed visual cycle will result in lower recovery of photopigment with a corresponding reduction in ERG a-wave amplitude recovery after photobleach.

Supplies/Reagents:
 ERG system: Diagnosys, Espion E2 console with Color-Dome full field ganzfeld stimulator
 Ketamine
 Xylazine
 2.5% phenylephrine
 1% cyclopentolate
 0.5% proparacaine
 Active electrode: Gold loop contact lens electrode (Mayo, part number N30)
 Reference electrode: Nasopharyngeal electrode (Grass, part number F-ERG-G)
 Ground electrode: Platinum needle electrode (Grass, part number F-E2)
 Hydrating drops: Novartis, Genteal Mild to Moderate
 Syringe pump: Harvard Apparatus, part number Pump 11 Plus Protocol:

Mice are placed in the dark overnight for approximately 20 hours before baseline ERGs are recorded. Immediately preceding recording, eyes are dilated with 1-2 drops of 1% cyclopentolate and 1-2 drops of 2.5% phenylephrine. 1-2 drops of 0.5% proparacaine (a topical anesthetic) are also applied. Mice are then anesthetized with an intraperitoneal injection of a cocktail of ketamine and xylazine (100-150 mg/kg and 5-10 mg/kg, respectively). Three electrodes are then placed to enable recording an ERG from one eye per mouse. The active electrode on the eye is a gold loop contact lens, the reference is a nasopharyngeal electrode placed in the mouth and the ground is a subdermal platinum needle electrode placed on the back just behind the head. Eyes are kept moist and electrical contact is maintained through continuous application of hydrating drops with a syringe pump (300 µl/hour). ERG amplitude is recorded by averaging the electrical response to three white flashes (2.7 log scotopic candela second per square meter) delivered by the xenon lamp in the ganzfeld dome. A-wave amplitude reported is the voltage measured 5 ms after the xenon flash as assessed using software analysis routines developed for this purpose (Mathworks, Matlab).

Dark adaptation is assessed by quantifying the ERG a-wave amplitude 4 hours after a photobleach. These experiments typically occur 48 hours after baseline determination. Mice are first housed in the dark overnight just as with the baseline measurements so that ERG recordings occur approximately 20 hours later. Eyes are dilated with 1-2 drops of 2.5% phenylephrine and 1-2 drops of 1% cyclopentolate immediately preceding photobleach. A sequence of 16 flashes of light (3.7 log scotopic candela second per square meter) is then delivered to the eye resulting in a photopigment bleach. Mice are placed back in the dark for 4 hours to recover visual function. ERGs are then recorded utilizing the same protocol used for the baseline determination. The recovery of visual function for each eye is defined as:

$$DA = \frac{a\text{-wave amplitude 4 hours post-bleach}}{\text{baseline } a\text{-wave amplitude}}$$

Figure 2:
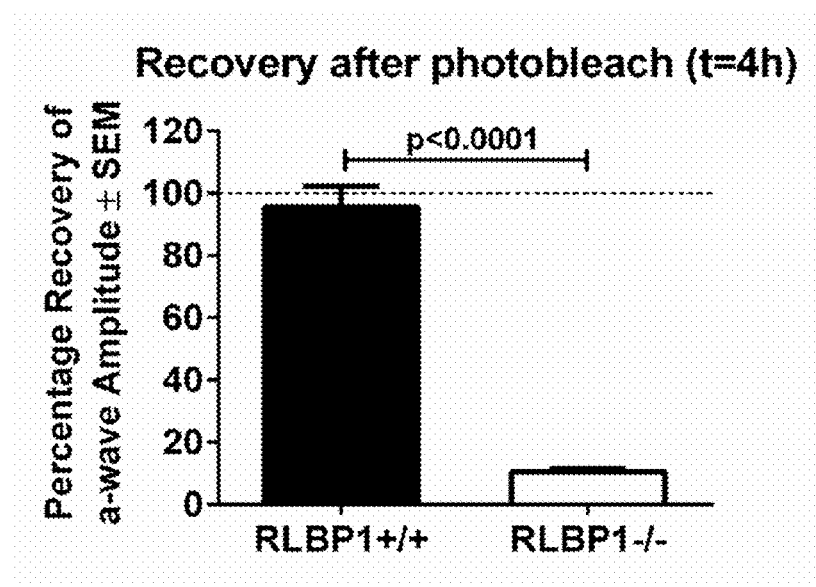
FIG. 2. Dark adaptation in RLBP1 KO (−/−) and wild-type (+/+) mice.

FIG. 2 illustrates the results of the assay when applied to RLBP1-/- and RLBP1+/+mice. RLBP1+/+mice exhibit nearly full recovery (up to 96%) 4 hours post-bleach. In contrast, RLBP1-/- mice recover minimal visual function (11%) at the same time point due to severely delayed visual cycle kinetics (Saari et al 2001). This 8-9 fold window between RLBP1+/+and -/- mice is the assay window achievable for testing vectors injected into RLBP1-/- mice.

Using the ERG-based dark adaptation assay described above, the improvement of dark adaptation efficiency is tested in RLBP1 knockout (KO) mice where therapeutic vectors are introduced subretinally. Since the subretinal injection involves the displacement of neural retina from the RPE, it is crucial to determine if the neural retina is reattached to the RPE to avoid false negative results for the test articles in the ERG assay. One week after subretinal injection of viral vectors into mouse eyes, optical coherence tomography (OCT) is performed to visualize the condition of the retina. Eyes with unresolved retinal detachment were excluded from ERG measurement.

At each time point, mice were dark adapted overnight (>12 hours) and the ERG a-wave amplitude from each eye was established as the maximum dark adapted response to light (100%). The fully dark adapted eyes were then exposed to a series of bright flashes (as described in previous section) and a-wave amplitude was quantified 4 hours later. The term "percentage of normal" is defined as the percentage of the second a-wave recovery measurement with respect to the value obtained from the maximum a-wave recovery measurement.

Positive efficacy, or efficacious effect, is defined as the difference between test measurement and negative (naïve) control being statistically significant at a given time point post-injection.

Test Articles Used in this Example Includes:
 NVS1 viral vector
 NVS2 viral vector
 NVS3 viral vector
 NVS4 viral vector
 NVS5 viral vector
 NVS11 viral vector FIGS. 3A-D illustrate that viral vectors expressing RLBP1 improve the rate of dark adaptation in RLBP1 KO mice. Efficacy assessments were performed for each group vs. naïve controls with statistics calculated using a one way ANOVA with a Newman-Keuls multiple comparison test. The mean+3 standard deviations (SD) for naïve (uninjected) eyes and eyes receiving $1 \times 10^9$ vg/eye of the negative control AAV-null vector (NVS11) for all related studies are shown to indicate the approximate threshold for efficacy (a-wave recoveries above this line typically exhibit statistically significant efficacy). This approach for displaying the degree of efficacy is similar to that presented in gene therapy publications (Jacobson et al. 2006 and Roman et al. 2007).

Figure 3:
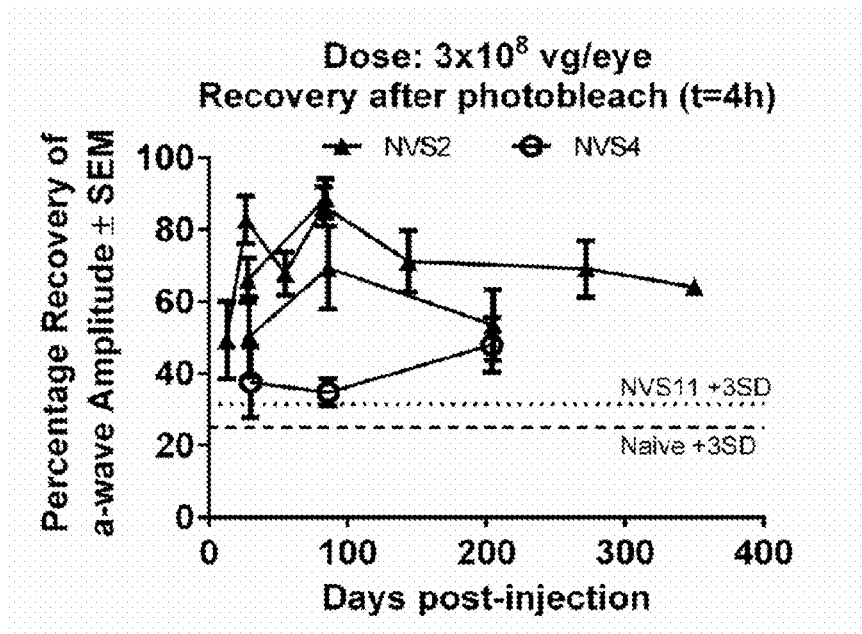
FIG. 3. Measurement of rate of dark adaptation of RLBP1 KO mice treated with various viral vectors: NVS1 (3B), NVS3 (3A and 3C), NVS3 (3B and 3D), NVS4 (3A and 3C) and NVS5 (3B and 3D).
Figure 3:
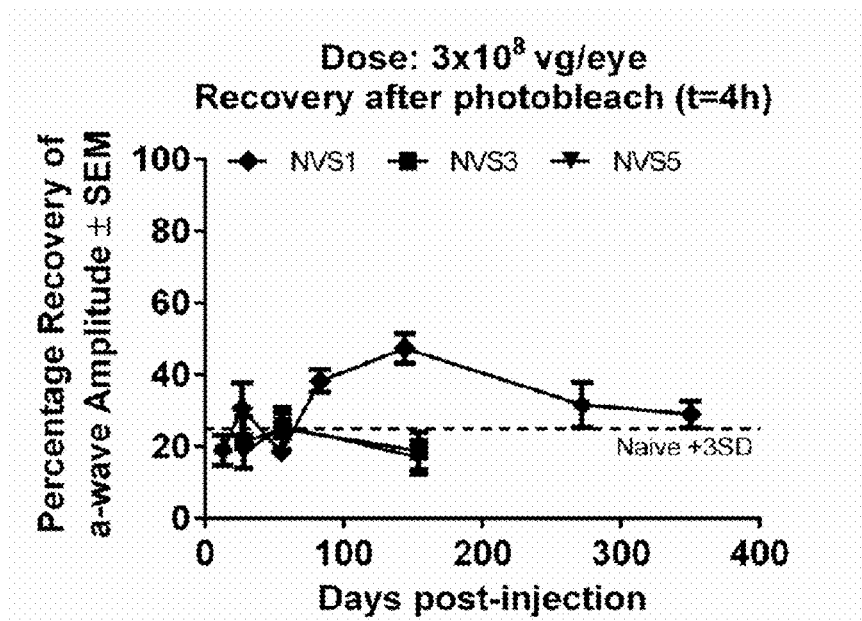
Figure 3:
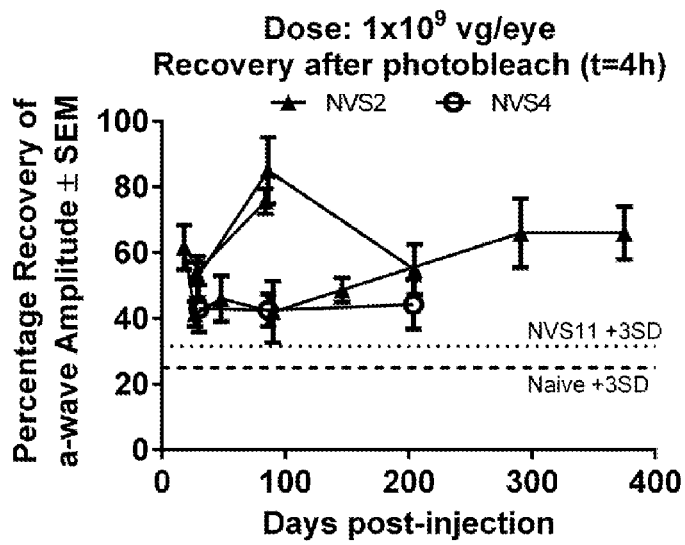
Figure 3:
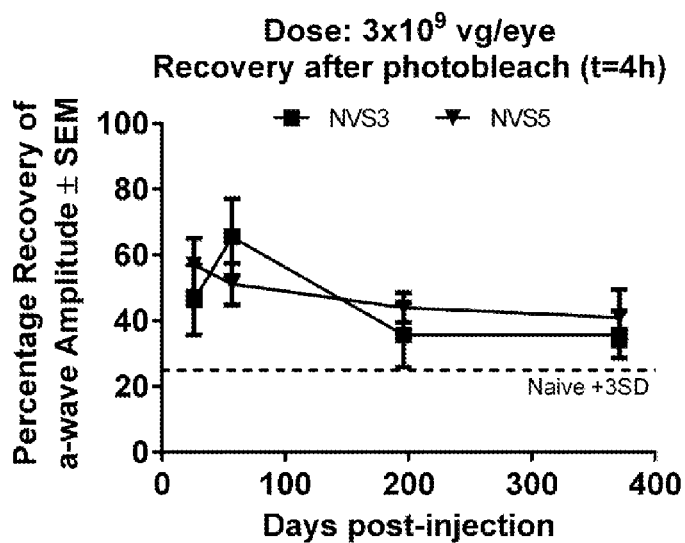

FIG. 3A shows that at a dose of $3 \times 10^8$ vg/eye, NVS2 is efficacious in improving the rate of dark adaptation as early as 14 days post treatment, and the efficacy endures at least 350 days. A dose of $3 \times 10^8$ vg/eye of NVS4 is also efficacious for at least 30-204 days post-treatment. NVS2 at the dose of approximately $3 \times 10^8$ vg/eye has been tested in RLBP1 KO mouse model in 3 independent experiments. In each experiment at all time points tested up to 350 days post injection the vector demonstrated efficacy.

FIG. 3B shows that NVS1 at the same dose ($3 \times 10^8$ vg/eye) demonstrated efficacy starting 84 days post-injection, with efficacy enduring to at least 350 days. NVS5 and NVS3 at the same dose did not demonstrate efficacy for up to 154 days post drug administration. Data presented in FIGS. 3A and 3B suggested that even though the viral vector genome is equivalent, the vector can be of different potency when packaged in different AAV capsid serotype (NVS1 versus NVS2). In addition, the specific combination of vector serotype, promoter, and vector genome conformation can affect the potency of the vector (NVS1 carries a self-complementary genome while NVS3 and NVS4 carry a single-stranded genome, all with different promoter sequences). This result further confirms that the combination of genome conformation and capsid serotype can affect the efficiency of recovery outcome.

FIG. 3C shows that, at the dose of $1\times10^9$ vg/eye, NVS2 is efficacious as early as 18 days post treatment, and the efficacy endures at least 375 days. At the dose of $1\times10^9$ vg/eye, NVS11, which is a negative control AAV-null vector, did not show significant difference in improvement of rate of dark adaptation when compared to uninjected control (individual data points not shown, but the historical mean+3SD line is displayed for comparison). A dose of $1\times10^9$ vg/eye of NVS4 is also efficacious for at least 30-204 days post-treatment.

FIG. 3D shows that at a dose of $3\times10^9$ vg/eye, NVS3 and NVS5, respectively, are efficacious in improving the rate of dark adaptation as early as day 26 post-treatment, and the efficacy endures at least 371 days.

Figure 4:
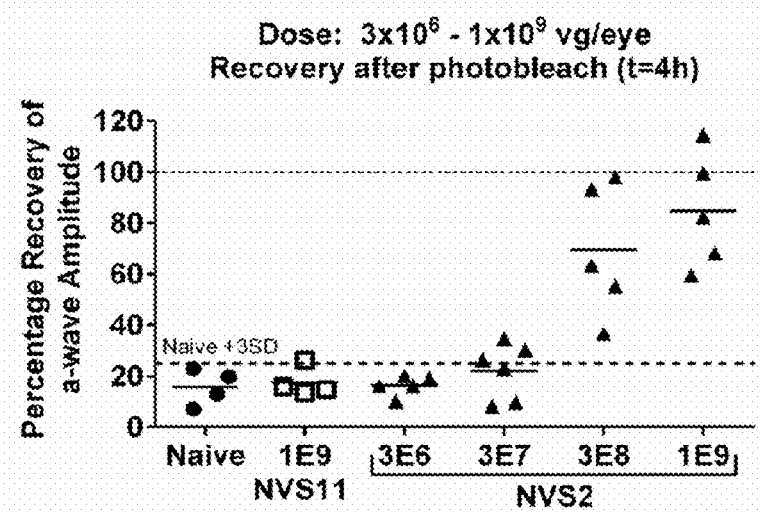
FIG. 4. Measurement of increased rate of dark adaptation of RLBP1 KO mice treated with various doses of NVS2 and NVS11 is shown in panel 4A. Panel 4B illustrates treatment efficacy of NVS2. Horizontal axis doses are indicated in scientific notation (for example, $3E6=3 \times 10^6$).
Figure 4:
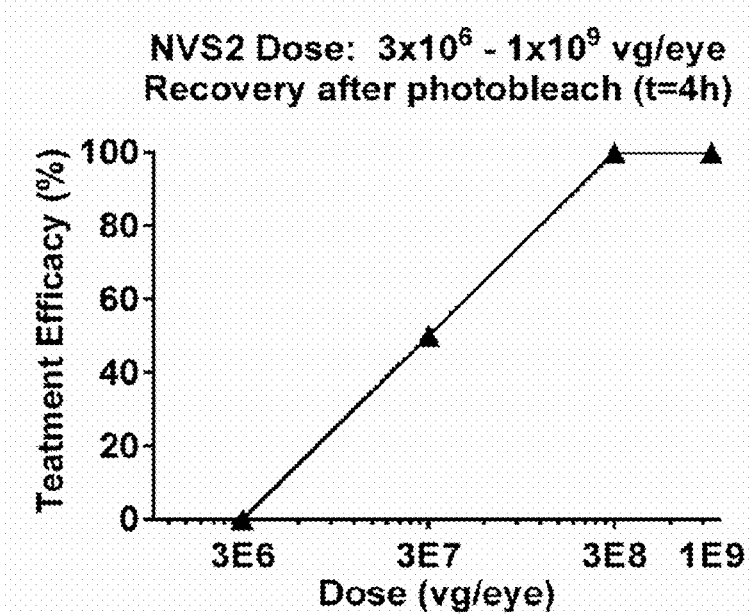

FIG. 4A demonstrates that NVS2 at multiple doses is efficacious at improving the rate of dark adaptation for at least 94 days post-injection. Both the $3\times10^8$ and $1\times10^9$ vg/eye groups were efficacious compared to naïve controls based on a one way ANOVA with a Newman-Keuls multiple comparison test. FIG. 4B displays the data from FIG. 4A in a different format. In this case, the plot displays the percentage of eyes/group with an a-wave recovery greater than that defined by the mean+3SD of the naïve group from several experiments. The results indicate that for NVS2, 50% of $3\times10^7$ vg/eye treated eyes and 100% of $3\times10^8$ and $1\times10^9$ vg/eye treated eyes demonstrated efficacious a-wave recovery, and that a dose-response curve is established.

Figure 5:
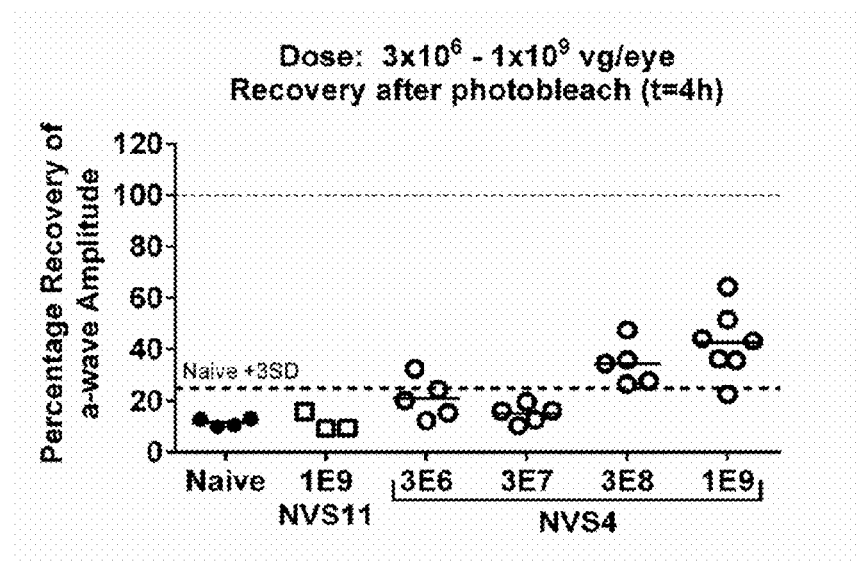
FIG. 5. Measurement of increased rate of dark adaptation of RLBP1 KO mice treated with various doses of NVS4 and NVS11 is shown in panel 5A. Panel 5B illustrates treatment efficacy of NVS4. Horizontal axis doses are indicated in scientific notation (for example, $3E6=3 \times 10^6$).
Figure 5:
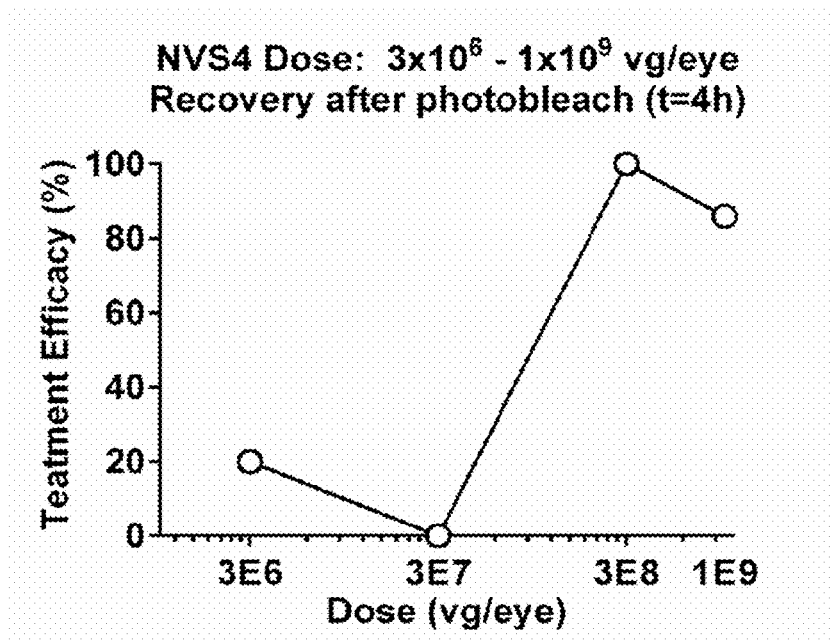

FIG. 5A demonstrates that NVS4 at multiple doses is efficacious at improving the rate of dark adaptation for at least 93 days post-injection. Both the $3\times10^8$ and $1\times10^9$ vg/eye groups were efficacious compared to naïve controls based on a one way ANOVA with a Newman-Keuls multiple comparison test. FIG. 5B displays the data from FIG. 5A in a different format. In this case, the plot displays the percentage of eyes/group with an a-wave recovery greater than that defined by the mean+3SD of the naïve group from several experiments. The results suggest that for NVS4, 85% of eyes treated with $3\times10^8$ and $1\times10^9$ vg/eye exhibited an increase in dark adaptation rate.

Figure 6:
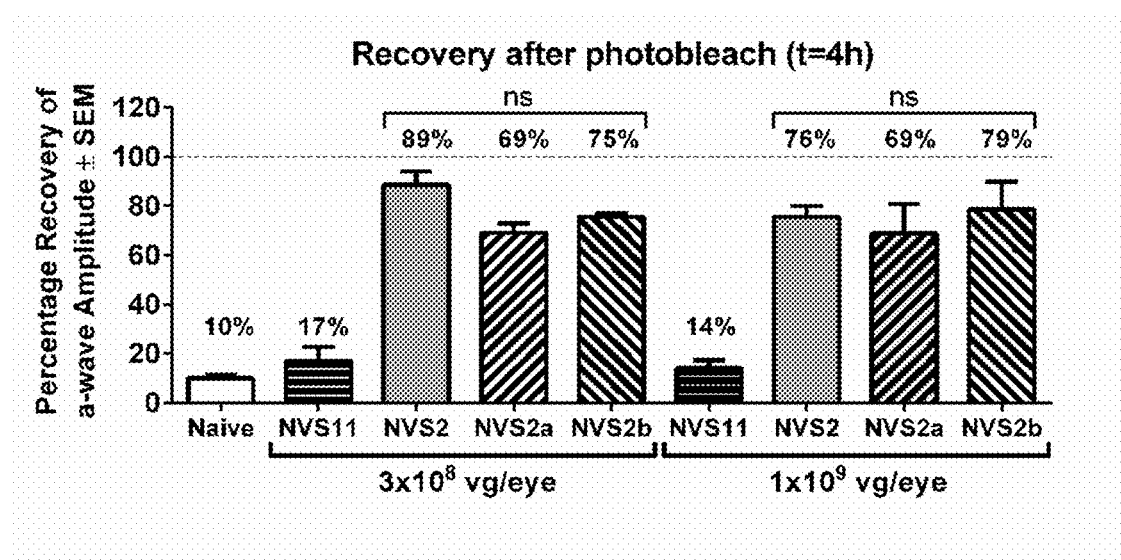
FIG. 6. Measurement of increased rate of dark adaptation of RLBP1 KO mice treated with NVS2 prepared with different purification methods.

FIG. 6 demonstrates the increase in dark adaptation rate achieved with vector NVS2 generated by various production methods. NVS2 and NVS2a were both produced using two different CsCl gradient centrifugation methods while NVS2b was purified using column chromatography. Efficacy achieved 84 days post-injection with all three purification methods is indistinguishable based on a one way ANOVA with a Tukey's test. This result indicates that 3 independent productions of NVS2 in 2 independent laboratories yielded functional material resulting in similar efficacy in RLBP1 KO mice.

Summary of Example 4 Results:
  Eyes injected with viral vector NVS2 exhibit an increased rate of dark adaption at doses ranging from $3\times10^7$ to $1\times10^9$ vg/eye, where efficacy lasts for at least 350 days post injection in the RLBP1 KO mouse model.
  Eyes injected with viral vector NVS4 exhibit an increased rate of dark adaption at doses ranging from $3\times10^8$ to $1\times10^9$ vg/eye and the efficacy endures at least 204 days at both doses.
  Eyes injected with viral vector NVS1 exhibit an increased rate of dark adaptation at the dose of $3\times10^8$ vg/eye and the efficacy endures at least 350 days.
  Eyes injected with viral vector NVS3 and NVS5 exhibit an increased rate of dark adaptation at the dose of $3\times10^9$ vg/eye and efficacy endures at least 371 days. Efficacy of NVS3 and NVS5 was not observed at $3\times10^8$ vg/eye for any time point tested.

Conclusion:
  Viral vector NVS2 exhibits higher maximum recovery than equivalent doses of the other vectors tested. Additionally, the NVS2 vector-mediated efficacy appears to be indistinguishable when prepared using CsCl or column chromatography purification.

Summary of Results:
  The results demonstrated that self-complementary AAV8-pRLBP1(short)-eGFP vector, the reporter gene surrogate version of the therapeutic vector NVS2, leads to RPE and Müller cell type specific expression with no detectable off-target expression, where the therapeutic vector NVS2 leads to at least 350 days of visual function recovery measured by a-wave recovery in RLBP1 mice at doses ranging from $3\times10^7$ to $1\times10^9$ vg/eye. This specific gene cassette when packaged in a single-stranded genome and packaged with the same serotype capsid 8 exhibits significantly lower level of gene expression in mice, as demonstrated by the measurement of mRNA expression level. The same self-complementary genome as NVS2 and packaged in AAV2 capsid, which is NVS1, demonstrated efficacious a-wave recovery (i.e.: an increased rate of dark adaption) at the dose of $3\times10^8$ vg/eye for at least 350 days. This result suggests that NVS2 is a more potent viral vector than NVS1, which is likely due to the more efficient infection of AAV8 capsid than AAV2 capsid to the target cell types.

The results also demonstrated that AAV8-pRLBP1(long)-eGFP vector, the reporter gene surrogate version of the therapeutic vector NVS4, leads to RPE and Müller cell expression but also to photoreceptors. The therapeutic vector NVS4 leads to at least 204 days of efficacy at doses ranging from $3\times10^8$ to $1\times10^9$ vg/eye. The same genome in NVS4 but packaged in AAV 2 capsid, which is NVS3, leads to efficacious a-wave recovery at the dose of $3\times10^9$ but not at lower dose tested ($3\times10^8$ vg/eye). The results demonstrated that AAV8-pRPE65-eGFP vector, the reporter gene surrogate version of the therapeutic vector NVS6, leads to RPE cell type expression with extensive photoreceptor off-target expression. When therapeutic vector NVS5, which carries the same genome as NVS6 but packaged into AAV2 capsid, is tested in RLBP1 KO mouse efficacy model, the results demonstrated that NVS5 endures positive a-wave recovery efficacy at the dose of $3\times10^9$ vg/eye but not at lower dose tested ($3\times10^8$ vg/eye).

References
Burstedt M S, Forsman-Semb K, Golovleva I, et al (2001) Ocular phenotype of Bothnia dystrophy, an autosomal recessive retinitis pigmentosa associated with an R234W mutation in the RLBP1 gene. Arch Ophthalmol; 119:260-267.
Burstedt M S and Mönestam E (2010) Self-reported quality of life in patients with retinitis pigmentosa and maculopathy of Bothnia type. Clin Ophthalmol; 4:147-54.
Choi V W, Asokan A, Haberman R A, and Samulski R J (2007) Production of Recombinant Adeno-Associated Viral Vectors for In Vitro and In Vivo Use. CURRENT PROTOCOLS IN MOLECULAR BIOLOGY. 16:25, Supplement 78.
Choi V W, McCarty D M, and Samulski R J (2005) AAV Hybrid Serotypes: Improved Vectors for Gene Delivery. Curr Gene Ther; 5(3):299-310.
Demirci F Y K, Rigatti B W, Mah T S, et al (2004) A novel compound heterozygous mutation in the cellular retinaldehyde-binding protein gene (RLBP1) in a patient with retinitis punctata albescens. Am J. Ophthalmol.; 138:171-173.

Eichers E R, Green J S, Stockton D W, et al (2002) Newfoundland rod-cone dystrophy, an early-onset retinal dystrophy, is caused by splice-junction mutations in RLBP1. Am J Hum Genet; 70:955-964.

Ferrari F K, Xiao X, McCarty D et al (1997) New developments in the generation of Ad-free, high-titer rAAV gene therapy vectors. Nat Med 3(11); 1295-1297.

Fishman G A, Roberts M F, Derlacki D J, et al (2004) Novel mutations in the cellular retinaldehyde-binding protein gene (RLBP1) associated with retinitis punctata albescens: evidence of interfamilial genetic heterogeneity and fundus changes in heterozygotes. Arch Ophthalmol.; 122:70-75.

Golovleva I and Burstedt M (2012) Retinitis Pigmentosa in Northern Sweden—From Gene to Treatment. March 2012. Advances in Ophthalmology, chapter 25, p. 451-472. Published by InTech.

Golovleva I, Köhn L, Burstedt M, et al (2010) Mutation spectra in autosomal dominant and recessive retinitis pigmentosa in northern Sweden. Adv Exp Med Biol. 664:255-262.

Grieger J C, Choi V W and Samulski R J. (2006) Production and characterization of adeno-associated viral vectors. Nat Protoc. 1(3); 1412-1428.

He X, Lobsiger J and Stocker A (2009) Bothnia dystrophy is caused by domino-like rearrangements in cellular retinaldehyde-binding protein mutant R234W. Proc. Natl Acad Sci USA. 106(44): 18545-50.

Jacobson S G, Acland G M, Aguirre G D et al (2006) Safety of Recombinant Adeno-Associated Virus Type 2-RPE65 Vector Delivered by Ocular Subretinal Injection. Molecular Therapy. 13(6); 1074-1084.

Katsanis N, Shroyer N F, Lewis R A, et al (2001) Fundus albipunctatus and retinitis punctata albescens in a pedigree with an R150Q mutation in RLBP1. Clin Genet; 59:424-429.

Köhn L, Burstedt M S, Jonsson F, et al (2008) Carrier of R14W in carbonic anhydrase IV presents Bothnia dystrophy phenotype caused by two allelic mutations in RLBP1. Invest Opthalmol Vis Sci. 49(7): 3172-3177.

Lock M, Alvira M, Vandenberghe L H, et al. (2010) Rapid, Simple, and Versatile Manufacturing of Recombinant Adeno-Associated Viral Vectors at scale. Human Gene Therapy. 21; 1-13.

Maw M A, Kennedy B, Knight A, et al (1997) Mutation of the gene encoding cellular retinaldehyde-binding protein in autosomal recessive retinitis pigmentosa. Nat Genet; 17:198-200.

McCarty D M (2008) Self-Complementary AAV Vectors; Advances and Applications. Molecular Therapy. 16(10): 1648-1656.

McCarty D M, Fu H, Monohan P E et al (2003) Adeno-associated virus terminal repeat (TR) mutant generates self-complementary vectors to overcome the rate-limiting step t transduction in vivo. Gene Therapy. 10; 2112-2118.

Morimura H, Berson E L, Dryja T P (1999) Recessive mutations in the RLBP1 gene encoding cellular retinaldehyde-binding protein in a form of retinitis punctata albescens. Invest Ophthalmol Visual Sci; 40:1000-1004.

Muzyczka N and Berns K I (2001) Chapter 69, Fields Virology. Lippincott Williams & Wilkins.

Naz S, Ali S, Riazuddin S A, et al (2011) Mutations in RLBP1 associated with fundus albipunctatus in consanguineous Pakistani families. Br J Ophthalmol; 95:1019-24.

Nojima K, Hosono K, Zhao Y, et al (2011) Clinical features of a Japanese case with Bothnia dystrophy. Ophthalmic Genet [Epub ahead of print]

Phelan J K and Bok D (2000) A Brief Review of Retinitis Pigmentosa and the Identified Retinitis Pigmentosa Genes. Mol Vis; 6:116-124.

Roman A J, Boye S L, Aleman T S, et al (2007) Electroretinographic Analyses of RPE65-mutant rd12 Mice: Developing an In Vivo Bioassay for Human Gene Therapy Trials of Leber Congenital Amaurosis. Mol Vis. 13; 1701-1710.

Saari J C, Huang J, Possin D E, et al (1997) Cellular retinaldehyde-binding protein is expressed by oligodendrocytes in optic nerve and brain. Glia.; 21:259-268.

SAMBROOK et al (1989) MOLECULAR CLONING: A LABORATORY MANUAL 2nd Ed. (Cold Spring Harbor, N.Y)

Saari J C, Nawrot M, Kennedy B N et al. (2001) Visual Cycle Impairment in Cellular Retinaldehyde Binding Protein (CRALBP) Knockout Mice Results in Delayed Dark Adaptation. Neuron; 29:739-748.

Samulski R J, Srivastava A, Berns K I, et al. (1983) Rescue of adeno-associated virus from recombinant plasmids: gene correction within the terminal repeats of AAV. Cell. 33(1): 135-143.

Schmidt M, Vouteaakis A, Afione S et al. (2008) Adeno-Associated Virus Type 12 (AAV12): a Novel AAV Serotype with Sialic Acid- and Heparan Sulfate Proteoglycan-Independent Transduction Activity. J of Virology. 82(3): 1399-1406.

Smith R H, Levy J R and Kotin R M. (2009) A Simplified Baculovirus-AAV Expression Vector System Coupled with One-Step Affinity Purification Yields High-Titer rAAV Stocks from Insect Cells. Molecular Therapy. 17(11); 1888-1896.

Travis G H, Golczak M, Moise A R, et al (2007) Diseases caused by defects in the visual cycle: retinoids as potential therapeutic agents. Annu Rev Pharmacol Toxicol.; 47: 469-512.

Vandenberghe L H, Xiao R, Lock M, et al. (2010) Efficient Serotype-Dependent Release of Functional Vector into the Culture Medium During Adeno-Associated Virus Manufacturing. Human Gene Therapy. 21; 1251-1257.

Wang J and Kefalov J V (2011) The Cone-specific visual cycle. Progress in retinal and eye research. 30: 115-128.

The invention claimed is:

1. A viral vector comprising:
a vector genome comprising a retinaldehyde binding protein 1 (RLBP1) coding sequence comprising nucleic acid sequences in the 5' to 3' direction of: SEQ ID NO: 36, 62, 63, 64, 65, 66, 1, 3, 4, 5, 6, 8, and 9, and
an adeno-associated virus (AAV) serotype 2 or 8 capsid.

2. The viral vector of claim 1, wherein said vector comprises an adeno-associated virus (AAV) serotype 8 capsid.

3. A composition comprising the viral vector of claim 1.

4. The composition of claim 3 further comprising a pharmaceutically acceptable excipient.

5. A viral vector comprising:
an adeno-associated virus (AAV) serotype 2 or 8 capsid,
a vector genome comprising a retinaldehyde binding protein 1 (RLBP1) coding sequence comprising, in the 5' to 3' direction, nucleic acid sequences selected from the group consisting of:

a) SEQ ID NO: 2, 10, 5, 6, 8, and 9;
b) SEQ ID NO: 2, 11, 5, 6, 8, 14, 9;
c) SEQ ID NO: 2, 22, 5, 6, 8, 23, and 9; and
d) SEQ ID NO: 2, 3, 4, 5, 6, 8, 23, and 9.

6. A nucleic acid comprising a gene cassette, said gene cassette comprises, in the 5' to 3' direction:
(i) a 5' inverted terminal repeat (ITR) having a nucleic acid sequence of SEQ ID NO: 2 or a non-resolvable ITR having a nucleic acid sequence of SEQ ID NO: 1;
(ii) a recombinant nucleotide sequence comprising an RLBP1 coding sequence having a promoter nucleic acid sequence selected from: SEQ ID NO: 3, 10, 11, 12 and 22 operably linked to said RLBP1 coding sequence; and
(iii) a 3'ITR having a nucleic acid sequence of SEQ ID NO: 9.

7. The nucleic acid of claim 6 that is a plasmid.

8. The nucleic acid of claim 6, further comprising the nucleic acid sequence selected from SEQ ID NO: 26, 27, 28, 29, 30 and 50.

9. The nucleic acid of claim 6, wherein the gene cassette comprises, in the 5' to 3' direction, the sequences selected from:
  a) SEQ ID NO: 2, 10, 5, 6, 8, and 9,
  b) SEQ ID NO: 2, 11, 5, 6, 8, 14 and 9,
  c) SEQ ID NO: 2, 22, 5, 6, 8, 23 and 9,
  d) SEQ ID NO: 2, 3, 4, 5, 6, 8, 23 and 9, and
  e) SEQ ID NO: 1, 3, 4, 5, 6, 8, and 9.

\* \* \* \* \*